United States Patent
Lee

(10) Patent No.: US 12,319,955 B2
(45) Date of Patent: *Jun. 3, 2025

(54) MATERIALS AND METHODS FOR LOCALIZED DETECTION OF NUCLEIC ACIDS IN A TISSUE SAMPLE

(71) Applicant: The Regents of the University of Michigan, Ann Arbor, MI (US)

(72) Inventor: Jun Hee Lee, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 98 days.

This patent is subject to a terminal disclaimer.

(21) Appl. No.: 18/343,858

(22) Filed: Jun. 29, 2023

(65) Prior Publication Data

US 2024/0132936 A1 Apr. 25, 2024
US 2024/0229102 A9 Jul. 11, 2024

Related U.S. Application Data

(63) Continuation of application No. 17/708,981, filed on Mar. 30, 2022, now Pat. No. 11,713,480, and a continuation of application No. PCT/US2021/041725, filed on Jul. 15, 2021.

(60) Provisional application No. 63/141,254, filed on Jan. 25, 2021, provisional application No. 63/053,238, filed on Jul. 17, 2020.

(51) Int. Cl.
| | |
|---|---|
| *C12Q 1/68* | (2018.01) |
| *C12N 15/10* | (2006.01) |
| *C12Q 1/6806* | (2018.01) |
| *C12Q 1/6841* | (2018.01) |
| *C12Q 1/6874* | (2018.01) |

(52) U.S. Cl.
CPC ....... *C12Q 1/6806* (2013.01); *C12N 15/1065* (2013.01); *C12Q 1/6841* (2013.01); *C12Q 1/6874* (2013.01)

(58) Field of Classification Search
CPC .................................................. C12Q 1/6869
See application file for complete search history.

(56) References Cited

U.S. PATENT DOCUMENTS

| | | |
|---|---|---|
| 8,133,719 B2 | 3/2012 | Drmanac et al. |
| 10,774,374 B2 | 9/2020 | Frisen et al. |

(Continued)

FOREIGN PATENT DOCUMENTS

| | | |
|---|---|---|
| WO | WO 2012/140224 | 10/2012 |
| WO | WO 2016/162309 | 10/2016 |

(Continued)

OTHER PUBLICATIONS

International Search Report and Written Opinion for PCT/US21/41725. Mailed Nov. 15, 2021. 10 pages.

(Continued)

*Primary Examiner* — Kenneth R Horlick
(74) *Attorney, Agent, or Firm* — Casimir Jones, S.C.; Rikki A. Hullinger

(57) ABSTRACT

The present disclosure relates to materials and methods for spatial detection of nucleic acid in a tissue sample or a portion thereof. In particular, provided herein are materials and methods for detecting RNA so as to obtain spatial information about the localization, distribution or expression of genes in a tissue sample. In some embodiments, the materials and methods provided herein enable detection of gene expression in a single cell.

20 Claims, 95 Drawing Sheets

Specification includes a Sequence Listing.

(56) References Cited

U.S. PATENT DOCUMENTS

| | | | |
|---|---|---|---|
| 11,162,132 | B2 | 11/2021 | Frisen et al. |
| 11,299,774 | B2 | 4/2022 | Frisen et al. |
| 11,390,912 | B2 | 7/2022 | Frisen et al. |
| 2011/0065607 | A1 | 3/2011 | Kersey et al. |
| 2014/0066318 | A1 | 3/2014 | Frisen et al. |
| 2019/0203275 | A1 | 7/2019 | Frisen et al. |

FOREIGN PATENT DOCUMENTS

| | | |
|---|---|---|
| WO | WO 2020/047002 | 3/2020 |
| WO | WO 2021/168455 | 8/2021 |

OTHER PUBLICATIONS

Abbas et al., The eEF1A Proteins: At the Crossroads of Oncogenesis, Apoptosis, and Viral Infections. Front Oncol. Apr. 7, 2015;5:75. 10 pages.

Aizarani et al., A human liver cell atlas reveals heterogeneity and epithelial progenitors. Nature. Aug. 2019;572(7768):199-204.

Altmann. Morphological observations on mucus-secreting nongoblet cells in the deep crypts of the rat ascending colon. Am J Anat. May 1983;167(1):95-117.

Asp et al., A Spatiotemporal Organ-Wide Gene Expression and Cell Atlas of the Developing Human Heart. Cell. Dec. 12, 2019;179(7):1647-1660.e19.

Asp et al., Spatially Resolved Transcriptomes-Next Generation Tools for Tissue Exploration. Bioessays. Oct. 2020;42(10):e1900221. 16 pages.

Baccin et al., Combined single-cell and spatial transcriptomics reveal the molecular, cellular and spatial bone marrow niche organization. Nat Cell Biol. Jan. 2020;22(1):38-48.

Bahar Halpern et al., Nuclear Retention of mRNA in Mammalian Tissues. Cell Rep. Dec. 29, 2015;13(12):2653-62.

Bahar Halpern et al., Single-cell spatial reconstruction reveals global division of labour in the mammalian liver. Nature. Feb. 16, 2017;542(7641):352-356.

Baratta et al., Cellular organization of normal mouse liver: a histological, quantitative immunocytochemical, and fine structural analysis. Histochem Cell Biol. Jun. 2009;131(6):713-26.

Becht et al., Dimensionality reduction for visualizing single-cell data using UMAP. Nat Biotechnol. Dec. 3, 2018. 10 pages.

Ben-Moshe et al., Spatial heterogeneity in the mammalian liver. Nat Rev Gastroenterol Hepatol. Jul. 2019;16(7):395-410.

Bentley et al., Accurate whole human genome sequencing using reversible terminator chemistry. Nature. Nov. 6, 2008;456(7218):53-9.

Bergenstrahle et al., Seamless integration of image and molecular analysis for spatial transcriptomics workflows. BMC Genomics. Jul. 14, 2020;21(1):482. 7 pages.

Bergenstråhle et al., Super-resolved spatial transcriptomics by deep data fusion. Nat Biotechnol. Nov. 29, 2021. 7 pages.

Bolte et al., A guided tour into subcellular colocalization analysis in light microscopy. J Microsc. Dec. 2006;224(Pt 3):213-32.

Borenshtein et al., Decreased expression of colonic Slc26a3 and carbonic anhydrase iv as a cause of fatal infectious diarrhea in mice. Infect Immun. Sep. 2009;77(9):3639-50.

Callea et al., From immunohistochemistry to in situ hybridization. Liver. Aug. 1992;12(4 Pt 2):290-5.

Cho et al., Concurrent activation of growth factor and nutrient arms of mTORC1 induces oxidative liver injury. Cell Discov. Nov. 19, 2019;5:60. 18 pages.

Cho et al., Microscopic examination of spatial transcriptome using Seq-Scope. Cell. Jun. 24, 2021;184(13):3559-3572.e22.

Crosetto et al., Spatially resolved transcriptomics and beyond. Nat Rev Genet. Jan. 2015;16(1):57-66.

De Haan et al., Unraveling the transcriptional determinants of liver sinusoidal endothelial cell specialization. Am J Physiol Gastrointest Liver Physiol. Apr. 1, 2020;318(4):G803-G815.

Dobin et al., STAR: ultrafast universal RNA-seq aligner. Bioinformatics. Jan. 1, 2013;29(1):15-21.

Donne et al., Polyploidy in liver development, homeostasis and disease. Nat Rev Gastroenterol Hepatol. Jul. 2020;17(7):391-405.

Dou et al., Macrophage Phenotype and Function in Liver Disorder. Front Immunol. Jan. 28, 2020;10:3112. 11 pages.

Eckhardt et al., Intestinal epithelial serum amyloid A modulates bacterial growth in vitro and pro-inflammatory responses in mouse experimental colitis. BMC Gastroenterol. Nov. 10, 2010;10:133. 9 pages.

Farkas et al., Cryosectioning Method for Microdissection of Murine Colonic Mucosa. J Vis Exp. Jul. 12, 2015;(101):e53112. 6 pages.

Fischer et al., Differential expression of aquaporin 8 in human colonic epithelial cells and colorectal tumors. BMC Physiol. 2001;1:1. 5 pages.

Haber et al., A single-cell survey of the small intestinal epithelium. Nature. Nov. 16, 2017;551(7680):333-339.

Hildebrandt et al., Spatial Transcriptomics to define transcriptional patterns of zonation and structural components in the liver. bioRxiv. Jan. 12, 2021. 48 pages.

Hughes et al., Second-Strand Synthesis-Based Massively Parallel scRNA-Seq Reveals Cellular States and Molecular Features of Human Inflammatory Skin Pathologies. Immunity. Oct. 13, 2020;53(4):878-894.e7.

La Manno et al., RNA velocity of single cells. Nature. Aug. 2018;560(7719):494-498.

Levine et al., Normal histology of the colon. Am J Surg Pathol. Nov. 1989;13(11):966-84.

Liao et al., Uncovering an Organ's Molecular Architecture at Single-Cell Resolution by Spatially Resolved Transcriptomics. Trends Biotechnol. Jan. 2021;39(1):43-58.

Liu et al., High-Spatial-Resolution Multi-Omics Sequencing via Deterministic Barcoding in Tissue. Cell. Dec. 10, 2020;183(6):1665-1681.e18.

Mazzarini et al., Evolution and new frontiers of histology in bio-medical research. Microsc Res Tech. Feb. 2021;84(2):217-237.

Moor et al., Spatial Reconstruction of Single Enterocytes Uncovers Broad Zonation along the Intestinal Villus Axis. Cell. Nov. 1, 2018;175(4):1156-1167.e15.

Nestorowa et al., A single-cell resolution map of mouse hematopoietic stem and progenitor cell differentiation. Blood. Aug. 25, 2016;128(8):e20-31.

Okumura et al., Lypd8 promotes the segregation of flagellated microbiota and colonic epithelia. Nature. Apr. 7, 2016;532(7597):117-21.

Parikh et al., Colonic epithelial cell diversity in health and inflammatory bowel disease. Nature. Mar. 2019;567(7746):49-55.

Park et al., Holistic characterization of single-hepatocyte transcriptome responses to high-fat diet. Am J Physiol Endocrinol Metab. Feb. 1, 2021;320(2):E244-E258.

Park et al., The protein disulfide isomerase AGR2 is essential for production of intestinal mucus. Proc Natl Acad Sci U S A. Apr. 28, 2009;106(17):6950-5.

Pelaseyed et al., The mucus and mucins of the goblet cells and enterocytes provide the first defense line of the gastrointestinal tract and interact with the immune system. Immunol Rev. Jul. 2014;260(1):8-20.

Ro et al., Tumor suppressive role of sestrin2 during colitis and colon carcinogenesis. Elife. Feb. 25, 2016;5:e12204. 20 pages.

Rodriques et al., Slide-seq: A scalable technology for measuring genome-wide expression at high spatial resolution. Science. Mar. 29, 2019;363(6434):1463-1467.

Rothenberg et al., Identification of a cKit(+) colonic crypt base secretory cell that supports Lgr5(+) stem cells in mice. Gastroenterology. May 2012;142(5):1195-1205.e6.

Sack. Serum Amyloid A (SAA) Proteins. Subcell Biochem. 2020;94:421-436.

Saiman et al., The role of chemokines in acute liver injury. Front Physiol. Jun. 20, 2012;3:213. 12 pages.

Salmen et al., Barcoded solid-phase RNA capture for Spatial Transcriptomics profiling in mammalian tissue sections. Nat Protoc. Nov. 2018;13(11):2501-2534.

(56) References Cited

OTHER PUBLICATIONS

Sasaki et al., Reg4+ deep crypt secretory cells function as epithelial niche for Lgr5+ stem cells in colon. Proc Natl Acad Sci U S A. Sep. 13, 2016;113(37):E5399-407.

Singer et al., Comprehensive biodiversity analysis via ultra-deep patterned flow cell technology: a case study of eDNA metabarcoding seawater. Sci Rep. Apr. 12, 2019;9(1):5991. 12 pages.

Spencer et al., The human intestinal B-cell response. Mucosal Immunol. Sep. 2016;9(5):1113-24.

Stahl et al., Visualization and analysis of gene expression in tissue sections by spatial transcriptomics. Science. Jul. 1, 2016;353(6294):78-82.

Stickels et al., Highly sensitive spatial transcriptomics at near-cellular resolution with Slide-seqV2. Nat Biotechnol. Mar. 2021;39(3):313-319.

Stoeckius et al., Simultaneous epitope and transcriptome measurement in single cells. Nat Methods. Sep. 2017;14(9):865-868.

Storm et al., Designing Randomized DNA Sequences Free of Restriction Enzyme Recognition Sites. Biotechnol J. Jan. 2018;13(1):10.1002/biot.201700326. 14 pages.

Stuart et al., Comprehensive Integration of Single-Cell Data. Cell. Jun. 13, 2019;177(7):1888-1902.e21.

Tee et al., Dual phenotypic expression of hepatocytes and bile ductular markers in developing and preneoplastic rat liver. Carcinogenesis. Feb. 1996;17(2):251-9.

Vickovic et al., High-definition spatial transcriptomics for in situ tissue profiling. Nat Methods. Oct. 2019;16(10):987-990.

Werner et al., All-In-One: Advanced preparation of Human Parenchymal and Non-Parenchymal Liver Cells. PLoS One. Sep. 25, 2015;10(9):e0138655. 17 pages.

Xiong et al., Landscape of Intercellular Crosstalk in Healthy and NASH Liver Revealed by Single-Cell Secretome Gene Analysis. Mol Cell. Aug. 8, 2019;75(3):644-660.e5.

Zhou et al., Encoding Method of Single-cell Spatial Transcriptomics Sequencing. Int J Biol Sci. Jul. 30, 2020;16(14):2663-2674.

NGST Step 2: Random Primer Extension (RPE)

(SEQ ID NO: 22)

NGST Step 3: Secondary Strand Isolation (SEQ ID NO: 23)

(SEQ ID NO: 24)

FIG. 6A

NGST Step 4: Amplification by PCR (RPE-PCR)

(SEQ ID NO: 25)

NGST Step 5: RPE-PCR purification (SEQ ID NO: 26)

FIG. 6B

NGST Step 6: Indexing PCR (SEQ ID NO: 27)

5'-AATGATACGGCGACCACCGAGATCTACACTCTTTCCCTACACGACGCTCTTCCGATCT → → → → →
                                                              5'-GACCCTTTCCGATCT NNNNNNNNNNNNNNNN [n27] [oligo-dT_30] [NNNN] NNNNNNNNN AGATCGGAAGAGCACACGTCTGA-3'
                                                              3'-CTGCGAAGAGGCTAGA NNNNNNNNNNNNNNNN [n27] [oligo-dA_30] [NNNN] NNNNNNNNN TCTAGCTTCTCGTGTGCAGACT-5'
                                                                                                                            ← ← ← ← ←

NGST Step 7: Final Library Structure (SEQ ID NO: 28)

P5 sequence    NGST Barcode    Filler oligo-dT    [n27] [oligo-dT_30] [NNNN] NNNN    Tn5mosaic Ends    Index i5    P7 sequence

FIG. 6C

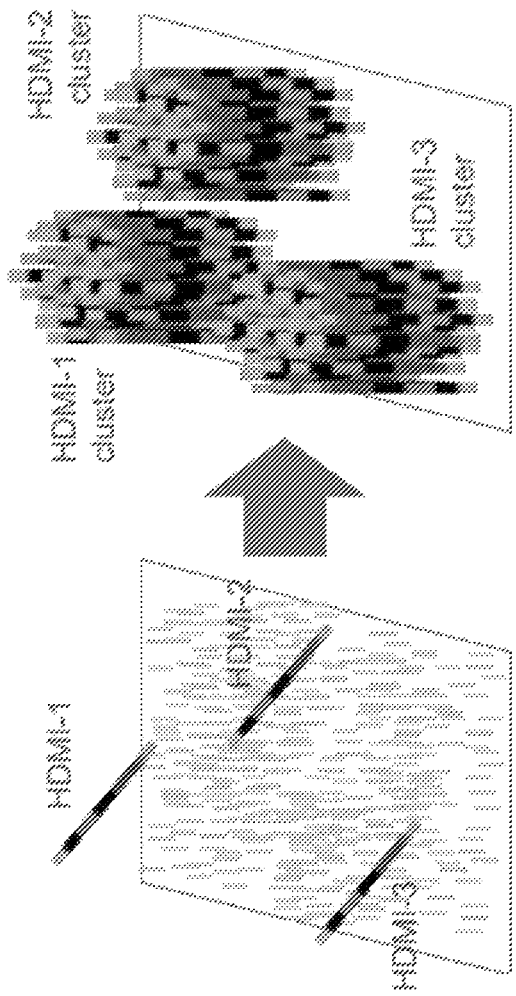
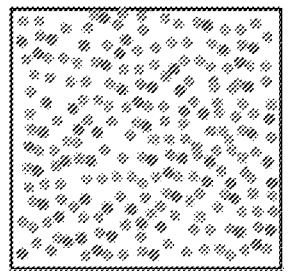
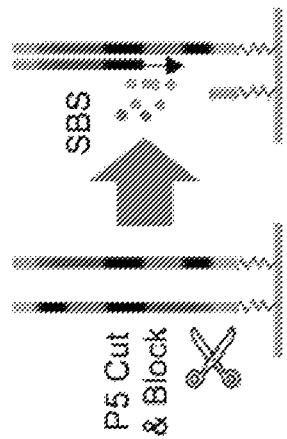
FIG. 8A
FIG. 8B
FIG. 8C

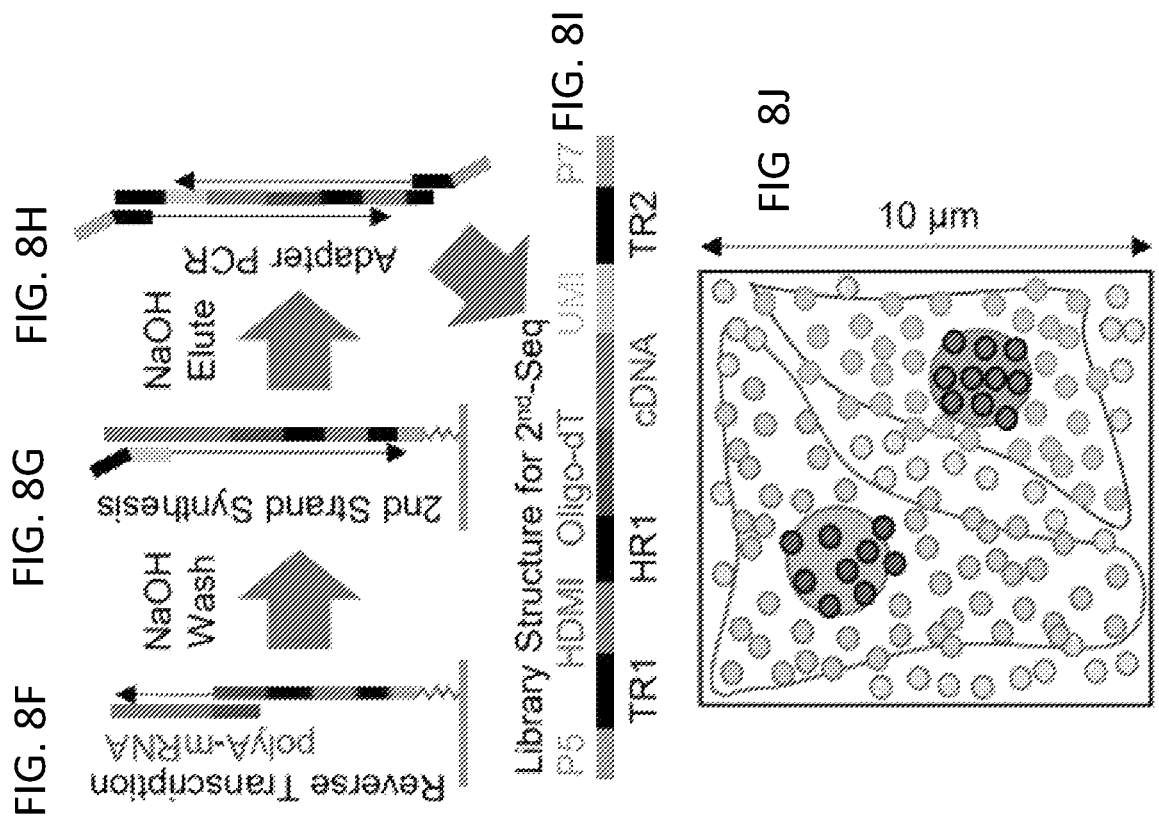
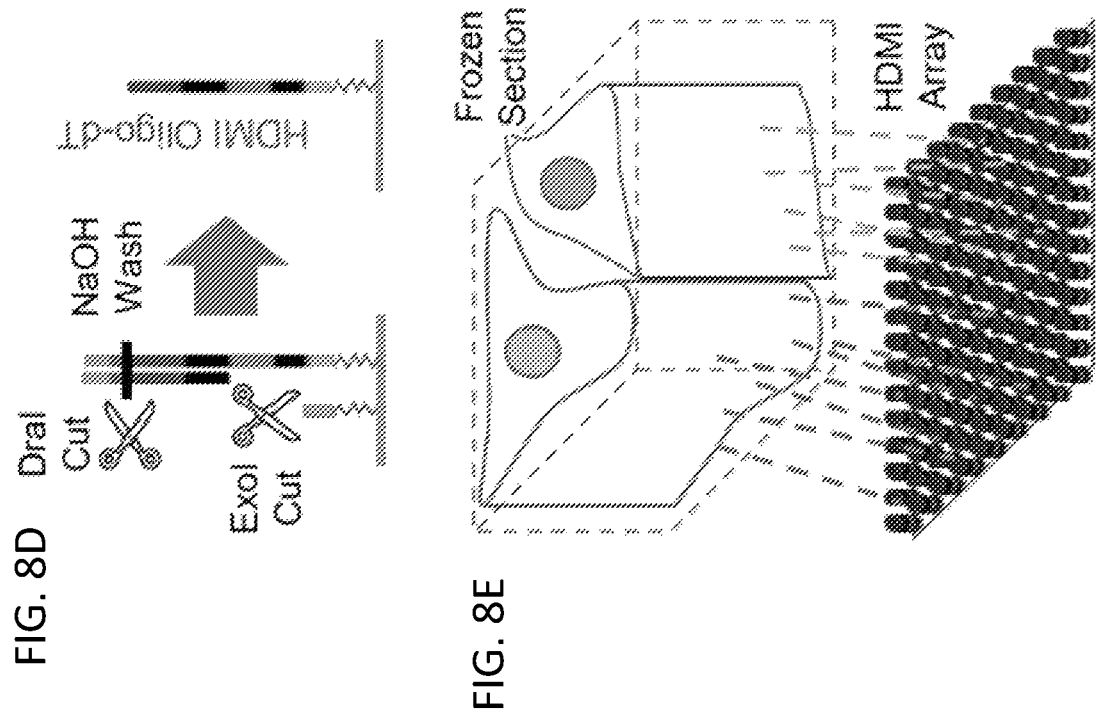

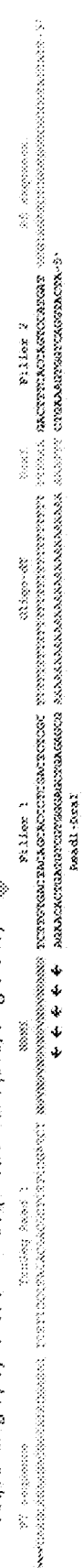
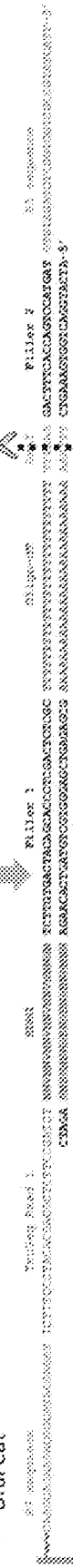
FIG. 9A

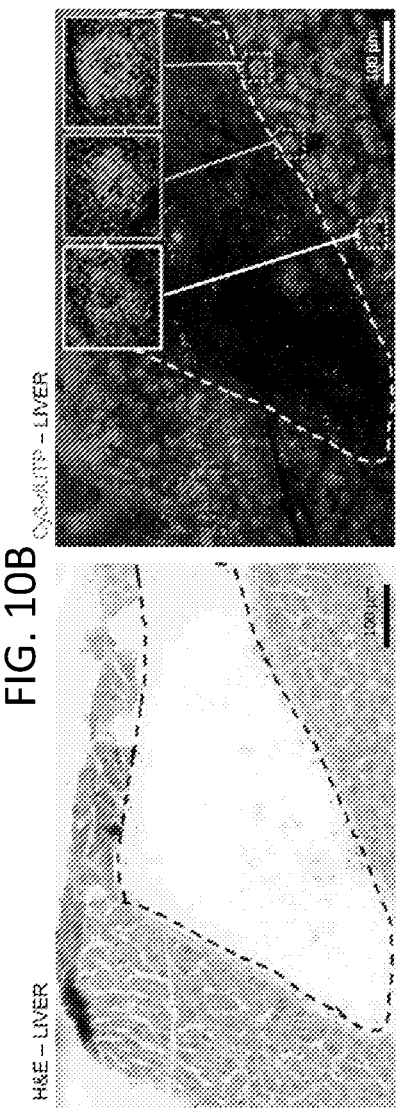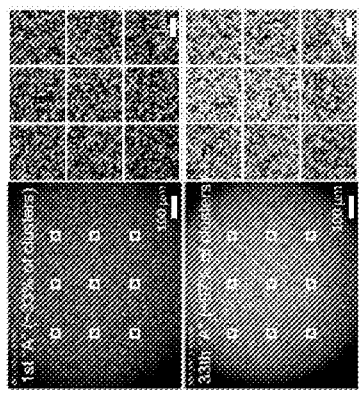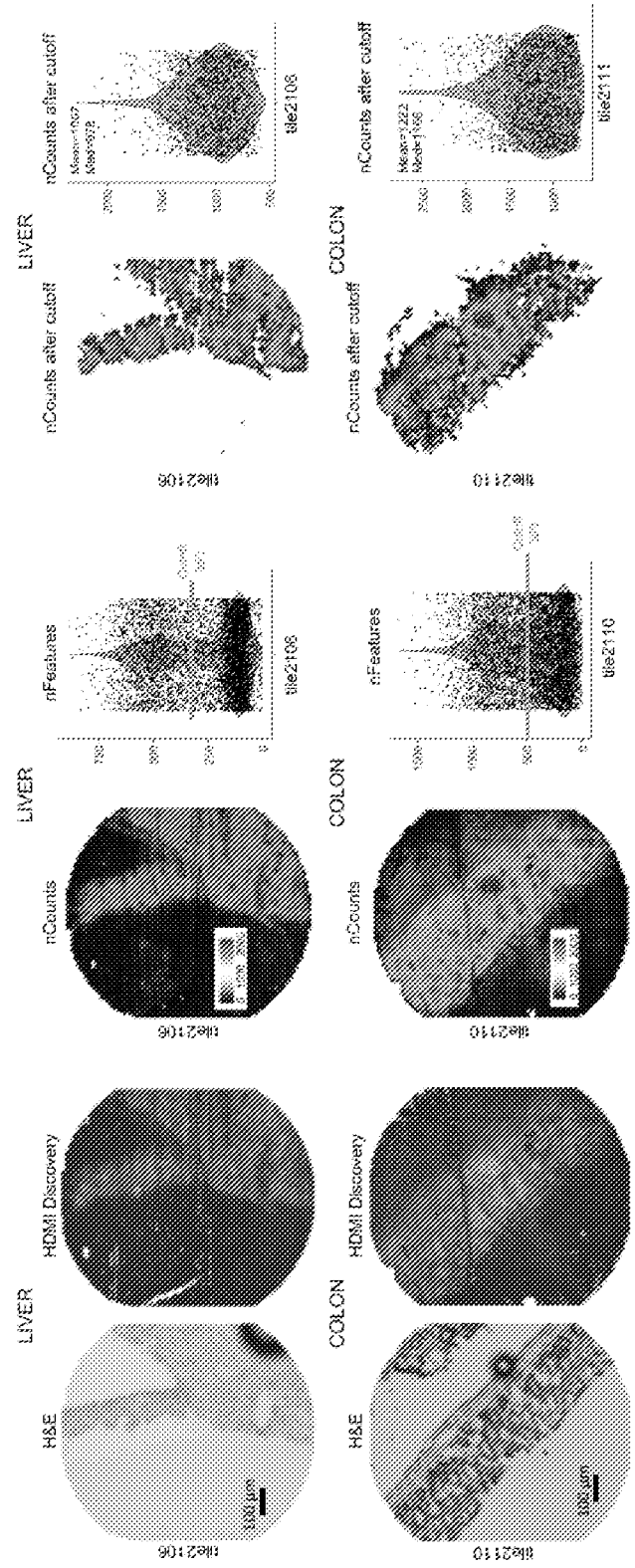
FIG. 10A
FIG. 10B
FIG. 10C
FIG. 10D
FIG. 10E

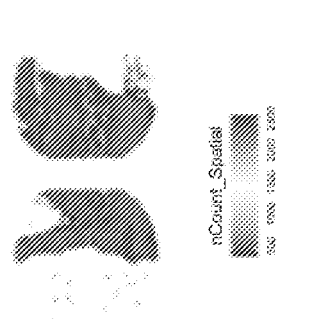
FIG. 11J
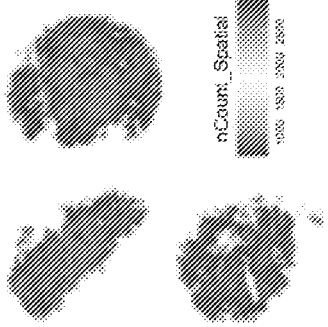
FIG. 11L
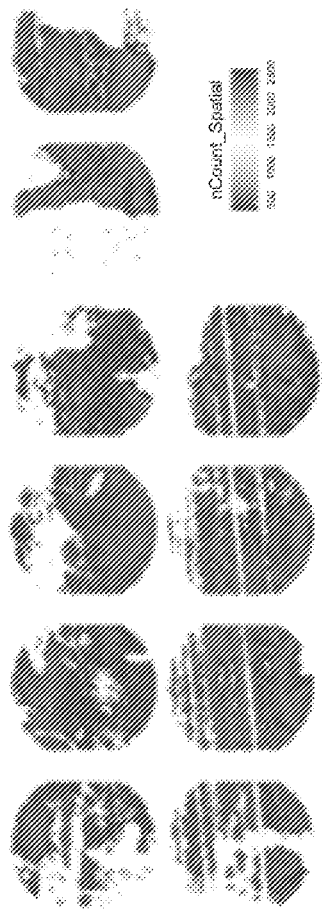
FIG. 11K
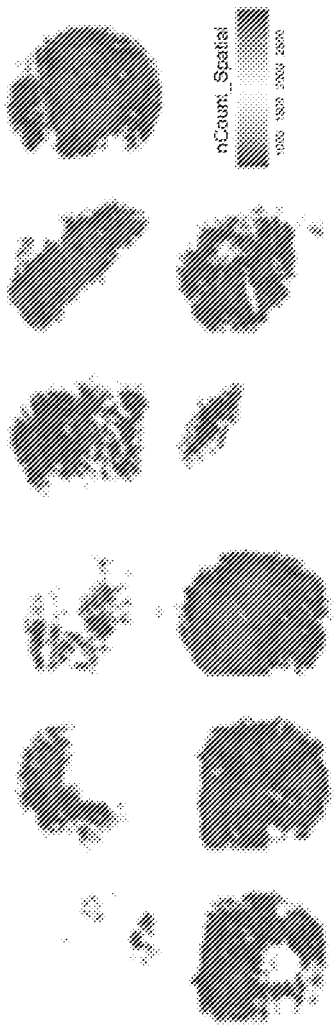
FIG. 11M
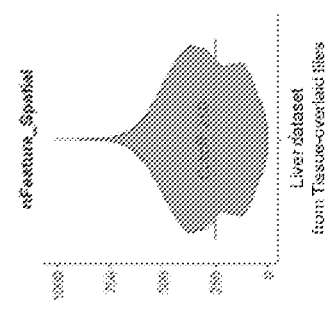
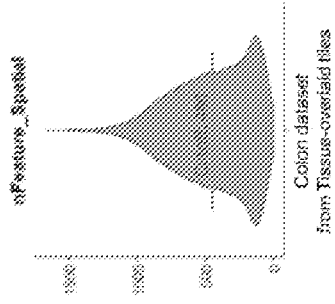

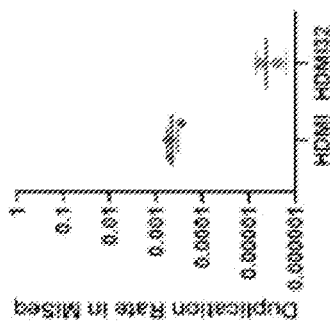
FIG. 11R
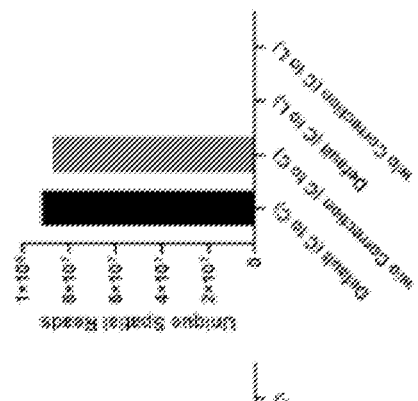
FIG. 11S
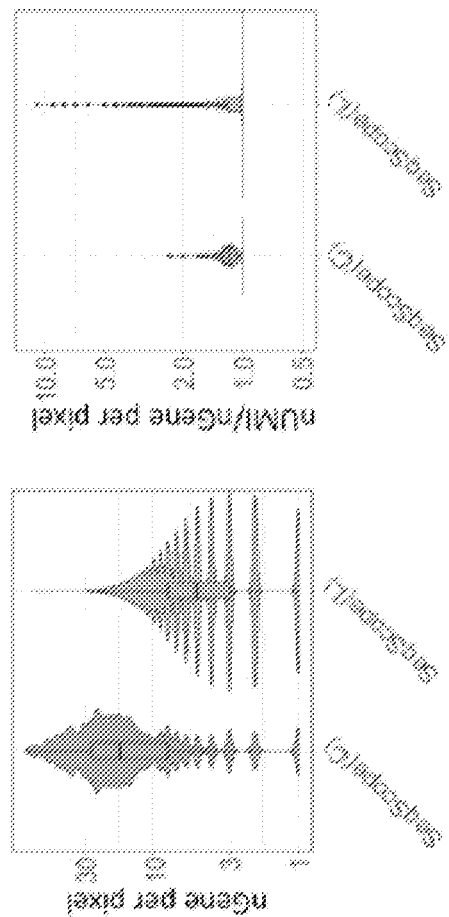
FIG. 11T
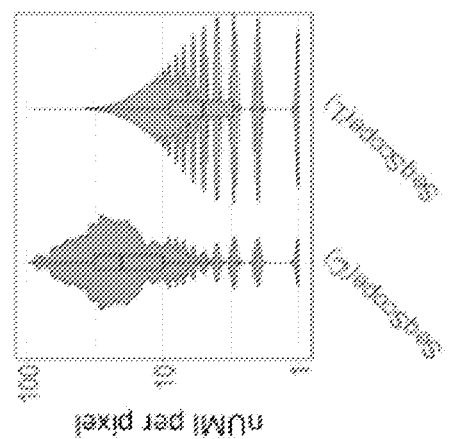

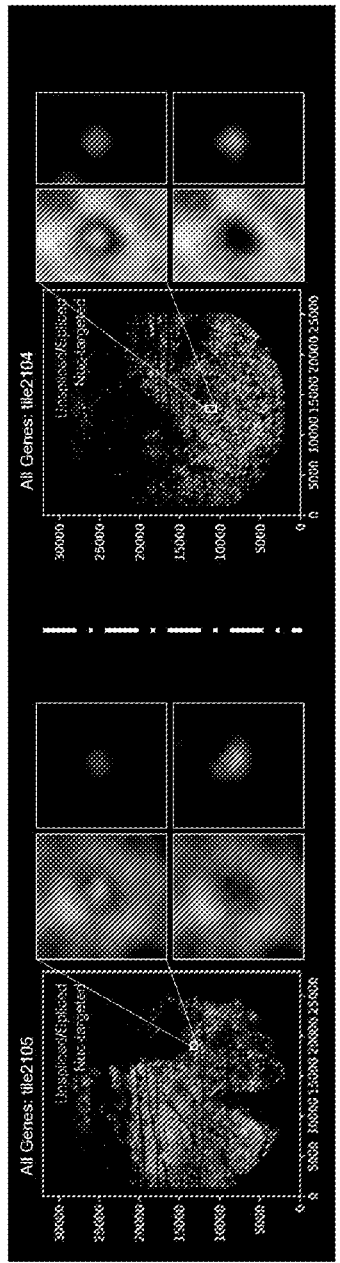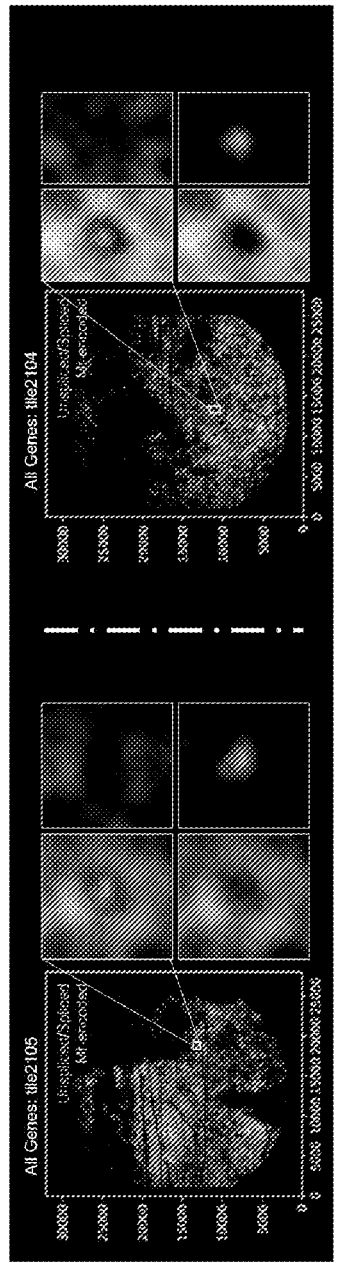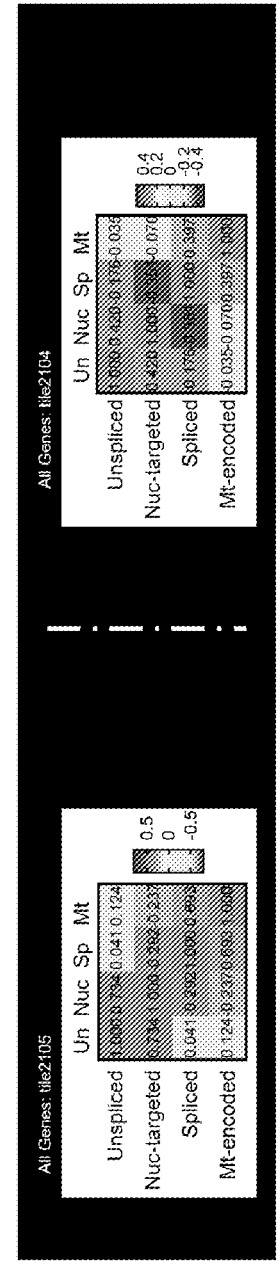
FIG. 13A
FIG. 13B
FIG. 13C

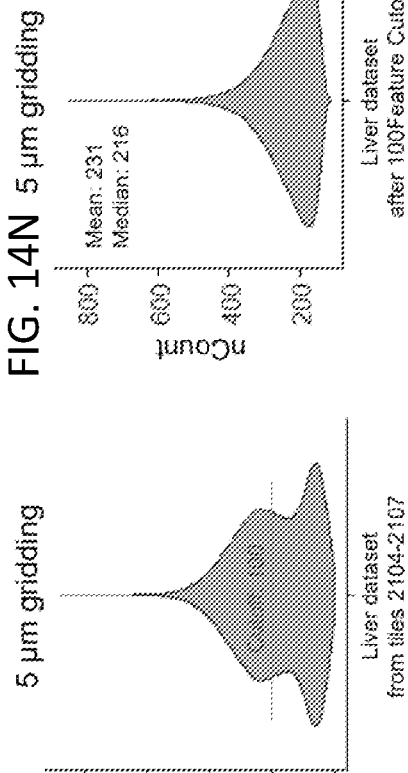
FIG. 14M
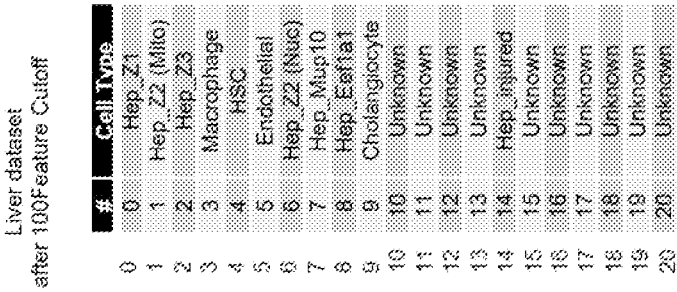
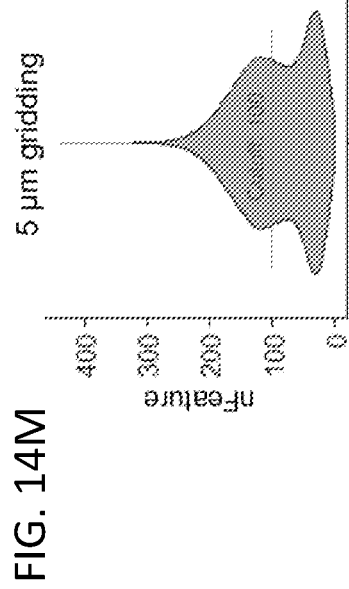
FIG. 14N
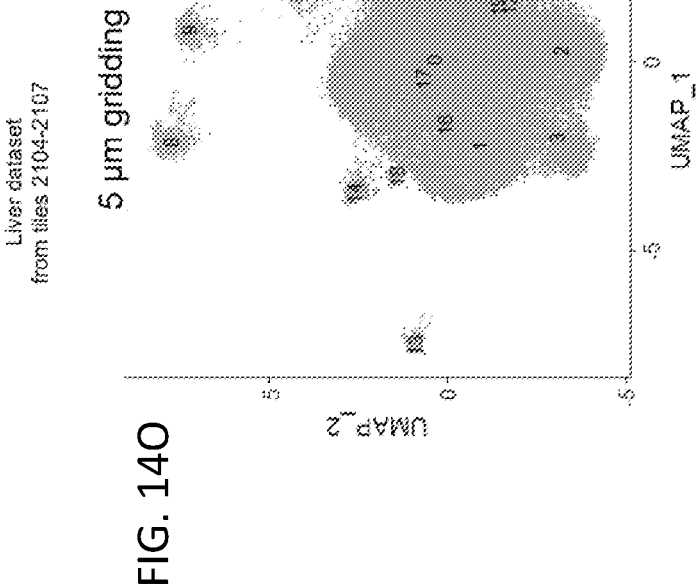
FIG. 14O

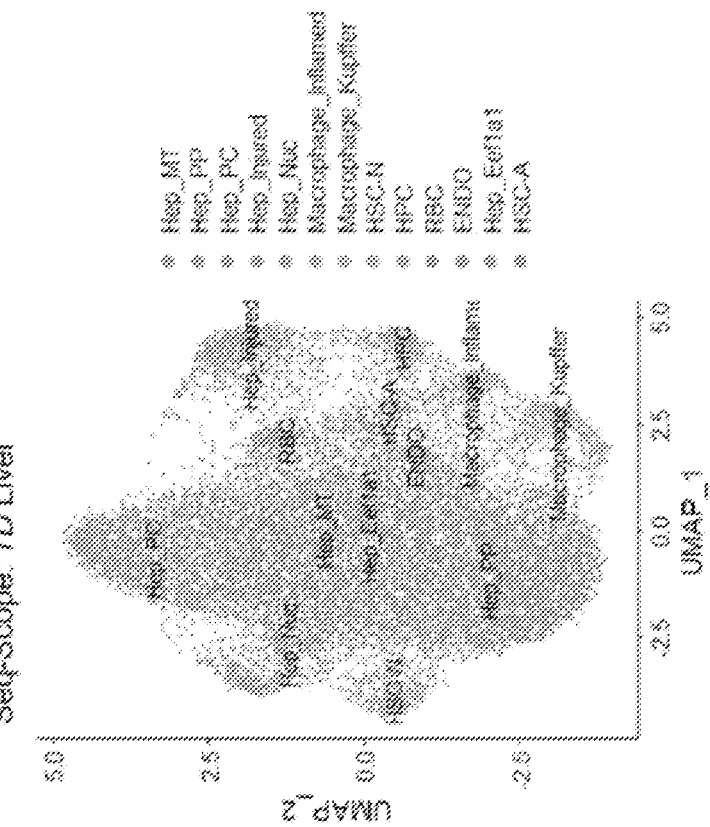
FIG. 16E
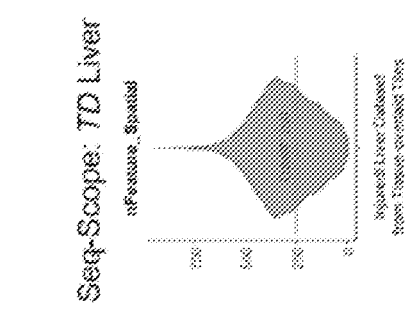
FIG. 16B
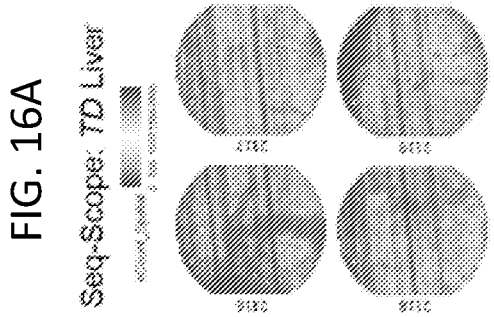
FIG. 16A
FIG. 16D
FIG. 16C
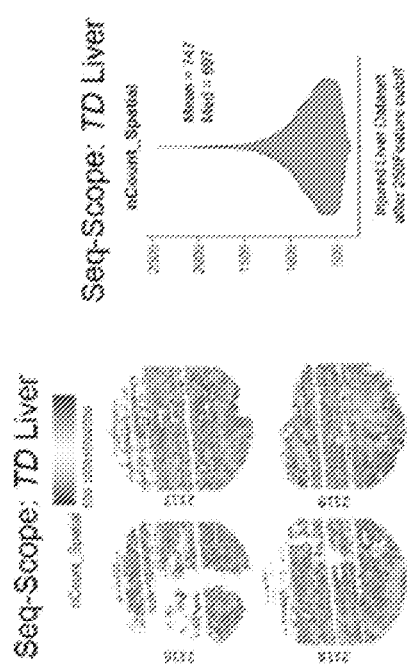

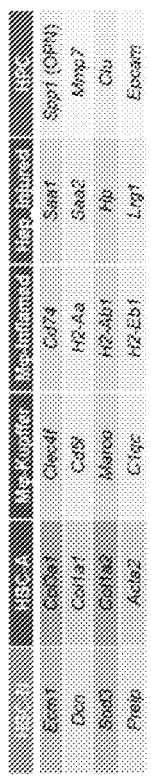
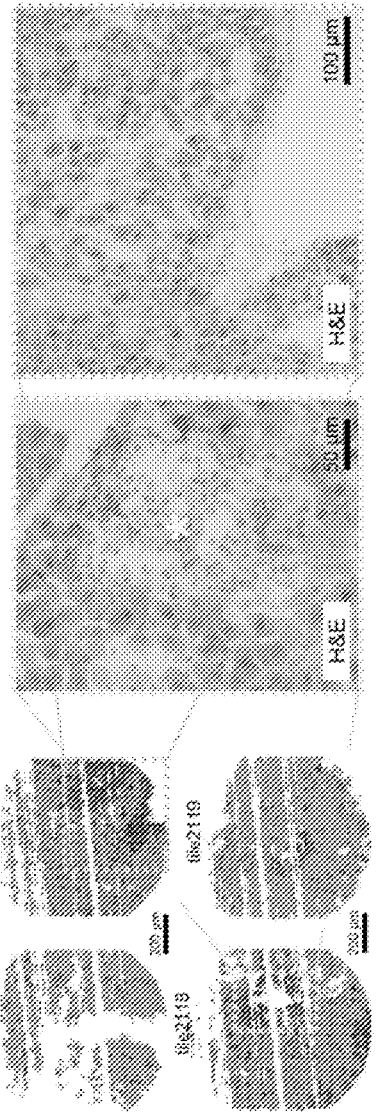
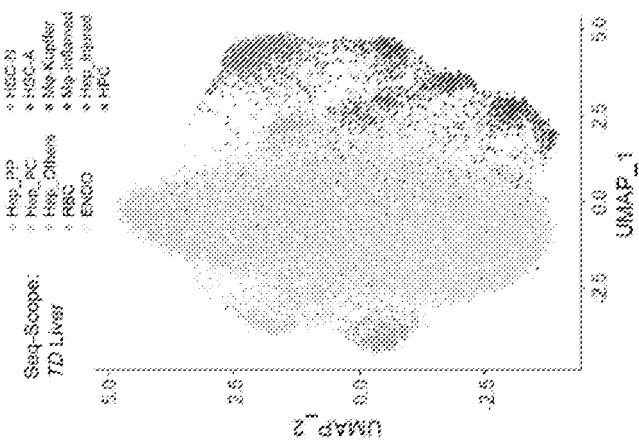

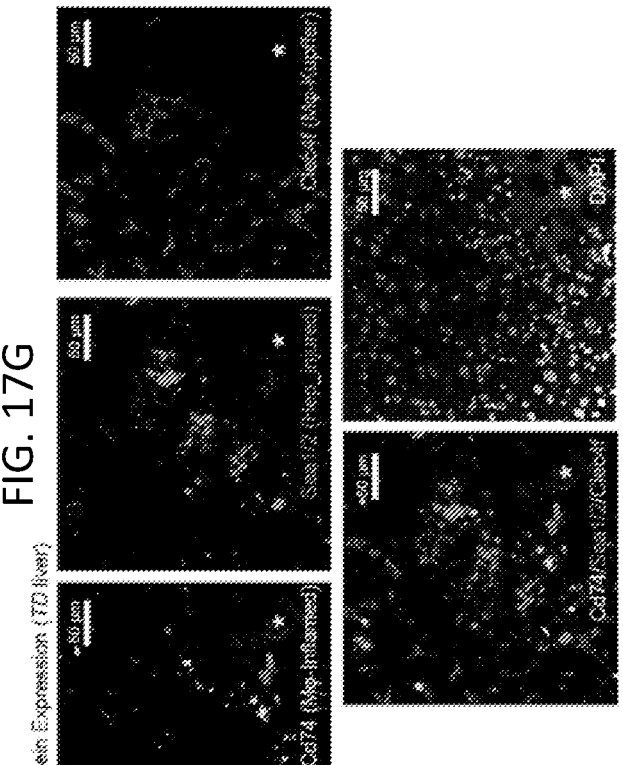
FIG. 17G
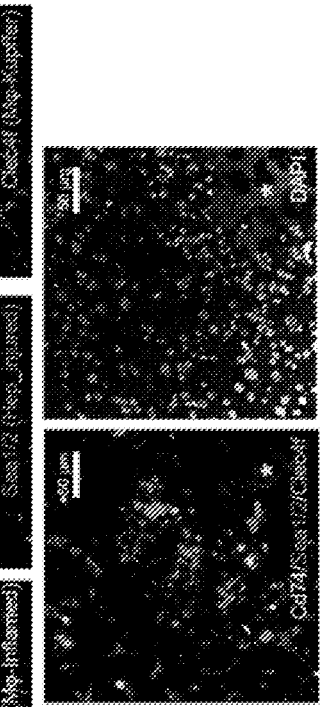
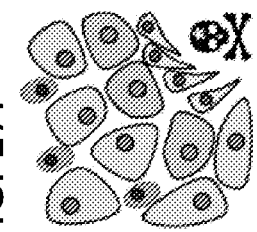
FIG. 17F
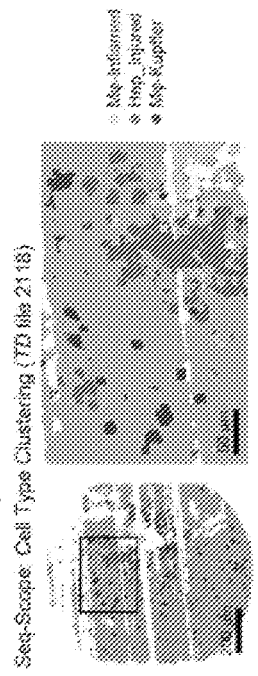
FIG. 17D
FIG. 17E

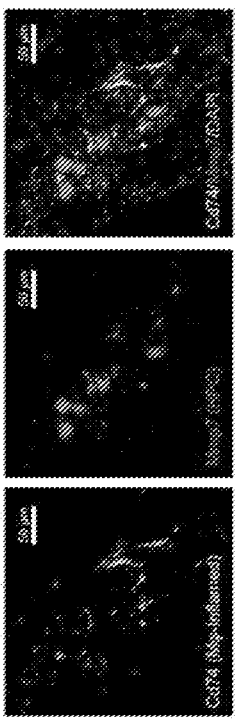
FIG. 17K
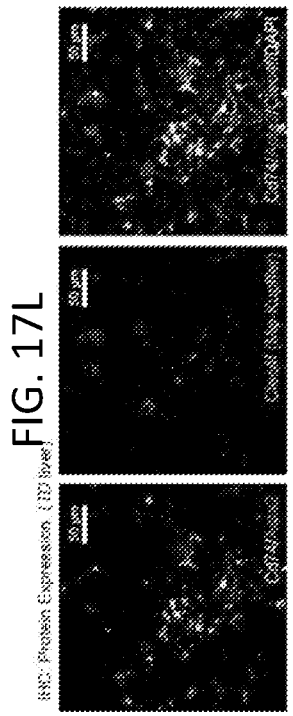
FIG. 17L
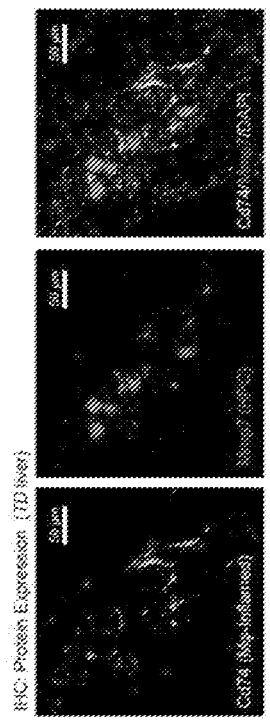
FIG. 17O
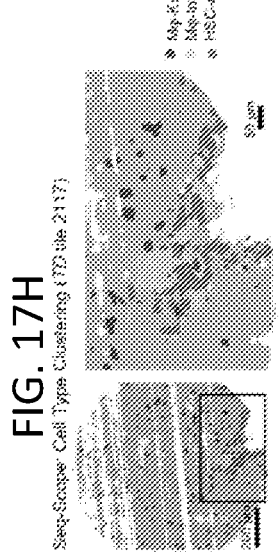
FIG. 17H
FIG. 17J
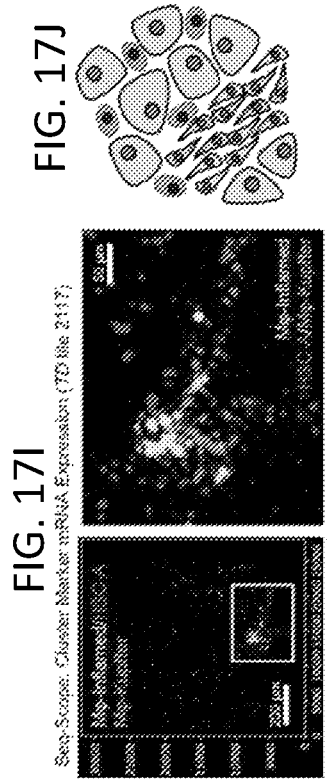
FIG. 17I
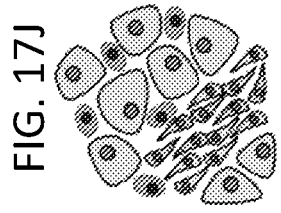
FIG. 17N
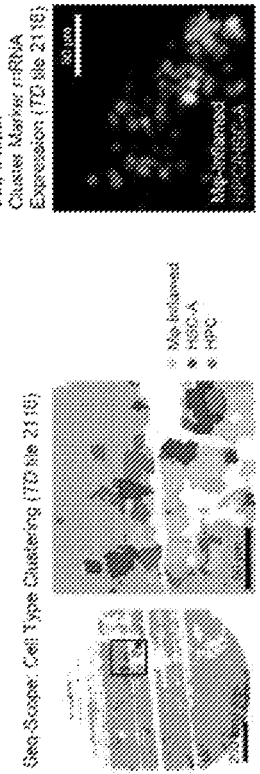
FIG. 17M

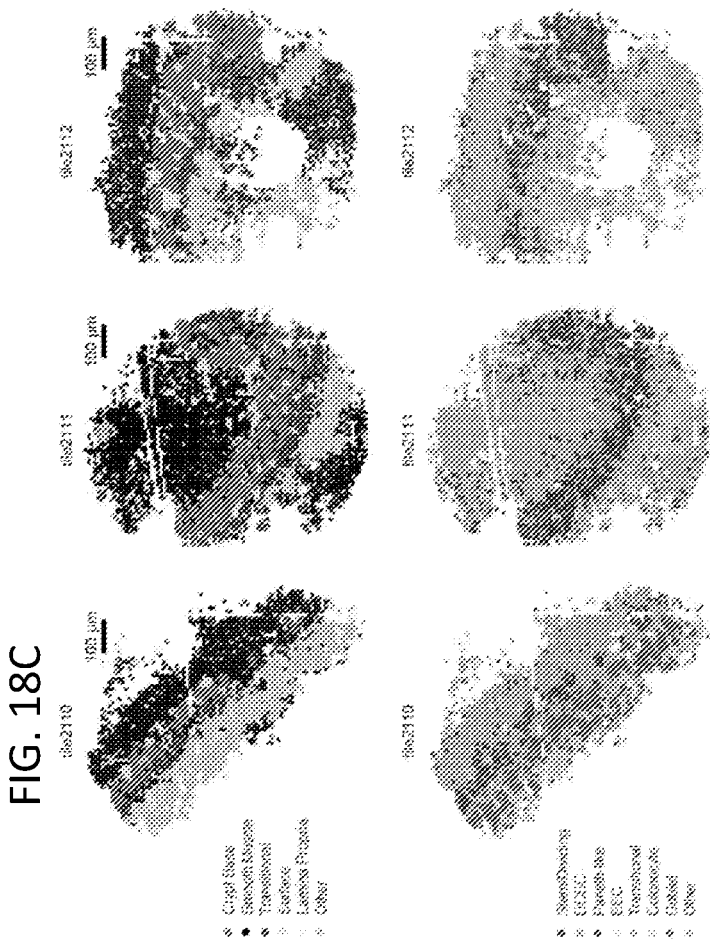
FIG. 18A  FIG. 18B  FIG. 18C
FIG. 18D  FIG. 18E  FIG. 18F

FIG. 18G
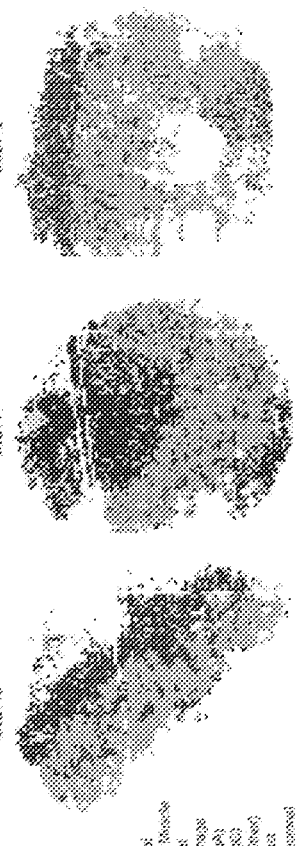
FIG. 18H
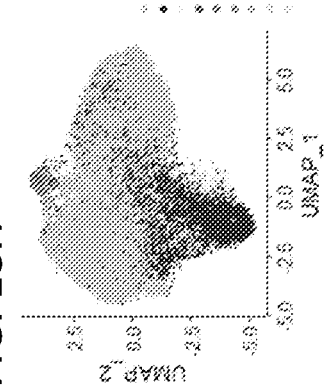
FIG. 18I
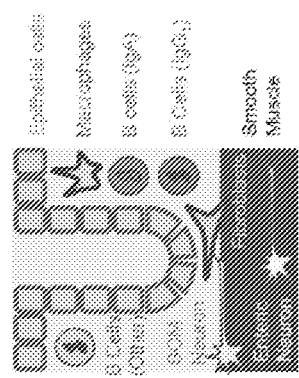
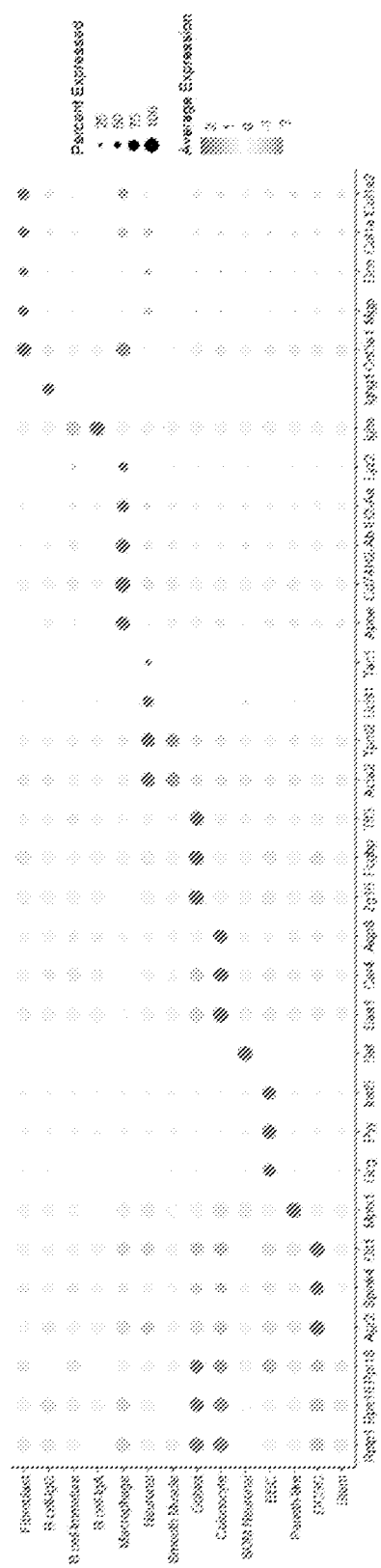
FIG. 18J

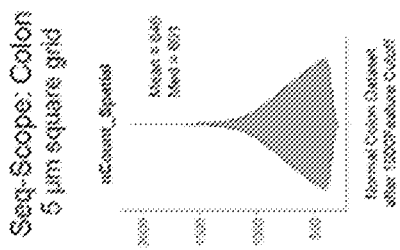
FIG. 19K
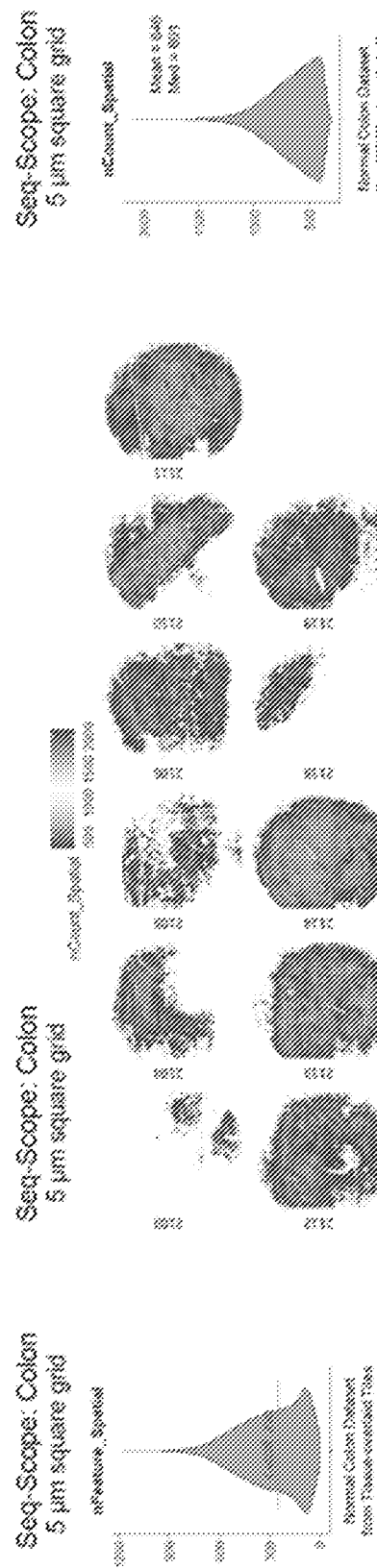
FIG. 19J
FIG. 19I
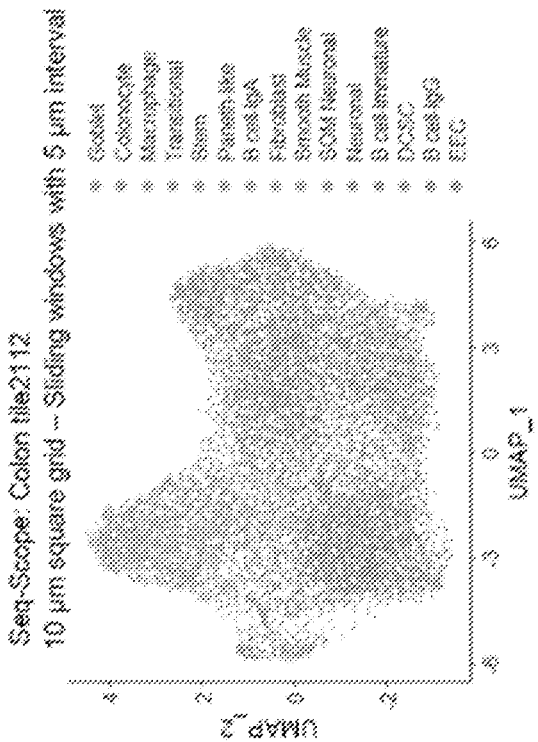
FIG. 19M
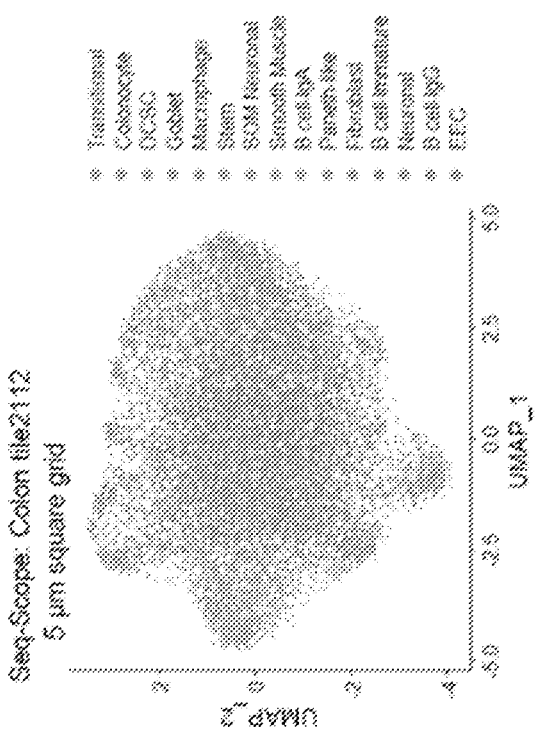
FIG. 19L

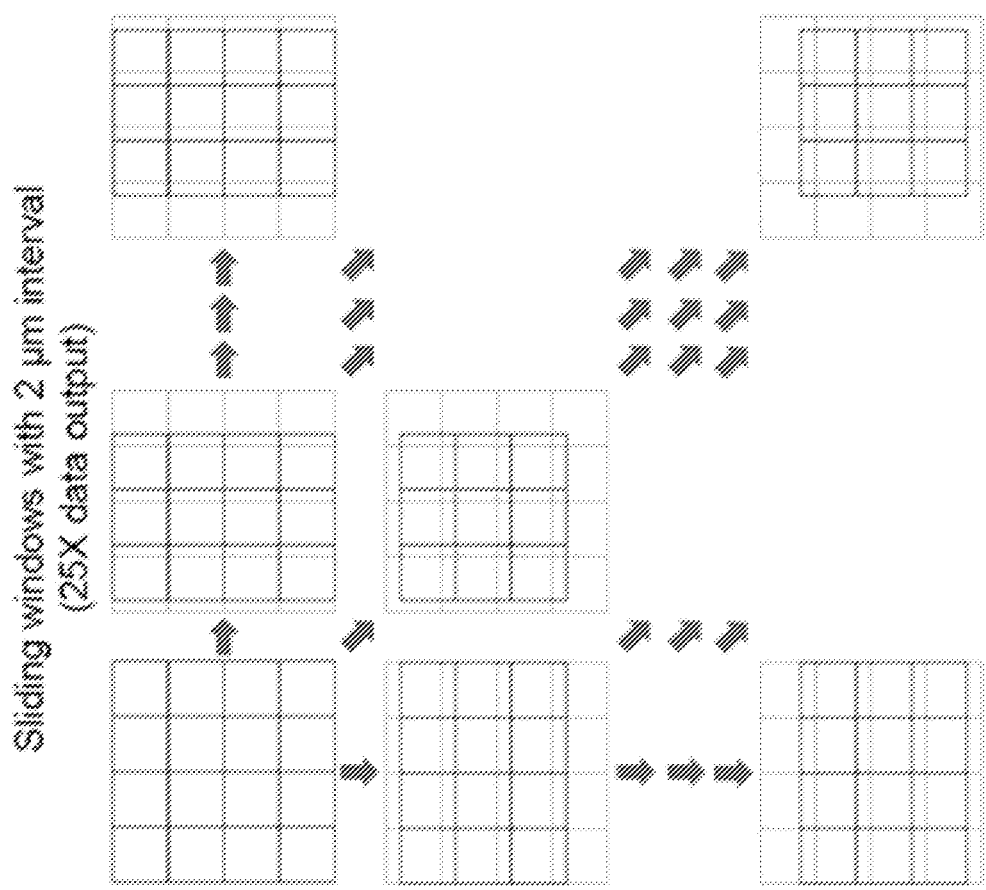
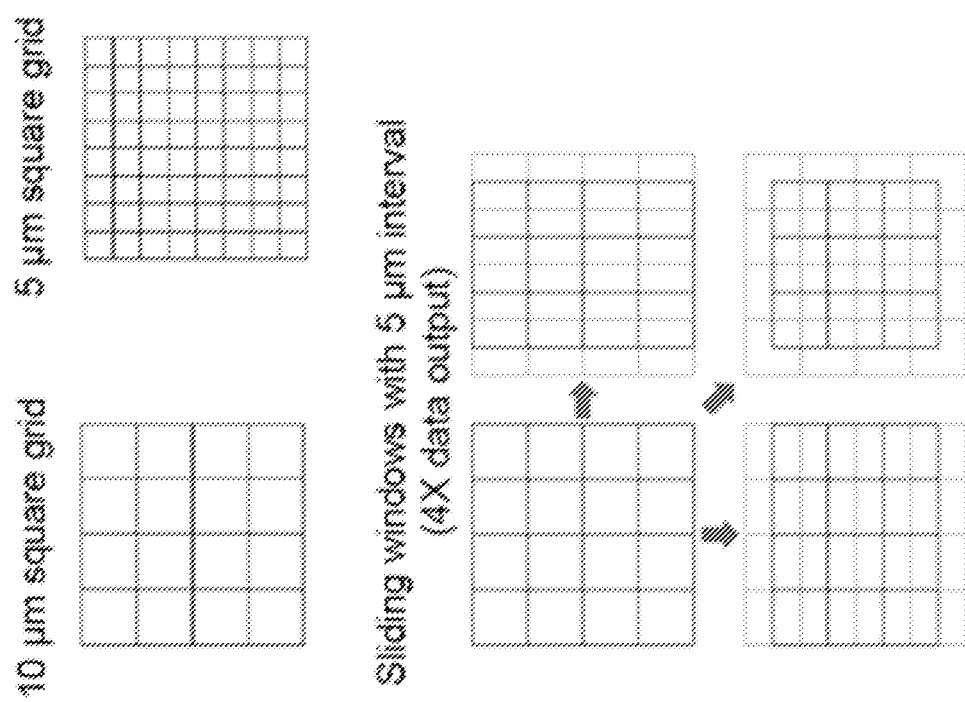
FIG. 190

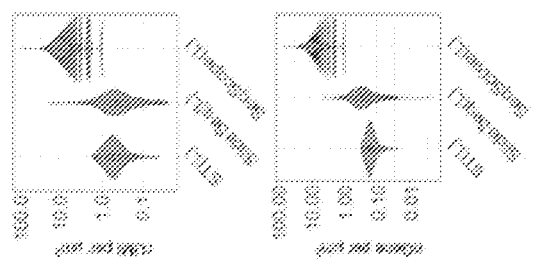
FIG. 20N  FIG. 20O
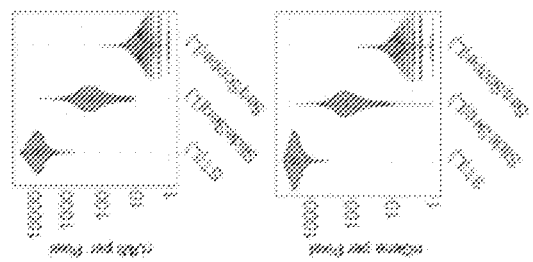
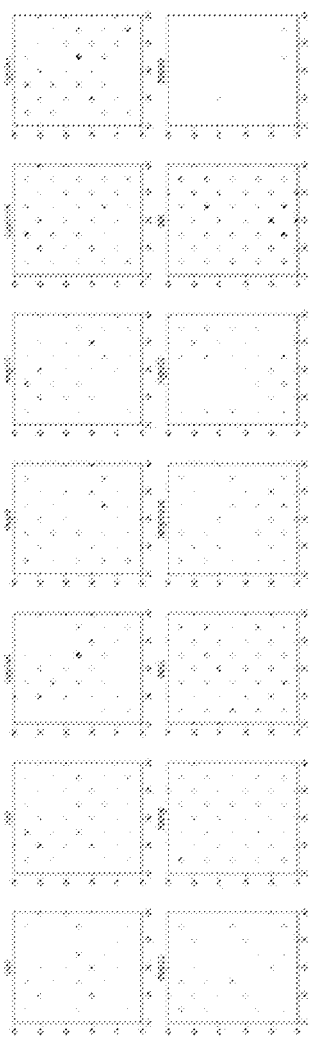
FIG. 20L
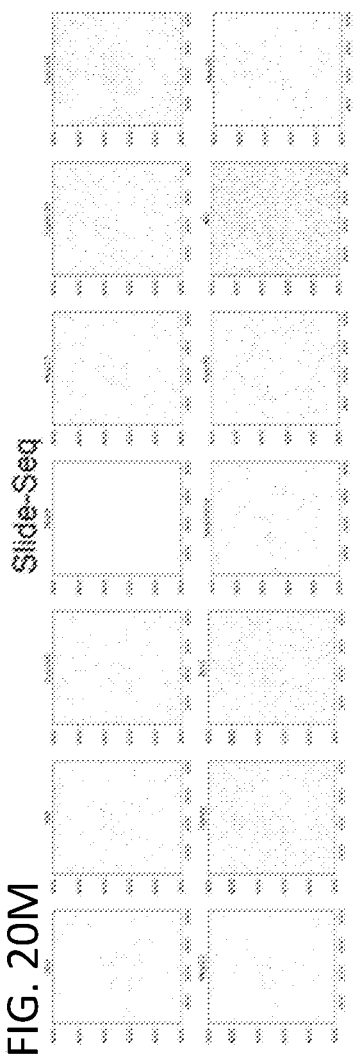
FIG. 20M

MATERIALS AND METHODS FOR LOCALIZED DETECTION OF NUCLEIC ACIDS IN A TISSUE SAMPLE

STATEMENT REGARDING RELATED APPLICATIONS

This application is a continuation of U.S. Track One patent application Ser. No. 17/708,981, filed Mar. 30, 2022, now granted as U.S. Pat. No. 11,713,480, which is a continuation of International Application No. PCT/US2021/041725, filed Jul. 15, 2021, which claims priority to U.S. Provisional Patent Application No. 63/053,238, filed Jul. 17, 2020, and U.S. Provisional Patent Application No. 63/141,254, filed Jan. 25, 2021, the entire contents of each of which are incorporated herein by reference.

STATEMENT OF GOVERNMENT FUNDING

This invention was made with government support under DK034933, DK102850, and DK114131 awarded by the National Institutes of Health. The government has certain rights in the invention.

SEQUENCE LISTING

The text of the computer readable sequence listing filed herewith, titled "UM_38589_305_Sequencelisting_Corrected", created Nov. 13, 2023, having a file size of 44.827 bytes, is hereby incorporated by reference in its entirety.

FIELD

The present disclosure relates to materials and methods for spatial detection of nucleic acid in a tissue sample or a portion thereof. In particular, provided herein are materials and methods for detecting RNA so as to obtain spatial information about the localization, distribution or expression of genes in a tissue sample. In some embodiments, the materials and methods provided herein permit detection of gene expression, as well as genome information, chromatin status, protein expression and developmental lineage information, at single cell resolution. In some embodiments, the materials and methods provided herein permit detection of gene expression (e.g. RNA) with subcellular resolution.

BACKGROUND

Methods for determining the spatial location of gene expression in a tissue sample, termed "spatial transcriptomics", have recently been developed. However, current methods for spatial transcriptomics are limited by poor resolution, low-throughput sequencing, or limited scalability. Accordingly, improved methods for determining the spatial location of gene expression in a tissue sample with high resolution and high throughput are needed.

SUMMARY

In some aspects, provided herein are substrates for spatial detection of nucleic acid in a tissue sample. The substrates comprise a plurality of capture probes immobilized on a surface of the substrate. In some embodiments, each capture probe comprises a capture domain and a spatial barcode. The plurality of capture probes may be arranged in clusters, each cluster comprising multiple capture probes. In some embodiments, each capture probe in a cluster comprises the same spatial barcode, and the spatial barcode for each cluster is unique.

In some embodiments, each cluster comprises at least 200 capture probes. In some embodiments, each cluster comprises at least 500 capture probes. In some embodiments, each cluster comprises at least 800 capture probes.

In some embodiments, each cluster has an average diameter of 200-1200 nm. For example, each cluster may have an average diameter of 1 µm. As another example, In some embodiments, the substrate comprises 0.8-1.2 million clusters per 1 $mm^2$ of surface. For example, the substrate may comprise about 1 million clusters per 1 $mm^2$ of surface. In some embodiments, each cluster has an average diameter of 400-800 nm. In some embodiments, the substrate comprises 1.2-2 million clusters per 1 $mm^2$ of surface.

The substrate may comprise any suitable surface. The surface may be porous or non-porous. The substrate may be planar or non-planar. In some embodiments, the surface of the substrate comprises a material selected from glass, silicon, poly-L-lysine coated materials, nitrocellulose, polystyrene, cyclic olefin copolymers (COCs), cyclic olefin polymers (COPs), polypropylene, polyethylene and polycarbonate.

In some embodiments, the capture domain for each capture probe is the same. In some embodiments, the capture domain comprises a poly-T oligonucleotide comprising at least 10 deoxythymidine residues. In some embodiments, the capture domain comprises a DNA sequence complementary to a nucleotide sequence of a target nucleic acid. In some embodiments, a single cluster could have multiple different capture domains to capture different sequences. In some embodiments, different clusters have different capture domains.

In some embodiments, each capture probe further comprises a sequencing barcode. In some embodiments, each capture probe further comprises one or more filler sequences. In some embodiments, each capture probe further comprises a cleavage domain. For example, the cleavage domain may comprise a binding site for a restriction endonuclease. In some embodiments, each capture probe further comprises a unique molecular identifier barcode.

In some embodiments, the nucleic acid detected in the tissue sample is RNA. In some embodiments, the nucleic acid detected in the tissue sample is DNA, which can be either natural or synthetic.

In some aspects, provided herein are methods for replicating the substrate described herein. In some embodiments, provided herein is a method comprising replicating a substrate as described herein to a second media to produce a second substrate. For example, the substrate may be used as a template substrate for replication onto multiple second substrates. The second substrates may be used for detection of nucleic acid in a tissue sample by a method as described herein.

In some aspects, provided herein are methods for spatial detection of RNA in a tissue sample. The methods comprise contacting a substrate as described herein with a tissue sample and allowing RNA molecules of the tissue sample to bind to the capture domain of the capture probes. The methods further comprise generating cDNA molecules from the bound RNA molecules, and sequencing the cDNA molecules.

In some embodiments, the method further comprises determining the location of each cluster of capture probes on the substrate prior to contacting the substrate with the tissue sample. In some embodiments, determining the location of each cluster comprises determining the sequence of the spatial barcode for at least one capture probe in each cluster, and assigning the sequence to a location on the substrate. In some embodiments, the sequence of the spatial barcode is determined by next generation sequencing. In some embodiments, the methods further comprise correlating the sequence of the spatial barcode for each sequenced cDNA molecule with the location of the cluster of capture probes on the substrate having a corresponding spatial barcode.

In some embodiments, the method further comprises imaging the tissue before or after generating the cDNA molecules. In some embodiments, the method further comprises determining the spatial location of the RNA molecules within the tissue sample by correlating the location of the cluster of capture probes on the substrate with a corresponding location within the tissue sample.

In some aspects, provided herein are methods for spatial detection of nucleic acid in a tissue sample. The methods comprise contacting a substrate as described herein with a tissue sample and allowing nucleic acid molecules of the tissue sample to bind to the capture domain of the capture probes. The methods further comprise sequencing the bound nucleic acid molecules. In some embodiments, the methods further comprise determining the location of each cluster of capture probes on the substrate prior to contacting the substrate with the tissue sample. In some embodiments, determining the location of each cluster comprises determining the sequence of the spatial barcode for at least one capture probe in each cluster, and assigning the sequence to a location on the substrate. In some embodiments, the sequence of the spatial barcode is determined by next generation sequencing. In some embodiments, the methods further comprise correlating the sequence of the spatial barcode for each sequenced nucleic acid molecule with the location of the cluster of capture probes on the substrate having a corresponding spatial barcode.

In some embodiments, the methods further comprise imaging the tissue before or after sequencing the nucleic acid molecules. In some embodiments, the methods further comprise determining the spatial location of the nucleic acid molecules within the tissue sample by correlating the location of the cluster of capture probes on the substrate with a corresponding location within the tissue sample.

In some aspects, provided herein are kits comprising a substrate as described herein.

In some aspects, provided herein are uses of a substrate as described herein for determining the spatial location of nucleic acid molecules within a tissue sample. The nucleic acid molecules may be RNA molecules.

In some aspects, provided herein are methods of determining RNA expression in a single cell in a tissue sample. The methods comprise contacting the tissue sample with a substrate as described herein.

DESCRIPTION OF THE DRAWINGS

FIG. 6A, FIG. 6B, and FIG. 6C show an example of suitable steps that may be performed following first strand cDNA generation, including (FIG. 6A) random primer extension (e.g., second strand cDNA synthesis), (FIG. 6A) second strand isolation, (FIG. 6B) second strand amplification, and (FIG. 6B) second strand purification. Additional standardized steps for constructing cDNA libraries, such as template switching or transposase-induced tagmentation may be also utilized.

FIGS. 8A-J shows an overview of one embodiments of a method described herein. (FIG. 8A) Schematic representation of the HDMI-oligo library structure. This library is used as an input of $1^{st}$-Seq, described below in (FIG. 8B) and (FIG. 8C). P5/P7, PCR adapters; TR1, TruSeq Read 1; HDMI, high-definition map location identifier; HR1, HDMI Read 1. (FIG. 8B) Solid-phase amplification of different HDMI-oligo molecules on the flow cell surface. During $1^{st}$-Seq, a single "seed" molecule from the HDMI-oligo library forms a cluster of oligonucleotides that contain unique HDMI sequences. (FIG. 8C and FIG. 8D) Illumina sequencing by synthesis (SBS) determines HDMI sequence and XY coordinates of each cluster (FIG. 8C). Then, HDMI oligonucleotide clusters are modified to expose oligo-dT, the RNA-capture domain (FIG. 8D). (FIGS. 8E-I) HDMI-array captures RNA released from the overlying frozen section (FIG. 8E). Then, cDNA footprint is generated by reverse transcription of mRNA hybridized with oligo-dT domain (FIG. 8F). After that, secondary strand is synthesized using random priming method on the HDMI-cDNA chimeric molecule (FIG. 8G). Finally, adapter PCR (FIG. 8H) generates the sequencing library for $2^{nd}$-Seq (FIG. 8I), where paired-end sequencing using TR1 and TR2 reveals cDNA sequence and its matching HDMI barcode. TR2, TruSeq Read 2; UMI, unique molecule identifier. (FIG. 8J) HDMI-array contains up to 150 HDMI clusters in 100 µm² are Each cluster has over 1,000 RNA capture probes with unique HDMI sequences.

FIGS. 9A-G shows an exemplary workflow for a method described herein. (FIG. 9A and FIG. 9B) Chemistry workflow for generating HDMI-array in $1^{st}$-Seq (FIG. 9A), and using the HDMI-array for constructing library for $2^{nd}$-Seq (FIG. 9B). The $2^{nd}$-Seq library is subjected to the standard next-generation sequencing workflow in Illumina and BGI platforms. See Experimental Procedures for details. (FIGS. 9C-E) Bioinformatics workflow for estimating tissue boundaries (FIG. 9C), visualizing and analyzing spatial gene expression (FIG. 9D), and determining nuclear and cytoplasmic areas (FIG. 9E). See Experimental Procedures for details. (FIG. 9F) Chemistry workflow for generating UMI-encoded HDMI-array in $1^{st}$-Seq. (FIG. 9G) Evaluation of UMI-encoding methods based on either random priming (UMI_Randomer) or array encoding (UMI_Array). The number of HDMI with multiple read counts was efficiently reduced by either UMI_Randomer- or UMI_Array-based collapsing methods.

FIGS. 10A-K. Generation and Analysis of Spatial cDNA Footprint from Tissue-Derived RNA. (FIG. 10A) Representative images of HDMI clusters in the HDMI-array, retrieved from the Illumina sequence analysis viewer. Upper panel visualizes "A" intensity at the $1^{st}$ cycle of the $1^{st}$-Seq SBS, where 33% of HDMI clusters exhibit fluorescence. Lower panel visualizes "A" at the $33^{rd}$ cycle of the $1^{st}$-Seq SBS, where over 97% of HDMI clusters exhibit fluorescence. Yellow squares in the left panels are magnified in the right panels. (FIG. 10B) H&E staining and its corresponding Cy3-dCTP labeling fluorescence images from fragmented liver section. Gross tissue boundaries (dotted lines) are well preserved in the underlying cDNA footprint. Box insets in the right panel highlights single cell-like patterns in the cDNA footprint. (FIG. 10C) H&E staining and its corresponding HDMI discovery plot drawn from the analysis of $1^{st}$-Seq and $2^{nd}$-Seq outputs. Brighter color in the HDMI discovery plot indicates that more number of HDMI was found from the corresponding pixel area. (FIG. 10D and FIG. 10E) Number of UMI counts (FIG. 10D, left; nCounts) and gene features (FIG. 10D, right; nFeatures) discovered across the indicated tiles of liver (upper) and colon (lower) dataset, binned using 10 µm square grids. Setting a 350 (liver) or 500 (colon) cutoff for these tiles isolated grid pixels covered by the tissue area (FIG. 10E, left), each of which presents approximately 1,000 UMIs (FIG. 10E, right). (FIGS. 10F-K) Performance comparison of different ST solutions. The values were derived from each pixel (FIG. 10F and FIGS. 10H-K) or gridded area (FIG. 10G). nUMI, number of UMI; nGene, number of gene features; SeqScope (FIG. 10L) and SeqScope (FIG. 10C), liver and colon Seq-Scope data.

(FIG. 11A) Representative images of HDMI clusters in the HDMI-array, retrieved from the Illumina sequence analysis viewer. Each picture visualizes "A" intensity at the $21^{st}$ cycle of the $1^{st}$-Seq SBS, where over 97% of HDMI clusters exhibit fluorescence. (FIGS. 11J-O) Violin plot depicting the distribution of the number of gene feature (nFeature) across the 10 µm square grids (FIG. 11J and FIG. 11L). Setting a 250 (liver) or 480 (colon) cutoff for these tiles isolated grid pixels covered by the tissue area (FIG. 11K and FIG. 11M), each of which presents between 600 and 1,200 UMIs (FIG. 11N and FIG. 11O). Both liver (FIG. 11J, FIG. 11K and FIG. 11N) and colon (FIG. 11L, FIG. 11M and FIG. 11O) datasets were analyzed. (FIG. 11R) Duplication rate of HDMI (standard 25-mer) and HDMI32 (extended 32-mer) in the MiSeq platform. HDMI duplication rate was very low at around 0.05%, and all duplicates were removed from the 1st-Seq whitelist dataset before it was used for the Seq-Scope analysis. Data are presented as mean±SD with individual values. (FIG. 11S) Reciprocal misassignment analysis of HDMI spatial mapping. Liver 2nd-Seq dataset was analyzed with Liver 1st-Seq dataset (L to L) or Colon 1st-Seq dataset (L to C), and Colon 2nd-Seq dataset was analyzed with Colon 1st-Seq dataset (C to C) or Liver 1st-Seq dataset (C to L). Alignment was performed with default error correction algorithm of STARsolo (Default) or without any error correction implementation (w/o Correction). Liver and colon 2nd-Seq datasets that were obtained from the separate lanes of the sequencer were selected for these analyses to eliminate the potential interference between the two datasets. (FIG. 11T) The number of UMI (nUMI) per HDMI pixel (left), the number of gene features (nGene) per HDMI pixel (center), and the nUMI/nGene ratio per pixel (right) are presented in violin plot. (FIG. 11U) Exterior appearance (left) and SYBR Gold staining pattern (right) of the exemplarily disassembled MiSeq flow cell FIGS. 12A-H. Visualization of Subcellular Spatial Transcriptome.

FIGS. 13A-E. Visualization of Nuclear/Mitochondrial/Cytoplasmic Subcellular Architecture. (FIG. 13A) Spatial plot of all unspliced and spliced transcripts, as well as RNA species that are known to localize to nucleus in liver tissue (Nuc-targeted; Malat1, Neat1 and Mlxip1). (FIG. 13B) Spatial plot of all unspliced and spliced transcripts, as well as RNA species that are encoded by mitochondrial genome (Mt-encoded). (FIG. 13C) Pearson correlations (r) between the indicated transcript intensities were presented as a heat map. (FIG. 13D) Spatial plot of unspliced and spliced transcript in three independent subsets of genes (Gene Subset 1-3). Pearson correlations (r) between these transcript intensities were presented as a heat map. S1-3, Spliced 1-3; U1-3, Unspliced 1-3. For all spatial plots, width and height of the imaging areas are 800 µm and 1 mm, respectively. (FIG. 13E) Potential reasons of why some segmented hepatocellular area did not exhibit nuclear/unspliced RNA-enriched area. Section slice may not contain nucleus for the cell (left). Nuclear position in the section may not be ideal for the unspliced RNA capture (middle). Transcriptionally inactive nuclei may express reduced levels of unspliced RNAs (right).

FIGS. 14A-R. Identification of Diverse Cell Types and Subtypes Present in Normal Liver. (FIGS. 14A-D) From the normal liver dataset binned with 10 µm square grids, a UMAP plot visualizing all clusters (FIG. 14A), UMAP plots visualizing expression of indicated genes across the gridded pixels (FIG. 14B), and dot plots visualizing cluster-specific expression of liver zonation (FIG. 14C) and cell type (FIG. 14D) markers are presented. (FIGS. 14M-R) Number of gene features (FIG. 14M, nFeatures) and UMI counts (FIG. 14N, nCounts; after nFeatures cutoff at 100) were calculated across the indicated tiles of liver dataset, binned using 5 µm square grids. From this dataset, a UMAP plot visualizing all clusters (FIG. 14O), UMAP plots visualizing expression of indicated genes across the gridded pixels (FIG. 14P), a UMAP plot visualizing cell type-assigned clusters (FIG. 14Q) and its associated spatial plots (FIG. 14R) are presented. Grid numbers, as well as mean and median UMI counts per grid pixel, were provided (FIG. 14R). For all spatial plots, width and height of the imaging areas are 800 µm and 1 mm, respectively.

FIGS. 15A-D) Spatial single-cell analysis of Seq-Scope data through histology-guided hepatocyte segmentation. (FIG. 15A) Single hepatocyte segmentation based on H&E staining. (FIG. 15B) Comparison of Seq-Scope single-cell output with those obtained from MARS-Seq and Drop-Seq. (FIG. 15C) Cell-type clustering revealed multiple layers of hepatocellular zonation (Hep_PC1-3 and Hep_PP1-3), as well as a small number of non-parenchymal (NPC) and injured (Hep_injured) transcriptome phenotypes. PC, pericentral; PP, periportal. UMAP (upper) and heatmap (lower) analyses are shown. (FIG. 15D) Spatial map of different hepatocellular clusters (left) was overlaid with H&E staining and cell segmentation images (right). PV, portal vein; CV, central vein. (FIG. 15E) Spectrum of genes exhibiting different zone-specific expression patterns were examined by spatial plot analysis. PC-specific genes are depicted in warm (red-orange-yellow) colors, whereas PP-specific genes are depicted in cold (blue-purple) colors. (FIGS. 15F-I) Detection of NPC transcriptome through histology-agnostic segmentation with 10-mm grids. (FIG. 15F) Schematic diagram depicting cellular components of normal liver and their representation in a tissue section. (FIG. 15G and FIG. 15H) UMAP (FIG. 15G) and spatial plots (FIG. 15H) visualizing clusters of 10-mm grids representing indicated cell types. (FIG. 15I) 10-mm grid-based M4 and ENDO mapping data (first and second panel) are compared with spatial plot data of cluster-specific markers (third panel), H&E (fourth), and segmented H&E (fifth) data.

FIGS. 16A-O. Seq-Scope analysis of liver injury and inflammation. (FIGS. 16A-F) TD liver Seq-Scope dataset was analyzed by data binning with 10 mm-sided square grids. (FIG. 16A) Spatial density plot depicting the number of UMIs discovered across 10 mm square grids. (FIG. 16B) Violin plot depicting the number of gene features (nFeature) across the 10 mm square grids. Setting a 250 cutoff isolated grid units covered by the tissue area (FIG. 16C), each of which contains around 700 UMIs (FIG. 16D). A UMAP plot visualizing all clusters (FIG. 16E) and a dot plot (FIG. 16F) visualizing expression of cluster-specific markers. (FIGS. 16J-O) Spatial plots visualizing expression of indicated cell type marker genes in TD liver.

FIGS. 17A-O. Seq-Scope examines liver histopathology at microscopic and transcriptomic scales. Liver from a Tsc1Dhep/Depdc5Dhep (TD) mouse, which suffers severe liver injury and inflammation (Cho et al., 2019), was examined through Seq-Scope. (FIGS. 17A-C) UMAP (FIG. 17A) and spatial plots (FIG. 17C, left) visualize cell type clusters of 10-mm grids. NPCs and injury-responding populations are highlighted in darker colors, and their representative cell-type-specific marker genes are summarized in (FIG. 17B). H&E images (FIG. 17C, right) correspond to the boxed regions in (FIG. 17C, left). Yellow asterisk marks the injury area. (FIGS. 17D-0) Transcriptomic structure of liver histopathology around dead hepatocytes (FIGS. 17D-G) and fibrotic lesions (FIGS. 17H-0). (FIG. 17D, FIG. 17H, and FIG. 17M) Cell-type mapping analysis using sliding windows with 5-mm (left) and 2-mm (right) intervals. (FIG. 17E, FIG. 17I, and FIG. 17N) Spatial plotting of indicated cell-type-specific genes in histological coordinate plane. (FIG. 17F) Schematic arrangement of M4-Inflamed (green), M4-Kupffer (blue), Hep_Injured (red), and other cells (gray) around dead hepatocytes (black skull with yellow asterisk).

FIGS. 18A-J. Seq-Scope identifies various cell types from colonic wall histology. Spatial transcriptome of colonic wall was analyzed using Seq-Scope. 10-mm grid dataset was analyzed. (FIGS. 18A-I) Seq-Scope reveals major histological layers (FIGS. 18A-C), epithelial cell diversity (FIGS. 18D-F), and non-epithelial cell diversity (FIGS. 18G-I) through transcriptome clustering. (FIG. 18A, FIG. 18D, and FIG. 18G) Schematic representation of colonic wall structure. Clusters corresponding to the indicated cell types were visualized in UMAP manifold (FIG. 18B, FIG. 18E, and FIG. 18H) and histological space (FIG. 18C, FIG. 18F, and FIG. 18I). (FIG. 18J) Cluster-specific markers were examined in dot plot analysis. DCSC, deep crypt secretory cells; EEC, enteroendocrine cells; SOM Neuronal, somatostatin expressing neuronal cells.

(FIG. 19A) Spatial density plot depicting the number of UMIs discovered across 10 mm square grids. (FIG. 19I) Violin plot depicting the number of gene features (nFeature) across the 5 mm square grids. Setting a 250 cutoff isolated grid units covered by the tissue area (FIG. 19J), each of which contains around 600 UMIs (FIG. 19K) (FIG. 19L and FIG. 19M) UMAP plots constructed from 5 mm grid dataset (FIG. 19L) and sliding windows dataset of 10 mm grids with 5 mm intervals (FIG. 19M). Cell type annotation was guided through the original 10 mm grid dataset (FIG. 19E). (FIG. 19O) Schematic diagrams depicting the sliding windows analysis methodology. Compared to the 10 mm grid dataset, 5 mm grid dataset produces higher resolution; however, the transcriptome information revealed by 5 mm grid area is only 25% of what was recovered from 10 mm grid area. Correspondingly, 5 mm dataset produced substantial noises in cell type assignment. To overcome this, sliding windows analysis was performed to maintain transcriptome information per pixel while achieving higher resolution of cell type mapping by oversampling the data 4 times (5 mm interval), 25 times (2 mm interval) or 100 times (1 mm interval; scheme not shown).

FIGS. 20A-E) Comparison of Seq-Scope transcriptome with bulk RNA-Seq and scRNA-Seq transcriptome. Individual dots represent a single gene showing expression levels in both datasets. Correlations were evaluated in the Pearson coefficients between groups. (FIG. 20F) Segmented hepatocyte transcriptomes were clustered into periportal (PP) and pericentral (PC) populations. UMAP (upper) and heatmap (lower) analyses of clusters and cluster-specific genes were shown. (FIG. 20G) Spatial map of PP and PC hepatocellular populations. (FIG. 20H) Top 50 PP- and PC-specific genes overlap between Seq-Scope and two independent scRNA-seq data. (FIG. 20I) Clustering, UMAP (upper) and spatial plotting (lower) analyses were performed using only the top 50 PC/PP genes from Drop-Seq (left) and MARS-Seq (right). (FIGS. 20L-O) Spatial expressions of individual genes were plotted onto histological coordinate planes roughly covering 0.8 mm 3 1 mm area, using mouse liver ST (FIG. 20L) and Slide-Seq (FIG. 20M) datasets. These plots displayed substantially lower resolution and dynamic range with less obvious spatial details, when compared to the plots generated by Seq-Scope (FIG. 4E). RNA/gene capture output per pixel (FIG. 20N) or area (FIG. 20O) were compared between liver datasets produced using ST, Slide-Seq and Seq-Scope technologies. (FIG. 20P-V) Normal liver Seq-Scope dataset was analyzed by data binning with 10 mm-sided square grids. FIG. 20 (P) Spatial density plot depicting the number of UMIs discovered across 10 mm square grids. (FIG. 20Q) Violin plot depicting the number of gene features (nFeature) across the 10 mm square grids. Setting a 250 cutoff isolated grid units covered by the tissue area (FIG. 20R), each of which contains around 700 UMIs (FIG. 20S). A UMAP plot visualizing all clusters (FIG. 20T) and a dot plot (FIG. 20U) and UMAP plots (FIG. 20V) visualizing expression of cluster-specific markers are presented.

(FIGS. 21A-J) Marker genes for indicated cell types were plotted onto the coordinate space with indicated colors. Top row for each panel represents combined plotting of all listed markers onto the coordinate space. Bottom rows represent gene expression plotting of individual cell type marker genes. For all spatial plots, width and height of the imaging areas are 800 μm and 1 mm, respectively.

(FIGS. 22A-C) Spatial cell-type mapping was refined using multiscale sliding windows analysis with 5-mm (left), 2-mm (center), or 1-mm (right) intervals. (FIGS. 22D-H) Original Seq-Scope dataset was analyzed by spatial gene expression plotting, using indicated layer-specific (FIG. 22D), cell-type-specific (FIG. 22E and FIG. 22F), or cell-cycle specific (FIG. 22H) marker genes. These spatial transcriptome features were consistent with underlying H&E histology (FIG. 22G).

DEFINITIONS

Figure 1:
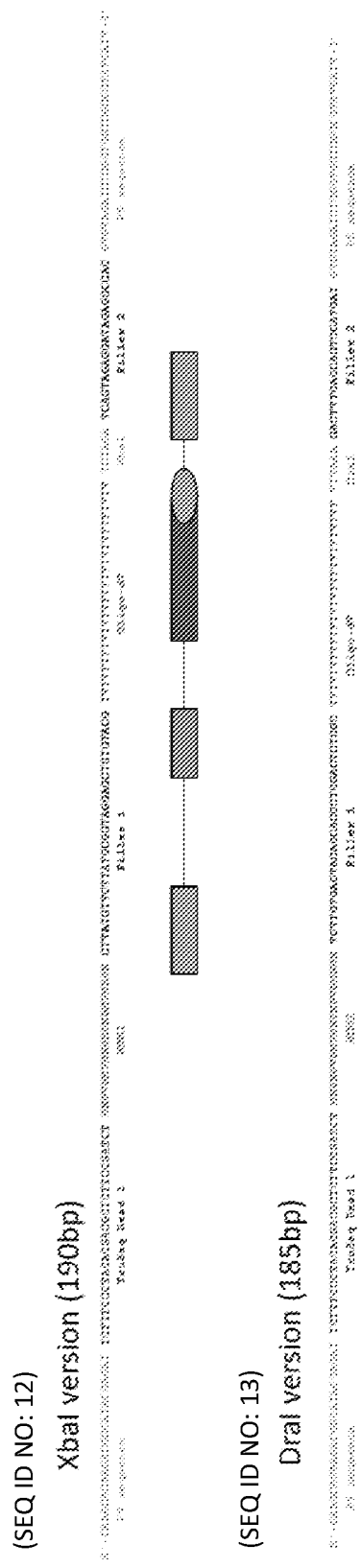
FIG. 1 shows representative capture probes that may be used in an exemplary substrate as described herein. The probes contain a spatial barcode (e.g. high density molecular identifier, HDMI) and a capture domain (e.g. oligo-dT). As shown in the drawing, the capture probes may additionally contain a cleavage domain (e.g., Xba1 binding site or a DraI binding site), a P7 sequence (ILLUMINA), and a P5 sequence (ILLUMINA). The P7 and P5 sequences (e.g. adapters) enable binding of the capture probes to the corresponding surface probes on the substrate and subsequent cluster generation (e.g., by bridge amplification).
Figure 2:
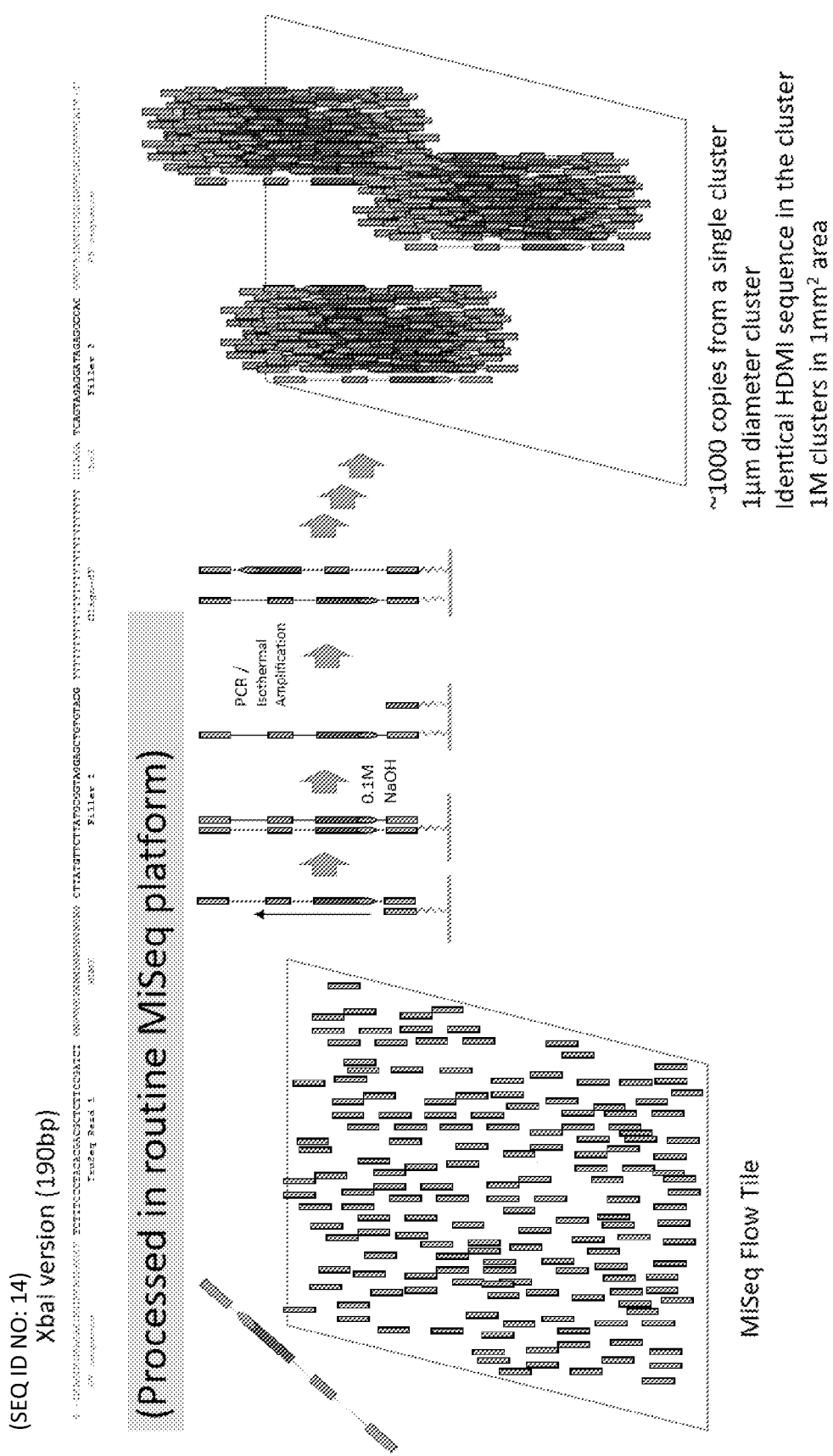
FIG. 2 shows a schematic representation of a suitable method for manufacturing a substrate as described herein. The substrate surface comprises a plurality of surface probes, such that the probes bind to the corresponding regions in the capture probes and clusters are generated by bridge amplification. The resulting substrate comprises millions of clusters, each cluster containing the same spatial barcode (e.g., HDMI sequence).
Figure 3:
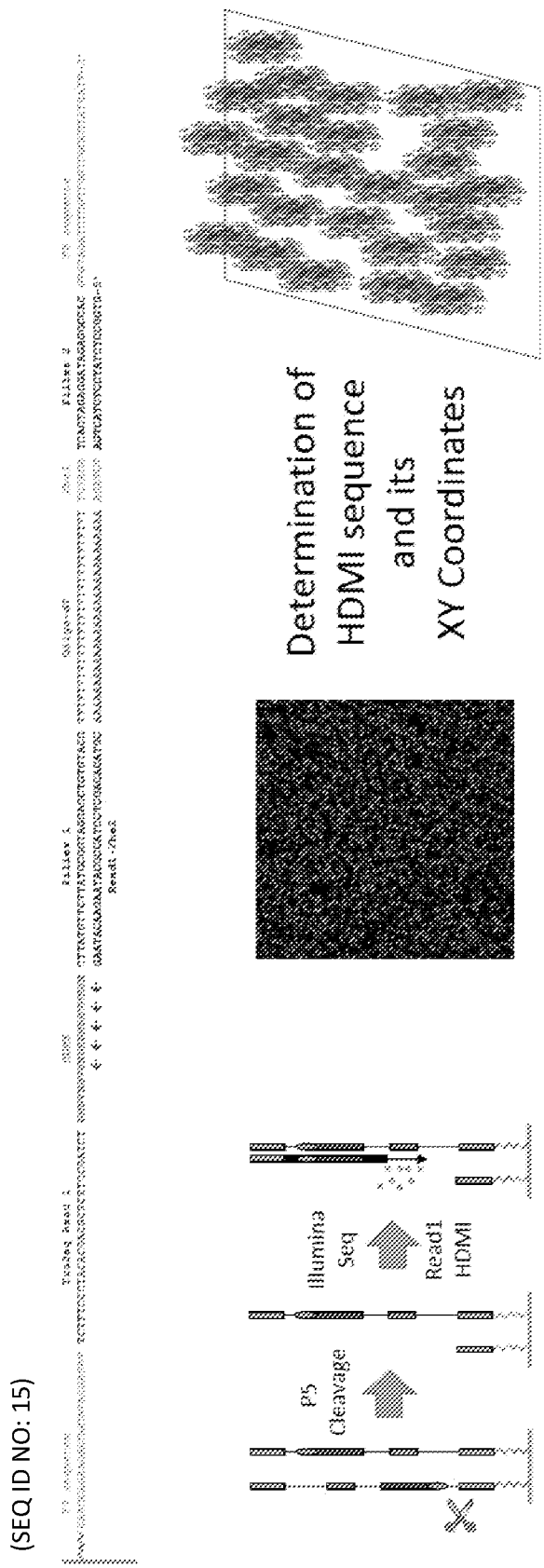
FIG. 3 shows a schematic representation of a suitable method for determining the location of each cluster on the substrate. The capture probe is bound to the substrate and clusters are generated (e.g., by bridge amplification). The P5 domain may be cleaved from the substrate and one or more wash steps may be performed, leaving only capture probes having a P7 domain bound to the substrate. Note that this is only exemplary, and in alternative embodiments the P7 domain may be cleaved from the substrate and one or more wash steps may be performed, leaving only capture probes having a P5 domain bound to the substrate. Suitable primer(s) may be added and the sequence of the remaining capture probes may be determined. In particular, the sequence of the spatial barcode may be determined for each cluster. The fluorescence image may be used to assign each cluster to a specific location on the substrate.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "substrate" is used herein it the broadest sense and refers to any substrate described herein. The "substrate" may also be referred to herein as a "flow cell surface". The substrate may be a part of a flow cell, wherein the flow cell comprises the flow cell surface (e.g. substrate) and one or more channels to facilitate adding liquids to the flow cell surface. In some embodiments, one or more components of the flow cell are detachable, such that an exposed flow cell surface (e.g. substrate) may be obtained without damaging the HDMI-array contained thereupon. In some embodiments, the term "substrate" refers to a substrate generated by methods described herein, such as bridge amplification. In some embodiments, the term "substrate" refers to a second substrate or a replicate substrate formed using an original substrate as a template, and copying the original substrate onto a second media. Methods for spatial detection of nucleic acid in a tissue sample as described herein may be performed using any substrate, including an original substrate and a second substrate.

DETAILED DESCRIPTION

In some aspects, provided herein are substrates for spatial detection of nucleic acids in a tissue sample. In some embodiments, provided herein are substrates for spatial detection of RNA molecules in a tissue sample. In some embodiments, the substrates may be used for spatial detection of RNA transcripts (e.g., mRNA) in a tissue sample.

In some embodiments, a substrate comprises a plurality of capture probes (e.g. "seeds" or "seed molecules") immobilized on a surface of the substrate. The probes may be immobilized on the surface of the substrate by any suitable means. In some embodiments, the surface of the substrate comprises binding partners for the capture probes. Binding partners for the capture probes are referred to herein as "surface probes". For example, the surface of the substrate may comprise a plurality of surface probes that bind to a complementary adapter region on the capture probe. In some embodiments, the surface of the substrate comprises multiple types of surface probes. For example, the surface of the substrate may comprise two types of surface probes, where the first type of surface probe is complementary to a first adapter region at the 3' end of the capture probe, and the second type of surface probe is complementary to a second adapter region at the 5' end of the capture probe. In such embodiments, clusters of capture probes may be generated on the surface of the substrate by a process known as bridge amplification.

In bridge amplification, the first adapter region at the 3' end of a capture probe binds to the complementary surface probe (e.g., the first type of surface probe). A polymerase enzyme creates a complementary strand to the hybridized capture probe, generating a double stranded molecule. The double stranded molecule is denatured (e.g., by addition of a denaturing agent, such as sodium hydroxide). One or more wash steps may be performed to wash away the original capture probe, leaving behind the complementary strand which is immobilized on the surface of the substrate. By random interaction, the second adapter region at the 5' end of the strand binds to the complementary surface probe (e.g., the second type of surface probe), thus causing the strand to bend, creating a "bridge". Polymerase enzymes generates the complementary strand, creating a double stranded bridge. The double stranded bridge is denatured, resulting in one capture probe having a 3' end bound to the first type of surface probe and an exposed 5' end, and another capture probe having a 5' end bound to the second type of surface probe and an exposed 3' end.

As described above, each capture probe may comprise an adapter region that binds to a complementary surface probe. In some embodiments, each capture probe comprises a capture domain. The capture domain may be any suitable domain capable of hybridizing to RNA or a transcript thereof, such as mRNA. In some embodiments, the capture domain comprises a poly-T oligonucleotide. A poly-T oligonucleotide comprises a series of consecutive deoxythymidine residues linked by phosphodiester bonds. A poly-T oligonucleotide is capable of hybridizing to the poly-A tail of mRNA. In some embodiments, the capture domain comprises a poly-T oligonucleotide comprising at least 10 deoxythymidine residues. The poly-T oligonucleotide may comprise at least 10, at least 11, at least 12, at least 13, at least 14, at least 15, at least 16, at least 17, at least 18, at least 19, at least 20, at least 25, at least 30, or more than 30 deoxythymidine residues. In some embodiments, the capture domain comprises nucleotides which are functionally or structurally analogous to poly-T and retain the functional property of binding to poly-A. For example, the capture domain may comprise a poly-U oligonucleotide.

In some embodiments, the capture domain is nonspecific (e.g., intended to capture all RNAs containing a poly-A tail). In some embodiments, the capture domain may further comprise additional sequences, such as random sequences, to facilitate the capture of specific subtypes of RNA. In some embodiments, the capture domain may further comprise additional sequences to capture a desired subtype of RNA, such as mRNA or rRNA. In some embodiments, the capture domain may further comprise additional sequences to facilitate the capture of a particular RNA (e.g., mRNA) corresponding to select genes or groups of genes. Such a capture probe may be selected or designed based on sequence of the RNA it is desired to capture. Accordingly, the capture probe may be a sequence-specific capture probe.

In some embodiments, the capture domain may target DNA, instead of RNA. In some embodiments, the capture domain may target non-specific or specific DNA sequences. For example, the capture domain may comprise a nucleic acid sequence to facilitate the capture of a target DNA sequence.

In some embodiments, the capture domain for each probe is the same. In some embodiments, the capture domain for one or more probes is different from the capture domain from at least one other probe.

In some embodiments, the capture probes additionally comprise a cleavage domain. In some embodiments, the cleavage domain is 3' of the capture domain, such that the capture domain is not exposed until the cleavage domain is cleaved. For example, the cleavage domain may comprise a binding site (e.g., a restriction site) for a restriction endonuclease. The cleavage domain may be intact (e.g., uncleaved) during binding of the capture probes to the surface of the substrate and cluster generation. Following cluster generation and/or determination of the location of each cluster on the substrate (e.g., by sequencing of the spatial barcode), an enzyme may be added to induce cleavage of the cleavage domain. For example, a restriction endonuclease (e.g., Xba1, Dra1, etc.) may be added to cut the cleavage domain and one or more wash steps may optionally be performed, thus exposing the capture domain.

In some embodiments, cleavage of the cleavage domain may allow for exposure of additional domain(s). For example, cleavage of the cleavage domain may expose the capture domain.

The capture probe comprises a spatial barcode. The spatial barcode may be an oligonucleotide of any suitable length. In some embodiments, the spatial barcode comprises 10-50 nucleotides. For example, the spatial barcode may comprise 10, 11, 12, 13, 14, 15, 16, 17, 18, 19, 20, 21, 22, 23, 24, 25, 26, 27, 28, 29, 30, 31, 31, 32, 33, 34, 35, 36, 37, 38, 39, 40, 41, 42, 43, 44, 45, 46, 47, 48, 49, or 50 nucleotides. In particular embodiments, the spatial barcode comprises 20 nucleotides.

In some embodiments, each capture probe comprises one or more sequencing barcodes (e.g., sequencing handles). For example, each capture probe may comprise a sequencing handle, such as an ILLUMINA TruSeq handle. The sequencing barcode may comprise any suitable number of consecutive nucleotides. In some embodiments, the sequencing barcode comprises 10-50 nucleotides. For example, the sequencing barcode may be about 10, 15, 20, 25, 30, 35, 40, 45, or 50 nucleotides in length.

In some embodiments, each capture probe further comprises one or more filler sequences. The filler sequence may comprise any suitable number of consecutive nucleotides. In some embodiments, the filler sequence comprises 10-50 nucleotides. For example, the filler sequence may be about 10, 15, 20, 25, 30, 35, 40, or 50 nucleotides in length.

The plurality of capture probes is arranged in clusters on the surface of the substrate, each cluster comprising multiple capture probes. Each capture probe in a cluster comprises the same spatial barcode. Additionally, the spatial barcode for each cluster is unique. For example, cluster A contains probes having spatial barcode A, cluster B contains probes having spatial barcode B, cluster C contains probes having spatial barcode C, etc.

In some embodiments, each capture probe in a cluster is engineered to comprise a unique molecular identifier (UMI) (also referred to herein as a "unique molecular identifier barcode" or a "UMI barcode"). Each capture probe in a cluster comprises different UMI barcode (UMI_Array). In some embodiments, UMI is not encoded by the capture probe, and instead obtained from the random priming site during secondary strand synthesis. For example, each cDNA will be paired with a secondary strand each of which is encoded by a unique random primer sequence, which is used as UMI (UMI_Randomer). UMI_Array and UMI_Randomer are both efficient in collapsing PCR duplicates from an amplified cDNA library. For example, the sequence of the spatial barcode for each cluster may be determined by next generation sequencing, and duplicate sequence reads may be collapsed through either the unique molecular identifier encoded by the array (UMI_Array) or by the random priming site (UMI_Randomer). In some embodiments, UMI_Randomer may be semi-random so that it has certain nucleotide patterns to make the secondary strand synthesis more efficient.

In some embodiments, each cluster comprises at least 200 capture probes. For example, each cluster may comprise at least 200, at least 300, at least 400, at least 500, at least 600, at least 700, at least 800, at least 900, or at least 1000 capture probes. In some embodiments, each cluster comprises 900-1100 capture probes. For example, each cluster may comprise 900, 910, 920, 930, 940, 950, 960, 970, 980, 990, 1000, 1010, 1020, 1030, 1040, 1050, 1060, 1070, 1080, 1090, or 1100 capture probes. In some embodiments, all capture probes in each cluster will be identical. In some embodiments, multiple different capture probes may be generated in a single cluster.

Each cluster may be roughly circular in shape. Each cluster may have an average diameter of about 200-1200 nm. For example, each cluster may be roughly circular in shape with an average diameter of 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, 1050 nm, 1100 nm, or 1200 nm. In some embodiments, each cluster is roughly circular in shape with an average diameter of 950-1050 nm. For example, the average diameter may be 950 nm, 960 nm, 970 nm, 980 nm, 990 nm, 1000 nm, 1010 nm, 1020 nm, 1030 nm, 1040 nm, or 1050 nm. In particular embodiments, the average diameter is 600 nm (0.6 microns).

The surface of the substrate may comprise any suitable number of clusters. In some embodiments, the surface of the substrate comprises 0.3-2 million clusters per 1 $mm^2$ of surface. In some embodiments, the surface of the substrate comprises 0.8-1.2 million clusters per 1 $mm^2$ of surface. In some embodiments, the surface of the substrate comprises about 1 million clusters per 1 $mm^2$ of surface.

The surface of the substrate may comprise any suitable material. In some embodiments, the surface of the substrate is porous. In some embodiments, the surface of the substrate is non-porous. In some embodiments, the surface comprises a material selected from glass, silicon, poly-L-lysine coated materials, nitrocellulose, polystyrene, polyacrylamide, cyclic olefin copolymers (COCs), cyclic olefin polymers (COPs), polypropylene, polyethylene and polycarbonate. In some embodiments, the surface comprises glass.

In some embodiments, the substrate may be a part of a flow cell, wherein the flow cell comprises a flow cell surface (e.g. the substrate) and one or more channels to facilitate adding liquids to the flow cell surface. For example, a flow cell may contain one or more channels, such that the channels direct the flow of liquid towards the flow cell surface (e.g. the substrate). Such embodiments may facilitate various wash steps, incubation steps, etc. In some embodiments, the flow cell is detachable, such that an exposed flow cell surface (e.g. substrate) may be obtained without damaging the HDMI-array contained thereupon.

In some embodiments, the substrate (e.g. flow cell surface) comprises a planar surface. For example, the substrate may comprise a slide (e.g., a glass slide). In some embodiments, the substrate comprises a non-planar (e.g. convex or concave) surface. In some embodiments, the substrate comprises a gel (e.g. a hydrogel). In some embodiments, the substrate comprises a tube or a capillary. Such embodiments may be particularly useful for simultaneous processing of multiple tissue samples. In some embodiments, the substrate comprises beads (e.g. microscopic beads). For example, the capture probes may be immobilized on the surface of the substrate via interaction with beads, which are attached to the surface of the substrate.

In some embodiments, the substrate is not a multi-well substrate. Rather, the substrate may comprise a planar surface coated with surface probes, and the generation of clusters may occur on the surface of the substrate through bridge amplification constrained by the random interaction of the capture probes with the surface probes. In some embodiments, avoiding the use of a multi-well substrate enables the generation of a substrate with a suitable cluster density, spacing, and number of clusters to achieve single cell resolution. Accordingly, the substrates described herein may enable spatial detection of nucleic acid (e.g. RNA) in a tissue sample with single cell resolution.

In some embodiments, the substrate (e.g. flow cell surface) may be patterned. For example, the substrate may be patterned with defined groups of surface probes, such that the interaction (e.g. bridge amplification) between the capture probes and the surface probes results in more defined clusters. Such patterning may facilitate improved definition of the spatial location of individual clusters on the substrate. In some embodiments, the substrate is patterned with nanowells (e.g. a multi-well substrate) containing defined groups of surface probes held within each nanowell.

In some embodiments, the substrate may be engineered to generate additional nucleic acids with a localized pattern. For example, clusters may encode RNA polymerase binding sequences, such as T7 RNA polymerase promoter sequences, to produce RNA sequences encoded by the clusters, amplifying the sequence information.

In some embodiments, the substrate may comprise additional capture moieties. For example, the substrate may comprise additional capture moieties for the capture of non-nucleic acid targets (e.g. targets other than RNA or DNA). Such embodiments enable multiplex detection of nucleic acid and non-nucleic acid targets. For example, such embodiments enable multiplex detection of DNA and/or RNA, and non-nucleic acid targets such as proteins. In some embodiments, the substrate may comprise antibodies against a target protein of interest. As another example, the substrate may comprise other molecular probes recognizing specific biomolecules, organelles, or cells. In some embodiments, the additional capture moieties (e.g. antibodies, probes) may be conjugated to the surface of the substrate. In some embodiments, natural DNA molecules may be fragmented and labeled with moieties that can be captured by the substrate. In some embodiments, the additional capture moieties may be conjugated to the surface of the substrate such that each cluster of capture probes contains one or more additional capture moieties integrated within the cluster. As another example, the additional capture moieties may be conjugated to the capture probe itself. For example, the additional capture moieties may be conjugated to a suitable portion of the capture probe by a suitable linker. In some embodiments, the additional capture moieties may be conjugated to tissue targets. For example, small microRNAs can be labeled with capture moieties, such as poly-adenine, so that they can be captured by the substrate.

In some embodiments, the substrate is replicated onto a second substrate. The second substrate is also referred to herein as a "replicate substrate". The substrate (e.g. flow cell surface) used for generation of a second substrate is referred to herein as an "original substrate" or a "template substrate". For example, an "original substrate" or a "template substrate" may be generated by a method described herein. In some embodiments, the capture domain of each capture probe is exposed in the template substrate. In some embodiments, the capture domain of each capture domain is not exposed in the template substrate (e.g. the cleavage domain is intact). The "template substrate" may be replicated onto a second media to form a "second substrate". For example, the template substrate may replicated onto the second substrate through additional PCR or isothermal amplification methods such as bridge amplification. Subsequent processing of the nucleic acid may expose capture domain in the replicate substrate. In some embodiments, the original substrate induces the localized synthesis and release of nucleic acid transcripts, such as RNA, which is captured by a second media to form a second substrate. Such embodiments may be advantageous in allowing a small number of template substrates to serve as a template for replication to form a large number of second substrates. The second substrates may be used for methods of spatial detection of nucleic acid in a tissue sample as described herein.

The replicate substrate may comprise any suitable material or form as described above for the original substrate. For example, the replicate substrate may be porous or non-porous. The replicate substrate may be planar or non-planar. For example, the replicate substrate may comprise a planar surface coated with surface probes. The replicate substrate may also comprise a 3 dimensional structure with increased surface area, such as convoluted surface or porous surface. The surface of the replicate substrate may comprise a material selected from glass, silicon, poly-L-lysine coated materials, nitrocellulose, polystyrene, cyclic olefin copolymers (COCs), cyclic olefin polymers (COPs), polypropylene, polyethylene, polycarbonate and polyacrylamide. In some embodiments, the replicated surface comprises polyacrylamide. In some embodiments, the replicate substrate comprises a gel. In some embodiments, the replicate substrate comprises beads. Any DNA polymerase suitable for PCR or isothermal amplification can be used for replicating the substrate. Suitable enzymes include: Taq polymerase, Pfu polymerase, Bst polymerase, KAPA HIFI DNA Polymerase™, Herculase™, and Phusion DNA Polymerase™. In some aspects, provided herein are methods for spatial detection of nucleic acid in a tissue sample. Although methods are frequently described herein for spatial detection of RNA in a tissue sample, it is understood that the substrates, methods, and kits described herein may also be used for spatial detection of DNA in a tissue sample. Additionally, the methods may comprise multiplex detection of nucleic acid (e.g. RNA, DNA) and non-nucleic acid (e.g. protein, cells, organelles, etc.) targets. The type of target may depend on the specific capture domain used and/or the presence of additional capture moieties on the substrate. For example, capture domains comprising a poly-dT tail are suited for spatial detection of RNA with poly-A tail. RNA that does not have poly-A tail may be labeled with poly-A before being captured by the substrate.

In some embodiments, synthetic nucleotides are sequence-specifically hybridized to natural RNA and/or DNA in the tissue. In these embodiments, such synthetic nucleotides are engineered to contain the target sequences for the capture domain, such as poly-A tail. Sequencing of the synthetic nucleotides captured by the substrate may enable spatial detection of target RNA and/or DNA that are present in the tissue.

Capture domains comprising a nucleic acid sequence against a target DNA sequence are useful for spatial detection of DNA. Substrates comprising a capture probe and an additional capture moiety (e.g. an antibody targeting protein or DNA/RNA probes targeting specific nucleic acid sequence) are useful for multiplex detection of nucleic acid and non-nucleic acid targets.

The methods for spatial detection of nucleic acid in a tissue sample comprise contacting the sample with a substrate as described herein. In some embodiments, the method comprises contacting the substrate with a tissue sample and allowing nucleic acid (e.g. RNA) molecules of the tissue sample to bind to the capture domain of the capture probes. For example, the poly-A tail of RNA molecules (e.g. mRNA) may bind to the exposed poly-dT (or functionally equivalent) domain of the capture probes.

As another example, target DNA molecules may bind to a capture domain comprising a sequence complementary to the nucleic acid sequence of the target DNA molecule. For methods for spatial detection of DNA, the target DNA (e.g. the DNA that binds to the capture domain) may be sequenced by a suitable sequencing method. For example, the capture probes may be extended using suitable primers, and the sequence of the target DNA may be determined. Suitable sequencing methods include those described below in relation to sequencing cDNA molecules, such as PCR-based methods, ILLUMINA platforms, pyrosequencing, and the like.

In some embodiments, the methods further comprise generating cDNA molecules from the bound RNA molecules. The cDNA generated is considered to be indicative of the RNA present in a cell at the time in which a tissue sample was taken. Therefore, cDNA represents all or some of the genes that were expressed in the cell at the time the tissue sample was taken. The capture probe acts as a primer for reverse transcription, such that the sequence of the capture probe is incorporated into the sequence of the first strand cDNA molecule along with the sequence complementary to the captured RNA strand. Accordingly, the spatial barcode of the capture probe is incorporated into the sequence of the first strand cDNA molecule.

Generating cDNA molecules from the bound RNA molecules may be performed by any suitable method. For example, generating cDNA molecules from the bound RNA molecules may be performed by addition of a reverse transcriptase to facilitate reverse transcription of the RNA (e.g., mRNA) to generate a complementary or copy DNA (i.e., cDNA). The cDNA resulting from the reverse transcription of RNA is referred to herein as "first strand cDNA". First strand cDNA synthesis (e.g., reverse transcription) may be performed directly on the substrate.

In some embodiments, the reverse transcription reaction includes a reverse transcriptase, dNTPs and a suitable buffer. The reaction mixture may comprise other components, such as RNase inhibitor(s). Each dNTP is typically present in an amount ranging from about 10 to 5000 μM, usually from about 20 to 1000 μM. Any suitable reverse transcriptase enzyme may be used. Suitable enzymes include: M-MLV, MuLV, AMV, HIV, ArrayScript™, MultiScribe™ ThermoScript™, and Superscript® I, II, and III enzymes. The reverse transcriptase reaction may be carried out at any suitable temperature, which is dependent on the properties of the enzyme. Typically, reverse transcriptase reactions are performed between 37-55° C., although temperatures outside of this range may also be appropriate. The reaction time may be as little as 1, 2, 3, 4 or 5 minutes or as much as 48 hours. Typically, the reaction is carried out for between 3-12 hours, although other suitable reaction times (e.g., overnight) may be used.

In some embodiments, a strand complementary to the first strand cDNA may be developed. The strand complementary to the first strand cDNA is referred to herein as "second strand cDNA". The term "cDNA" as used herein is used in the broadest sense and refers to any cDNA, including first strand cDNA and second strand cDNA.

In some embodiments, "generating cDNA" comprises performing second strand synthesis (e.g., following the reverse transcription reaction) to generate second strand cDNA. In some embodiments, second strand cDNA synthesis may occur without increasing the number of copies of the second strand cDNA (e.g., without amplifying the second strand). In other embodiments, second strand cDNA may be synthesized and amplified, resulting in multiple copies of the second strand. Second strand cDNA synthesis, if performed, may be performed on the substrate (e.g., while the cDNA is immobilized on the substrate). Alternatively, the first strand cDNA may be released from the substrate and second strand cDNA synthesis may be performed in solution.

The second strand cDNA comprises a complement of the capture probe and therefore comprises a complement of the spatial barcode sequence of the capture probe. The second strand cDNA may be amplified using a suitable primer or combination of primers upstream of the complement to the spatial barcode sequence, such that the complement of the spatial barcode sequence is presence in each amplified second strand cDNA.

In some embodiments, second strand cDNA synthesis is performed using random primers. For example, the first strand cDNA may be incubated with random primers, such as hexamer primers, and a DNA polymerase, under conditions sufficient for synthesis of the complementary DNA strand (e.g., second strand cDNA) to form.

In some embodiments, the use of random primers yields cDNA molecules of varying lengths and is unlikely to yield full-length cDNA molecules (e.g., cDNA molecules corresponding to the entire RNA strand from which they were synthesized). If it is desirable to generate full-length cDNA molecules, alternative methods may be employed. For example, the 3' end of the first stand cDNA may be modified such that a complement of the entire first strand cDNA is generated. For example, a linker or adaptor may be ligated to the 3' end of the cDNA molecules. This may be achieved using single stranded ligation enzymes such as T4 RNA ligase or Circligase™ (LUCIGEN). Alternatively, a helper probe (a partially double stranded DNA molecule capable of hybridizing to the 3' end of the first strand cDNA molecule), may be ligated to the 3' end using a double stranded ligation enzyme such as T4 DNA ligase. Other enzymes appropriate for the ligation step are known in the art and include, e.g., Tth DNA ligase, Taq DNA ligase, Thermococcus sp. (strain 9° N) DNA ligase (9° N™ DNA ligase, New England Biolabs), and Ampligase™ (LUCIGEN). In some embodiments, the helper probe comprises a specific sequence from which the second strand cDNA may be primed using a primer that is complementary to the part of the helper probe that is ligated to the first cDNA strand. A further alternative comprises the use of a terminal transferase active enzyme to incorporate a polynucleotide tail, e.g. a poly-A tail, at the 3' end of the first strand of cDNA. Second strand synthesis may be primed using a poly-T primer, which may also comprise a specific amplification domain for further amplification.

Another suitable method for generating full-length cDNA is referred to as template switching, e.g., using the SMART™ technology from Clontech®. SMART (Switching Mechanism at 5' End of RNA Template) technology is well established and is based that the discovery that reverse transcriptase enzymes, e.g. Superscript® II (Invitrogen), are capable of adding a few nucleotides at the 3' end of an extended cDNA molecule to produce a DNA/RNA hybrid with a single stranded DNA overhang at the 3' end. The DNA overhang may provide a target sequence to which an oligonucleotide probe can hybridize to provide an additional template for further extension of the cDNA molecule. The oligonucleotide probe that hybridizes to the cDNA overhang contains an amplification domain sequence, the complement of which is incorporated into the synthesized first strand cDNA product. Primers containing the amplification domain sequence, which will hybridize to the complementary amplification domain sequence incorporated into the first strand cDNA, can be added to the reaction mix to prime second strand synthesis using a suitable polymerase enzyme and the cDNA first strand as a template. This method avoids the need to ligate adaptors to the 3' end of the cDNA first strand. While template switching was originally developed for full-length mRNAs, which have a 5' cap structure, it has since been demonstrated to work equally well with truncated mRNAs without the cap structure. Thus, template switching may be used in the methods of the invention to generate cDNA molecules.

In some embodiments, the second strand cDNA may be synthesized such that one or more additional features are added to the second strand. These additional features may be present in the primers used for second strand synthesis (e.g., the random primers). For example, the second strand cDNA may be synthesized such that a primer binding site for subsequent amplification is added to the second strand. In some embodiments, one or more sequencing handles (e.g., sequencing barcodes) may be incorporated into the second strand cDNA. For example, second strand cDNA synthesis may comprise a sequencing handle, such as an ILLUMINA TruSeq handle, which may be added to the second strand cDNA. In some embodiments, the sequencing barcode comprises 10-50 bases. For example, the sequencing barcode may be about 10, 15, 20, 25, 30, 35, 40, 45, or 50 bases in length. In some embodiments, the second strand cDNA may be synthesized such that a unique molecular identifier (UMI) sequence is added to the second strand. The UMI may be any suitable sequence of nucleic acids of any suitable length. In some embodiments, the second strand may contain both a UMI and a sequencing handle. The addition of these additional features (e.g., primer binding site, unique molecular identifier, and/or sequencing handle) to the second strand cDNA may facilitate future steps, such as future amplification, purification, or detection steps, in the disclosed method.

In some embodiments, the second strand cDNA may be isolated, purified and amplified following synthesis. For example, the second strand cDNA may be synthesized by a suitable method as described above (e.g., using random primers). In some embodiments, the secondary strand cDNA may be isolated through DNA denaturation through 0.1N NaOH, 0.1N KOH, or any solutions with high pH and/or organic solutions that can denature the DNA. In some embodiments, the secondary strand cDNA may be isolated through heat denaturation. The isolated second strand may be purified, and then amplified by PCR. Primers for PCR amplification of the second strand cDNA may be any suitable primers, including primers targeting the additional features (e.g., primer binding sites, sequencing barcodes, unique molecular identifiers) added to the second strand cDNA. Any suitable number of isolation, amplification, and purification steps may be performed to generate the final library of cDNA prior to sequencing.

In some embodiments, the capture probes used for the initial capture of RNA (e.g., mRNA) may contain one or more additional features (e.g., additional to the spatial barcode and capture domain) that facilitate sequencing library preparation. For example, the capture probes may contain a sequencing handle (e.g., sequencing barcode). Therefore, the complement of the sequencing barcode will be present in the cDNA. Accordingly, cDNA generated by the methods described herein may comprise two distinct sequencing barcodes. For example, the cDNA may comprise sequencing barcode(s) compatible with an ILLUMINA sequencing platform (e.g., TruSeq Read 1 handle, TruSeq Read 2 handle). In some embodiments, the cDNA comprises sequencing barcode(s), a spatial barcode, and/or a unique molecular identifier. These additional features may facilitate library preparation, sequencing, and spatial detection of RNA by the methods described herein.

In some embodiments, the generated cDNA may be sequenced with no intervening treatment steps prior to sequencing. For example, in tissue samples that comprise large amounts of RNA, generating the cDNA may yield a sufficient amount of cDNA such that it may be sequenced directly. In other embodiments, it may be desirable to generate double stranded cDNA and/or generate multiple copies of the DNA prior to sequencing. Such methods may be performed while the cDNA is bound to the substrate, or the cDNA may be released from the substrate and subsequently treated to generate double stranded copies and/or amplify the DNA. In some embodiments, it may be desirable to generate double stranded DNA without increasing the number of double stranded DNA molecules. In other embodiments, it may be desirable to generate double stranded DNA and generate multiple copies of the second strand. For example, one or multiple amplification reactions may be conducted to generate multiple copies of single stranded or double stranded DNA.

In some embodiments, generation of cDNA (e.g., by reverse transcription of the RNA bound to the capture probes) may take place on the substrate and the generated cDNA may be released from the substrate prior to subsequent treatment steps. For example, the cDNA may be generated on the substrate and the generated DNA may be released from the substrate and collected in a tube. Subsequent steps (e.g., second strand cDNA synthesis, amplification, sequencing, etc.) may be performed in solution. In some embodiments, RNA may be removed prior to subsequent treatment of the cDNA strand. For example, RNA may be removed using an RNA digesting enzyme (e.g., RNase). In some embodiments, no specific RNA removal step is necessary, as RNA will degrade naturally and/or removal of the tissue from the substrate is sufficient for RNA removal.

In some embodiments, the methods for spatial detection of nucleic acid (e.g. RNA) in a tissue sample further comprise sequencing the cDNA molecules. The cDNA molecules may be sequenced on the substrate or may be released and collected into a suitable device (e.g., a tube) prior to sequencing. Sequencing may be performed by any suitable method. Sequencing is generally performed using one or multiple amplification steps, such as polymerase chain reaction (PCR). In some embodiments, sequencing may be performed using next-generation sequencing methods. High-throughput sequencing is particularly useful in the methods described herein, as it enables a large number of nucleic acids to be sequenced or partially sequenced in relatively short period of time. In some embodiments, sequencing may be performed using ILLUMINA technology (e.g., "sequencing by synthesis" technology). For example, the sequencing reaction may be based on reversible dye-terminators, such as used in the ILLUIMNA technology. The sequencing primer may be added to the sample containing cDNA and the primer may bind to the corresponding region on the cDNA molecule. The sequence of the primer is extended one nucleotide at a time, each nucleotide containing a fluorescent label. After the addition of each consecutive nucleotide to the growing chain, a characteristic fluorescent signal is determined, until the desired sequence data is obtained. Using this technology, thousands of nucleic acids may be simultaneously sequenced on a single substrate.

In some embodiments, other sequencing methods may be used to determine the sequence of the cDNA molecules. For example, the sequence of the cDNA molecules may be determined by pyrosequencing. In this method, the cDNA is amplified inside water droplets in an oil solution (emulsion PCR), with each droplet containing a single cDNA template attached to a single primer-coated bead that then forms a clonal colony. The sequencing machine contains many wells, each containing a single bead and sequencing enzymes. Pyrosequencing uses luciferase to generate light for detection of the individual nucleotides added to the nascent cDNA and the combined data are used to generate sequence read-outs.

In some embodiments, the full length of the cDNA molecules may be sequenced. In some embodiments, less than the full length of the cDNA molecules may be sequenced. The claimed methods are not limited to sequencing the entire length of each cDNA molecule. For example, the first 100 nucleotides from each end of the cDNA molecules may be sequenced and used to identify the gene expressed. In some embodiments, sequencing may be performed to determine the sequence of the spatial barcode and at least about 20 bases of RNA transcript specific sequence data. For example, the sequencing may be performed to determine the sequence of the spatial barcode and at least 10, 25, 30, 35, 40, 45, 50 bases of RNA transcript specific sequence data. Additional bases of RNA transcript specific sequence data may be obtained. For example, the sequencing may be performed to determine the sequence of the spatial barcode and at least 50, 60, 70, 80, 90, or 100 bases of RNA transcript specific data.

In some embodiments, the methods for spatial detection of nucleic acid (e.g. RNA) in a tissue sample further comprise determining the location of each cluster of capture probes on the surface of the substrate prior to contacting the substrate with the tissue sample. In some embodiments, the location of each cluster of capture probes may be provided. For example, a kit comprising a substrate as described herein may contain information regarding the location of each cluster of capture probes on the substrate. In some embodiments, determining the location of each cluster of capture probes on the surface of the substrate comprises determining the spatial barcode for at least one capture probe in each cluster, and assigning the sequence to a specific location on the substrate.

In some embodiments, the location of each cluster of capture probes on the surface of the substrate is determined during manufacture of the substrate itself. For example, the substrate may be manufactured by immobilizing one or more capture probes on the surface of the substrate (e.g., by binding to a surface probe on the substrate) and generating clusters (e.g., by bridge amplification), as described above. The capture probes may comprise a spatial barcode and a capture domain, as described above. After cluster generation, the determination of the location of each cluster of capture probes on the surface may be determined by sequencing the capture probes on the substrate. For example, sequencing may be performed using an ILLUMINA system. In particular, sequencing primers targeting the spatial barcode may be utilized, and the sequence of the spatial barcode may be determined. The sequence of the spatial barcode for each cluster may be assigned to a specific location on the substrate (e.g., an XY coordinate on the substrate) from which the detected sequencing was obtained. In some embodiments, a high-resolution map of the substrate may be generated based upon the signal detected during sequencing (e.g., the fluorescent signal) and used to assign an XY coordinate to each cluster on the substrate.

In some embodiments, the methods for spatial detection of nucleic acid (e.g. RNA) in a tissue sample further comprise correlating the sequence of the spatial barcode for each sequenced cDNA molecule with the location of the cluster of capture probes on the substrate having the corresponding spatial barcode. The first strand cDNA will contain the same spatial barcode as the capture probe, whereas the second strand cDNA will contain the complement to the spatial barcode of the capture probe. "Corresponding" as used herein covers each of these possibilities, depending on which cDNA strand is sequenced. For instance, if the second strand cDNA is sequenced, the sequence of the second strand cDNA is correlated with the location of the cluster of capture probes on the substrate having the complementary spatial barcode. Alternatively, if the first strand cDNA is sequenced (e.g., no intermittent steps of second strand synthesis and/or amplification are performed prior to sequencing the cDNA), the sequence of the first strand cDNA is correlated with the location of the cluster of capture probes on the substrate having the same spatial barcode.

In some embodiments, the methods for spatial detection of nucleic acid (e.g. RNA) in a tissue sample further comprise imaging the tissue after contacting the tissue with the substrate. Imaging the tissue may assist in the determination of the spatial location of RNA molecules within the tissue sample. In some embodiments, imaging the tissue is performed before generating cDNA. In some embodiments, imaging the tissue is performed after generating cDNA. Imaging the tissue may be performed using any suitable technique, including light, bright field, dark field, phase contrast, fluorescence, reflection, interference, confocal microscopy, or a combination thereof.

In some embodiments, one or more fiducial marks may be introduced on the flow cell surface. The term "fiducial mark" as used herein refers to a mark or object placed in the field of view of an imaging system for use as a point of reference or a measure. For example, a fiducial mark may be produced by physically removing clusters or by overlaying a blocking material that obscures the capture domain functionality. Physical removal or blocking of clusters may be detected in both optical images and digitally reconstructed transcriptome images after sequencing. In some embodiments, fiducial marks may be used to align the optical images and digitally reconstructed transcriptome images.

Methods for spatial detection of nucleic acid (e.g. RNA) in a tissue sample may optionally comprise imaging the cDNA molecules prior to release of the cDNA from the substrate. Imaging the cDNA molecules may assist in the determination of the spatial location of the corresponding RNA molecules from which the cDNA molecules were generated within the tissue sample. For example, the first strand or second strand cDNA molecules may be labeled during synthesis to facilitate subsequent imaging. The cDNA molecules may be labeled with a directly detectable label or an indirectly detectable label. A directly detectable label is one that can be directly detected without the use of additional reagents, while an indirectly detectable label is one that is detectable by employing one or more additional reagents, e.g., where the label is a member of a signal producing system made up of two or more components. Exemplary directly detectable labels include fluorescent labels, colored labels (e.g., dyes), radioisotopic labels, chemiluminescent labels, and the like. Any spectrophotometrically or optically-detectable label may be used. In other embodiments the label may require the addition of further components to generate signal. For instance, the label may be capable of binding a molecule that is conjugated to a signal giving molecule.

In some embodiments, the cDNA is labelled by the incorporation of a labelled nucleotide when the cDNA is synthesized. The labelled nucleotide may be incorporated in the first and/or second strand synthesis. In a particularly preferred embodiment, the labelled nucleotide is a fluorescently labelled nucleotide. Thus, the labelled cDNA may be imaged by fluorescence microscopy. Fluorescent molecules that may be used to label nucleotides are well known in the art, e.g. fluorescein, the cyanine dyes, such as Cy3, Cy5, Alexa 555, Bodipy 630/650, and the like. In some embodiments, fluorescently tagged CTP (such as Cy3-dCTP, Cy5-dCTP) is incorporated into the cDNA molecules synthesized on the surface of the substrate. Other suitable labels include dyes, nucleic acid stains, metal complexes, and the like.

In some embodiments, the substrate may comprise markers to facilitate the orientation of the tissue sample or the image thereof in relation to the clusters of capture probes on the substrate. Any suitable means for marking the array may be used such that they are detectable when the tissue sample is imaged. For instance, a molecule, e.g. a fluorescent molecule, that generates a signal, preferably a visible signal, may be immobilized directly or indirectly on the surface of the array. Preferably, the array comprises at least two markers in distinct positions on the surface of the substrate, further preferably at least 3, 4, 5, 6, 7, 8, 9, 10, 12, 15, 20, 30, 40, 50, 60, 70, 80, 90 or 100 markers. In some embodiments, several hundred or even several thousand markers may be used. In some embodiments, tens of thousands of markers may be used. The markers may be provided in a pattern, for example the markers may make up an outer edge of the portion of the substrate on which the capture probes are immobilized. Other informative patterns may be used, such as lines sectioning the array. Such markers may facilitate aligning an image of the tissue sample to the signal detected from the labelled cDNA molecules, (e.g. the image of the labelled cDNA molecules), and/or to the location of clusters of the capture probes on the substrate. The markers may be detected prior to, simultaneously with, or after imaging of the tissue sample. In some embodiments, the markers are detectable when the tissue sample is imaged. Thus, the marker may be detected using the same imaging conditions used to visualize the tissue sample. In some embodiments, the marker is detectable when the labelled cDNA is detected.

In some embodiments, determining the spatial location of the RNA molecules within the tissue sample comprises correlating the location of the cluster of capture probes on the substrate with a corresponding location within the tissue sample. In some embodiments, the spatial location of the RNA molecules in the tissue sample may be ultra-high resolution, allowing identification of a single cell expressing the RNA molecules.

In some embodiments, the techniques described herein allow for detection of gene expression within subcellular compartments within a single cell. For example, the methods described herein may allow for ultra-high resolution investigations of gene expression (e.g. RNA expression) in subcellular compartments including the nucleus, cytoplasm, and/or mitochondria of a single cell. For example, mRNA is transcribed and poly-A modified in the nucleus. Before it can be transported to cytoplasm, it is spliced, and intronic sequences are removed. Therefore, the nuclear area will have higher concentration of unspliced mRNA sequences, while the cytoplasmic area will have higher concentration of spliced mRNA sequences. Such differences may be utilized in order to investigate nuclear vs. cytoplasmic expression of various sequences in a single cell. For example, plotting of spliced and unspliced transcripts may be performed in conjunction with the methods described herein (e.g. in conjunction with the methods for spatial detection of RNA expression in a sample) to determine the nuclear-cytoplasmic structure of RNA (e.g. mRNA) expression. As another example, mitochondrial expression may be determined by investigating mitochondrial-encoded gene transcripts. Suitable methods for investigating nuclear, cytosolic, and/or mitochondrial expression patterns are described in Example 2. In some embodiments, antibodies or other molecular probes labeling plasma membrane and cell surface proteins could be used to mark the cell boundaries, enabling precise single cell segmentation. In some embodiments, optical images, including fluorescence images, are used for single cell segmentation. In some embodiments, the techniques described herein may be used to investigate various cell populations based upon zones within a given tissue type. For example, different zone markers (e.g. such as for hepatocytes) may be used to identify gene expression within a given zone, as described in Example 2. Other suitable combinations of markers may be used in order to investigate gene expression in a desired area and/or subcellular compartment.

In representative embodiments, the methods described herein may comprise each of the following steps (in no particular order):
a. providing a substrate described herein;
b. determining the sequence of the spatial barcode for at least one capture probe in each cluster on the substrate;
c. assigning each cluster a location (e.g., XY coordinate) on the substrate based upon the sequence of the spatial barcode;
d. contacting the substrate with a tissue sample and allowing RNA molecules in the tissue sample to bind to the capture probes;
e. imaging the tissue sample while the sample is bound to the substrate;
f. generating cDNA molecules from the RNA molecules bound to the capture probes;
g. determining the sequence of the spatial barcode for the cDNA molecules and correlating this sequence with the location of a corresponding cluster on the substrate (e.g., cluster of capture probes containing the corresponding spatial barcode);
h. correlating the location of the corresponding cluster of capture probes on the substrate with a corresponding location within the tissue sample, thus identifying the spatial location of RNA (e.g., gene) expression in the sample.

In representative embodiments, the methods described herein may comprise each of the following steps (in no particular order):
a. providing a substrate described herein;
b. determining the sequence of the spatial barcode for at least one capture probe in each cluster on the substrate;
c. assigning each cluster a location (e.g., XY coordinate) on the substrate based upon the sequence of the spatial barcode;
d. contacting the substrate with a tissue sample and allowing RNA molecules in the tissue sample to bind to the capture probes;
e. imaging the tissue sample while the sample is bound to the substrate;
f. generating first strand cDNA molecules from the RNA molecules bound to the capture probes (e.g., by reverse transcription)
g. generating, isolating, purifying, and amplifying second strand cDNA molecules from the first strand cDNA molecules, thus creating multiple second strand cDNA molecules from each first strand cDNA molecules;
h. determining the sequence of the spatial barcode for the second strand cDNA molecules and correlating this sequence with the location of a corresponding cluster on the substrate (e.g., cluster of capture probes containing the complementary spatial barcode to the spatial barcode of the second strand cDNA);
i. correlating the location of the corresponding cluster of capture probes on the substrate with a corresponding location within the tissue sample, thus identifying the spatial location of RNA (e.g., gene) expression in the sample.

Sequencing of the cDNA molecules enables determination of gene expression in the tissue sample, as cDNA is considered indicative of RNA expression in the tissue at the time it was isolated. Accordingly, determining the location within the tissue to which the sequence of the spatial barcode for the cDNA molecules corresponds allows for localized, spatial detection of RNA expression in the tissue sample. In some embodiments, the methods described herein have a high enough resolution to enable determination of gene expression in a single cell.

In some embodiments, the methods may further comprise analyzing the tissue sample for the presence of one or more additional targets, such as targets bound to the additional capture moieties on the substrate. For example, the methods may further comprise determining whether the tissue sample additionally contains one or more proteins of interest, which may be detected by an antibody conjugated capture moiety on the substrate. In some embodiments, the location of the additional capture moieties on the substrate may be known and thus used to determine the corresponding location of the additional target in the tissue sample. For example, the location of the additional capture moieties on the substrate may be known based upon the location of the cluster of capture probes in which the additional capture moieties are integrated.

The methods and substrates described herein may be used to determination of gene expression in any suitable tissue sample. The tissue may be fresh or frozen. In some embodiments, the tissue may be fixed (e.g. formalin fixed).

In some aspects, provided herein are kits for use in methods of spatial detection of RNA in a tissue sample. In some embodiments, the kit comprises a substrate as described herein. For example, the kit may comprise a substrate comprising a plurality of capture probes as described herein immobilized on a surface of the substrate.

In some embodiments, each capture probe on the substrate comprises a capture domain and a spatial barcode. In some embodiments, the plurality of capture probes are arranged in clusters, wherein each cluster comprises multiple capture probes, each capture probe in a cluster comprises the same spatial barcode, and the spatial barcode for each cluster is unique.

In some embodiments, the kit further comprises additional reagents for spatial detection of RNA in a tissue sample. For example, the kit may further comprise additional reagents for generation of cDNA, imaging of the tissue sample and/or cDNA on the substrate, and/or sequencing of cDNA. For example, the kit may further comprise enzymes (e.g. reverse transcriptases, ligases, etc.), dNTPs, buffers, RNAse inhibitors, primers, probes, labels (e.g. fluorescent dyes), and the like. In some embodiments, the kit further comprises additional reagents for spatial detection of DNA in a tissue sample. In some embodiments, the kit further comprises additional reagents for spatial detection of specific cellular and tissue-level features, which could be conjugated with a specific nucleic acid sequence, such as proteins that are detected by nucleic acid-conjugated antibodies. Individual member components of the kits may be physically packaged together or separately. The kits can also comprise instructions for using the components of the kit. The instructions are relevant materials or methodologies pertaining to the kit. Instructions can be supplied with the kit or as a separate member component, either as a paper form or an electronic form which may be supplied on computer readable memory device or downloaded from an internet website, or as recorded presentation. It is understood that the disclosed kits can be employed in connection with the substrates, methods, and systems described herein.

Further provided herein are systems which may be used to collect, store, and/or display information regarding the spatial location of RNA in a sample. Such systems may be used in combination with a substrate, method, or kit as described herein. In some embodiments, systems include software containing instructions for performing one or more steps in a method described herein. For example, the system may include software designed to execute a program for imaging cDNA, imaging tissue, performing PCR, performing sequencing, and the like. In some embodiments, the system includes a memory for storing data collected during one or more steps in a method as described herein. For example, the memory may store sequencing and/or imaging data collected by a method as described herein. In some embodiments, the system includes a computer (e.g., a controller), which may comprise the software and/or memory component.

Exemplary substrates and methods of making and using the same are provided in Cho et al., (2021) Cell 184. 3559-3572, the entire contents of which are incorporated herein by reference for all purposes.

EXAMPLES

Example 1

Capture probes containing a high density molecular identifier (HDMI), an oligo-dT domain, and a cleavage domain (Xba1 or Dra1 restriction site) were immobilized on the surface of a glass slide. The probes contained an ILLUMINA P5 or P7 sequence, and were bound to the surface of the glass slide by interactions with a corresponding surface probe on the slide surface. Capture probes were amplified by bridge amplification, resulting in the generation of multiple clusters of capture probes on the surface of the slide. The resulting substrate comprises millions of clusters, each cluster containing the same spatial barcode (e.g., HDMI sequence).

The P5 domain may be cleaved from the substrate and one or more wash steps may be performed, leaving only capture probes having a P7 domain bound to the substrate. Alternatively, the P7 domain may be cleaved from the substrate and one or more wash steps may be performed, leaving only capture probes having a P5 domain bound to the substrate.

Following cleavage of the P5 or the P7 domain, sequencing may be performed to determine the sequence of the HDMI for each cluster. The sequence may be used to assign each cluster to a specific location on the substrate.

Figure 4A:
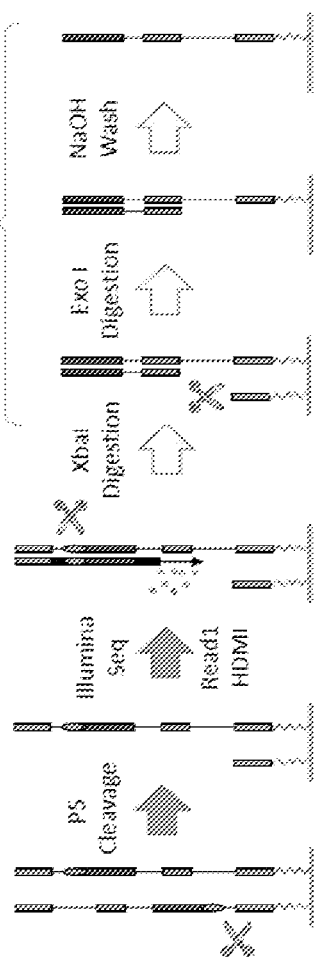
FIG. 4A shows a schematic representation of a suitable method for preparing the bound capture probes for RNA capture. The capture probe may contain a cleavage domain which protects the capture domain from damage/degradation during substrate manufacture. After cluster generation, sequencing, and assignation of a location on the substrate to each cluster (as shown in FIG. 2-3), one or more digestion and wash steps may be performed to cut the cleavage domain and expose the binding domain. The resulting substrate ("HR-slide") contains clusters of capture probes, each cluster having a unique spatial barcode and a known location on the substrate, and each cluster containing a plurality of capture probes with exposed binding domains such that RNA may bind to the capture probes.
Figure 4B:
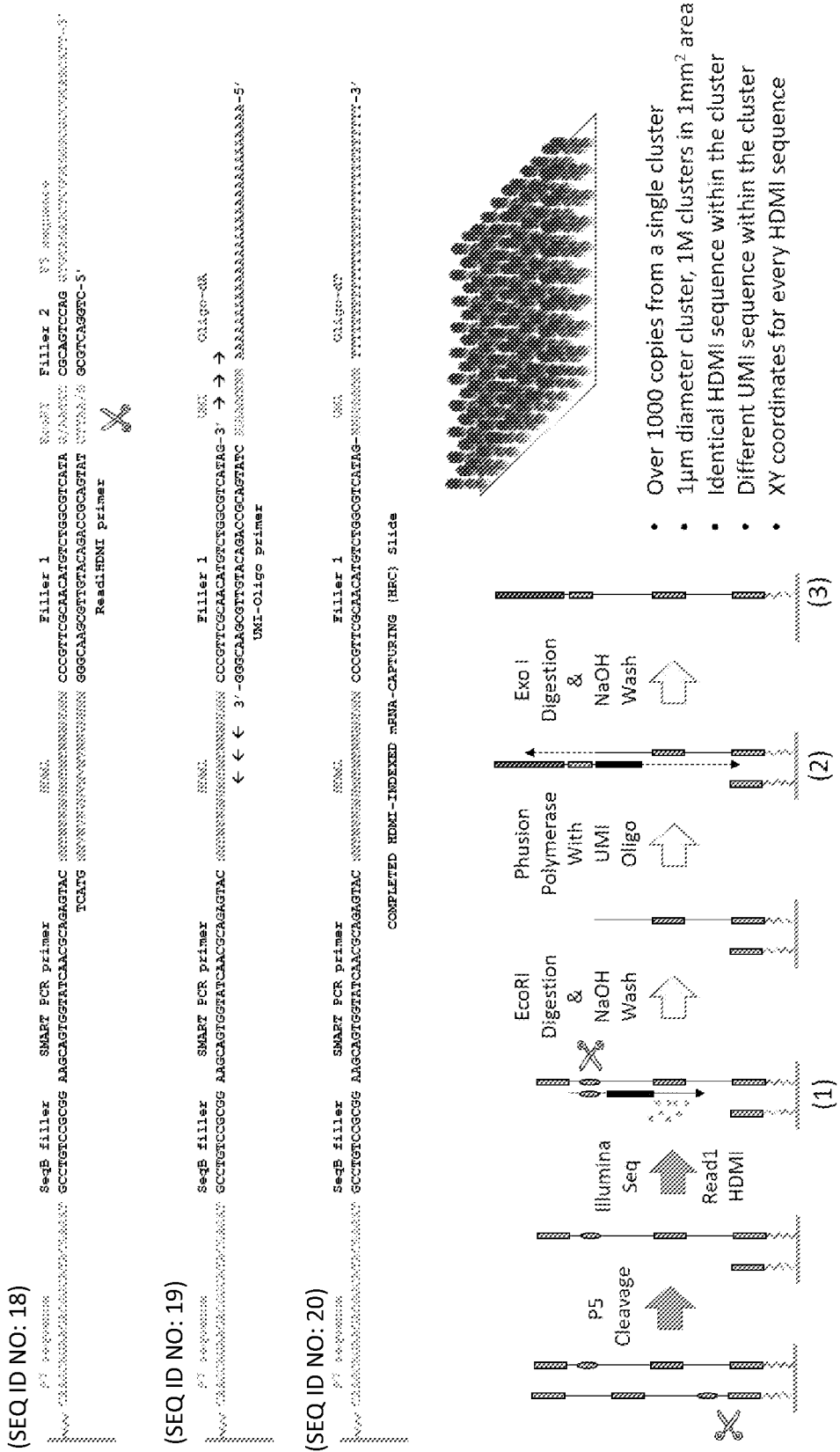
FIG. 4B shows a schematic representation of an alternative method for preparing the RNA capture probes with unique molecular identifier (UMI). In this method, the capture probe sequence is encoded by two separate oligonucleotides: HDMI-oligo and UMI-oligo. HDMI-oligo is used for cluster generation and sequencing processes as described above in FIG. 4A. After cluster generation and sequencing, HDMI-oligo is cleaved (1) and attached to UMI-oligo (2). The resulting substrate contains clusters of capture probes, each cluster having a unique spatial barcode (HDMI) and a known location on the substrate, and each cluster containing a plurality of capture probes with exposed binding domains as well as different UMI sequences.
Figure 4C:
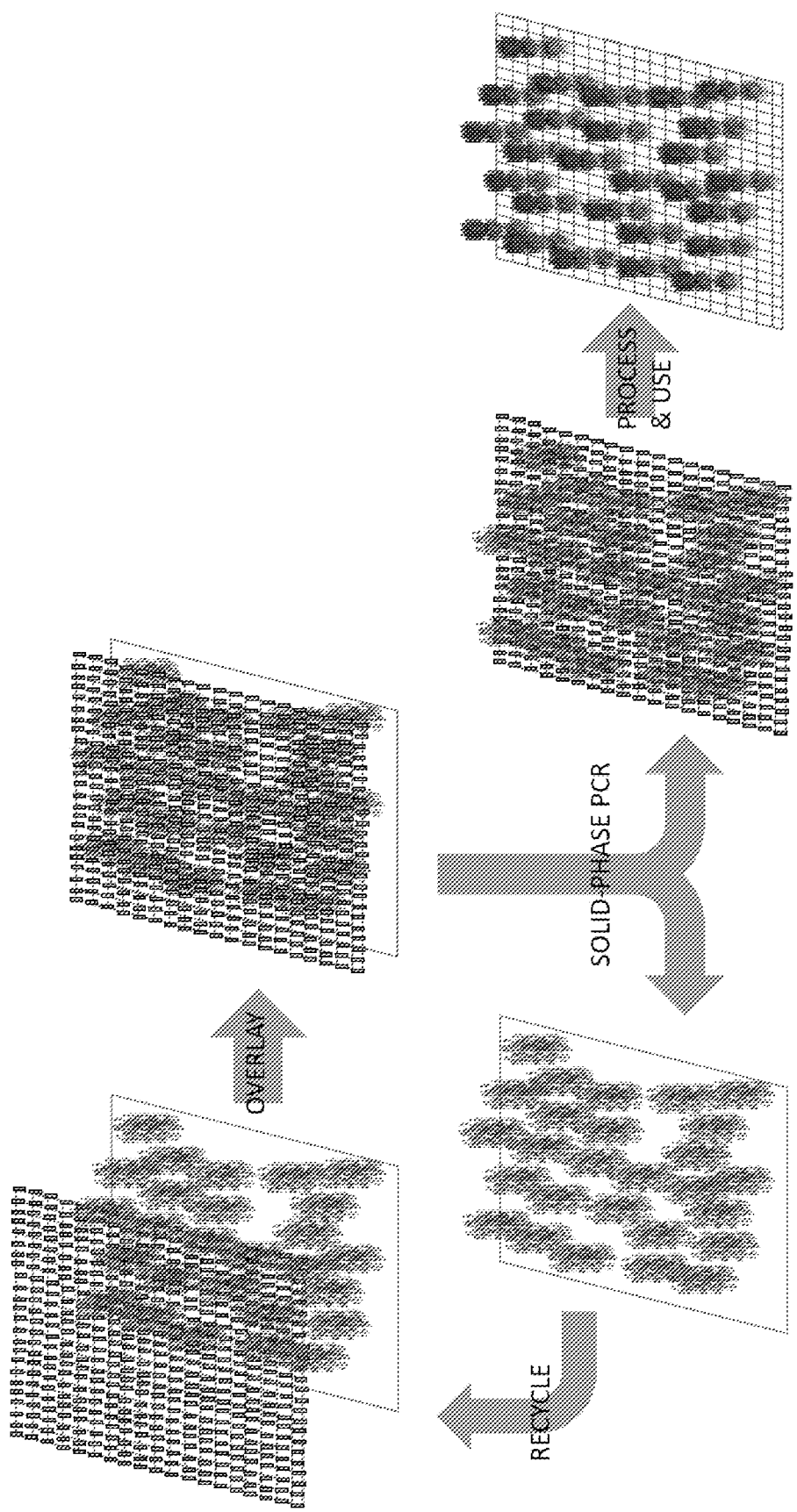
FIG. 4C shows a schematic representation of a method that can replicate the clusters containing HDMI-encoded clusters. Through overlaying a media attached with appropriate PCR primers (e.g. polymer structure) and performing solid-phase PCR, HDMI-encoded clusters can be replicated into a new media while preserving the spatial information for the capture probes. The new media can be processed to generate a substrate that is similar to the original substrate (e.g. "HR-slide") described above. The generated substrate is referred to herein as a "second substrate" or a "replicate substrate". The second substrate can be used for RNA capturing while the original substrate can be recycled for repeated generation of the replicate substrates.
Figure 5:
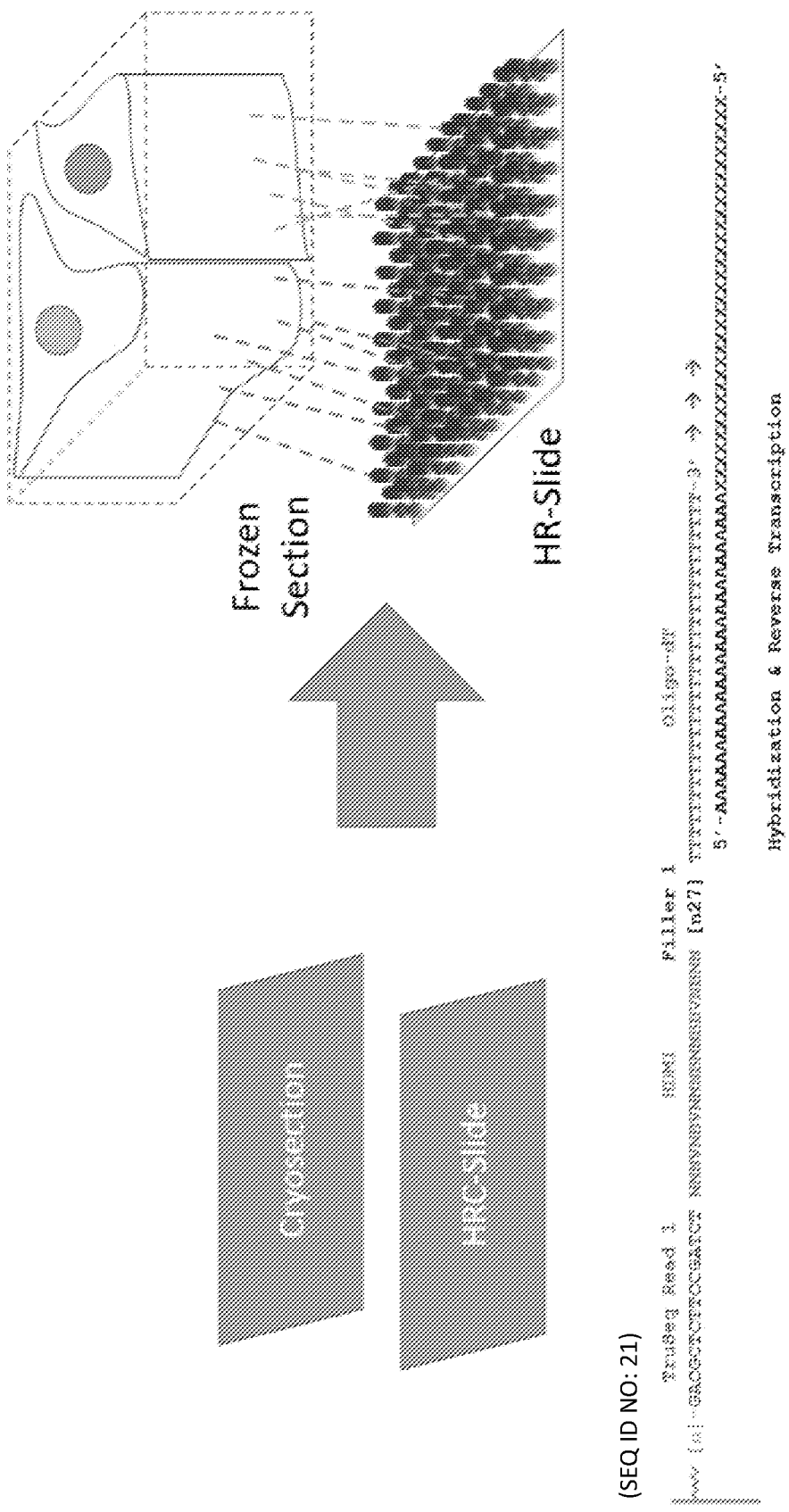
FIG. 5 shows a schematic representation of a suitable method for spatial detection of RNA expression in a tissue sample. The frozen tissue section (e.g., cryosection) may be contacted with the substrate (e.g., "HR-slide"). The poly-A tail of RNA in the tissue binds to the oligo-dT binding domain of the capture probe, and the first strand cDNA is generated by reverse transcription.

Following amplification and determination of the HDMI sequence, the oligo-dT tail may be exposed. For example (FIG. 4A), the oligo-dT tail may be exposed by the addition of suitable restriction enzymes (e.g., Xba1) to cut the cleavage domain, and one or more wash steps (e.g., NaOH wash) or enzymatic steps (e.g. exonuclease digestion) may be performed. The resulting capture probe comprises the P5 (or P7 domain) bound to the surface of the slide, the HDMI sequence, and an exposed oligo-dT tail. In the second example (FIG. 4B), the oligo-dT tail may be synthesized on the HDMI sequence by hybridization of separate oligonucleotide that encodes oligo-dA tract. In the third example (FIG. 4C), the HDMI sequence clusters may be replicated into a new substrate by PCR or isothermal amplification, which may be further processed to expose the oligo-dT tail.

Figure 7:
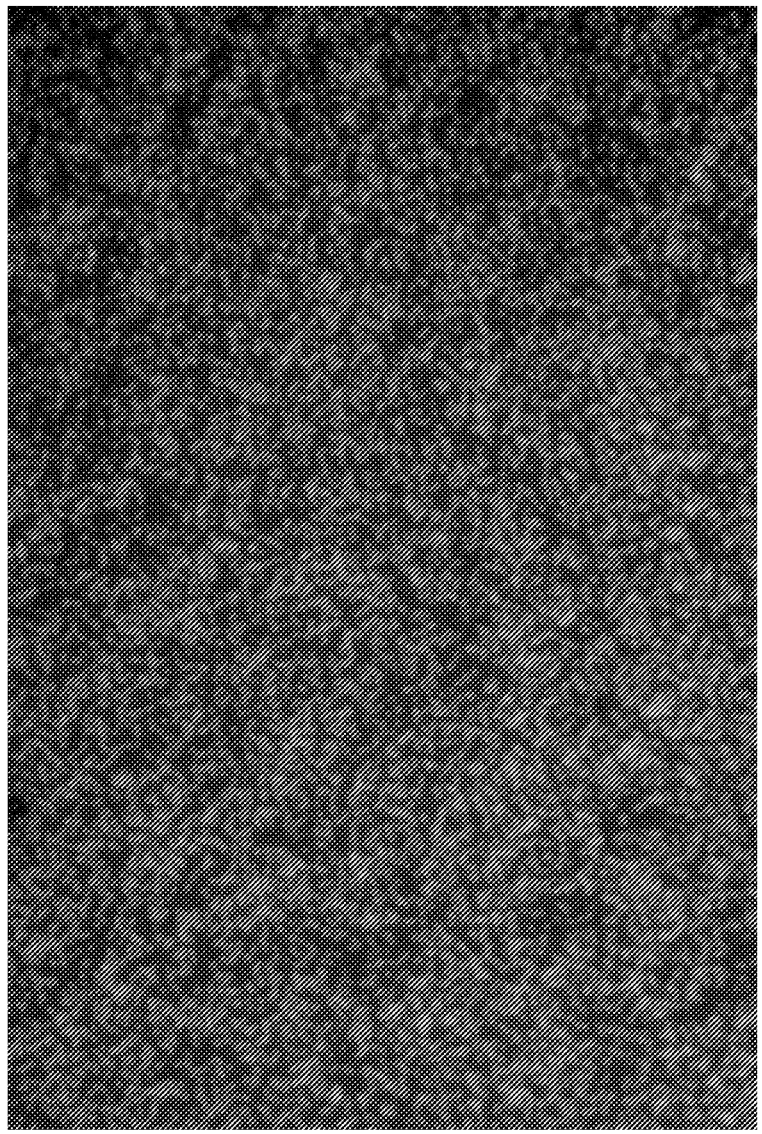
FIG. 7 shows Cy3 fluorescence of an exemplary slide that captured poly-A mRNA and generated Cy3-labeled cDNA. The slide was manufactured by a method as described herein to contain clusters of capture probes, and the sequence and spatial location of the cluster probes were determined. The oligo-dT tail of the capture probe was exposed, and the slide was subjected to reverse transcription (RT) reaction with 1 ug total RNA purified from the mouse liver, in the presence of fluorescence-labeled deoxynucleotide (Cy3-dCTP). Cy3-dCTP was incorporated into the cDNA sequence which was synthesized on the HDMI molecules during the RT reactions. This resulted in a very bright Cy3 staining in all the HDMI clusters (picture attached below), indicating that these clusters are indeed capable of synthesizing cDNAs.

FIG. 7 shows an exemplary slide containing clusters of capture probes. The oligo-dT tail of the capture probe was exposed, and the slide was subjected to reverse transcription (RT) reaction with 1 ug total RNA purified from the mouse liver, in the presence of fluorescence-labeled deoxynucleotide (Cy3-dCTP). Cy3-dCTP was incorporated into the HDMI molecules during the RT reactions. This resulted in a very bright Cy3 staining in all the HDMI clusters (FIG. 7) indicating that these clusters are suitable for synthesizing cDNAs and subsequent analysis.

Example 2

Experimental Procedures

Part I. Experimental Implementation

Generation of Seed HDMI-Oligo Library

Methods described herein are initiated with generation of a HDMI-oligo seed library (FIGS. 8A and 9A). In the current report, two versions of the library—HDMI-DraI and HDMI32-DraI, whose sequences are provided below, were used. The libraries have the same backbone structure with different length of HDMI sequences. HDMI is a sequence of random nucleotides that are designed to avoid DraI digestion site using Cutfree software [52]. HDMI32-DraI is an improved version of HDMI-DraI; however, for the liver and colon studies, HDMI-DraI was used. HDMI-DraI was generated by IDT as Ultramer oligonucleotides, while HDMI32-DraI was generated by Eurofins as Extremer oligonucleotides.

Backbone:
(P5 sequence) (TR1: TruSeq Read 1) (HDMI) (HRI:

HDMI Read 1) (Oligo-dT) (DraI) (DraI adapter)

-continued (P7 sequence)

HDMI-DraI:
(SEQ ID NO: 1)
CAAGCAGAAGACGGCATACGAGATTCTTTCCCTACACGACGCTCTTCCGAT

CTNNVNNVNNVNNVNNVNNVNNNNNTCTTGTGACTACAGCACCCTCGACTCTCG

CTTTTTTTTTTTTTTTTTTTTTTTTTTTTAAAGACTTTCACCAGTCCAT

GATGTGTAGATCTCGGTGGTCGCCGTATCATT

HDMI32-DraI:
(SEQ ID NO: 2)
CAAGCAGAAGACGGCATACGAGATTCTTTCCCTACACGACGCTCTTCCGAT

CTNNVNBVNNVNNVNNVNNVNNVNNVNNVNNVNNNNNTCTTGTGACTACAGCAC

CCTCGACTCTCGCTTTTTTTTTTTTTTTTTTTTTTTTTTTTAAAGACTT

TCACCAGTCCATGATGTGTAGATCTCGGTGGTCGCCGTATCATT

HDMI-oligo Cluster Generation and Sequencing through MiSeq (1st-Seq)

HDMI-DraI or HDMI32-DraI was used as ssDNA library, and sequenced in MiSeq by using Read1-DraI as the custom Read1 primer. The Read1-DraI sequence is provided below.

Read1-DraI:
(SEQ ID NO: 3)
ATCATGGACTGGTGAAAGTCTTTAAAAAAAAAAAAAAAAAAAAAAAAAAA

AAGCGAGAGTCGAGGGTGCTGTAGTCACAAGA

Read1-DraI has a complementary sequence covering HR1, Oligo-dT, DraI and DraI-adapter sequences of HDMI-DraI and HDMI32-DraI ssDNA libraries.

Figure 10J:
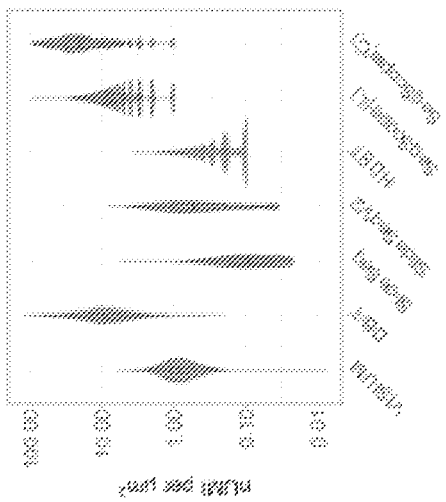
Figure 11A:
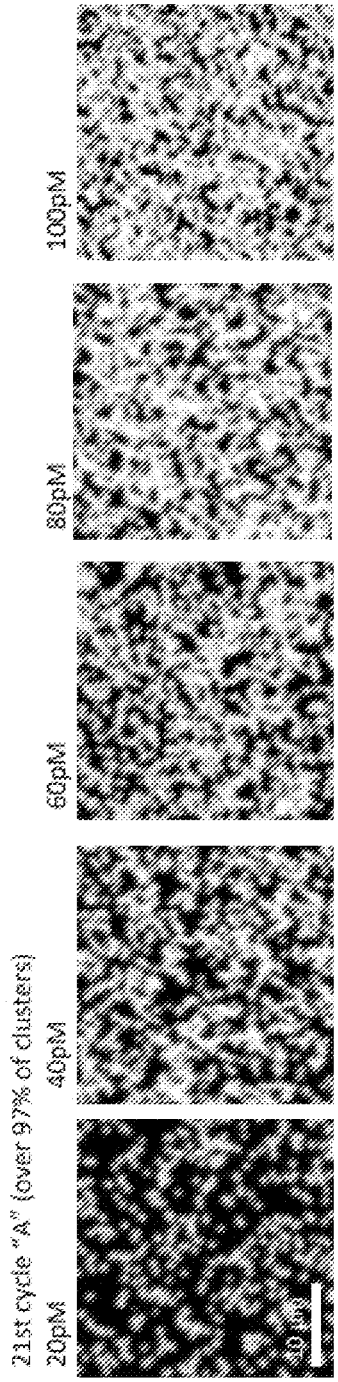
FIGS. 11A-U shows various performance metrics for the methods described herein.
Figure 11B:
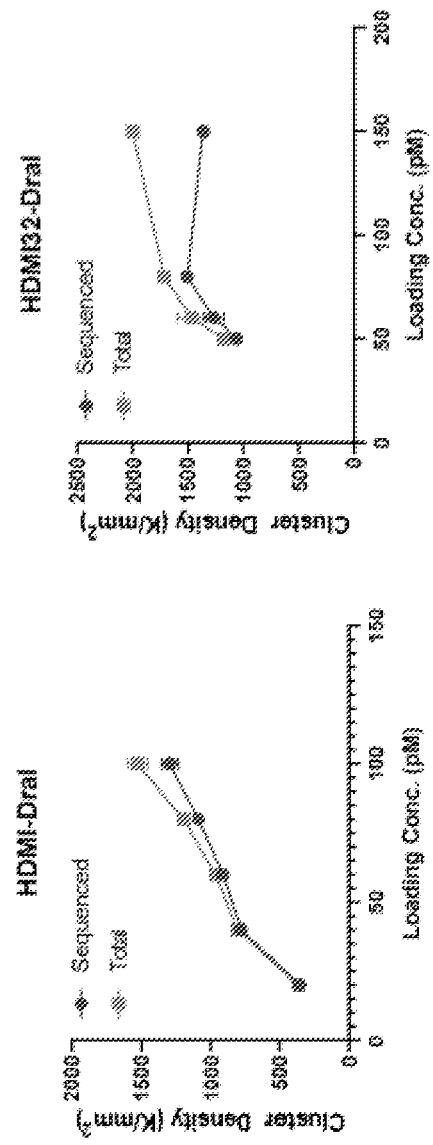
(FIG. 11B) Titration of HDMI-oligo library loading concentration for obtaining maximum number of sequenced clusters. Total (red) and sequenced (blue) cluster numbers were presented for indicated $1^{st}$-Seq conditions. Data are presented as mean±SEM.

Initially, the libraries were sequenced using MiSeq v2 nano platform to titrate the concentration of the ssDNA library to generate the largest possible number of confidently-sequenced HDMI clusters (FIGS. 11A and 11B). After several rounds of optimization, HDMI-DraI was loaded at 100 pM while HDMI32-DraI was loaded at 60-80 pM. For actual implementation, MiSeq v3 regular platform was used. MiSeq was performed in a manual mode: 25 bp single end reading (for HDMI-DraI) or 37 bp single end reading (for HDMI32-DraI). The MiSeq runs were completed right after the first read without denaturation or re-synthesis steps. The flow cell (e.g. substrate) was retrieved right after the completion of the single end reading steps. The MiSeq result was provided as a FASTQ file that has the HDMI sequence followed by 5-base adapter sequence in TR1. The adapter sequence concordance is over 96% for all MiSeq results used in the method described in this Example. Thumbnail images of clusters, visualized using Illumina Sequencing Analysis Viewer, were used to inspect the cluster morphology and density (FIGS. 10A, 11A and 11B).

The HDMI sequences contain 20-32 random nucleotides, which can produce 260 billion (20-mer in HDMI-DraI) or 1 quintillion (32-mer in HDMI32-DraI) different sequences. Due to this extreme diversity, duplication rate of the HDMI sequence was extremely low (less than 0.1% of total HDMI sequencing results), even though the MiSeq identified more than 30 million HDMI clusters.

Figure 11C:
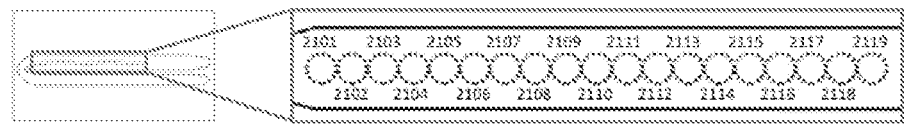
(FIG. 11C) Schematic diagram depicting the tile arrangement in the bottom surface of MiSeq v3 regular flow cell.

MiSeq has total 38 rectangular imaging areas, which are called as "tiles". 19 tiles are on the top of the flow cell, while the other 19 tiles are on the bottom of the flow cell (FIG. 11C; tiles 2101-2119). For each sequencing output, tile number and XY coordinates of the cluster where the sequence is originated from, can be found in the FASTQ output file of MiSeq. Only the bottom tiles were used for analysis because the top tiles were destroyed during the flow cell disassembly.

Processing MiSeq Flow Cell into the HDMI-Array

After 1st-Seq, the MiSeq flow cell was further processed to convert HDMI-containing clusters to HDMI-array that can capture mRNAs released from the tissue (FIG. 8D). The flow cell retrieved from the MiSeq run was washed with nuclease-free water 3 times. Then the flow cell was treated with DraI enzyme cocktail (1 U DraI enzyme (#R0129, NEB) in 1× CutSmart buffer), 37° C. overnight, to completely cut out the P5 sequence and expose oligo-dT. Then the flow cell was loaded with exonuclease I cocktail (1 U Exo I enzyme (#M2903, NEB) in 1×Exo I buffer), 37° C. 45 min, to eliminate P5 primer lawn and other non-specific ssDNA. P7-bound HDMI-DraI oligonucleotides will make a duplex with Read1-DraI, so will be protected from the Exo I digestion. Then the flow cell was washed with water 3 times, 0.1N NaOH 3 times (each with 5 min incubation at room temperature, to denature and eliminate the Read1-DraI primer), 0.1M Tris (pH7.5, to neutralize the flow cell channel) 3 times (each with brief wash), and then water 3 times (each with brief wash).

HDMI-Array Disassembly

Figure 11D:
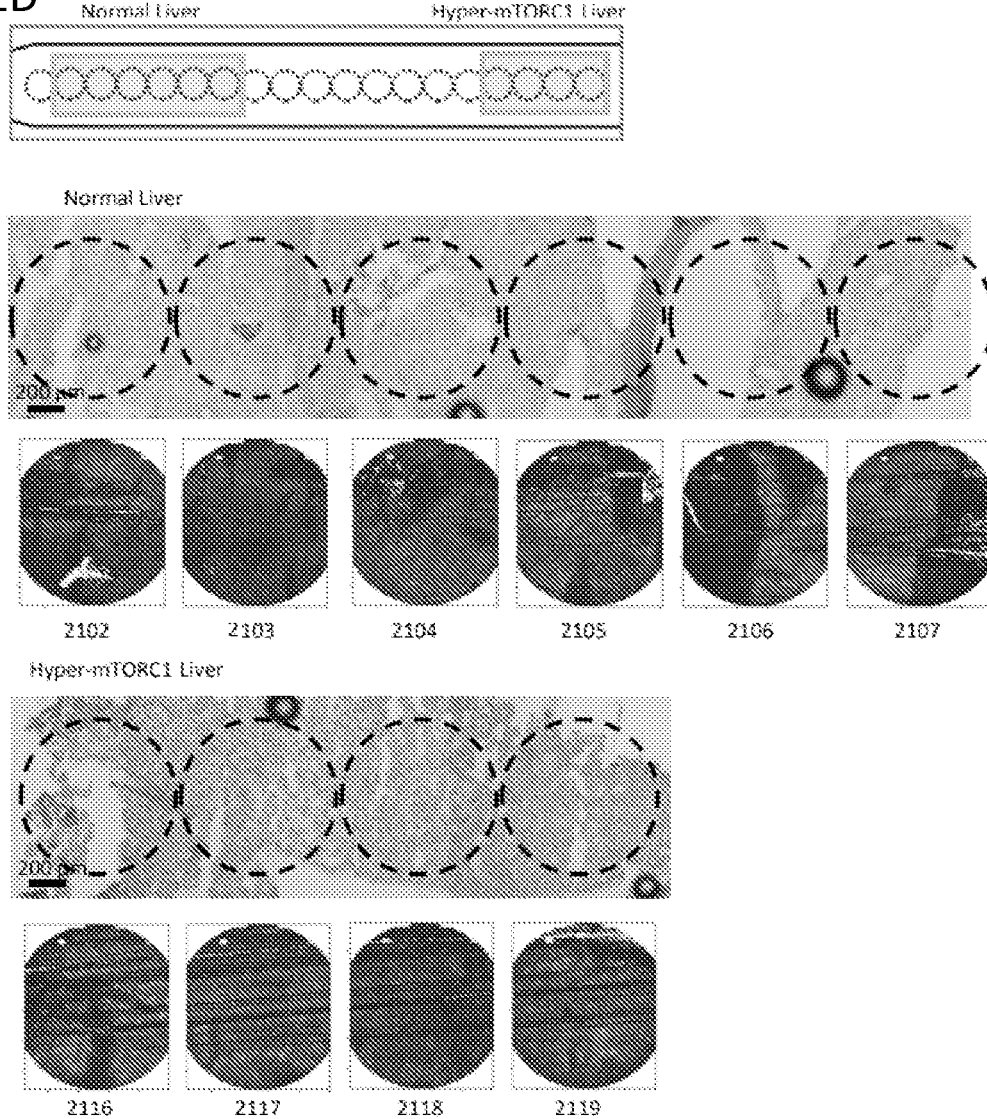
(FIG. 11D and FIG. 11E) Schematic diagram visualizes the tiles which were attached to the indicated liver (FIG. 11D, top) or colon (FIG. 11E, top) tissues. On the bottom, H&E staining images (upper) and their corresponding HDMI discovery plots (lower) were presented.
Figure 11E:
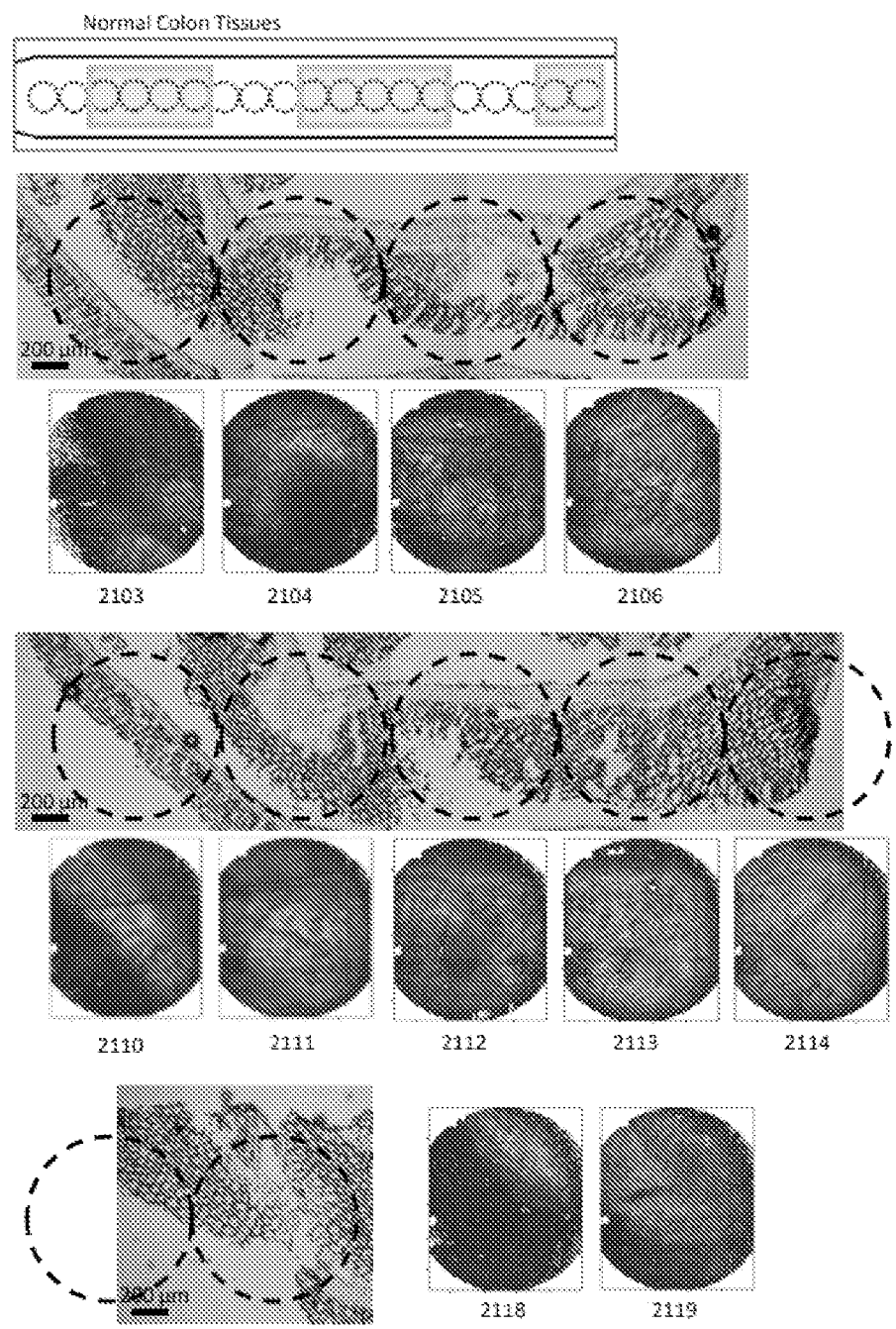
Figure 11G:
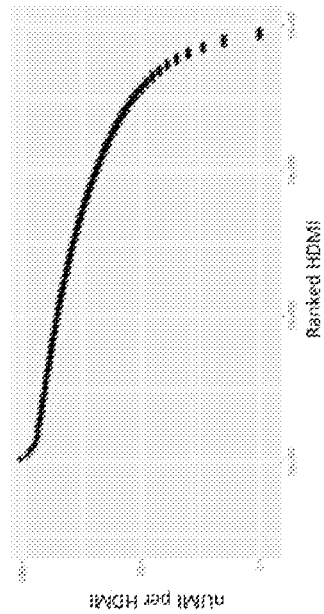
(FIG. 11F and FIG. 11G) Knee plots depicting the distribution of all HDMI discovered from $2^{nd}$-Seq and the number of UMIs (nUMI) discovered per each HDMI molecule. Both liver (FIG. 11F) and colon (FIG. 11G) datasets were analyzed.
Figure 11F:
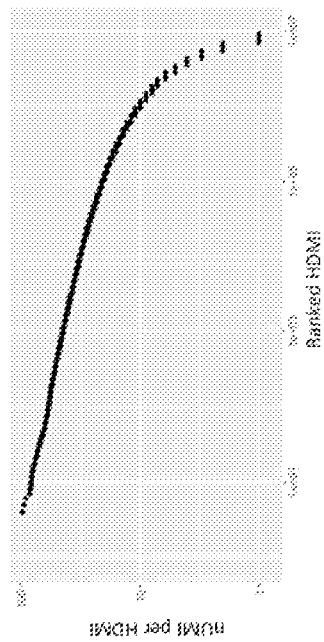
Figure 11H:
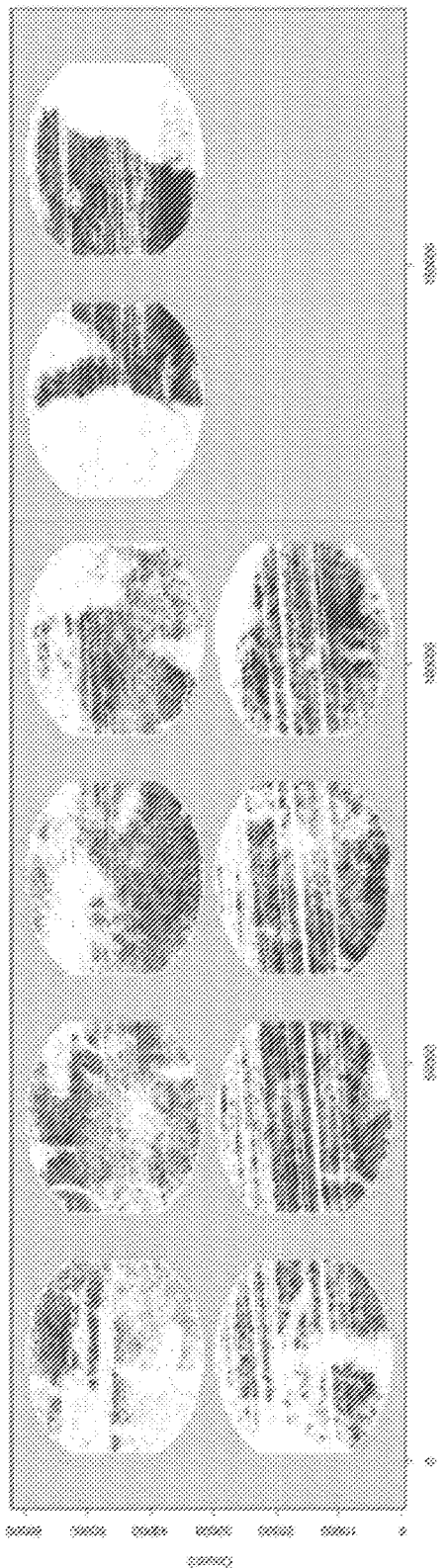
(FIG. 11H and FIG. 11I) Spatial density plots of the gridded dataset depicting the number of UMIs discovered from indicated 10 µm square grids.
Figure 11I:
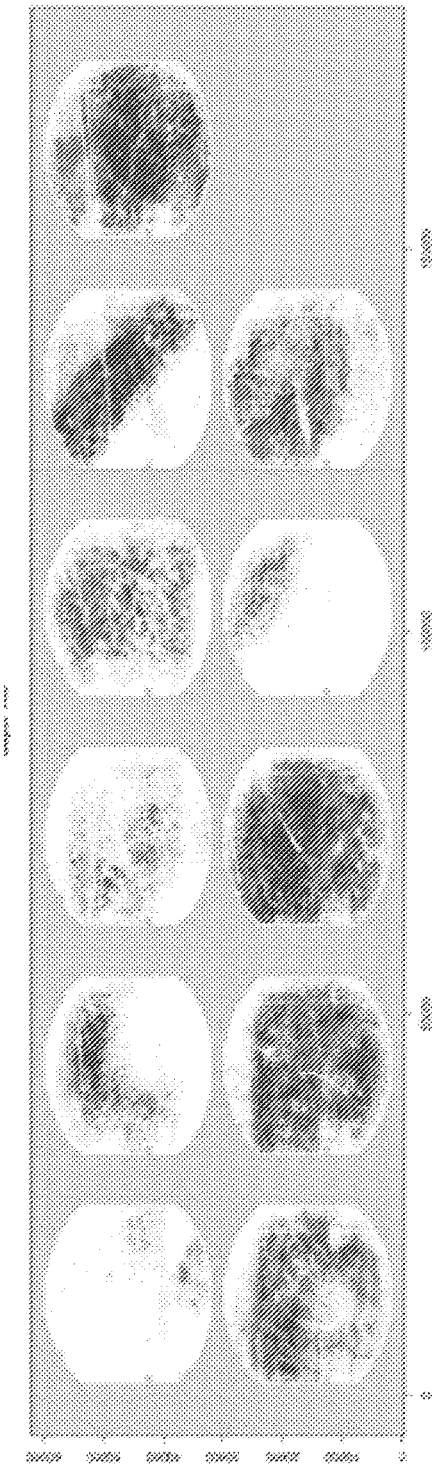
Figure 11N:
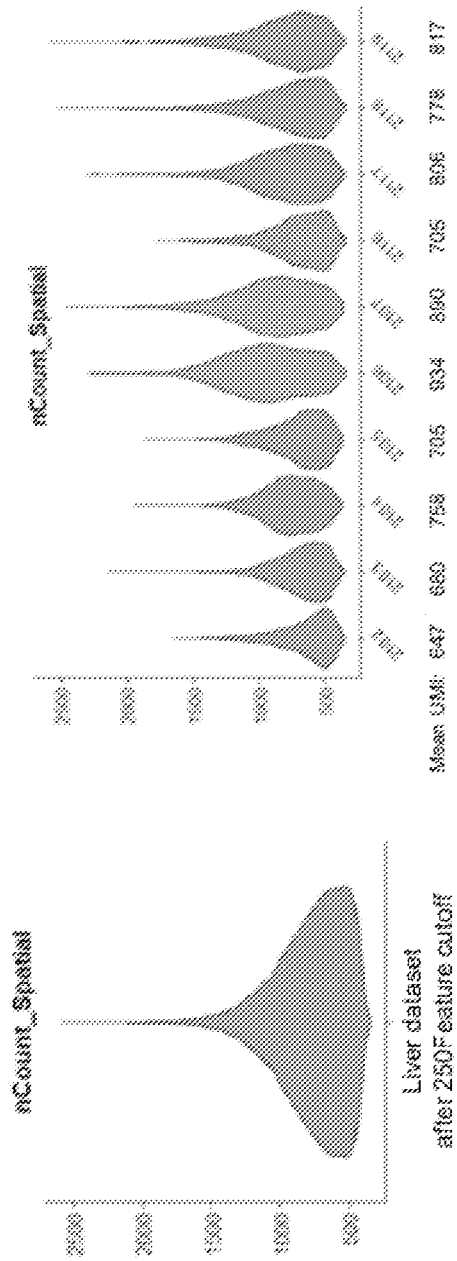
Figure 11O:
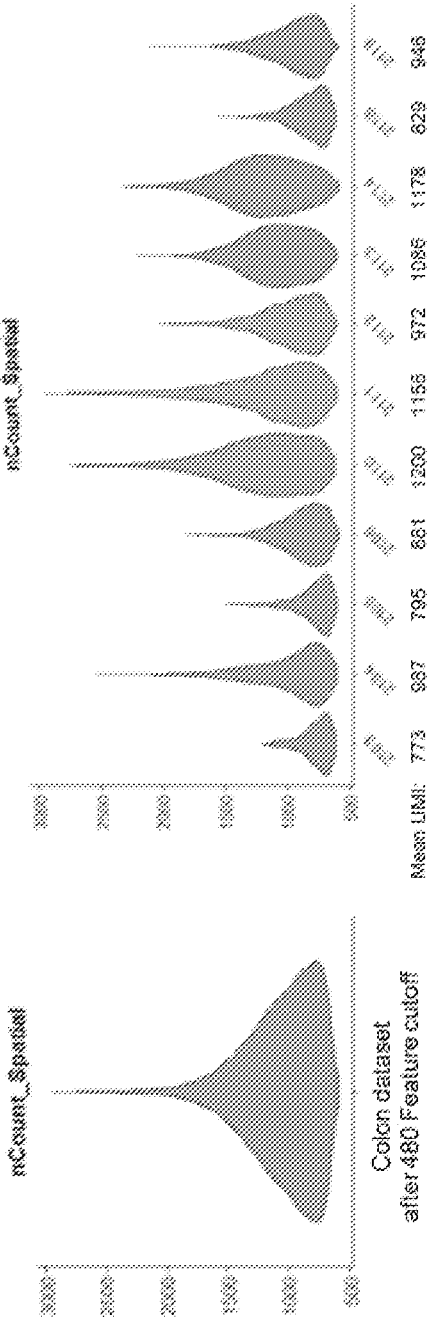
Figure 11N:
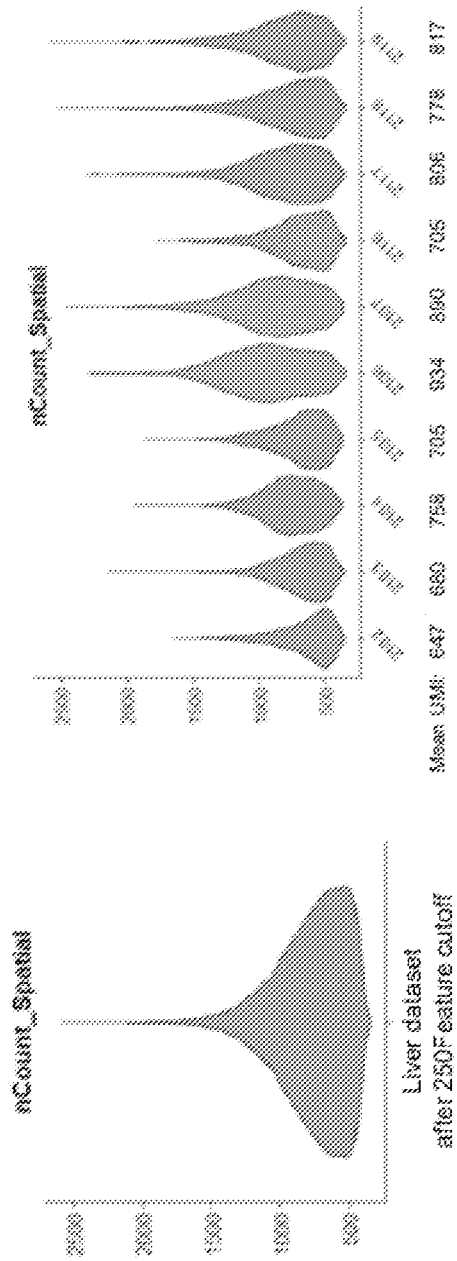
Figure 11O:
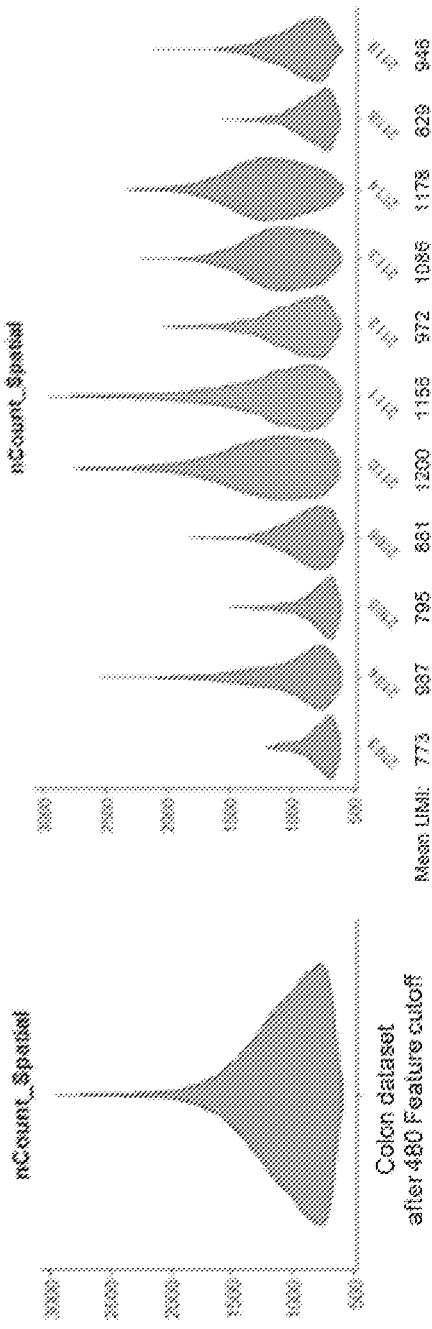
Figure 11P:
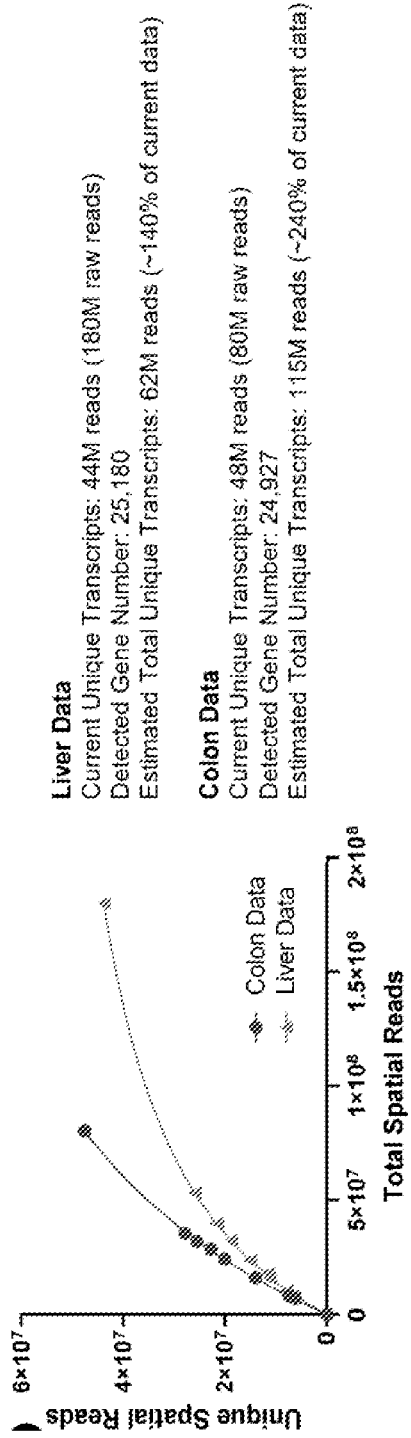
(FIG. 11P) Saturation analysis of liver (red) and colon (blue) dataset. For all spatial plots, width and height of the imaging areas are 800 µm and 1 mm, respectively.

Then the flow cell was disassembled so that the HDMI-array was exposed to outside and can be attached to tissue sections. To protect the HDMI-array, agarose hydrogel (BP160, Fisher) was used to fill the flow cell channel before disassembly (for the colon dataset). 1.5% agarose suspension was prepared in water, and incubated in 95° C. 1 min. The resulting 1.5% melted agarose solution was loaded into the flow cell, and chilled to solidify the gel. Using the Tungsten Carbide Tip Scriber (IMT-8806, IMT), all the boundary lines of the channel (corresponding to the imaging area) were scored. Additional lines inside of the boundaries were scored to help break the glass into small pieces. Then, the pressure was applied around the scored lines to break the glass out. Then, the glass particles and agarose debris were removed by washing with water. The top-exposed flow cell (HDMI-array; FIG. 11U, left) was then ready for tissue attachment. The disassembly process could be practiced with used MiSeq flow cells, which could be obtained as a byproduct of conventional sequencing. After the practice flow cell was disassembled, the quality of cluster arrays could be inspected by staining with DNA dye, such as SYBR Gold. An exemplary SYBR Gold staining image of the disassembled flow cell with minimal array damage was provided as a reference (FIG. 11U, right). It is critical to avoid scratches that damage the HDMI cluster array.

Tissue Samples

Liver and colon samples were from recent studies [32, 53]. Livers were collected from 8 week-old control (Depdc5$^{F/F}$/Tsc1$^{F/F}$, male) and TD (Alb-Cre/Depdc5$^{F/F}$/Tsc1$^{F/F}$, female) mice [32]. Colons are from 8-week-old C57BL/6 wild-type male mice [53].

Tissue Sectioning, Attachment and Fixation

OCT-mounted fresh frozen tissue was sectioned in a cryostat (Leica CM3050S, −20 C) at a 5° cutting angle and 10 m thickness. The tissues were maneuvered onto the HDMI-array from the cutting stage (FIG. 8E). The tissue-HDMI-array sandwich was moved to room temperature, and tissues were fixed in 4% formaldehyde (100 μl, diluted from the EM-grade 16% paraformaldehyde (#15170, Electron Microscopy Sciences)) for 10 min.

Tissue Imaging and mRNA Release

The tissues were incubated 1 min in 100 µl isopropanol, and then stained with 80 µl hematoxylin (S3309, Agilent) for 5 min. After washing with water, the tissues were treated with 80 µl bluing buffer (CS702, Agilent) for 1 min. After washing with water, the tissues were treated with buffered eosin (1:9=eosin (HT110216, Sigma): 0.45M Tris-Acetic buffer (pH 6.0)). After washing with water, the tissues were dried and mounted in 85% glycerol. The tissues were then imaged under a light microscope (MT6300, Meiji Techno). To release RNAs from the fixed tissues, the tissues was treated with 0.2 U/uL collagenase I at 37° C. 20 min, and then with 1 mg/mL pepsin in 0.1M HCl at 37° C. 10 min, as previously described [7].

Reverse Transcription

The tissue was washed with 40 µl 1×RT buffer containing 8 µl Maxima 5×RT Buffer (EP0751, Thermofisher), 1 µl RNase Inhibitor (30281, Lucigen) and 31 µl water. Subsequently, reverse transcription (FIGS. 8F and 9B) was performed by incubating the tissue-attached HDMI-array in 40 µl RT reaction solution containing 8 µl Maxima 5×RT Buffer (EP0751, Thermofisher), 8 µl 20% Ficoll PM-400 (F4375-10G, Sigma), 4 µl 10 mM dNTPs (N0477L, NEB), 1 µl RNase Inhibitor (30281, Lucigen), 2 µl Maxima H-RTase (EP0751, Thermofisher), 4 µl Actinomycin D (500 ng/l, A1410, Sigma-Aldrich) and 13 µl water. The RT reaction solution was incubated at 42° C. overnight.

Tissue Digestion

Next day, the RT solution was removed and the tissue was submerged in the exonuclease I cocktail (1 U Exo I enzyme (#M2903, NEB) in 1×Exo I buffer) and incubated at 37° C. for 45 min, to eliminate DNA that did not hybridize with mRNA. Then the cocktail was removed and the tissues were submerged in 1× tissue digestion buffer (100 mM Tris pH 8.0, 100 mM NaCl, 2% SDS, 5 mM EDTA, 16 U/mL Proteinase K (P8107S, NEB). The tissues were incubated at 37° C. for 40 min.

Secondary Strand Synthesis and Purification

After tissue digestion, the HDMI-array was washed with water 3 times, 0.1N NaOH 3 times (each with 5 min incubation at room temperature), 0.1M Tris (pH7.5) 3 times (each with brief wash), and then water 3 times (each with brief wash). This will eliminate all mRNA from the HDMI-array.

After washing steps, secondary strand synthesis mix (18 µl water, 3 µl NEBuffer-2, 3 µl 100 µM Truseq Read2-conjugated Random Primer with TCA GAC GTG TGC TCT TCC GAT CTN NNN NNN NN sequence (SEQ ID NO: 4) (IDT), 3 µl 10 mM dNTP mix (N0477, NEB), and 3 µl Klenow Fragment (exonuclease-deficient; M0212, NEB). Then the HDMI-array was incubated at 37° C. 2 hr in a humidity-controlled chamber.

After secondary strand synthesis (FIG. 8G), the HDMI-array was washed with water 3 times to remove all DNAs that were taken off from the HDMI-array, so that each HDMI molecule can correspond to each single copy of secondary strand. Then the HDMI-array was treated with 30 µl 0.1 N NaOH to elute the secondary strand. The elution step was duplicated to collect total 60 µl of the secondary strand product. The 60 µl secondary strand product was neutralized by mixing with 30 µl 3 M potassium acetate, pH5.5.

The volume of neutralized secondary strand product was increased up to 100 µl with water. Then the solution was subjected to AMPure XP purification (A63881, Beckman Coulter) using 1.8× bead/sample ratio, according to the manufacturer's instruction. The final elution was performed using 40 µl water.

Library Construction and Sequencing ($2^{nd}$-Seq)

First-round library PCR was performed using Kapa HiFi Hotstart Readymix (KK2602, KAPA Biosystems) in 100 µl reaction volume with 40 µl secondary strand product as a template and forward (TCT TTC CCT ACA CGA CGC*T*C (SEQ ID NO: 5)) and reverse (TCA GAC GTG TGC TCT TCC*G*A (SEQ ID NO: 6)) primers at 2 µM. PCR condition: 95° C. 3 min, 13-15 cycles of (95° C. 30 sec, 60° C. 1 min, 72° C. 1 min), 72° C. 2 min and 4° C. infinite. PCR products were purified using AMPure XP in 1.2× bead/sample ratio.

Second-round library PCR (FIG. 8H) was performed using Kapa HiFi Hotstart Readymix (KK2602, KAPA Biosystems) in 100 µl reaction volume with 10 µl of 2 nM first-round PCR product as a template and forward (AAT GAT ACG GCG ACC GAG ATC TAC ACT CTT TCC CTA CAC GAC GCT CT*T*C (SEQ ID NO: 7)) and reverse (CAA GCA GAA GAC GGC ATA CGA GAT [8-mer index sequence] GTG ACT GGA GTT CAG ACG TGT GCT CTT CC*G*A (SEQ ID NO: 8)) primers at 1 µM. PCR condition: 95° C. 3 min, 8-9 cycles of (95° C. 30 sec, 60° C. 30 sec, 72° C. 30 sec), 72° C. 2 min and 4° C. infinite. PCR products were purified using agarose gel elution for all products between 400-850 bp size, using Zymoclean Gel DNA Recovery Kit (D4001, Zymo Research) according to the manufacturer's recommendation. Then the elution products were further purified using AMPure XP in 0.6×-0.7× bead/sample ratio. The pooled libraries were subjected to paired-end (100-150 bp) sequencing in Illumina and BGI platforms at AdmeraHealth Inc., Psomagen Inc., and Beijing Genome Institute. The HDMI discovery plot assessments indicated that all sequencing platforms worked well for analyzing final output data.

cDNA Labeling Assay

To label cDNAs on the HDMI-array, all the steps were identically performed as described above, except that, after mRNA release, the HDMI array was subjected to cDNA labeling assay instead of library generation procedures [7]. After mRNA release, the tissue-attached HDMI array was incubated in 40 uL fluorescent reverse transcription solution containing 13 µl water, 8 µl Maxima 5×RT Buffer (EP0751, Thermofisher), 8 µl 20% Ficoll PM-400 (F4375-10G, Sigma), 0.8 µl 100 mM dATP (from 0446S, NEB), 0.8 µl 100 mM dTTP (from 0446S, NEB), 0.8 µl 100 mM dGTP (from 0446S, NEB), 0.1 µl 100 mM dCTP (from 0446S, NEB), 1.5 µl 6.45 mM Cy3-dCTP (B8159, APExBIO), 1 µl RNase Inhibitor (30281, Lucigen), 4 µl Actinomycin D (500 ng/l, A1410, Sigma-Aldrich) and 2 µl Maxima H-RTase (EP0751, Thermofisher). Reverse transcription was performed at 42° C. overnight.

Then the cocktail was removed and the tissues were submerged in 1× tissue digestion buffer (100 mM Tris pH 8.0, 100 mM NaCl, 2% SDS, 5 mM EDTA, 16 U/mL Proteinase K (P8107S, NEB). The tissues were incubated at 37° C. 40 min. After washing the HDMI-array surface with water 3 times, it was mounted in 80% glycerol, and then observed under a fluorescent microscope (Meiji).

Generation and Testing of UMI-Encoded HDMI-Array

Figure 9B:
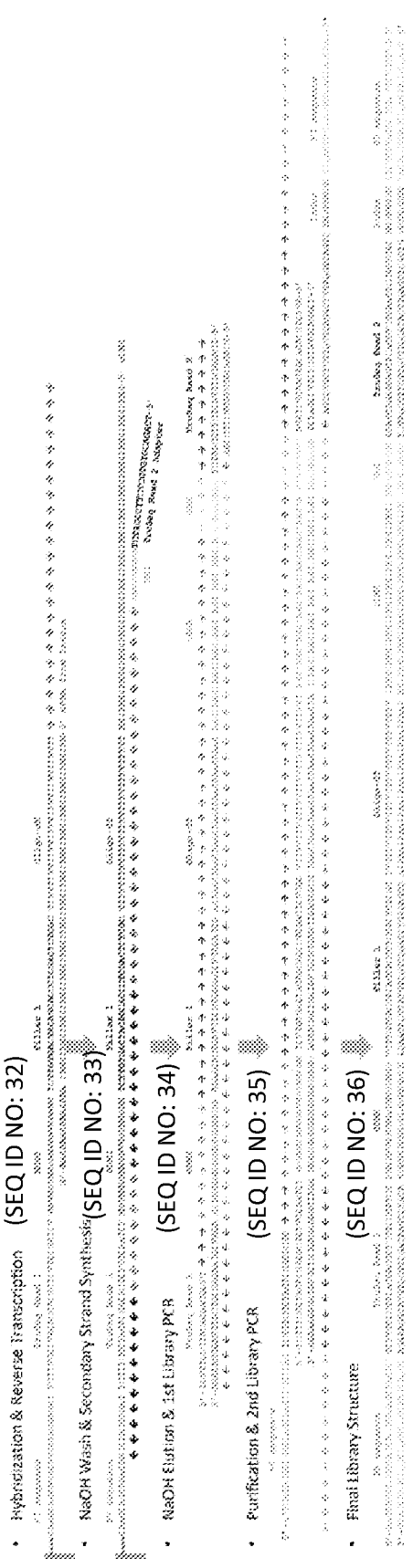
Figures 9C, 9D:
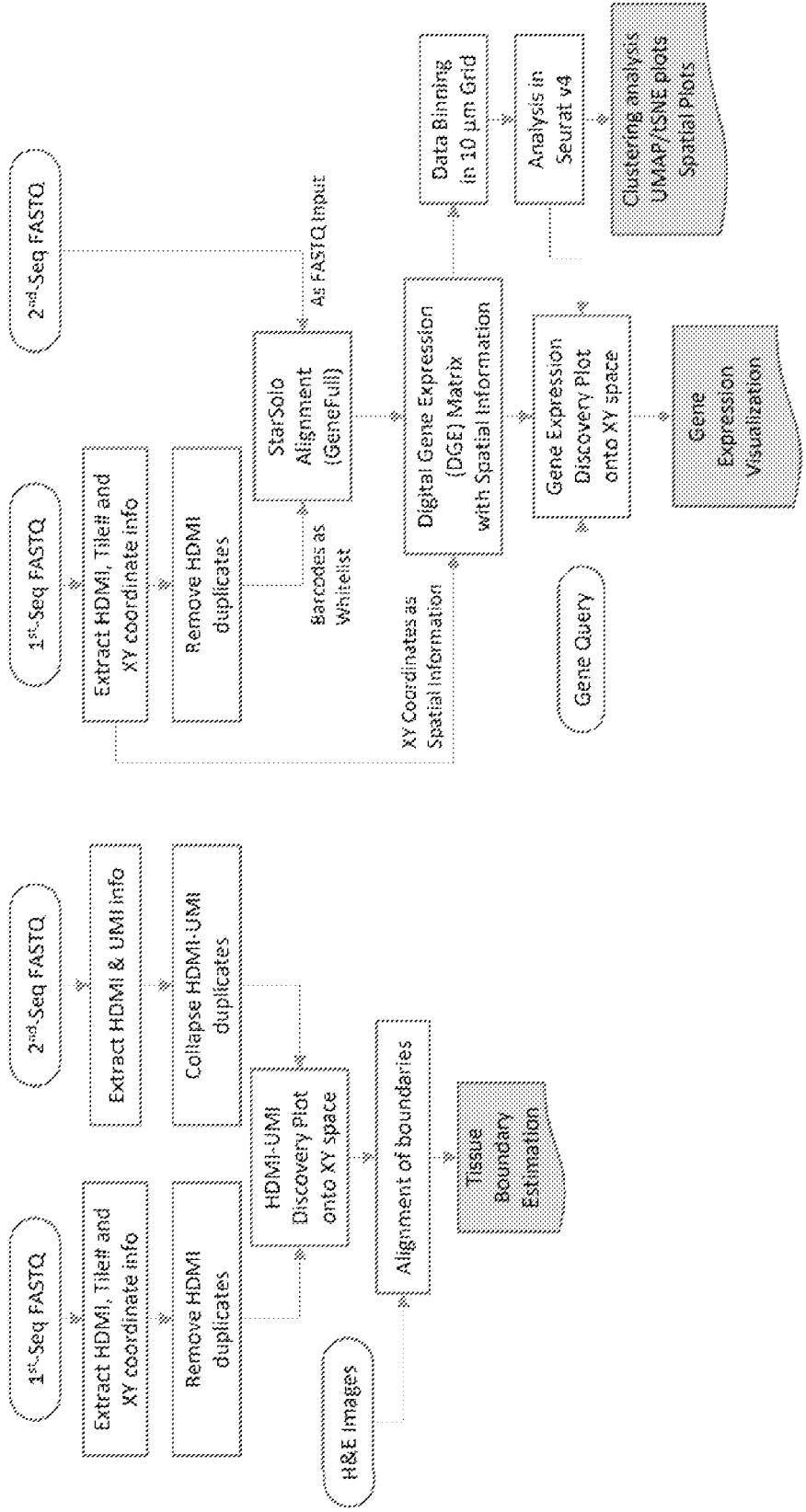
Figure 9E:
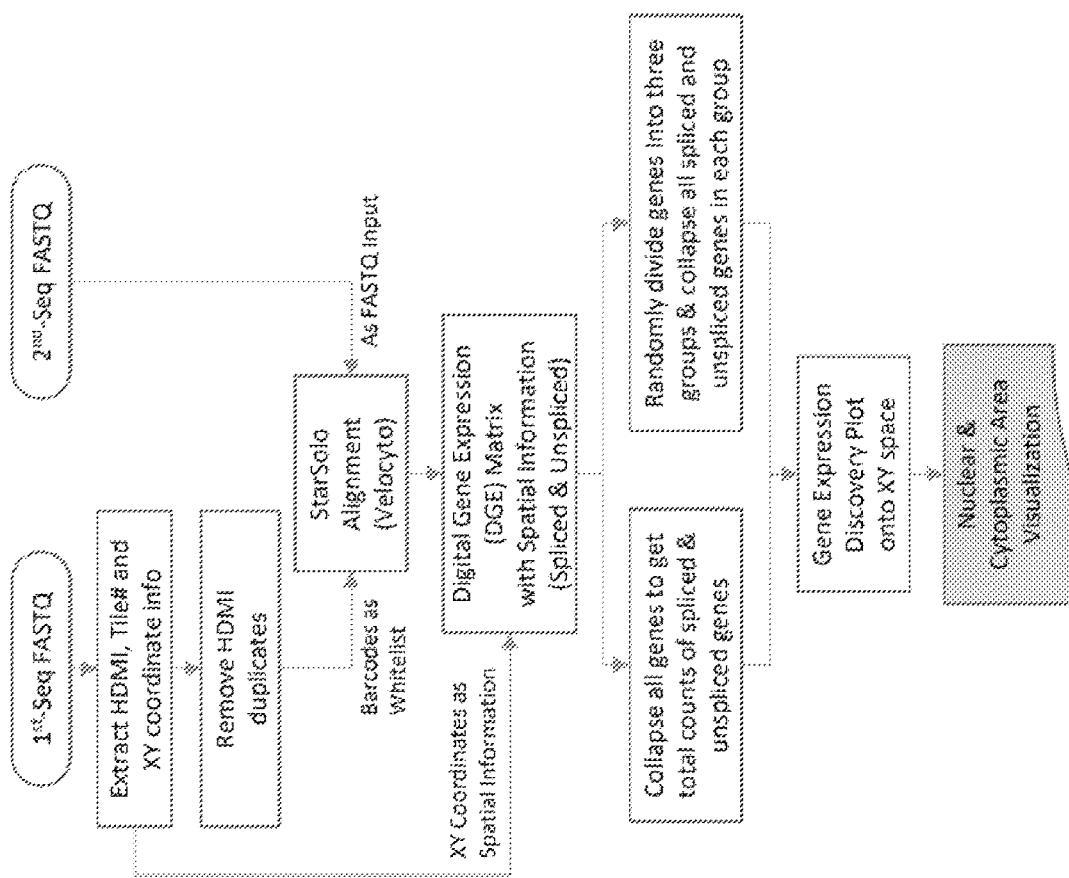
Figure 9F:
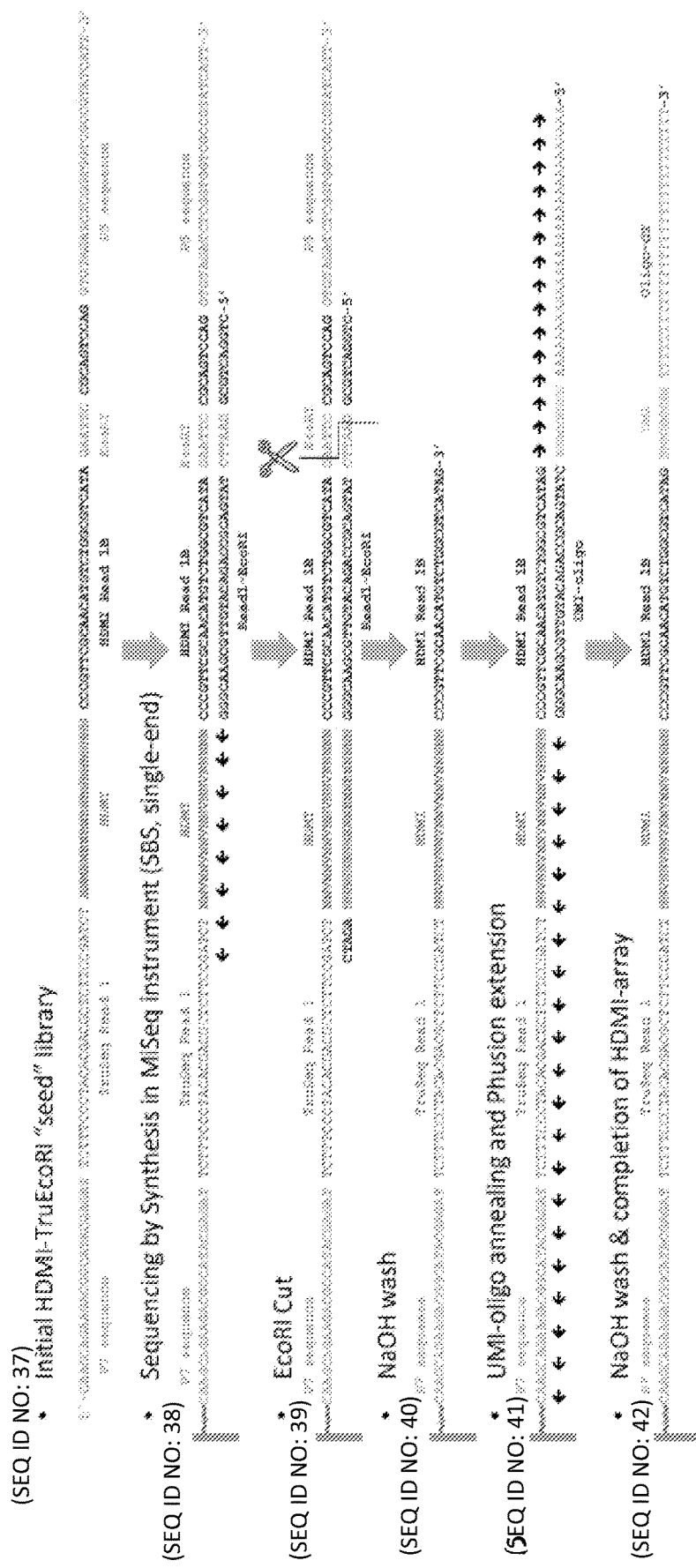

UMI-encoded HDMI array was generated using HDMI-TruEcoRI library, which is similar to the ssDNA libraries described above, but does not have an oligo-dT sequence (FIG. 9F).

Backbone:
(P5 sequence) (TR1: TruSeq Read 1) (HDMI) (HR1B:
HDMI Read 1B) (EcoRI) (EcoRI adapter) (P7 sequence)

HDMI-TruEcoRI:
(SEQ ID NO: 9)
CAAGCAGAAGACGGCATACGAGATTCTTTCCCTACACGACGCTCTTCCGAT

CTHNNBNBNBNBNBNBNBNNNNCCCGTTCGCAACATGTCTGGCGTCATAGA

ATTCCGCAGTCCAGGTGTAGATCTCGGTGGTCGCCGTATCATT

For MiSeq running, Read1-EcoRI was used as the read 1 primer.

Backbone:
(EcoRI adapter) (EcoRI) (HR1B)

Read1-EcoRI:
(SEQ ID NO: 10)
CTGGACTGCG GAATTC TATGACGCCAGACATGTTGCGAACGGG

The library was sequenced using MiSeq v2 nano platform at 100 pM concentration, and generated 1.4 million sequenced HDMI clusters per mm². MiSeq was performed in a manual mode, 25 bp single end reading, using the Read1-EcoRI as the custom Read 1 primer. The flow cell was retrieved right after the completion of the single end reading step. The MiSeq result was provided as a FASTQ file that has the HDMI sequence followed by 5-base adapter sequence in TR1.

Then the MiSeq flow cell was processed to attach UMI and oligo-dT sequences to the HDMI clusters. The flow cell was washed with water 3 times, and then loaded with EcoRI-HF cocktail (1 U EcoRI-HF (R3101, NEB) in 1× CutSmart NEB buffer) to cut out the P5 sequence. After 37° C. overnight incubation, the flow cell was washed with water 3 times, 0.1N NaOH 3 times (each with 5 min incubation at room temperature), 0.1M Tris (pH 7.5) 3 times, and then water 3 times. The flow cell was then loaded with 1× Phusion Hot Start II High-Fidelity Mastermix (F565S) containing 5 µM of UMI-oligo (sequence provided below).

Backbone:
(oligo-dA) (UMI) C (HR1B)

UMI-Oligo:
(SEQ ID NO: 11)
AAAAAAAAAAAAAAAAAAAAAAAAAAAAANNNNNNNNNCTATGACGCCAGA

CATGTTGCGAACGGG

The flow cell was then incubated at 95° C. 5 min, 60° C. 1 min and 72° C. 5 min. Then, the flow cell was loaded with exonuclease I cocktail (see above for composition), and incubated 45 min at 37° C. The flow cell was then washed with water 3 times, 0.1N NaOH 3 times (each with 5 min incubation at room temperature), 0.1M Tris (pH 7.5) 3 times, and then water 3 times. This completed the generation of the UMI-encoded HDMI-array.

Performance of the UMI-encoded HDMI-array was tested using 2 µg total RNA purified from mouse liver, using the same reverse transcription and library preparation method described above (but without the tissue slice). The library prepared from the total liver RNA and UMI-encoded HDMI-array was sequenced in Illumina HiSeqX and HiSeq4000 platforms.

Immunohistochemistry

For immunohistochemistry, frozen liver sections were fixed with 4% paraformaldehyde, blocked with 1% BSA, 0.01% Triton X-100 in DPBS, and incubated with primary antibodies detecting indicated proteins, followed by staining with Alexa fluorescence-conjugated secondary antibodies and DAPI. Immunofluorescence was detected in Nikon A1 confocal microscope.

Part II. Computational Analysis of Data.

Input Data

There are three experimental outputs, which serve as input data for downstream computational analysis. (1) HDMI sequence, tile and spatial coordinate information from $1^{st}$-Seq, (2) HDMI sequence, coupled with cDNA sequence from $2^{nd}$-Seq, and (3) Histological image obtained from H&E staining of the tissue slice.

Tissue Boundary Estimation

To estimate the tissue boundary, the HiSeq data were joined into MiSeq data according to their HDMI sequence. As a result, for each of the HiSeq data whose HDMI was found from MiSeq, the tile number and XY coordinates were assigned. Finally, using a custom python code, an HDMI discovery plot was generated to visualize the density of HiSeq HDMI in a given XY space of each tile (FIG. 9C). The density plots were manually assigned to the corresponding H&E images (FIG. 10C, FIG. 11D, and FIG. 11E).

Read Alignment and Generation of Digital Gene Expression Matrix

Read alignment was performed using STAR/STARsolo 2.7.5c (Dobin et al., 2013), from which the digital gene expression (DGE) matrix was generated. From MiSeq data, HDMI sequences of clusters located on the bottom tile were extracted and used as a "white-list" for the cell (HDMI) barcode after reverse complement conversion. The first 20 (HDMI-DraI version) or 30 (HDMI32-DraI) basepairs of HiSeq data Read 1 were considered as the cell (HDMI) barcode. HDMI assignments were performed using the default error correction method implemented in STARsolo (1 MM_multi). Details about the spatial barcode assignment and error correction methods are described below in separate sections.

Due to the extensive washing steps after secondary strand synthesis, it was expected that each single molecule of HDMI-cDNA hybrid would lead to one secondary strand in the library. Therefore, the first 9-mer of Read 2 sequence, which is derived from the Randomer sequence, could serve as a proxy of the unique molecular identifier (UMI). Accordingly, the first 9 basepairs of HiSeq Read 2 data were copied to Read 1 and used as the unique molecular identifier (UMI). Read 2 was trimmed at the 30 end to remove polyA tails of length 10 or greater and was then aligned to the mouse genome (mm10) using the Genefull option with no length threshold and no cell filtering (FIG. 9D). For the genes whose expression could not be monitored by the Genefull option, the Gene option was used to generate the gene expression discovery plots. UMIs were deduplicated using the default error correction method implemented in STARsolo (1 MM_All), in which all UMIs with 1 mismatch distance to each other are collapsed (i.e., counted once).

For saturation analysis, multiple read alignments were performed using 25%, 50% and 75% subsets of the 2nd-Seq results. The alignment output values were plotted in a graph (Figure S2I) to generate a saturation curve in Graphpad Prism 8 (Graphpad Software, Inc.). Hyperbolic regression was used to estimate the total unique transcript number in the liver (60,292,407 to 96,899,822; 95% confidence interval) and colon (308,586,493 to 510,224,639; 95% confidence interval) Seq-Scope libraries.

Error Correction Methods for Spatial Barcodes

Although the possibility of per-base error is very low, Seq-Scope involves a multi-step processing of sequences and DNA samples, so it is possible that a small but non-negligible fraction of HDMI barcodes will contain errors. For example, the probability of "perfect barcode sequencing" without any errors throughout the 1st-Seq and 2nd-Seq steps (see below for details) was estimated to be 92.3%, with the remaining reads potentially leading to challenges in the correct barcode assignment. However, under stochastic assumptions of sequencing errors, it is estimated that only <1% will have multiple errors, and the error correction procedure is robust against occasional errors occurring only once throughout the 1st- and 2nd-Seq steps. In the current study, error correction and demultiplexing of HDMI barcodes were performed in STARsolo using the 2nd-Seq result as a FASTQ input, and the 1st-Seq result as a barcode whitelist. The STARsolo's default option was used (1 MM_multi), which implements a robust statistical error correction method similar to 10× CellRanger 2.2.0. In this method, HDMIs are allowed to have one mismatch, and the posterior probability calculation is used to choose the barcode when multiple mismatched sequences are present.

In empirical evaluation, when no error correction method was applied, 13.3% (liver) and 5.1% (colon) of HDMI barcodes no longer matched between 1st- and 2nd-Seq. These were comparable to the expected error rate of 7.7% and suggested that the error correction method employed substantially rescued potential false negatives. On the other hand, the error correction introduced only negligible false positives. With error correction, the total fraction of false positive HDMI matches between 1st- and 2nd-seq was estimated to be 0.2% (liver data) and 0.7% (colon data). Therefore, the Seq-Scope procedure, combined with a standard error correction method, is robust against producing false-positive barcode assignments and also rescues a significant number of false-negative barcodes from the dataset.

Potential Sources of PCR and Sequencing Errors in Seq-Scope Processes

In the whole Seq-Scope procedure, there are three potential sources of errors: 1st-Seq cluster generation step, 1st-Seq sequencing step, and 2nd-Seq library prep and sequencing steps. 1st-Seq cluster generation (2.3%): Even though the HDMI barcodes are randomly generated in a single-stranded oligonucleotide library, they were amplified on the flow cell surface so that every barcode in the cluster would have the same HDMI sequence. Based on the high fidelity of DNA polymerase, errors introduced during cluster generation are expected to be minimal. To estimate the extent of replication errors during cluster generation, a PCR fidelity estimator was used. After 25 cycles of solid-phase isothermal amplification by Bst DNA polymerase (error rate was set as 10-4), which generates approximately 1,000 copies of HDMI (20-mer nucleotide)-containing molecules per cluster, it was estimated that 97.7% of molecules will have no errors, and only 2.27% of molecules will have a single error. HDMI sequences with multiple errors will be less than 0.03%. Therefore, most of the HDMI sequences in a single cluster are expected to be error-free.

1st-Seq sequencing step (3%): Errors can be also introduced during the sequencing step; however, the Illumina SBS is well known to be one of the most reliable high-throughput sequencing technologies. During 1st-Seq, clusters were robustly filtered through the algorithms offered by the Real Time Analysis (RTA). Only the clusters passing filters (PF clusters) were used for the coordinate assignment. Randomly created HDMI sequences produced high and well-balanced base diversity, which enabled high quality sequencing at high-density library-loading conditions. Consequently, the Q30 rate (having >99.9% accuracy in base calling) was very high, at above 96% (96.89% for liver 1st-Seq and 96.21% for colon 1st-Seq). The Q20 rate (having >99% accuracy in base calling) was even higher than 99% (99.4% for liver 1st-Seq and 99.2% for colon 1st-Seq). The base composition of each sequencing position was perfectly consistent with the expected HDMI sequencing pattern (NNNNNBNNBNNBNNBNNBNN) for more than 99% of all sequenced clusters (FIG. 11Q); 99.08% for liver 1st-Seq and 99.09% for colon 1st-Seq. Based on the current Q30 and Q20 rates, the total 1st-Seq sequencing error rates for 20-mer HDMI were estimated as 3%.

2nd-Seq library preparation and sequencing steps (2.4%): A small number of barcode errors could be introduced during secondary strand synthesis, PCR-based library amplification, and 2nd-Seq sequencing reads. Based on the nature of these procedures, it was not expected that Seq-Scope will produce substantially more errors compared to the other available ST or scRNA-seq methods. For instance, the exonuclease-deficient Klenow enzyme produces 1 error per 10,000 bases. So, the error rate of 20-base HDMI will be less than 0.2%. The KAPA HIFI enzyme we used for library amplification has an extremely low error rate (1 error per 3.6 3 106 bases), so even after 21-25 total cycles of amplification, the error rate of 20-base HDMI will be again less than 0.2%. Finally, if it is supposed that every HDMI was sequenced in 2nd-Seq just at Q30 (>99.9% accuracy), there will be a 2% chance of producing an error in the sequence. Therefore, the total errors produced in the 2nd-Seq steps were estimated to be around 2.4%.

The total rate of errors (7.7%) was estimated by adding all the possible error rates of each step: 1st-Seq cluster generation (2.3%)+1st-Seq sequencing (3%)+2nd-Seq library prep and sequencing (2.4%). Therefore, 92.3% of the final HDMI sequences were estimated to be error-free. However, in real experiments, the actual rate of errors could vary at each step; therefore, it is expected that there will be substantial variations from this value. Most importantly, these barcode errors are unlikely to produce false positives because a whitelist from 1st-Seq is used to assign the spatial barcode. The errors will mostly contribute to a small fraction of false negatives, which are less problematic and can be recovered through error correction (see below) and/or additional sequencing.

Estimation of False-Negative and False-Positive Spatial Assignments During Error Correction To estimate the rate of mismatch errors that were corrected by the pipeline, spatial HDMI assignment was performed without an error correction method (w/o Correction). Removal of error correction (w/o Correction) decreased the total number of spatially assigned (whitelisted) unique transcripts by 13.3% (liver; L to L in Figure FIG. 11S) and 5.1% (colon; C to C in Figure FIG. 11S). These rates will be equal to the false-negative barcode assignment rate that was rescued by the error correction. The rate of multiple errors, which the current algorithm will not correct, can be estimated to be much lower than these rates (0.3% to 3%). False-positive spatial assignment could be more problematic and should also be avoided as much as possible. To understand the extent of potential false-positive spatial assignment, we performed a reciprocal misassignment analysis—liver 2nd-Seq results were analyzed using the colon 1st-Seq whitelist (L to C), which is not expected to have correctly matching HDMI. Likewise, colon 2nd-Seq results were analyzed using the liver 1st-Seq whitelist (C to L). For the misassignment analyses, liver and colon 2nd-Seq results that were obtained from the separate lanes of the sequencer were selected and used to eliminate the potential interference between the two datasets. Compared to the datasets with correct assignment (set as 100%; L to L and C to C), the misassigned dataset exhibited spatial assignment rates of 0.2% (L to C) and 0.7% (C to L), both of which are almost negligible (Figure S2H). Therefore, the rate of false-positive spatial assignment was estimated to be below 1%. All these analyses indicate that over 99% of Seq-Scope data are accurate in the spatial assignment.

Analysis of Spliced and Unspliced Gene Expression

To obtain separate read counts for spliced and unspliced transcripts, Velocyto [55] option in the Starsolo software (FIG. 9E) was used. All spliced or unspliced mRNA reads were plotted onto the imaging space to identify nuclear-cytoplasmic structure (see below in "Visualization of Spatial Gene Expression). To test the statistical significance of the nuclear-cytoplasmic image, all genes were randomly divided into three groups, and spliced and unspliced read counts were obtained independently. Independent images produced by plotting of spliced and unspliced read counts in each group were compared with each other to calculate Pearson's correlation coefficients in NIH ImageJ using Just Another Colocalization Plugin (JACoP) [56]. Abundances of nuclear-specific (Malat1, Neat1 and Mlxip1) and mitochondrial-encoded (all genes whose name start with "mt-") transcripts were also analyzed using the same statistical method. The correlation coefficients were assembled and presented in a heat map produced by Graphpad Prism 8 (Graphpad Software, Inc.).

Subcellular Transcriptome Analysis

Transcriptomic nuclear centers were identified from the unspliced RNA plot using watershed local maxima detection implemented in ImageJ. HDMI transcriptome was partitioned into 14 bins according to their mm distances from the nuclear center. Then, the genes that were most significantly enriched in the nuclear area (with 5 mm from the nuclear center) were isolated.

Image Segmentation for Single Cell Analysis

Figure 15C:
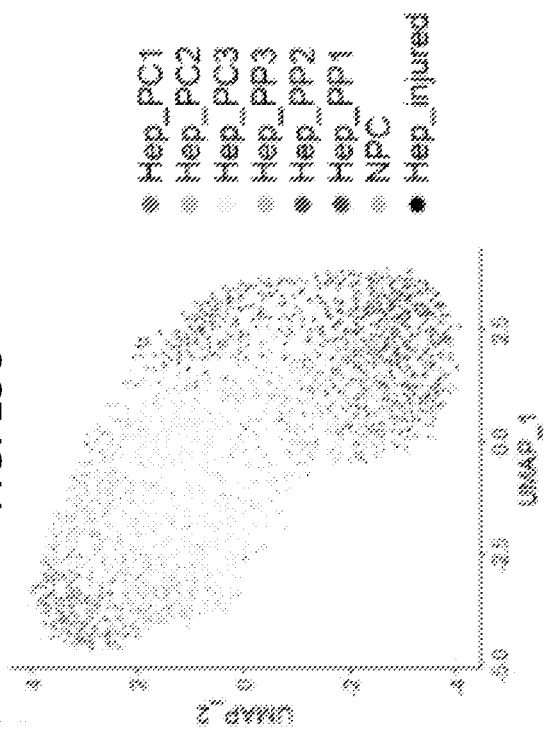
FIGS. 15A-I. Seq-Scope performs spatial single-cell analysis in normal mouse liver.
Figure 15A:
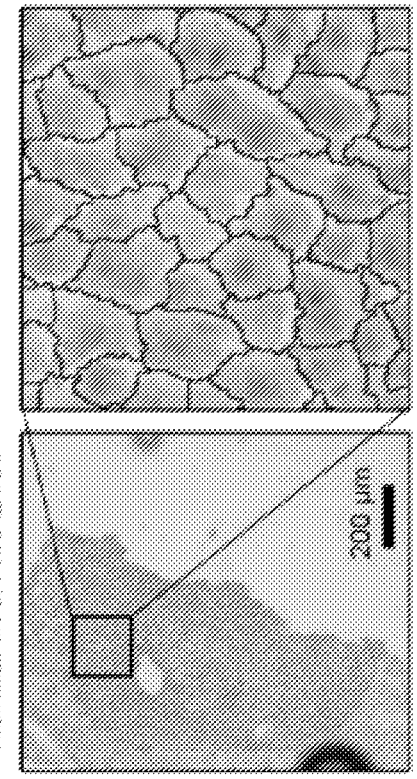

To perform cell segmentation using H&E histology images, the watershed algorithm implemented in ImageJ was utilized. The cell segmentation results isolated the single hepatocyte areas, which are consistent with the visual inspection of the H&E images (FIG. 15A). Cell boundary images and cell center coordinates were exported from ImageJ, and used to aggregate SeqScope data so that the transcriptome information from all HDMI pixels within each segmented area were collapsed into their corresponding cell center coordinate barcode, generating a single cell-indexed DGE matrix. The DGE matrix was used for clustering analysis as described below. Single cell segmentation data and the spatial single cell annotation data were overlaid onto the histology images or unspliced RNA plot images using Adobe Photoshop CC.

Data Binning Through Square Grids

Data binning was performed by dividing the imaging space into 100 mm2 (10 mm-sided) square grids and collapsing all HDMI-UMI information into one barcode per grid. Alternatively, data binning was also performed with 25 mm2 (5 mm-sided) square grids. After data binning, gene types were filtered to only contain protein-coding genes, lncRNA genes, and immunoglobulin/T cell receptor genes, to contain only the first-appearing splicing isoforms, and to exclude any hypothetical gene models (genes designated as Gm-number).

Cell Type Mapping (Clustering) Analysis

The binned and processed DGE matrix was analyzed in the Seurat v4 package. Feature number threshold was applied to remove the grids that corresponded to the area that was not overlaid by the tissue or was extensively damaged through scratches. Data were normalized using regularized negative binomial regression implemented in Seurat's SCTransform function. Clustering was performed using the shared nearest neighbor modularity optimization implemented in Seurat's FindClusters function. Clusters with mixed cell types were subjected to an additional round of clustering to get separation between the different cell types, while similar cell types were grouped together. UMAP manifold, also built in the Seurat package, was used to assess the clustering performance. Top markers from each cluster, identified through the FindAllMarkers function, were used to infer and annotate cell types. Then the clusters were visualized in the UMAP manifold or the histological space using DimPlot and SpatialDimPlot functions, respectively. Raw and normalized transcript abundance in each tile, cluster and spatial grid was visualized through the VlnPlot, DotPlot, FeaturePlot and SpatialFeaturePlot functions built in the Seurat package. Area-proportional Venn diagrams were made using BioVenn.

Analysis of Transcripts Discovered Outside of Tissue-Overlaid Region

Some RNAs were discovered in an area where the tissue was not overlaid. It is possible that a trace of tissue fluid or debris, as well as ambient RNAs released from the tissues, may have generated this pattern. Although the RNA discovery in these regions was scarce, the compositions of RNA discovered in tissue-overlaid (nFeature >250 in liver dataset) and non-overlaid regions (nFeature % 250 in liver dataset) were very similar to each other (r=0.9833 in Spearman coefficients). The minor differences between these two regions could be explained by the different rates of ambient RNA release/capture and the different composition of cell types in the tissue debris. Therefore, it is plausible that ambient and debris-derived RNAs generated the pattern of RNA discovery in the tissue non-overlaid region.

Multiscale Sliding Windows Analysis

Figure 19B:
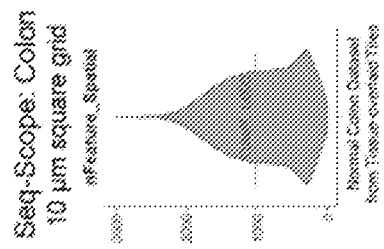
(FIG. 19B) Violin plot depicting the number of gene features (nFeature) across the 10 mm square grids. Setting a 1,000 cutoff isolated grid units covered by the tissue area (FIG. 19C), each of which contains around 2,700 UMIs (FIG. 19D). A UMAP plot visualizing all clusters (FIG. 19E) and spatial plots visualizing major histological layers (FIG. 19F), epithelial cell diversity (FIG. 19G), and non-epithelial cell diversity (FIG. 19H) are presented.
Figure 19D:
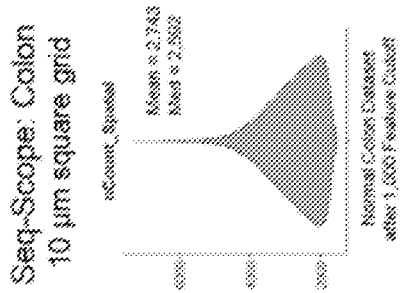
FIGS. 19A-O. Seq-Scope analysis of colonic spatial transcriptome. Colon Seq-Scope dataset was analyzed by data binning with 10 mm-sided square grids.
(FIGS. 19I-K) Colon Seq-Scope dataset was analyzed by data binning with 5 mm-sided square grids.
(FIG. 19N) Multi-scale cell type mapping combined with sliding window analysis identifies clear boundaries between different cell types with high resolution. Colon SeqScope dataset was analyzed using simple gridding with 10 mm-sided squares (left). Using the 10 mm dataset as an anchor, multi-scale cell type mapping was performed in 5 mm gridding dataset (center). Even though 5 mm gridding improved the resolution, the image was very noisy due to scarce genetic information in each grid. To overcome this, we performed the same analysis using a dataset produced by sliding windows analysis of 10 mm gridding dataset with 5 mm intervals. The output images (right) clearly visualize the boundaries between different cell types with high resolution. Cell type annotations depict major histological layers (upper), epithelial cell diversity (middle), and non-epithelial cell diversity (lower).
Figure 19A:
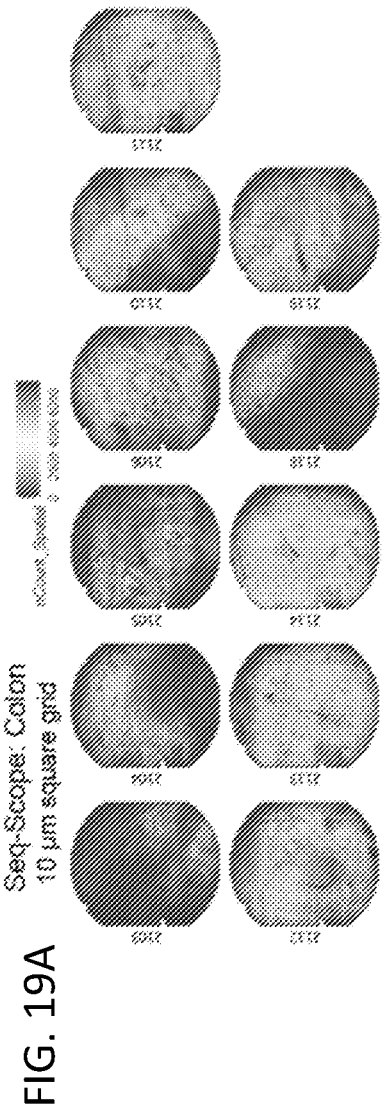
Figure 19C:
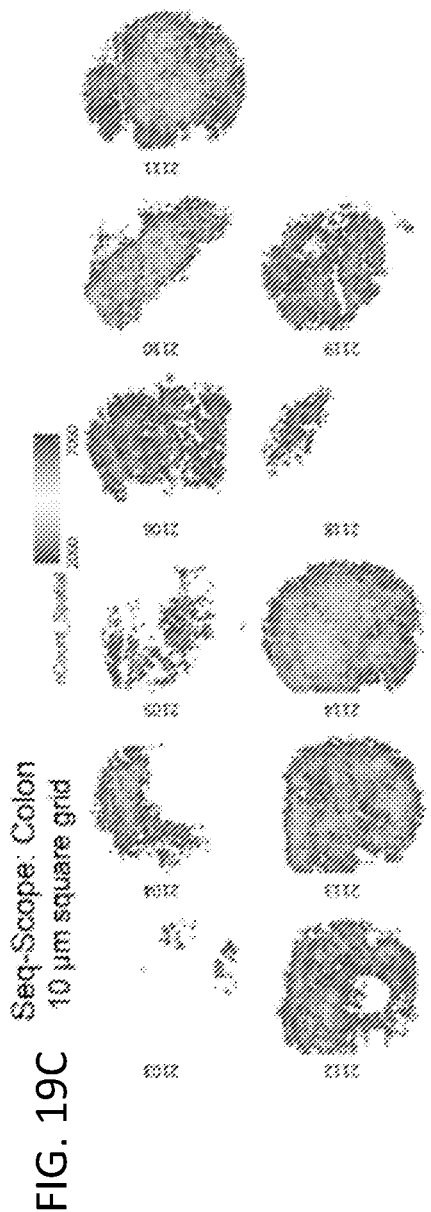
Figure 19E:
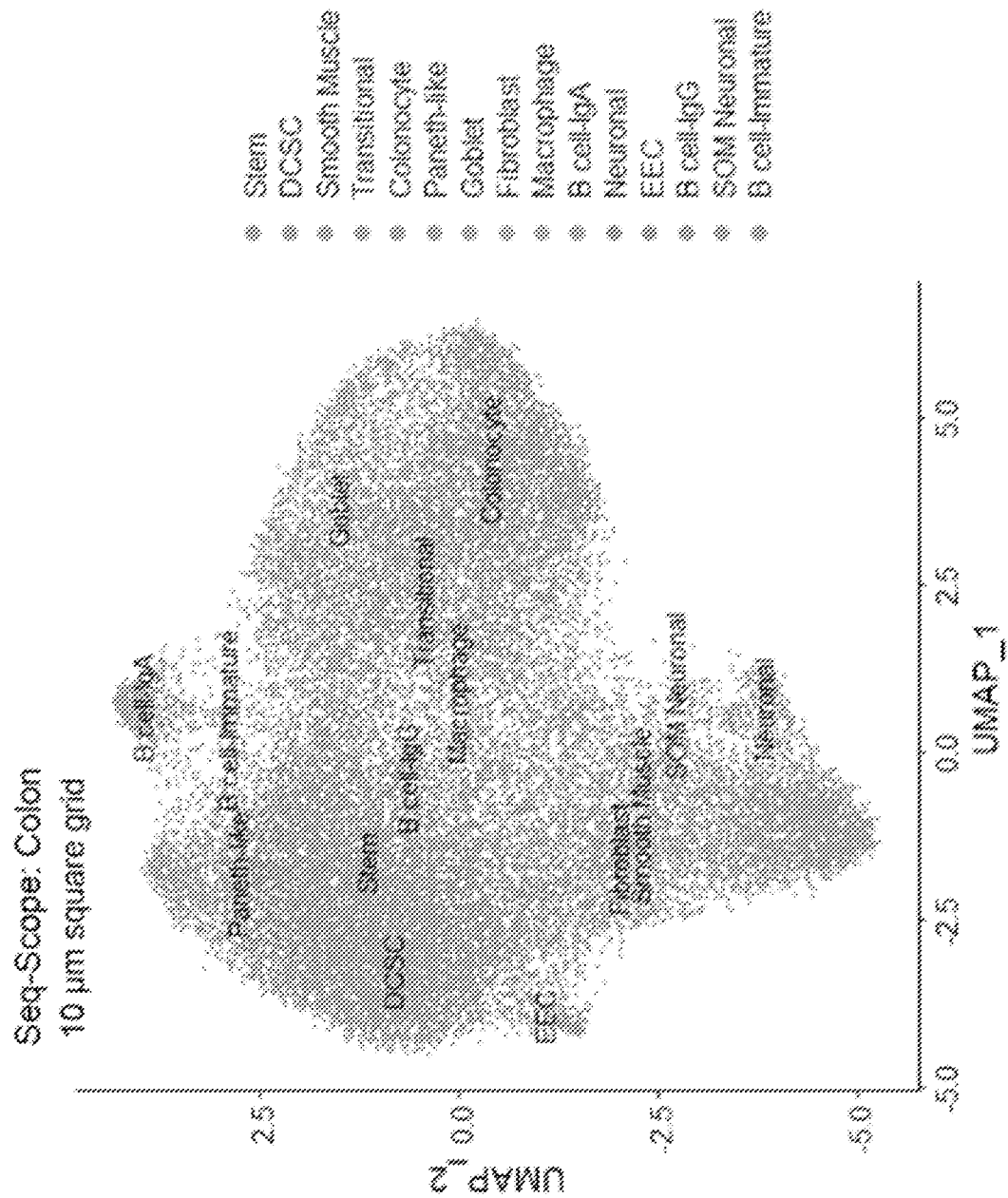
Figures 19F, 19G, 19H:
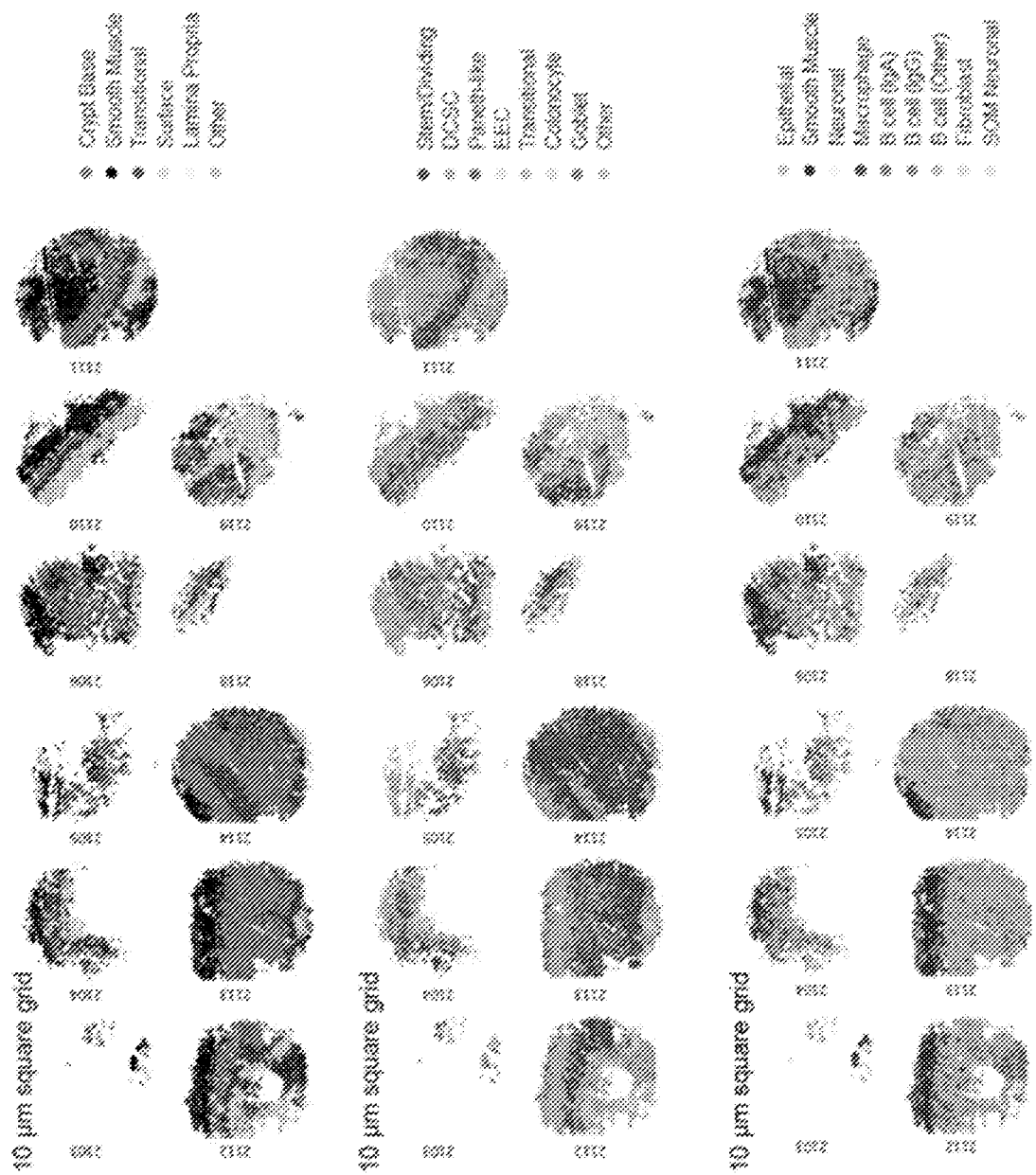
Figure 19N:
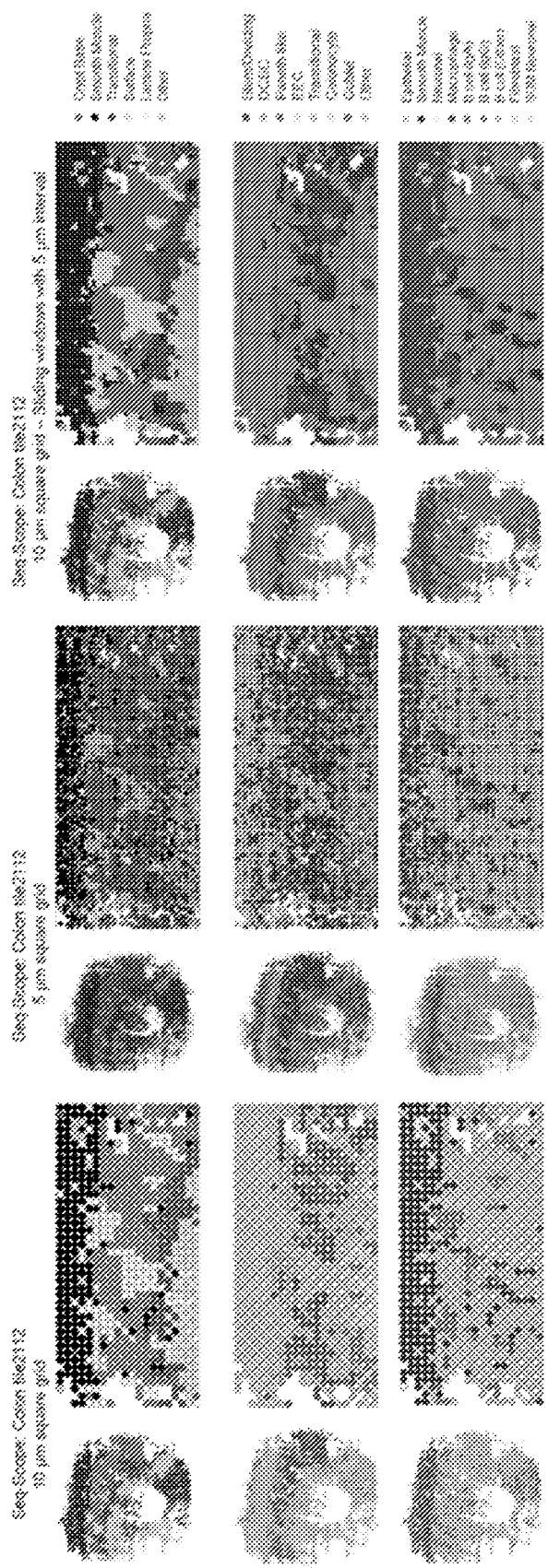

Multiscale analysis was employed to fine tune the annotation using FindTransferAnchors and TransferData functions implemented in Seurat. The anchors provided by the 10 mm grid dataset were used to guide other datasets produced from the same Seq-Scope result. Compared to the 10 mm grid dataset, the 5 mm grid dataset was much noisier in UMAP (FIG. 19L) and spatial (FIG. 19N, center) analyses even after multiscale fine tuning. To circumvent this problem, the sliding windows analysis was employed; after the initial 10 mm grid sampling, the grid was shifted both horizontally and vertically with 5 mm, 2 mm or 1 mm intervals, producing 4, 25 and 100 times more data, respectively (see FIG. 19O for a schematic illustration). Then, the original 10 mm grid dataset was used to guide these sliding windows datasets to perform high-resolution cell type annotation. Sliding windows analysis with 5 mm intervals (FIG. 19N, right) performed much better when compared to the 5 mm grid datasets (FIG. 19N, center), and showed the UMAP pattern (FIG. 19M) whose shape is more similar to the original 10 mm grid dataset (FIG. 19E).

Sliding windows analyses with 5 mm intervals were used to produce left panels in FIGS. 17D, 17H, 17I, 22A-22C, and 16I. Sliding windows analyses with 2 mm intervals were used to produce right panels in FIGS. 17D, 17H, 17I, and 16I, and middle panels in FIG. 22A-22C. Sliding windows analyses with 1 mm intervals were used to produce the right panels in FIG. 22A-22C.

Visualization of Spatial Gene Expression

Spatial gene expression was visualized using a custom python code. Raw digital expression data of the queried gene (or gene list) were plotted onto the coordinate plane according to their HDMI spatial index. Considering the lateral RNA diffusion distance of 1.7±2 mm (mean±SD) measured from the original ST study, gene expression densities were plotted as an about 3 mm-radius circle at a transparency alpha level between 0.005 and 0.5. In spatial gene expression images with a white background, the intensity of the colored spot indicates the abundance of transcripts around the spot location. Spatial gene expression images with a black background were created for genes or gene lists of high expression values, to make it easy to adjust the linear range of gene expression density and to overlay gene expression densities of different queries with different pseudo-color encoding. The inverse image of the greyscale plot was pseudo-colored with red, blue, green, or gray, and the image contrast was linearly adjusted to highlight the biologically relevant spatial features. Finally, different pseudo-colored images were overlaid together to compare the gene expression patterns in the same histological coordinate plane. Cell cycle-specific genes, such as S phase- and G2/M phase-specific gene lists were retrieved from the Seurat package, and their mouse homologs were identified using the biomaRt package.

Benchmark Analysis

The performance of Seq-Scope in liver and colon experiments were benchmarked against publicly available datasets produced by 10×VISIUM (https://support.10xgenomics.com/spatial-gene-expression/datasets/1.1.0/V1_Human_Brain_Section_1), DBiT-Seq (GEO: GSM4096261 in GSE137986), Slide-Seq (Single Cell Portal: 180819_11 in SCP354), Slide-SeqV2 (Single Cell Portal: 190921_19 in SCP815), and HDST (GEO: GSM4067523 in GSE130682). Liver Seq-Scope dataset was separately benchmarked against former liver datasets produced using original ST (Zenodo: 10.5281/zenodo.4399655) and Slide-Seq (Single Cell Portal: 1808038_8 in SCP354). The Seq-Scope dataset had a large area that was not covered by tissues, so the tissue-overlaid HDMI pixels were isolated and used for the benchmark analysis. Tissue-overlaid HDMI pixels were isolated from the 10 mm grid areas that were used for the cell type mapping analysis described above. Center-to-center resolution was calculated per each pixel as the distance from the closest pixel. For the technologies that have a defined pixel area (VISIUM, DBiT-Seq and HDST), pixel density was calculated as the inverse of the pixel area. For Slide-Seq, Slide-SeqV2 and Seq-Scope, pixel density was calculated in 150 mm grids (Slide-Seq and Slide-SeqV2) and 10 mm grids (Seq-Scope) of the final dataset. Grids that contained less than 10 pixels were excluded from the analysis. nUMI corresponds to the number of unique transcripts mapped to the transcriptome, and nGene corresponds to the number of gene features discovered per each pixel. nUMI/pixel and nGene/pixel values were multiplied by the average pixel density (pixel/mm2) to obtain the area-normalized nUMI and nGene (nUMI/mm2 and nGene/mm2, respectively) for each pixel.

UMI Efficiency Test

Figure 9G:
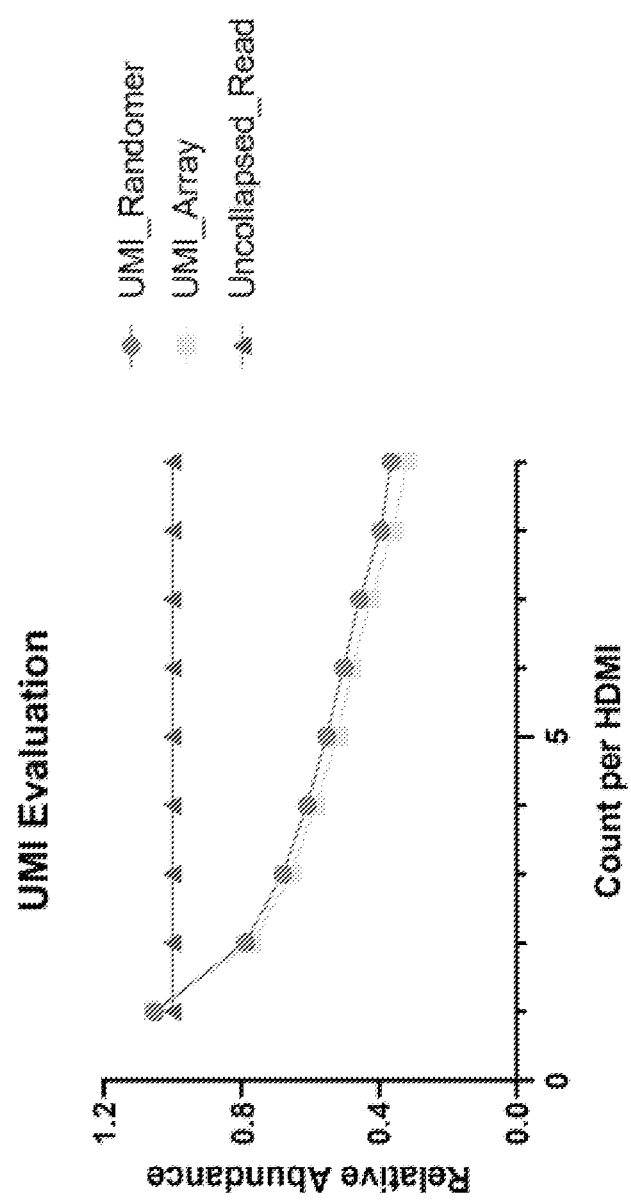

Efficiencies of UMI-encoding methods for collapsing duplicate read counts were evaluated using the data produced from the "Generation and Testing of UMI-encoded HDMI-array" section. UMI encoded by the HDMI-array (UMI_Array; $49^{th}$-$57^{th}$ positions of Read 1) and UMI encoded by the Random primed position (UMI_Randomer; $1^{st}$-$49^{th}$ positions of Read 2) was identified from the $2^{nd}$-Seq results. Uncollapsed read count, read count collapsed according to UMI_Array, and read count collapsed according to UMI_Randomer was calculated for all the HDMI sequences observed, and their relative abundances were presented in a line graph (FIG. 9G). The result indicates that both UMI_Array and UMI_Randomer are efficient in collapsing duplicate read count of $2^{nd}$-Seq results.

Results/Overview: The methods described herein, referred to as "Seq-Scope", are divided into two consecutive sequencing steps: "$1^{st}$-Seq" and "$2^{nd}$-Seq" (FIG. 8). $1^{st}$-Seq generates the physical array of spatially-barcoded RNA-capture molecules. $1^{st}$-Seq also generates the data table where the spatial coordinates of each barcode sequence in the physical array are defined. $2^{nd}$-Seq captures RNAs released from the tissue using the physical array produced by $1^{st}$-Seq, and sequences the captured molecules with both cDNA and spatial barcode information.

$1^{st}$-Seq starts with the solid-phase amplification of a single-stranded synthetic oligonucleotide library using an Illumina sequencing-by-synthesis (SBS) platform (MiSeq in the current study; FIG. 8A). The oligonucleotide "seed" molecule (e.g. the capture probe) contains the PCR/read adapter sequences, restriction enzyme-cleavable RNA-capture domain (oligo-dT), and the high-definition map location identifier (HDMI), the spatial barcode that is composed of a 20-32 nucleotide random sequence. The "seed" oligonucleotide library (e.g. capture probe library) was amplified on a lawn surface coated with PCR adapters (e.g. surface probes) (FIG. 8B), generating a number of clusters, each of which are derived from a single "seed" molecule. Each cluster has thousands of oligonucleotides that are identical clones of the initial oligonucleotide "seed" (FIG. 8B). The HDMI sequence and spatial coordinate of each cluster are determined through SBS (FIGS. 8C and 9A). After SBS, oligonucleotides in each cluster are processed to expose the nucleotide-capture domain (FIGS. 8D and 9A), producing an HDMI-encoded RNA-capturing array (HDMI-array; FIG. 8E).

$2^{nd}$-Seq begins with overlaying the tissue section slice onto the HDMI-array (FIG. 8E). The mRNAs from the tissue are used as a template to generate cDNA footprints on the HDMI-barcoded RNA capture molecule (FIGS. 8F and 9B). Then the secondary strand will be synthesized on the cDNA footprint using an adapter-tagged random primer (FIGS. 8G and 9B). Since each cDNA footprint is paired with a single random primer after washing, the random priming sequence is used as a unique molecular identifier (UMI; FIG. 9B). The secondary strand, which is a chimeric molecule of HDMI and cDNA sequences, is then collected and prepared as a library through PCR (FIGS. 8H and 9B). The paired-end sequencing of this library will reveal the cDNA footprint sequence, as well as its corresponding HDMI sequence (FIGS. 8I and 9B). The spatial coordinates of each discovered cDNA footprint are determined by joining the data tables from $1^{st}$-Seq and $2^{nd}$-Seq based on the matching HDMI sequences (FIG. 9C-9E). The combined digital gene expression (DGE) matrix is used for various analyses including gene expression visualization and spatial feature clustering assays (FIG. 9C-9E).

In sum, for each HDMI sequence, 1st-Seq provides spatial coordinate information whereas 2nd-Seq provides captured cDNA information. Correspondingly, the spatial gene expression matrix is constructed by combining the 1st-Seq and 2nd-Seq data, which is used for various analyses.

HDMI-Array Captures Spatial RNA Footprint of Tissues: Through a series of titration and optimization experiments, the HDMI-array with was produced a sequenced cluster density of up to 1.5 million clusters per mm$^2$ (FIGS. 10A, 11A and 11B). The distance between the centers of nearby clusters was estimated to be between 0.5-1 µm (FIGS. 10A and 11A). Since up to 150 HDMIs were generated in a 100 µm$^2$ area, visualization of the structure of single cell, as well as its subcellular structures such as nucleus and cytoplasm, is possible (FIG. 9J).

The RNA-capturing capability of the HDMI-array was first evaluated by performing Cy3-dCTP-mediated cDNA labeling assay using a fragmented frozen liver section. The HDMI-array successfully captured tissue transcriptome and generated a spatial cDNA footprint that preserves gross shape of the overlying tissue (FIG. 10B). Interestingly, the Cy3-dCTP labeling assay also revealed microscopic details of cDNA footprints that resemble a single cell morphology (FIG. 10B, insets), which has a fluorescence texture that is similar to the one produced by underlying clusters (FIGS. 10A and 11A).

The full Seq-Scope procedure ($1^{st}$-Seq and $2^{nd}$-Seq; FIG. 1) was subsequently performed on two representative gastrointestinal tissues, liver and colon. In each $1^{st}$-Seq experiment, the HDMI-array was produced in 1 mm-wide circular areas of the MiSeq flow cell, also known as "tiles" (2101 to 2119; FIG. 10C). Liver and colon tissue sections were overlaid onto the HDMI arrays, examined by H&E staining, and subjected to $2^{nd}$-Seq. Analysis of $1^{st}$-Seq and $2^{nd}$-Seq data (FIG. 9C) demonstrated that the RNA footprints were discovered mostly from the tissue-overlaid regions of each tile (FIGS. 10C, 11D and 11E), confirming that the procedure can indeed capture and analyze the spatial transcriptome from the tissues.

Figure 11Q:
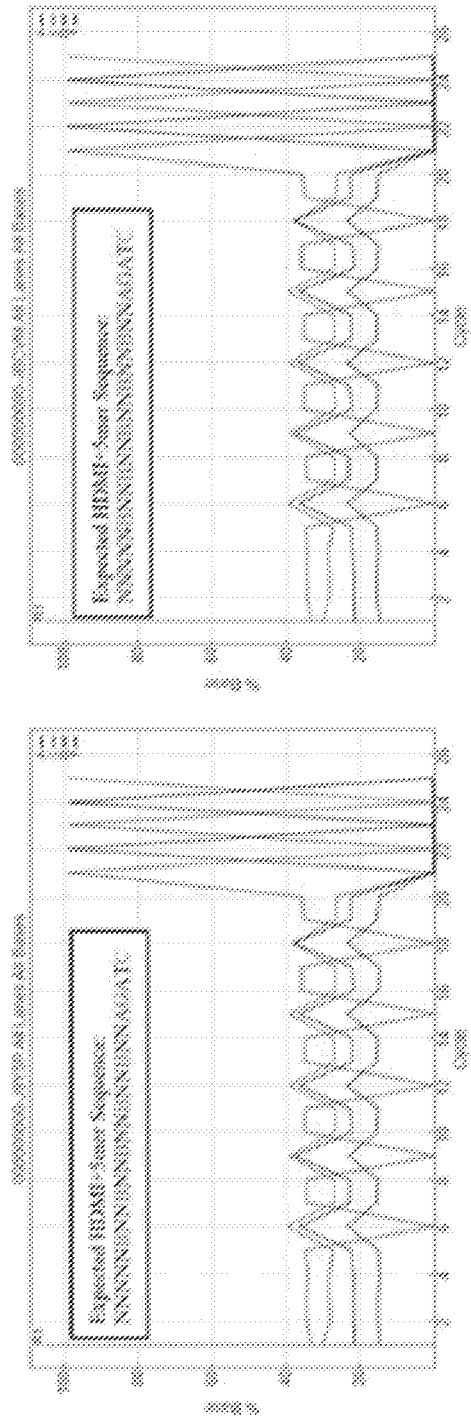
(FIG. 11Q) HDMI sequencing results from 1st-Seq. Base incorporation rate (%) at each location of the HDMI sequences in liver (left) and colon (right) 1st-Seq is presented in a line graph. Please note that we used standard machine mixing for making random oligonucleotides. In this method, even though A:C:G:T was dispensed at 25:25:25:25, random bases potentially have variations from the designated ratio (in this case, A>C>G>T) due to the different chemical properties of the bases. The sequence pattern of 1st-Seq is consistent with the expected sequence (NNNNNBNNBNNBNNBNNBNN) for more than 99% of sequenced clusters.
Figure 11U:
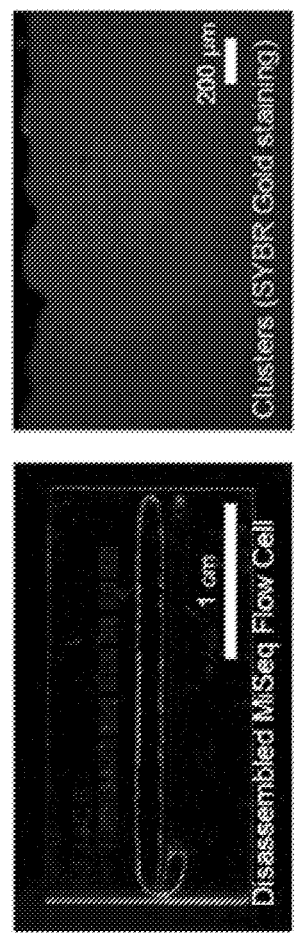

The Seq-Scope analysis was robust against PCR and sequencing errors; >99% of all spatial assignments were estimated to be accurate, as detailed in the STAR Methods (FIGS. 11Q-11S). The small number of transcripts discovered outside of the tissue-overlaid regions had a transcriptome profile similar to the tissue-covered area (r=0.9833); therefore, these transcripts are likely derived from tissue debris or ambient RNAs released from the tissue.

Figure 10K:
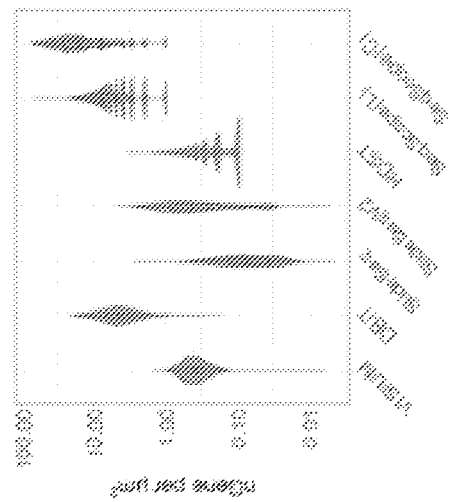

Capture of Transcriptome Information with High Efficiency: Compared to previous ST solutions, Seq-Scope offers a dramatic improvement in resolution (FIG. 10F) and pixel density (FIG. 10G); center-to-center distances between HDMI pixels were measured to be 0.633±0.140 mm (liver) and 0.630±0.132 mm (colon) (mean±SD) (FIG. 10F). Although each HDMI-barcoded cluster covers an extremely tiny area (less than 1 µm$^2$), many HDMI clusters were able to identify 10-100 unique transcripts from the overlying tissue section (FIGS. 11F and 11G). To compare the data output with other existing ST technologies, the number of gene features and unique transcripts in a 10 µm-sided square grid were quantified (FIGS. 11H and 11I). Since tissue-overlaid grid pixels distinctively displayed higher number of gene features and unique transcript counts (FIG. 10D), setting a simple gene feature cutoff was sufficient to isolate tissue-overlaid grid pixels (FIGS. 10E and 11J-11M); tissue-overlaid grid pixels identified up to 1,000-1,200 unique transcripts per individual pixel (FIGS. 10D, 10E, 11N and 11O).

Figure 10H:
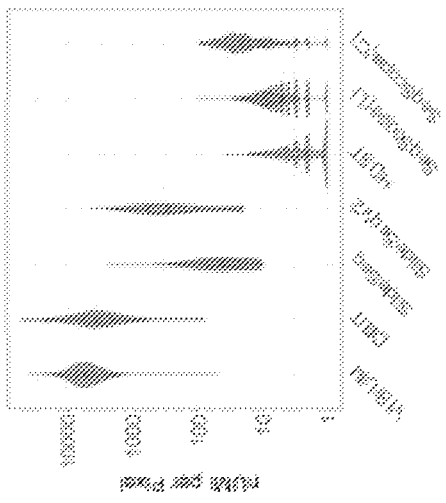
Figure 10I:
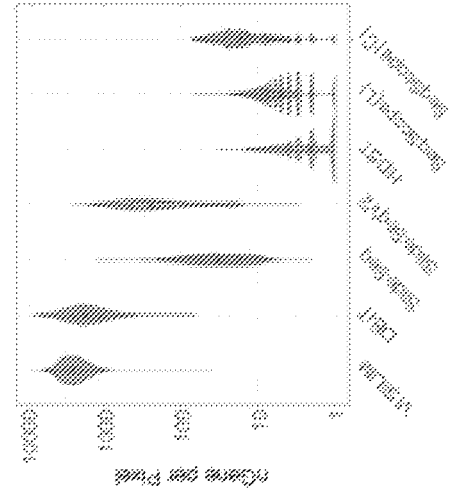
Figure 10F:
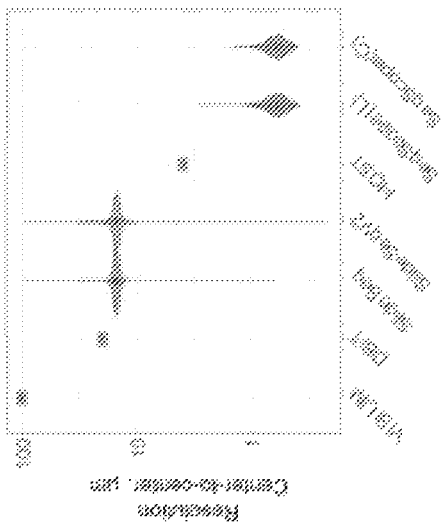
Figure 10G:
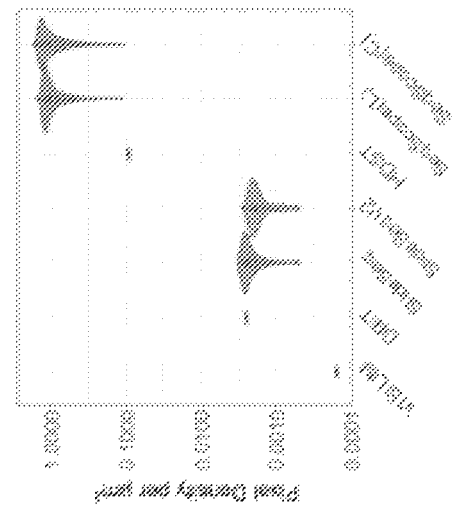

Indeed, although each HDMI-barcoded cluster covers an extremely tiny area (less than 1 µM$^2$) single HDMI pixel in tissue-covered region was able to capture 6.70±5.11 (liver) and 23.4±17.4 (colon) UMIs (mean±SD) (FIG. 10H). The number of gene features identified per HDMI pixel was 5.88±4.22 (liver) and 19.7±14.3 (colon) (mean±SD) (FIG. 10I). Per-pixel counts of UMIs and genes in Seq-Scope were larger than HDST but were smaller than other technologies (FIGS. 10H and 10I). However, after normalization using the pixel density, Seq-Scope showed the best transcriptome capture performance per area among the datasets we examined (FIG. 10J and FIG. 10K; colon dataset). Considering that the current data are estimated to cover about 60% (liver) and about 36% (colon) of the total library size (FIG. 11P), the maximum possible Seq-Scope capture efficiency should be even higher than the currently presented data. Therefore, Seq-Scope provides an outstanding mRNA capture output, in addition to providing an unmatched spatial resolution output.

Figure 12B:
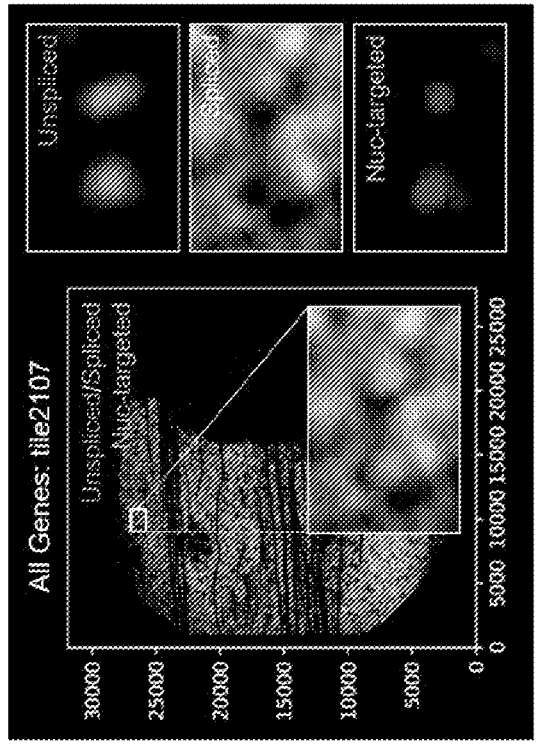
(FIGS. 12B-D) Spatial plot of all unspliced and spliced transcripts, as well as RNA species that are known to localize to nucleus in liver tissue (Nuc-targeted; Malat1 Neat1 and Mlxip1) (FIG. 12B). RNA species that are encoded by mitochondrial genome (Mt-encoded) were also analyzed (FIG. 12C). Pearson correlations (r) between these transcript intensities were presented as a heat map (FIG. 12D).
Figure 12D:
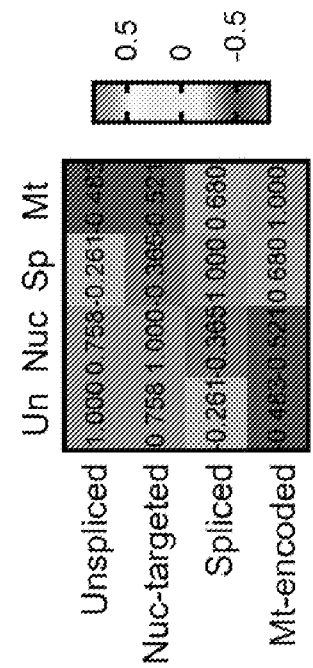
Figure 12A:
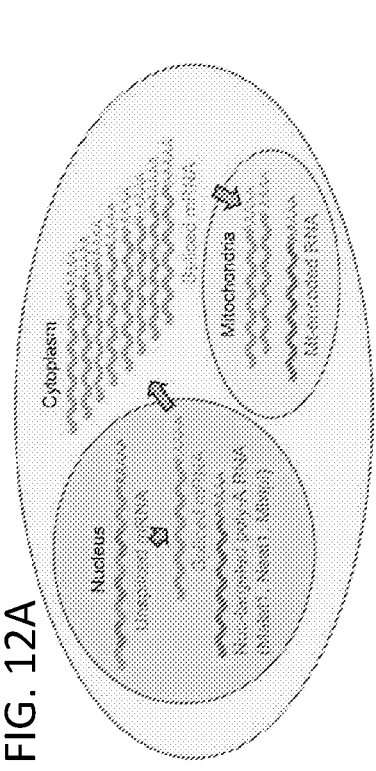
(FIG. 12A) Schematic diagram depicting the distribution of different RNA species in subcellular compartments.

Nuclear-Cytoplasmic Transcriptome Architecture from Tissue Sections: mRNA is transcribed and poly-A modified in the nucleus. Before it can be transported to cytoplasm, it is spliced, and intronic sequences are removed. Therefore, the nuclear area will have higher concentration of unspliced mRNA sequences, while the cytoplasmic area will have higher concentration of spliced mRNA sequences (FIG. 12A). In mouse liver, several RNA species, such as Malat1, Neat1 and Mlxip1, were found to show nuclear localization due to their strong attenuation in cytoplasmic transport (FIG. 12A) [18]. On the other hand, cytoplasm has mitochondria, which has a unique transcriptome structure with mitochondria-encoded RNAs (mt-RNA; FIG. 12A).

Figure 12C:
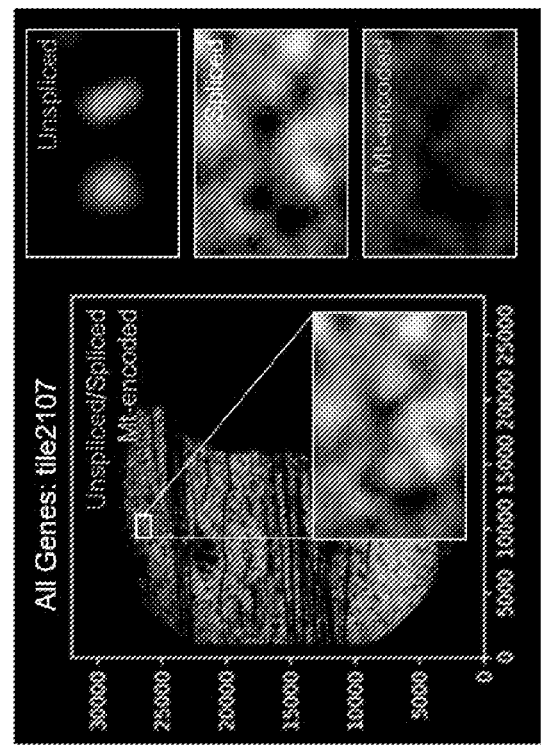
Figure 12E:
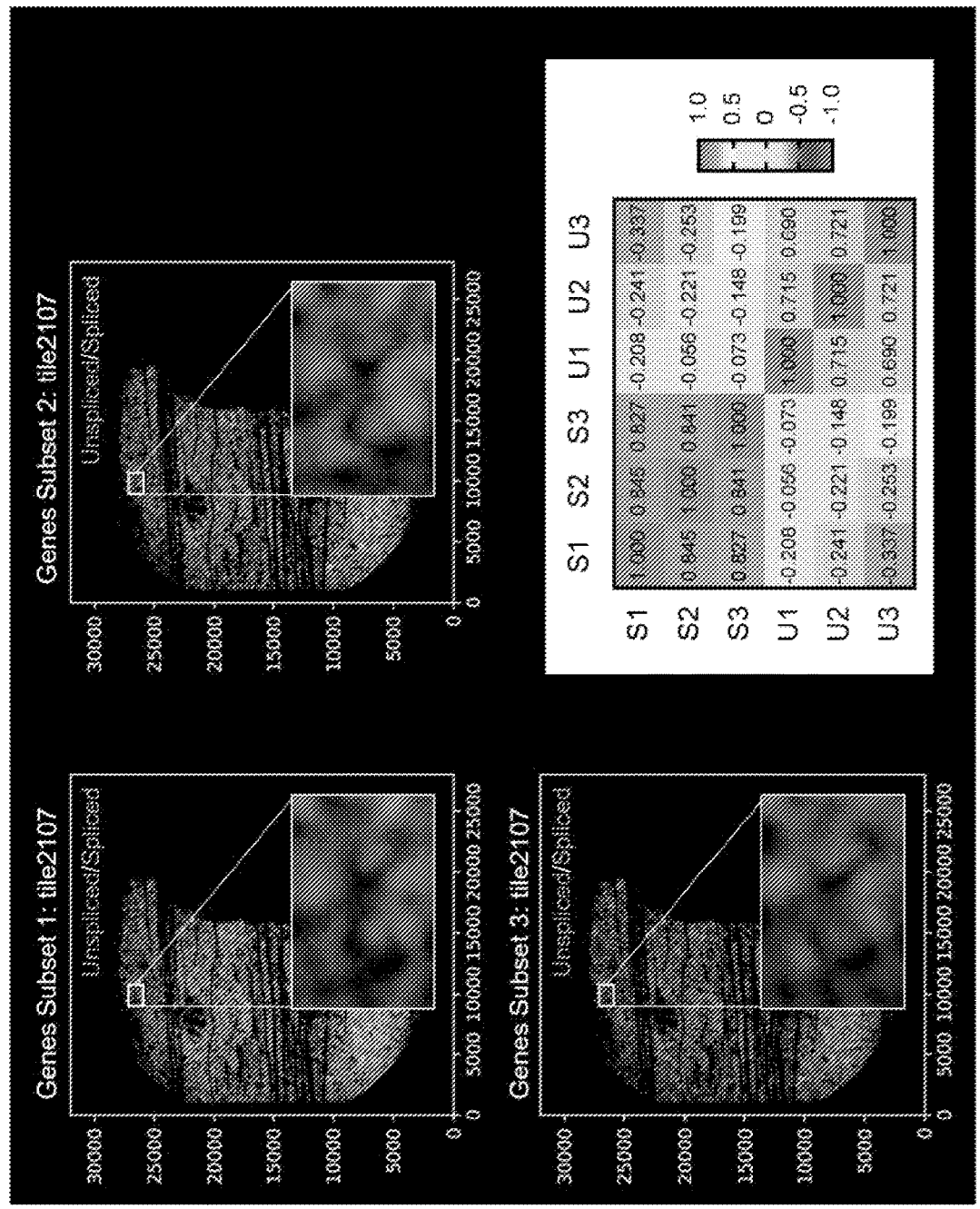
(FIG. 12E) Spatial plot of unspliced and spliced transcripts in three independent subsets of genes (Gene Subset 1-3). Pearson correlations (r) between these transcript intensities were presented as a heat map. S1-3, Spliced 1-3; U1-3, Unspliced 1-3.
Figure 13D:
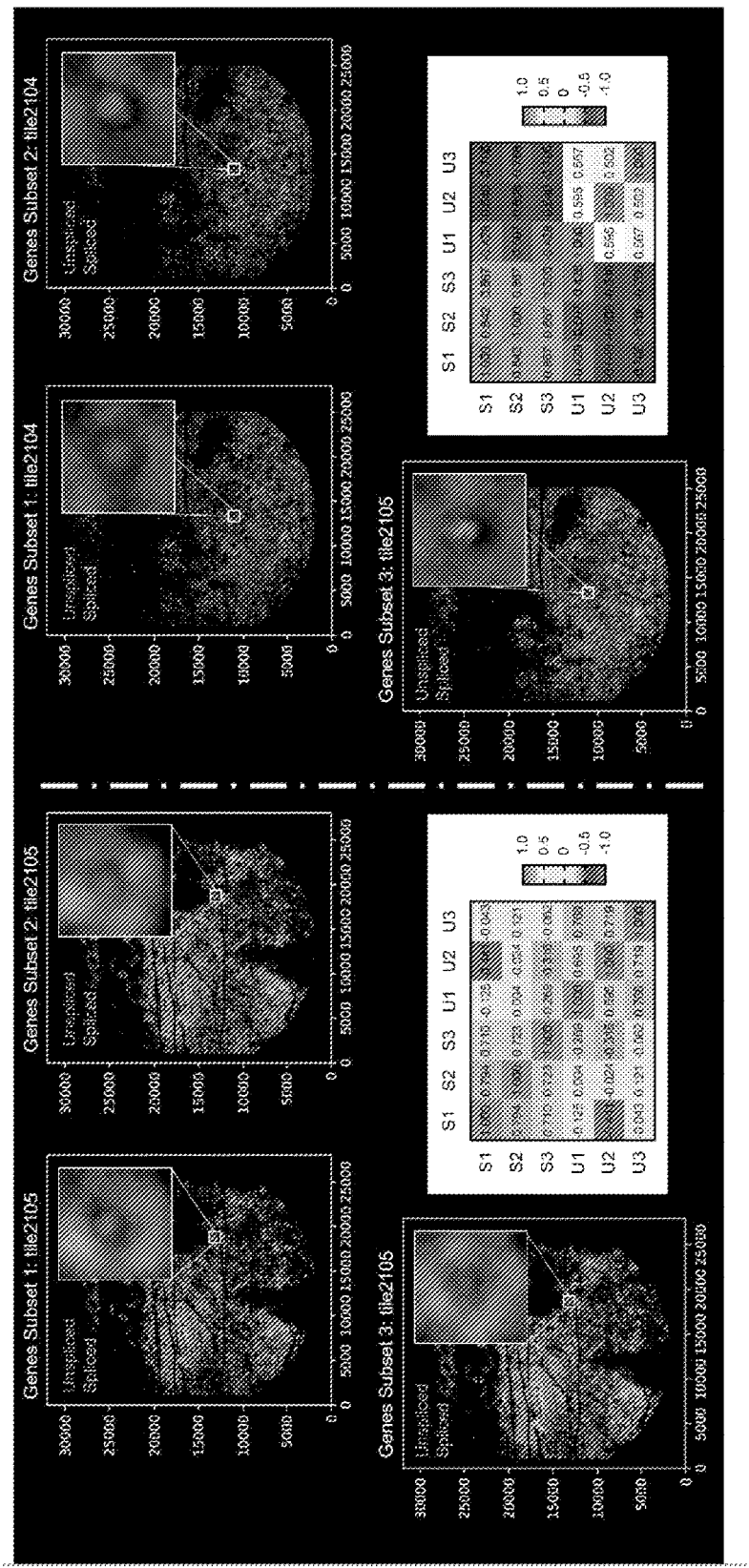

To know whether the technology disclosed herein is capable of examining subcellular-level spatial transcriptome (FIG. 8G), all spliced and unspliced transcripts were plotted in a two-dimensional coordinate space. Intriguingly, unspliced transcripts showed an interesting pattern as their expression was restricted in a number of tiny circles that have a diameter of approximately 10 µm, which is about the size of hepatocellular nuclei [19] (FIGS. 12B and 13A). More interestingly, spliced mRNAs were less frequently discovered in the unspliced area, while nuclear-localized RNAs, including Malat1, Neat1 and Mlxip1 [18], were more frequently found in the unspliced area (FIG. 12B). On the other hand, mt-RNAs were more frequently found in the spliced cytoplasmic area (FIGS. 12C and 13B). As a result, focused images covering the single cell area showed strong positive correlations between unspliced and nuclear-localized mRNAs and between spliced and mitochondrial mRNAs, while displaying strongly negative correlations between the opposite groups (FIGS. 12D and 13C). These data suggest that plotting of spliced and unspliced transcripts could be used to determine the nuclear-cytoplasmic structure from the dataset. To further test if these observations are robust and statistically significant, all genes were divided into three independent subsets, expressions of spliced and unspliced mRNAs from each gene subset were calculated, and each dataset was analyzed through the same plotting method. All three datasets similarly visualized nuclear-cytoplasmic structure with a strong statistical correlation (FIGS. 12E and 13D).

These results suggest that spliced and unspliced transcripts are useful to determine the nuclear-cytoplasmic structure from the Seq-Scope dataset. Indeed, when overlaid with H&E staining images, the unspliced RNA-enriched region generally agreed with the nuclear position (FIG. 12F; note that some hepatocytes are known to be multinucleate) (Donne et al., 2020). However, in some hepatocytes, the unspliced RNA-enriched regions were not observed (FIG. 12F), which can be explained by the absence of the cell's nucleus in the tissue slice (FIG. 13E, left), the inadequate positioning of the nucleus for RNA capture (FIG. 13E, middle), or the intrinsic variations in the rates of transcription, splicing, and nuclear export (FIG. 13E, right). To further test the robustness of these observations, all genes were randomly divided into three independent subsets and examined the expressions of spliced and unspliced mRNAs from each subset. All three datasets similarly visualized a nuclear-cytoplasmic structure with a strong correlation (FIG. 12E and FIG. 13D). Finally, nuclear centers were identified by using unspliced transcripts (FIG. 12G). Then, genes whose transcripts were enriched within 5 mm from the nuclear centers were searched for. Consistent with previous cell fractionation and RNA in situ hybridization studies (Bahar Halpern et al., 2015) and the observations described above, Malat1, Neat1, and Mlxip1 were identified as the top 3 genes enriched in the nuclear area (FIG. 12H). These results demonstrate that Seq-Scope can perform subcellular transcriptome studies.

Figure 14A:
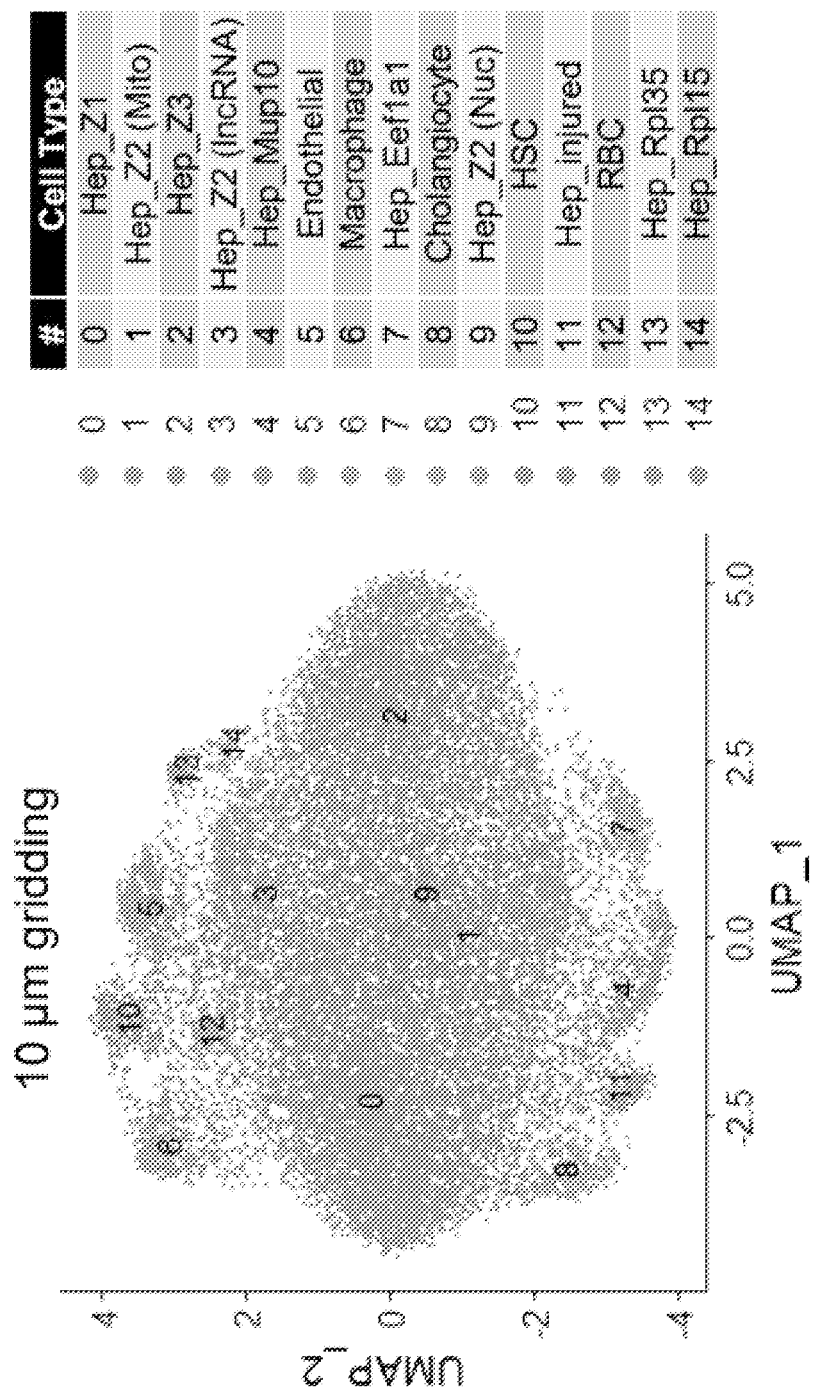
Figure 14B:
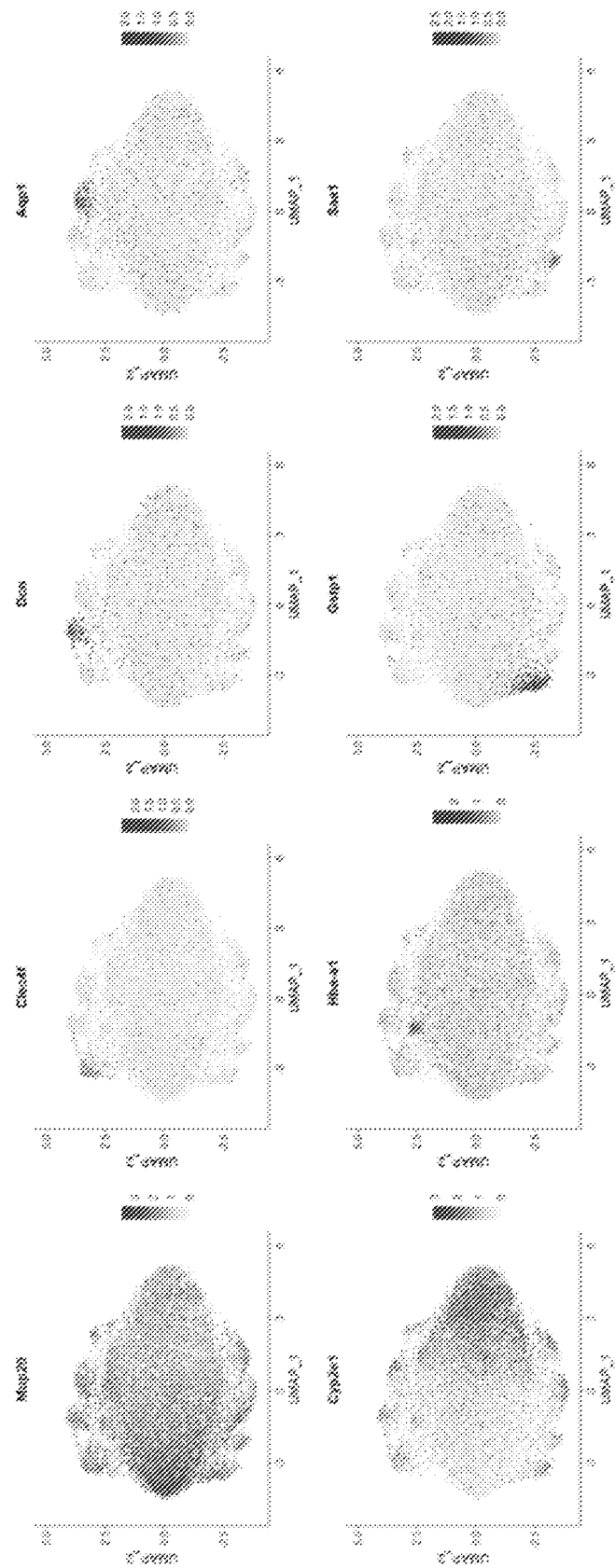
Figure 14C:
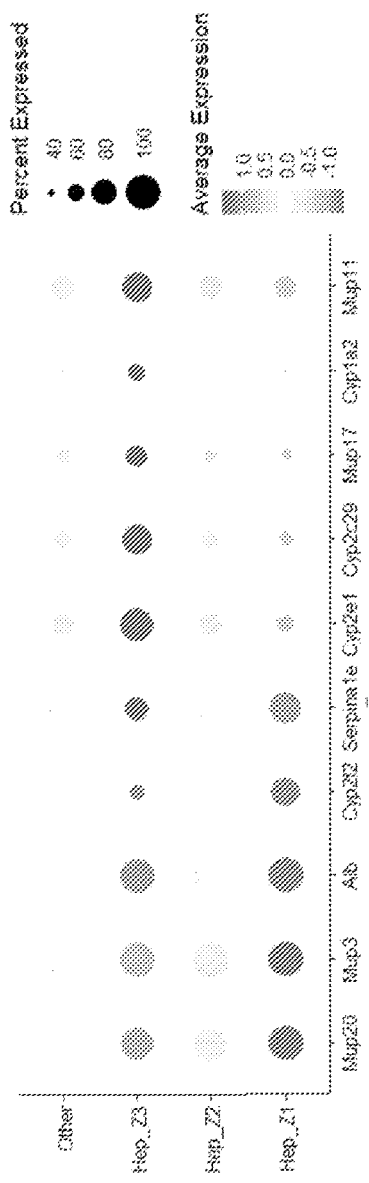
Figure 14D:
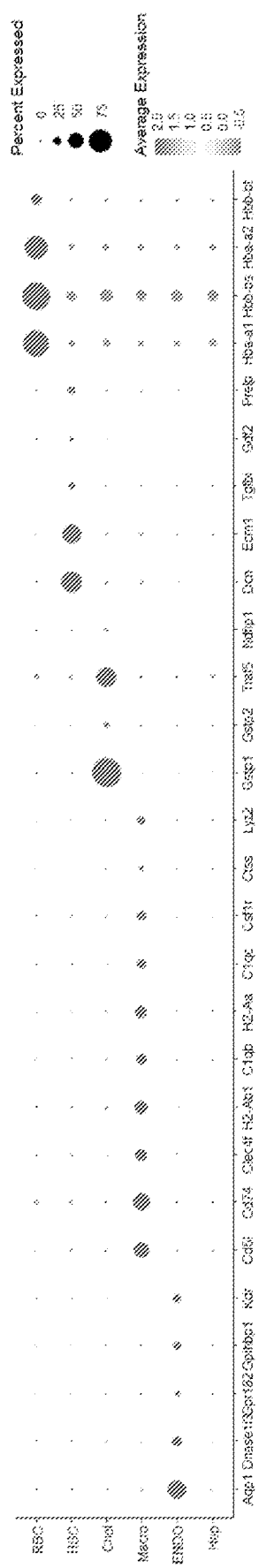

Spatial Transcriptomic Details of Metabolic Liver Zonation: It was then examined whether the methods described herein can reveal biologically relevant features of hepatic spatial transcriptome. To systematically approach the heterogeneity of liver cell transcriptome, the square-gridded dataset was analyzed (FIG. 10H-10O) with the standard scRNA-seq analysis pipeline [20]. Multi-dimensional clustering analysis identified many interesting cell types (FIG. 14A) with a long list of cluster-specific marker genes (FIG. 14B-14D).

Hepatocytes, the parenchymal cell type of liver, are exposed to varying gradients of oxygen and nutrients according to their histological locations, leading to metabolic zonation whereby cells express different genes to perform the zone-specific metabolic function (Zone 1-3 or Z1-3) [21]. Consistent with this, multi-dimensional clustering analysis identified zonated hepatocytes as the major clusters found from the dataset (FIG. 14A). Spatial plotting of the cluster identity clearly visualized zone 1-3 in the two dimensional grid space.

To fully utilize the submicrometer resolution performance, zone-specific molecular markers were directedly plotted into the raw coordinate plane. This revealed a spectrum of genes showing various zonation patterns, which cannot be explained by the three simple layers. For instance, the immediate pericentral hepatocytes specifically expressed extreme zone 3 markers such as Glul and Oat. Cyp2a5, Mup9 and Mup17 were also narrowly expressed in extreme pericentral hepatocytes; however, Mup9 and Mup17 displayed a lower expression at the immediate pericentral hepatocytes, forming a donut-like staining pattern. In contrast, general pericentral markers, such as Cyp2c29 and Cyp2e1, were broadly expressed across all pericentral hepatocytes. Several genes, such as Mup11 and Hamp, were not expressed in extreme zone 1 and zone 3 layers but showed higher expression in the intermediary layers. Likewise, different periportal markers, such as Ass1, Serpinale, Cyp2f2, Alb and Mup20, exhibited various levels of zone 1-specific expression patterns. Many of these observations are supported by previous scRNA-seq, RNA in situ hybridization [22, 23] and immunostaining results [24].

Figures 14E, 14F:
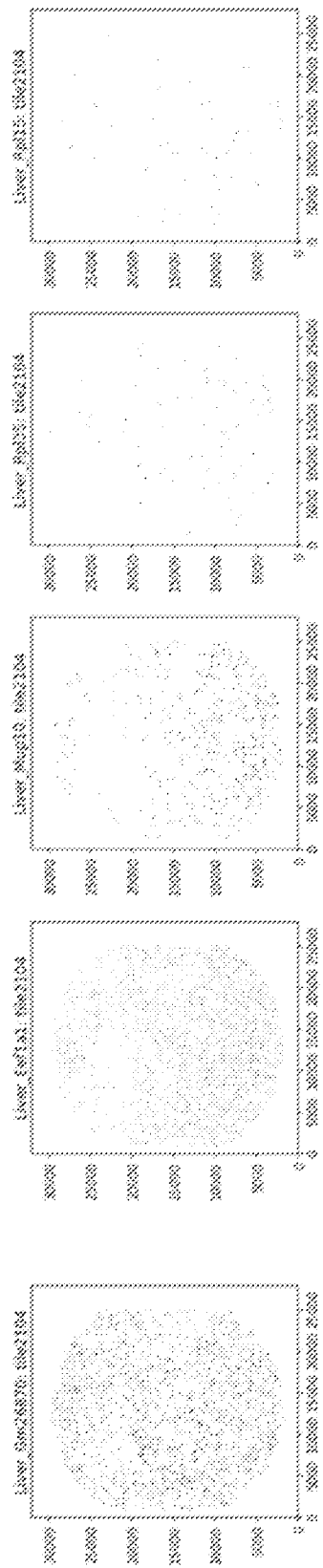
(FIG. 14E and FIG. 14F) Spatial plot of indicated transcripts on coordinate space.
Figures 14G, 14H:
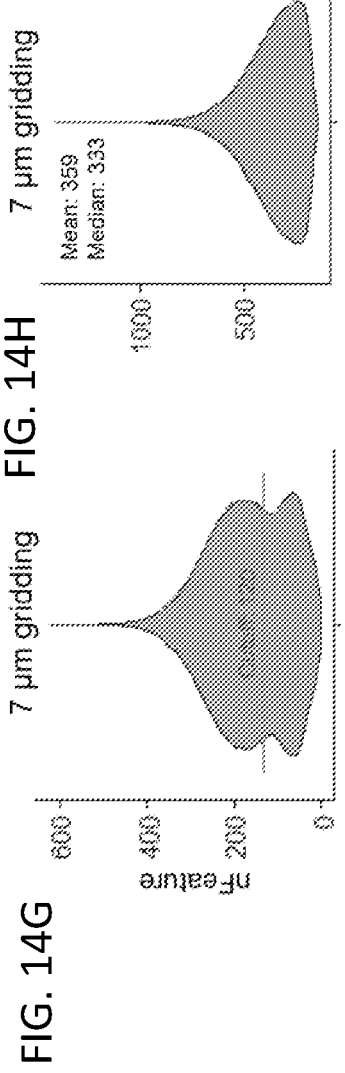
(FIGS. 14G-J) Number of gene features (FIG. 14G, nFeatures) and UMI counts (FIG. 14H, nCounts; after nFeatures cutoff at 120) were calculated across the indicated tiles of liver dataset, binned using 7 µm square grids. From this dataset, a UMAP plot visualizing all clusters (FIG. 14I), UMAP plots visualizing expression of indicated genes across the gridded pixels (FIG. 14J), a UMAP plot visualizing cell type-assigned clusters (FIG. 14K) and its associated spatial plots (FIG. 14L) are presented. Grid numbers, as well as mean and median UMI counts per grid pixel, were provided (FIG. 14L).
Figure 14I:
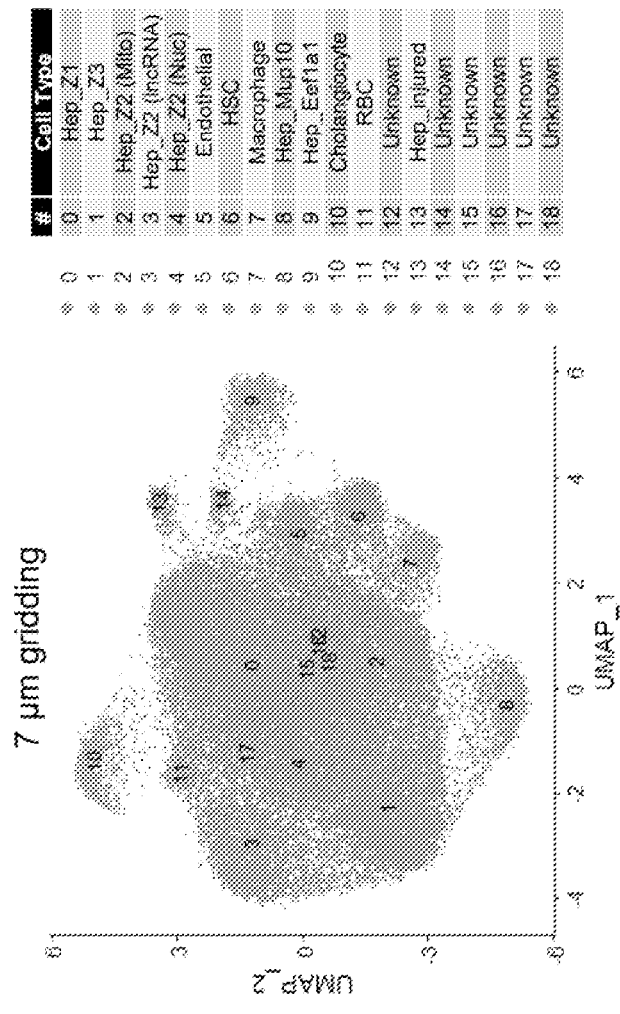
Figure 14J:
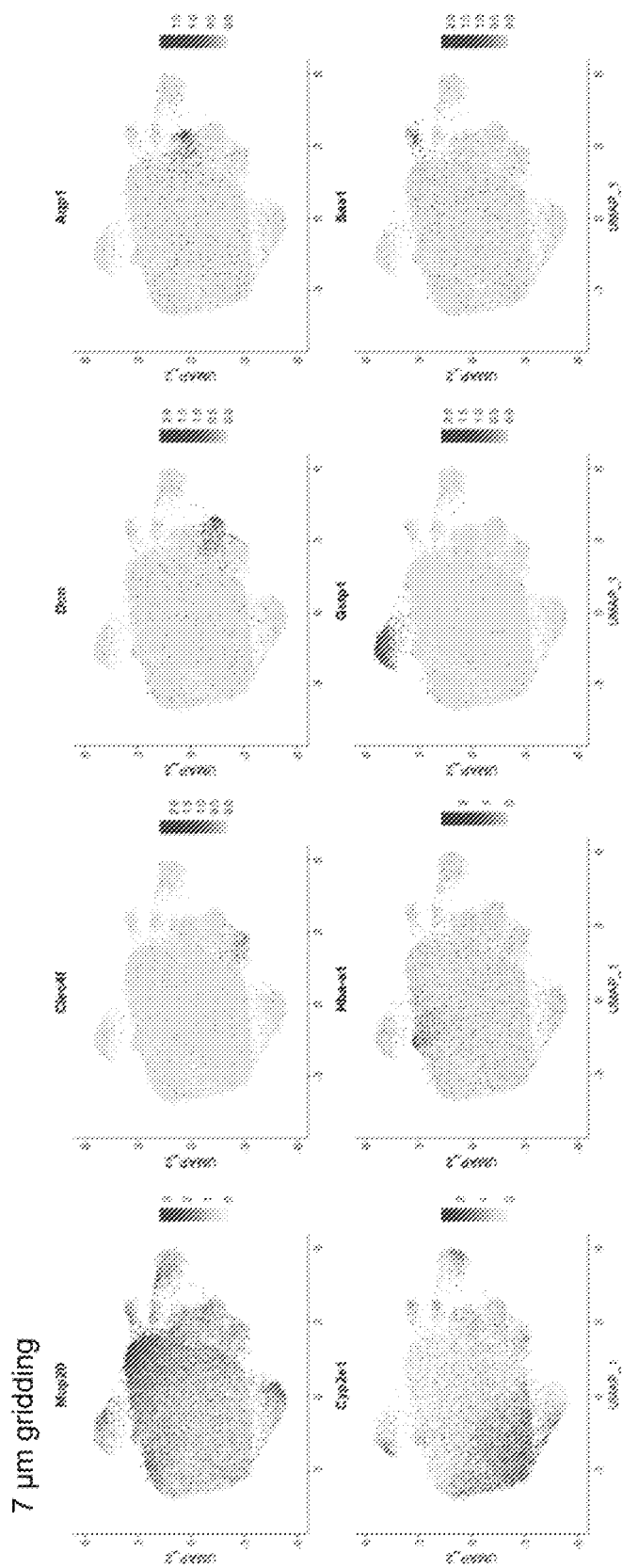
Figures 14K, 14L:
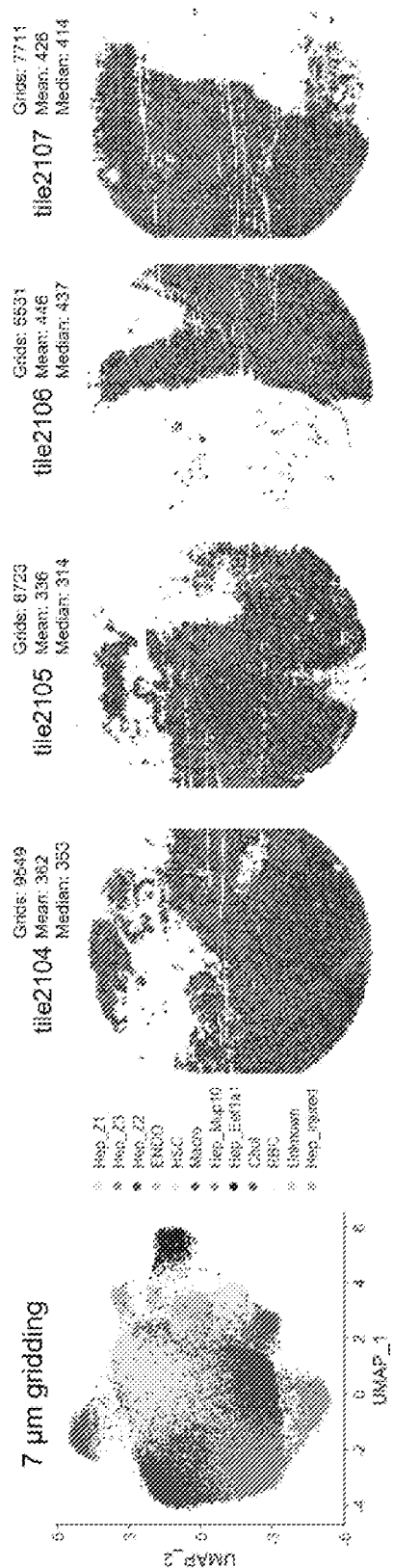
Figures 14P, 14Q, 14R:
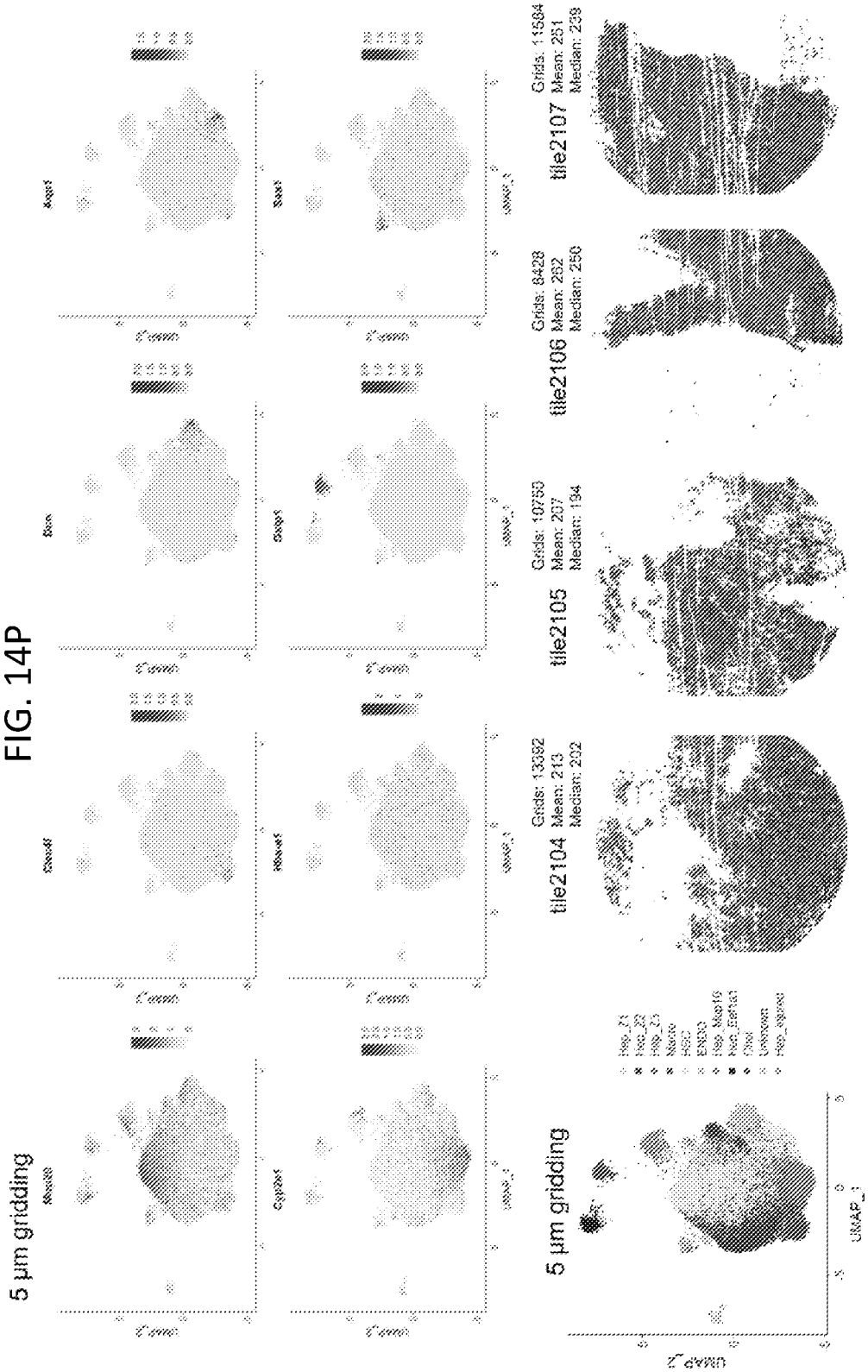

Interestingly, most of these zone 1- or zone 3-specific markers were found to be cytosolically located, as they did not overlap with the unspliced transcript-enriched area. This is consistent with the notion that zone-specific proteins are actively translated in the cytosol to perform zonated metabolic functions [21-24]. Consequently, zone 2 hepatocytes, which do not exhibit obvious periportal or pericentral transcriptome characteristics, were clustered based on the subcellular transcriptome heterogeneity; zone 2 hepatocytes were found in clusters enriched with nuclear transcripts (Malat1, Neat1 and Mlxip1 [18]; cluster 9 in FIG. 14A), mitochondrial transcripts (mtRNA; cluster 1 in FIG. 14A) and long non-coding RNA (lncRNA; cluster 3 in FIG. 14A) that show heterogeneous spatial gene expression patterns (FIG. 14E).

Seq-Scope Performs Spatial Single-Cell Analysis of Hepatocytes

Figure 12F:
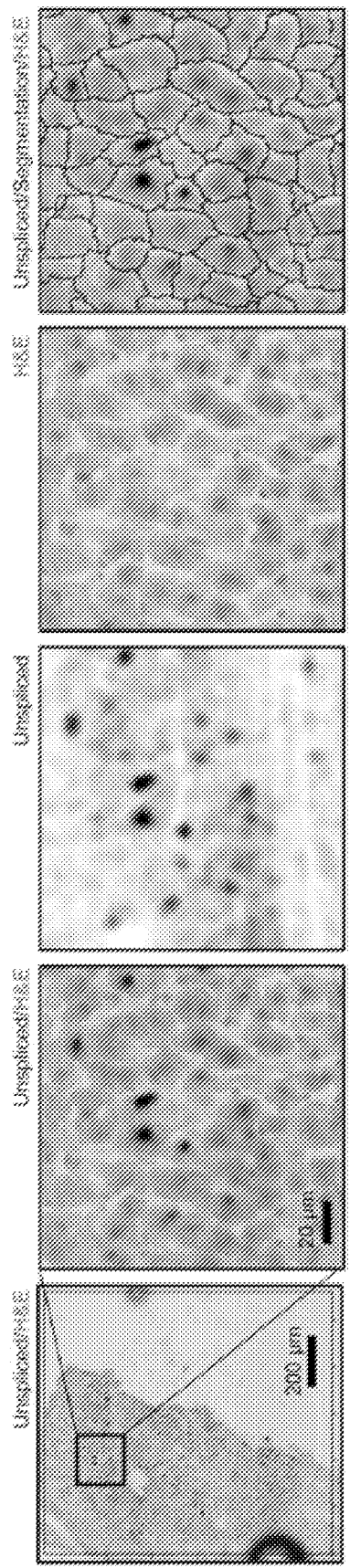
(FIG. 12F) Images displaying unspliced RNA discovery, H&E histology, and histology-based cell segmentation boundaries. Inset in the first panel is magnified in right panels.
Figure 12H:
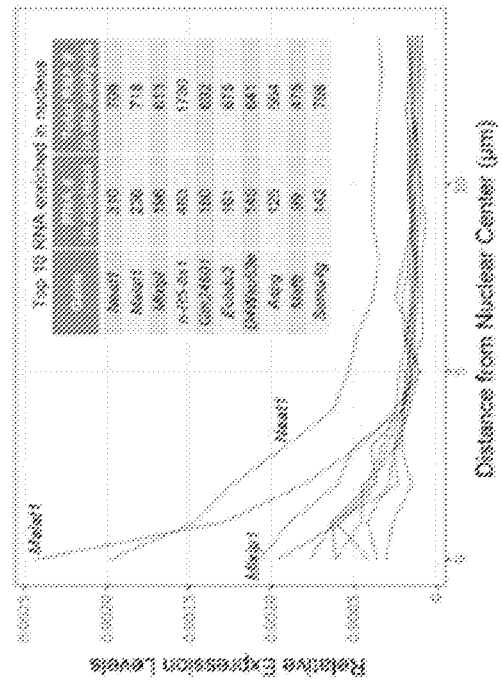
(FIG. 12H) Identification of nuclear-enriched RNA species. Top 10 nuclear-enriched RNAs are shown.
Figure 12G:
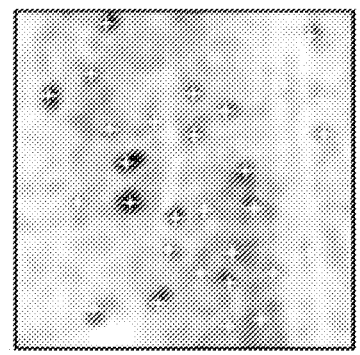
(FIG. 12G) Identification of transcriptomic nuclear centers (yellow crosses) through local maxima detection.
Figure 13E:
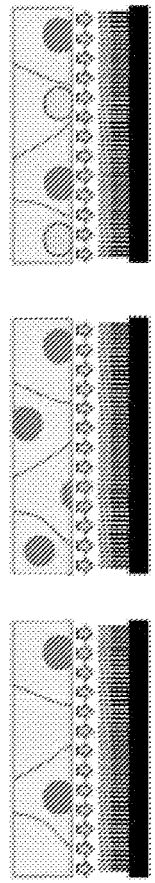
Figure 15B:
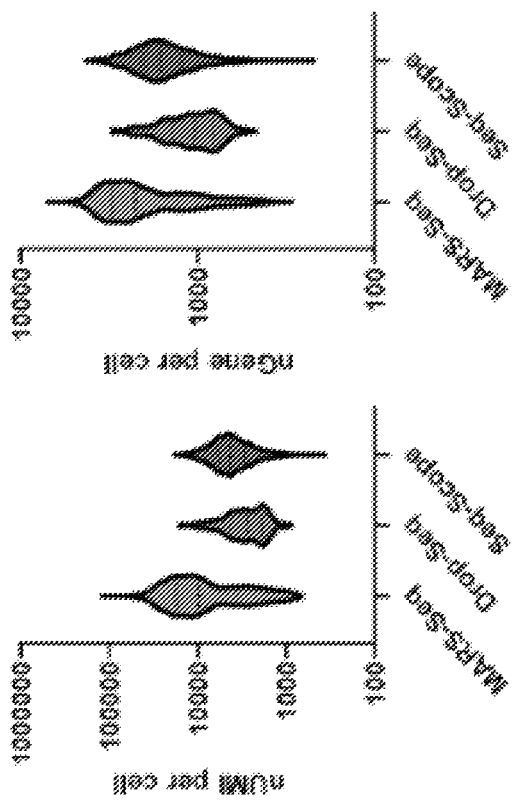
Figure 15D:
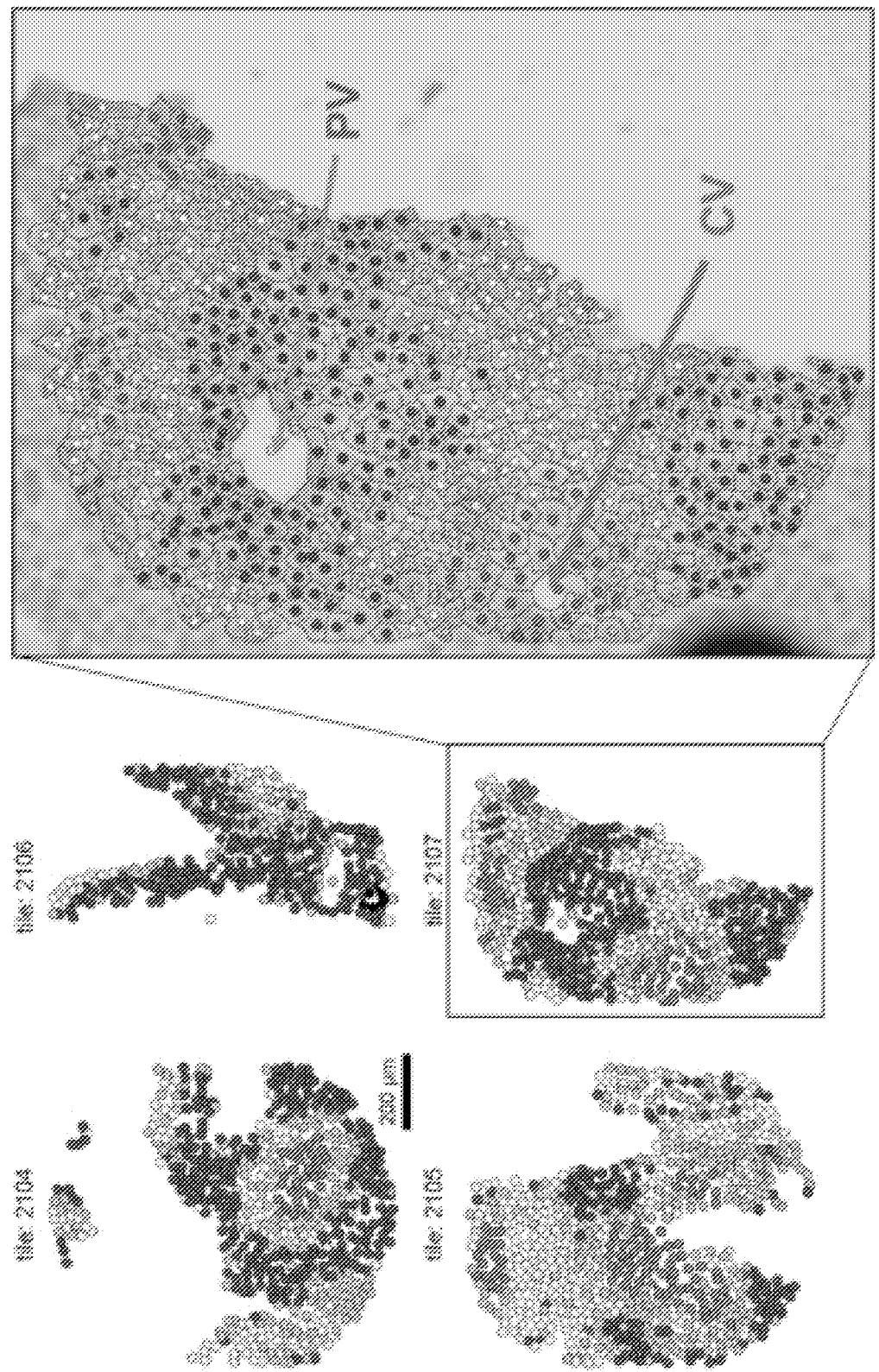
Figure 15E:
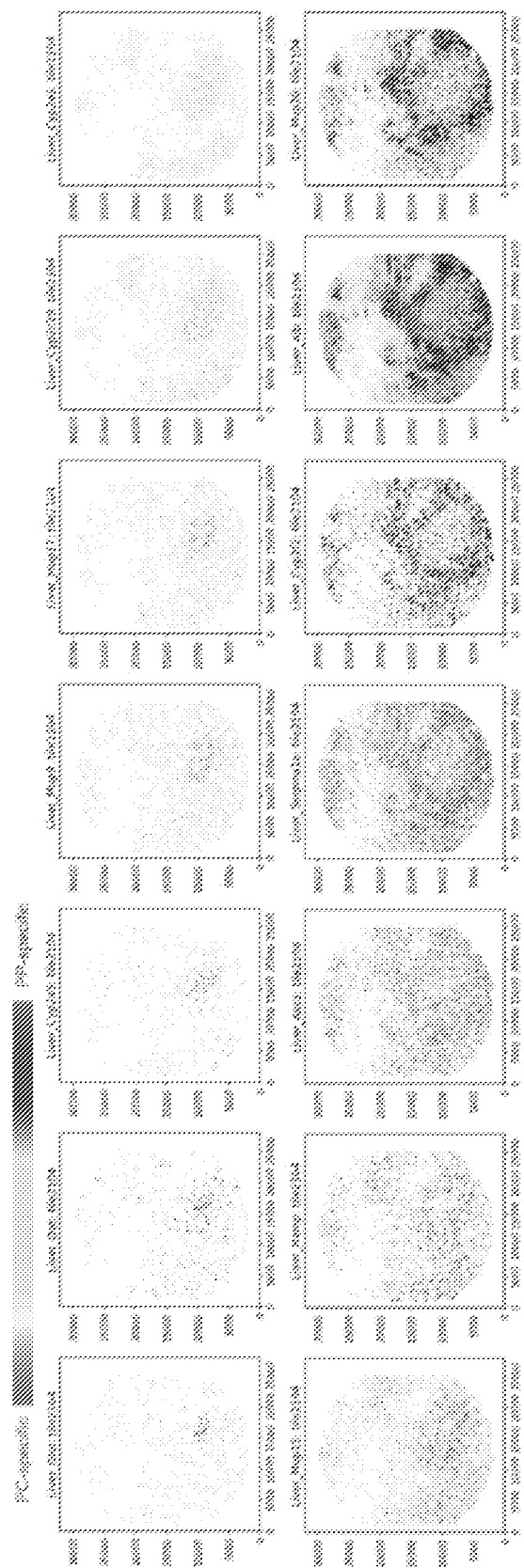
Figure 20C:
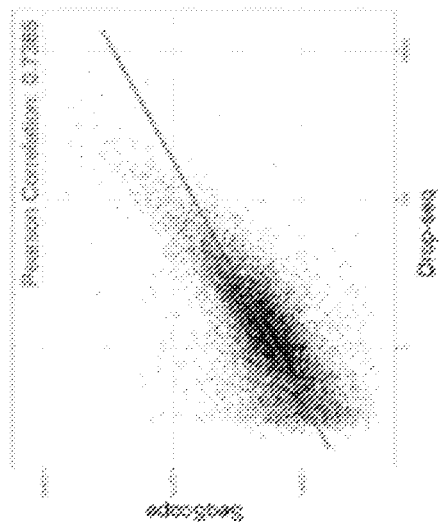
Figure 20B:
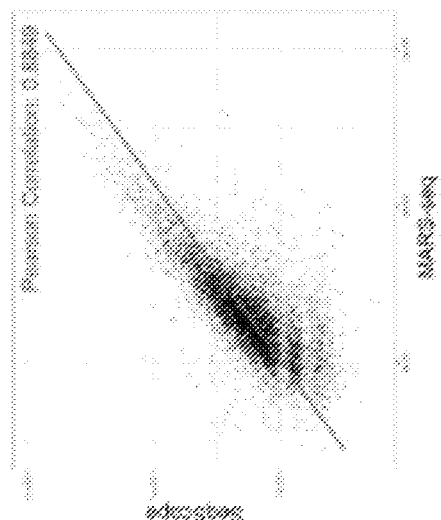
Figure 20A:
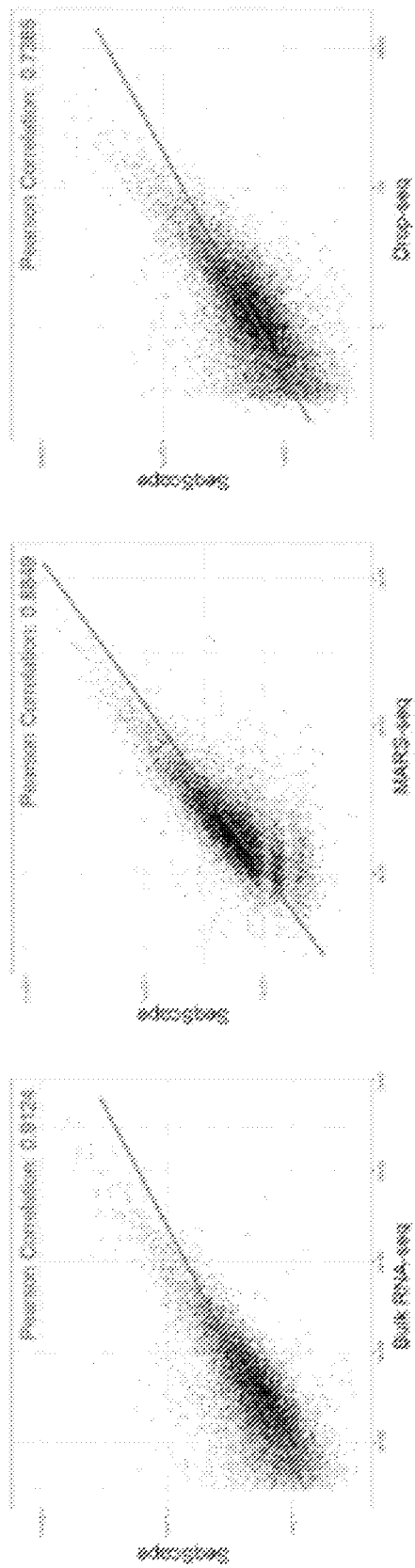
FIGS. 20A-V. Spatial single-cell analyses using Seq-Scope dataset of normal liver.
Figure 20E:
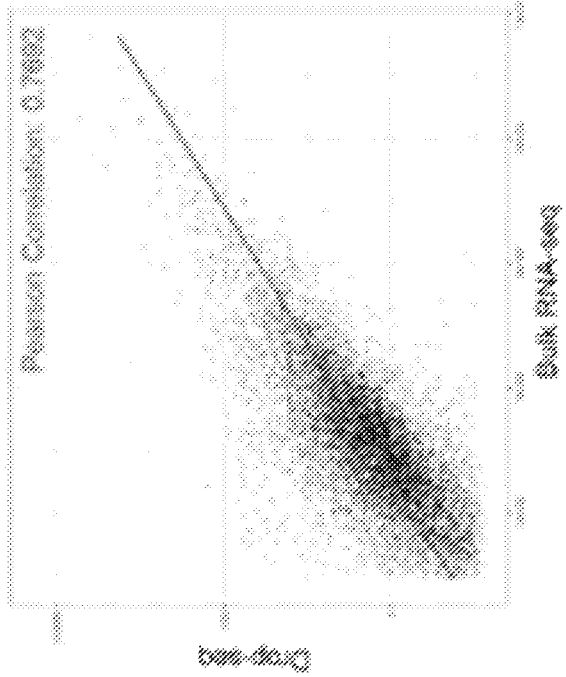
Figure 20D:
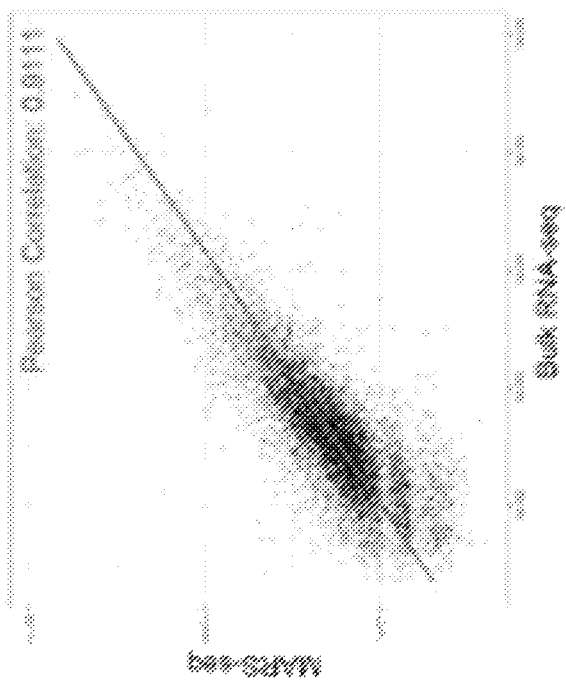
Figures 20F, 20G:
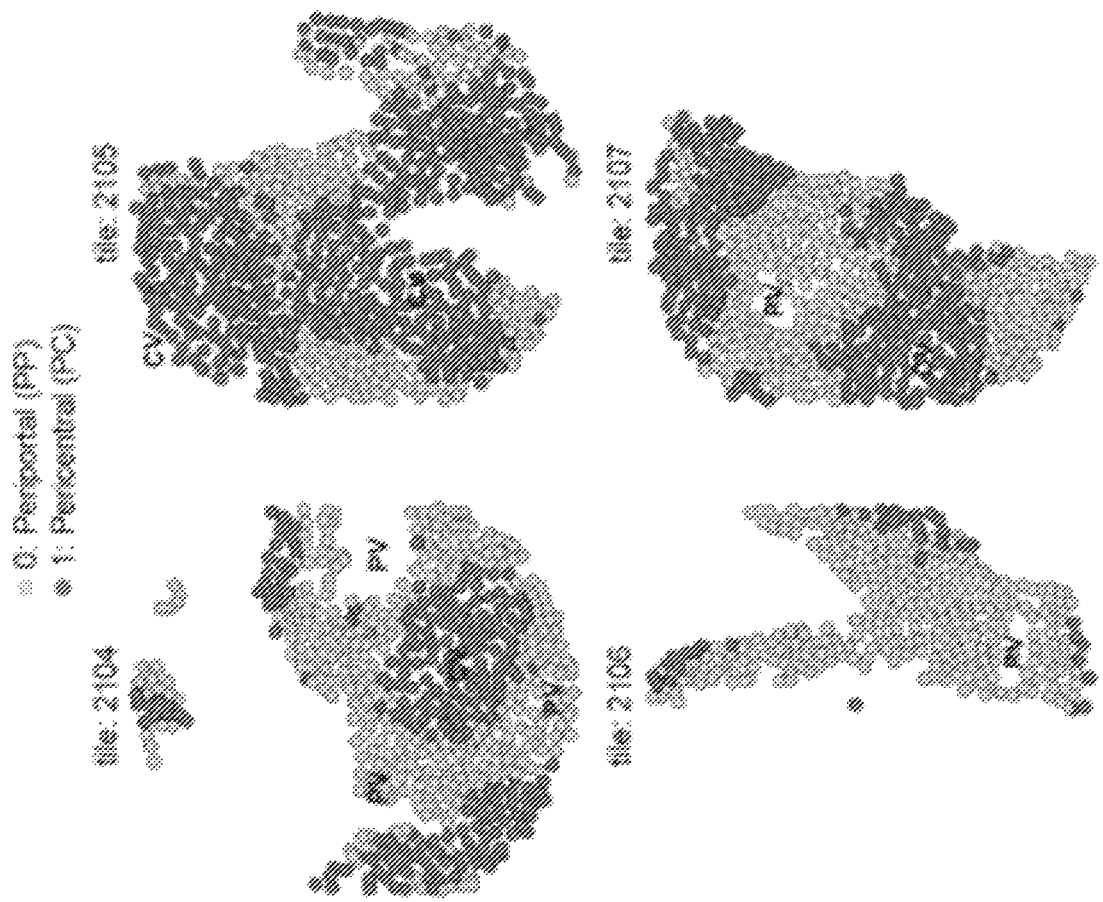
(FIGS. 20F-I) Single hepatocyte transcriptome analysis using Seq-Scope.
Figure 20I:
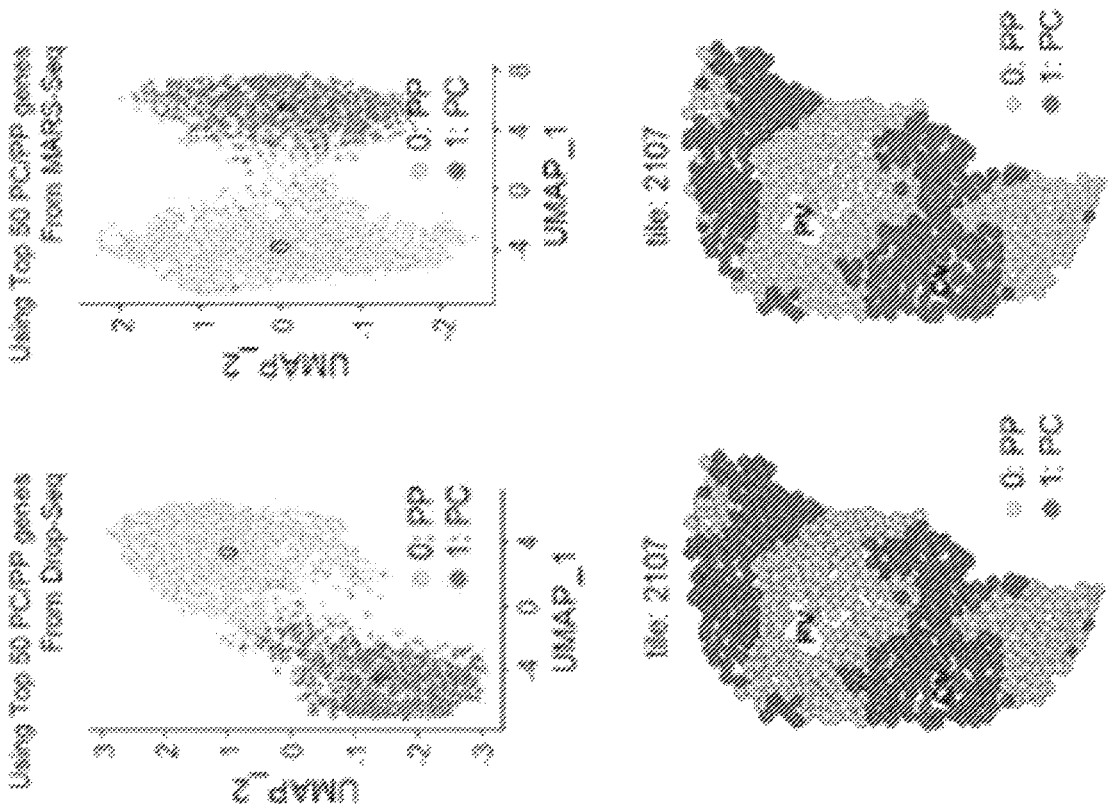
Figure 20H:
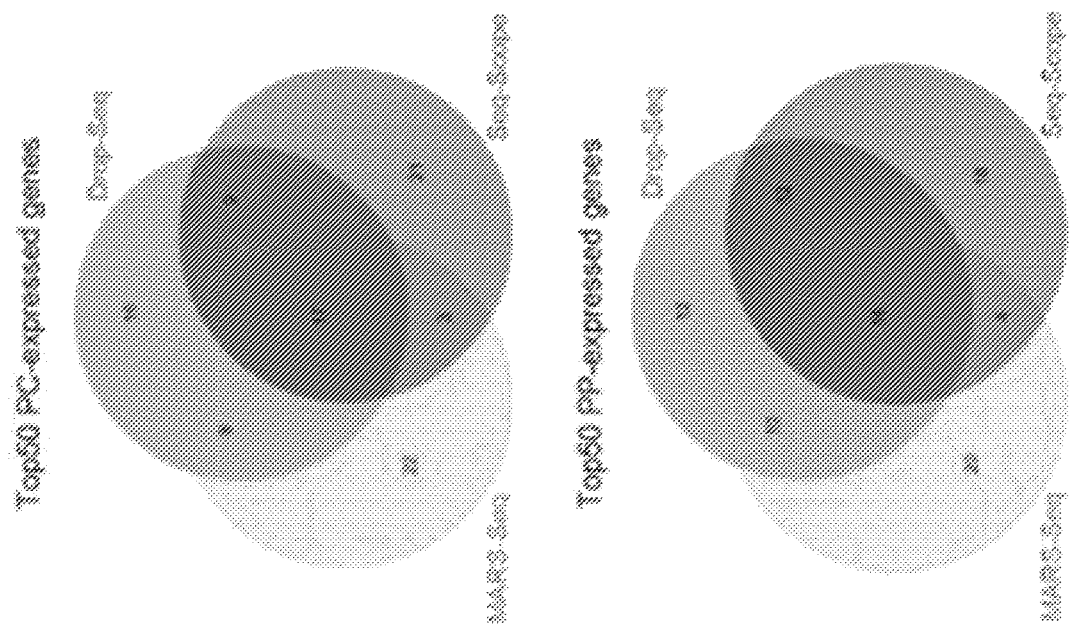
Figure 20J:
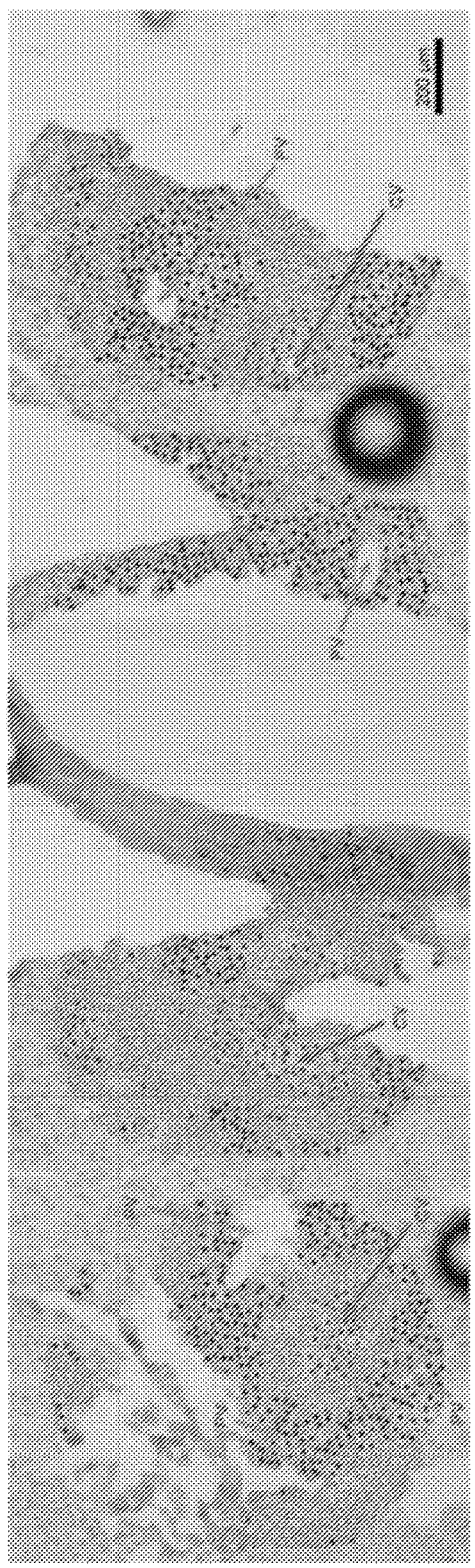
(FIG. 20J) Spatial map of different hepatocellular clusters described in FIG. 4D, overlaid with H&E staining and cell segmentation images. Four tiles, 2104-2107 (left to right), were analyzed. PV, portal vein; CV, central vein.
Figure 20K:
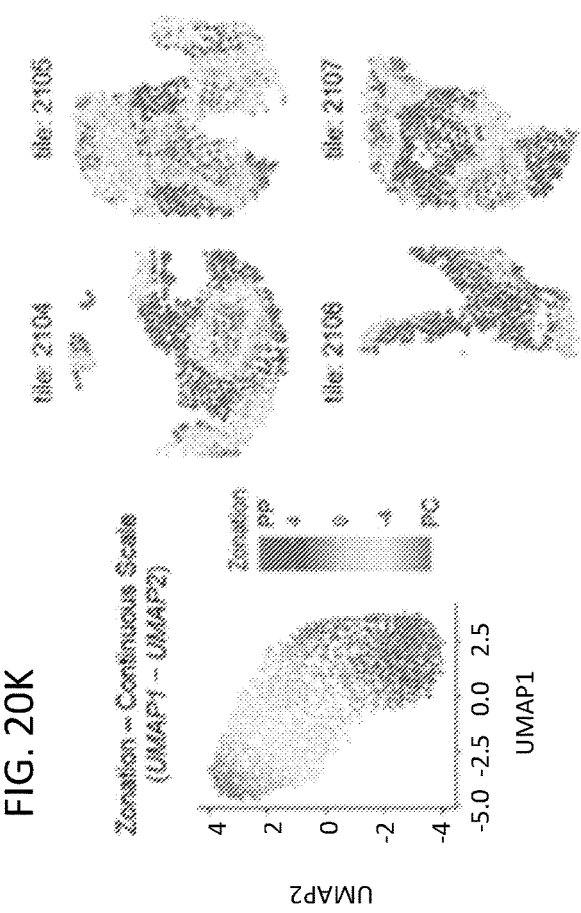
(FIG. 20K) UMAP (left) and spatial plotting (right) analysis colored with continuous zonation color map (UMAP1, UMAP2).
Figure 20P:
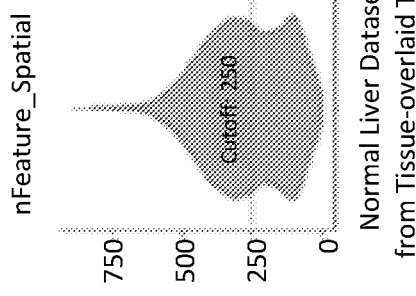
Figure 20Q:
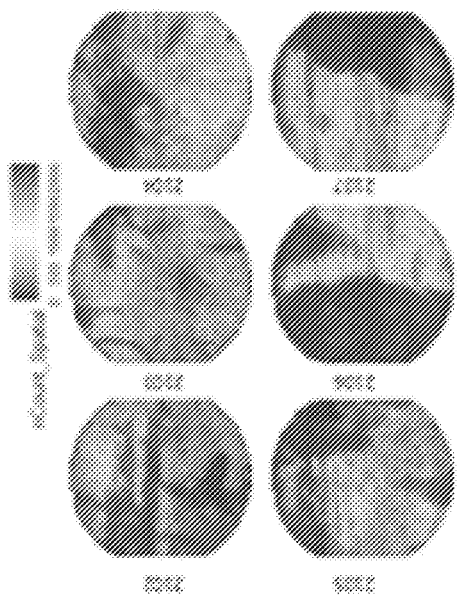
Figure 20R:
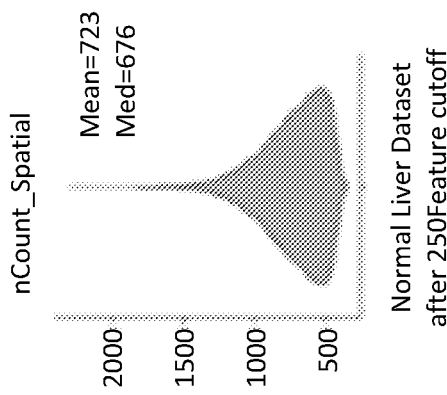
Figure 20S:
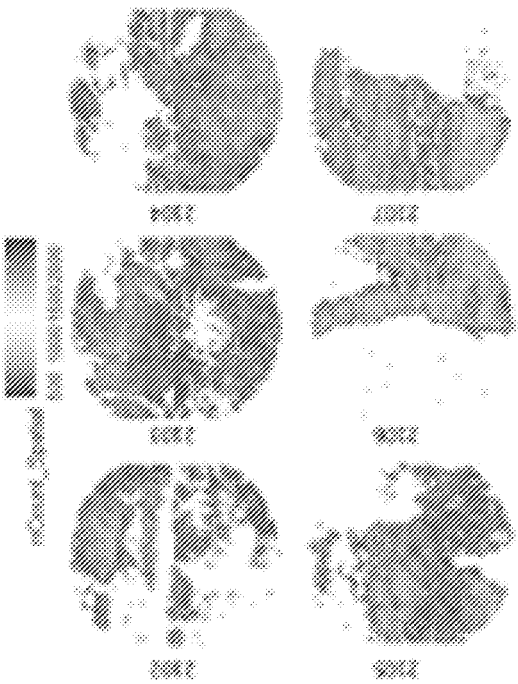

Using an image segmentation method (Sage and Unser, 2003), single hepatocellular areas were identified from the H&E image (FIGS. 12F and 15A). The single hepatocellular transcriptome from the segmented Seq-Scope data showed a substantial number of UMIs (4,294, median; 4,734±2,480, mean±SD) and genes (1,617, median; 1,673±631.7, mean±SD), which are comparable to the recent single hepatocyte transcriptome datasets obtained from MARS-Seq (Halpern et al., 2017) and DropSeq (Park et al., 2021) (FIG. 15B). The transcriptome content of Seq-Scope was similar to the results from the MARS-Seq, Drop-Seq, and Bulk RNA-seq analyses of the normal liver (FIGS. 20A-20E). Cell type mapping analysis of the segmented single hepatocyte dataset revealed the spatial structure of hepatocellular zonation, identifying both pericentral (PC) and periportal (PP) profiles (FIG. 20F), which were found in their corresponding spatial locations (FIG. 20G). PP- and PC-specific genes isolated from Seq-Scope were also found in MARS-Seq and Drop-Seq data (FIG. 20H). The top 50 PC/PP genes from Drop-Seq and MARS-Seq were sufficient to classify PC/PP cells in the Seq-Scope dataset (FIG. 20I). Therefore, Seq-Scope single-cell analysis agreed with the former scRNAseq results and revealed every single cell's actual spatial locations. A more detailed analysis of Seq-Scope data identified multiple transcriptome layers ordered across the portal-central zonation axis (FIG. 15C, FIG. 14D). Continuous mapping, instead of discrete clustering, also visualized a similar zonation pattern (FIG. 20K). Many of the cluster marker genes showed a spectrum of diverse zonation patterns between the PC and PP profiles (FIG. 15E). These gene expression patterns are consistent with the previous RNA in situ hybridization (Aizarani et al., 2019; Halpern et al., 2017) and immunostaining results (Park et al., 2021). However, previous studies using original ST (Hildebrandt et al., 2021) or Slide-Seq (Rodriques et al., 2019) were not able to uncover this level of detail (FIGS. 20L and 20M), possibly due to the limitations in resolution (FIG. 10F, FIG. 10G) and RNA capture efficiency (FIGS. 20N and 20O).

Figure 15F:
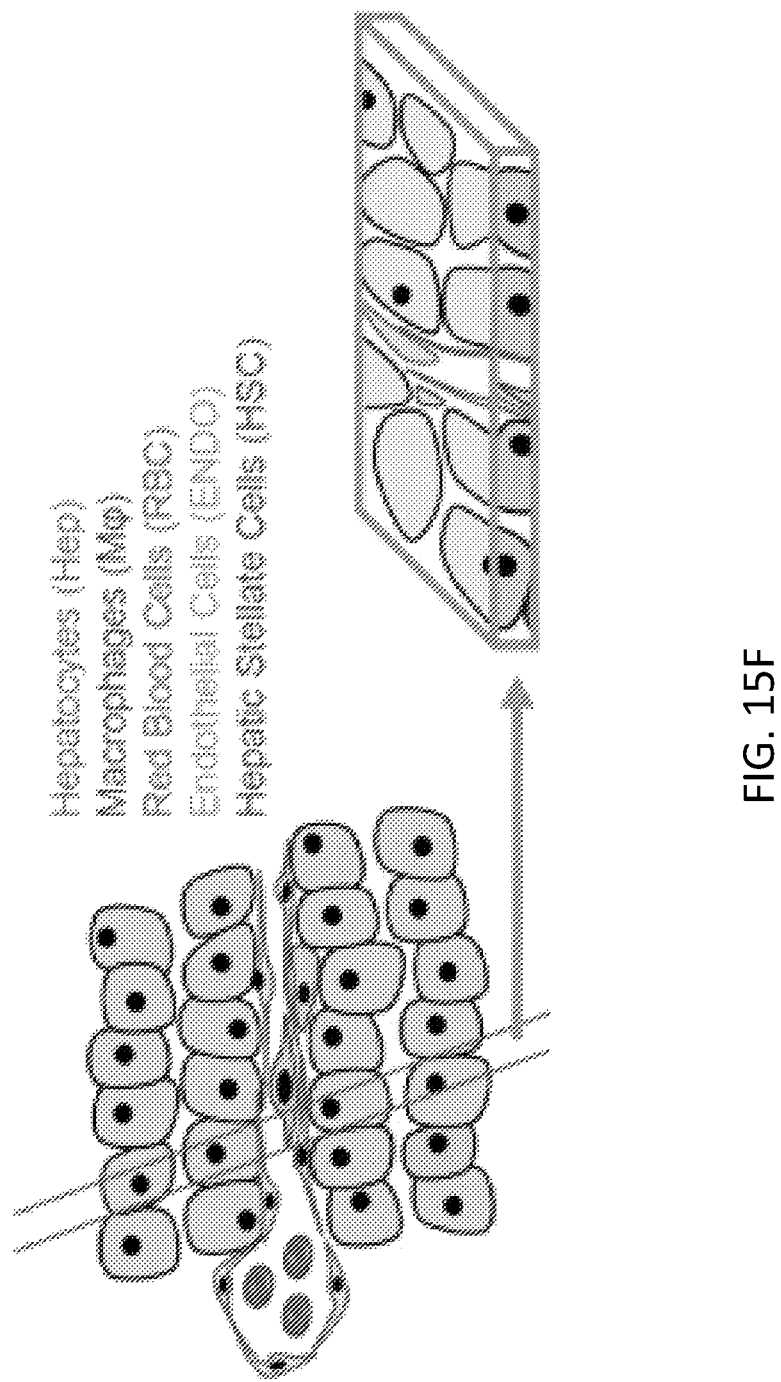
Figure 15G:
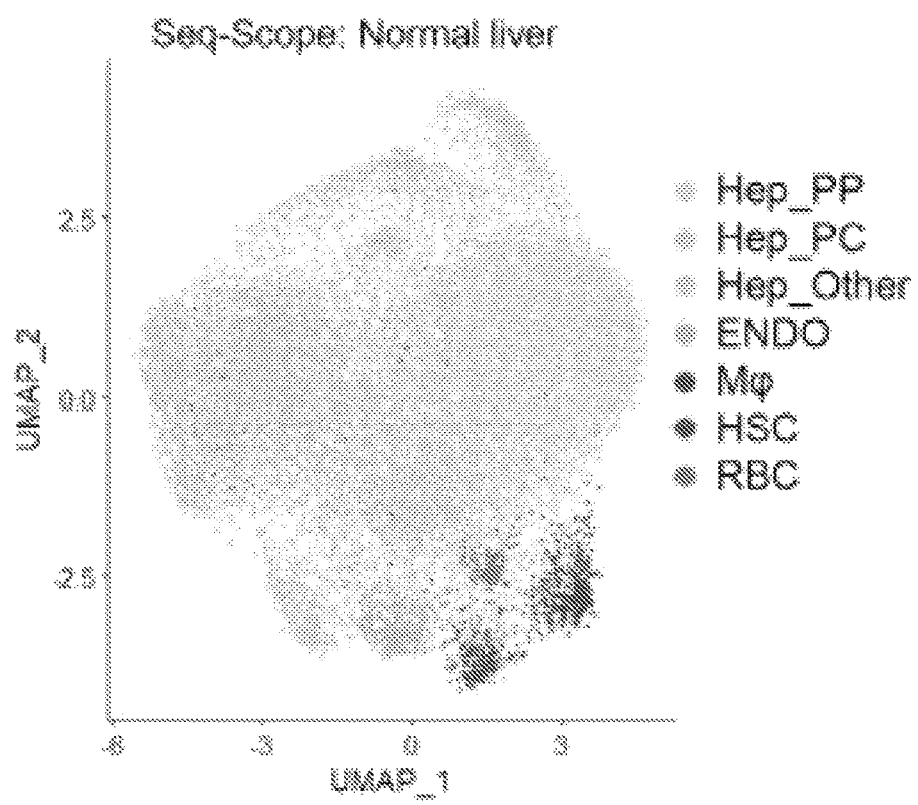
Figure 15H:
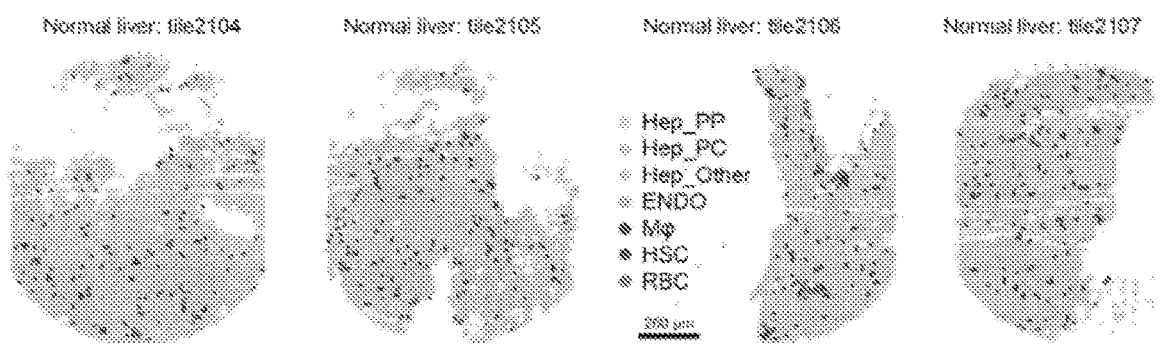
Figure 15I:
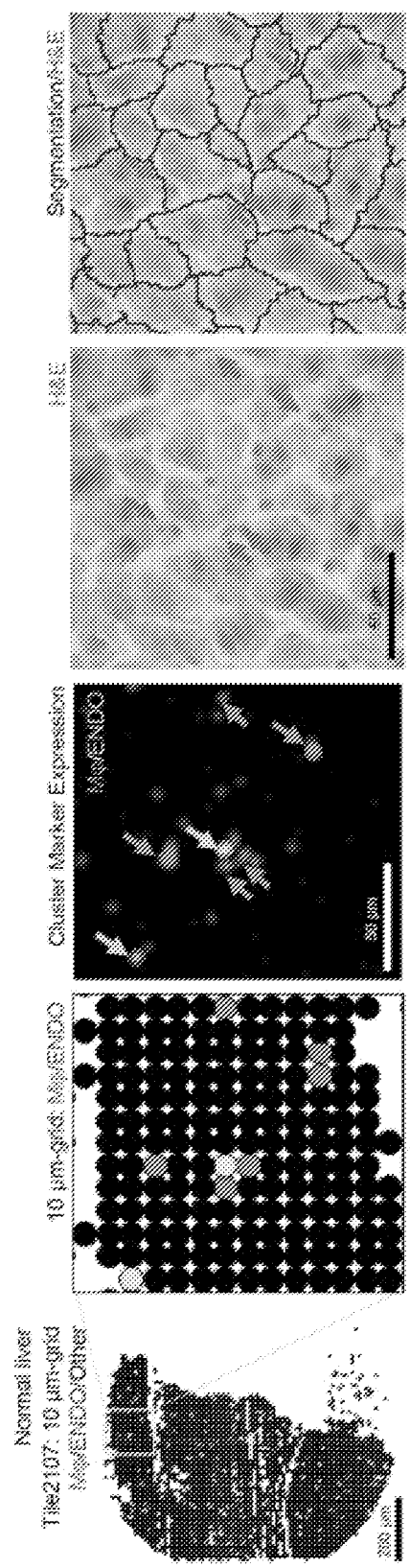
Figures 20T, 20U:
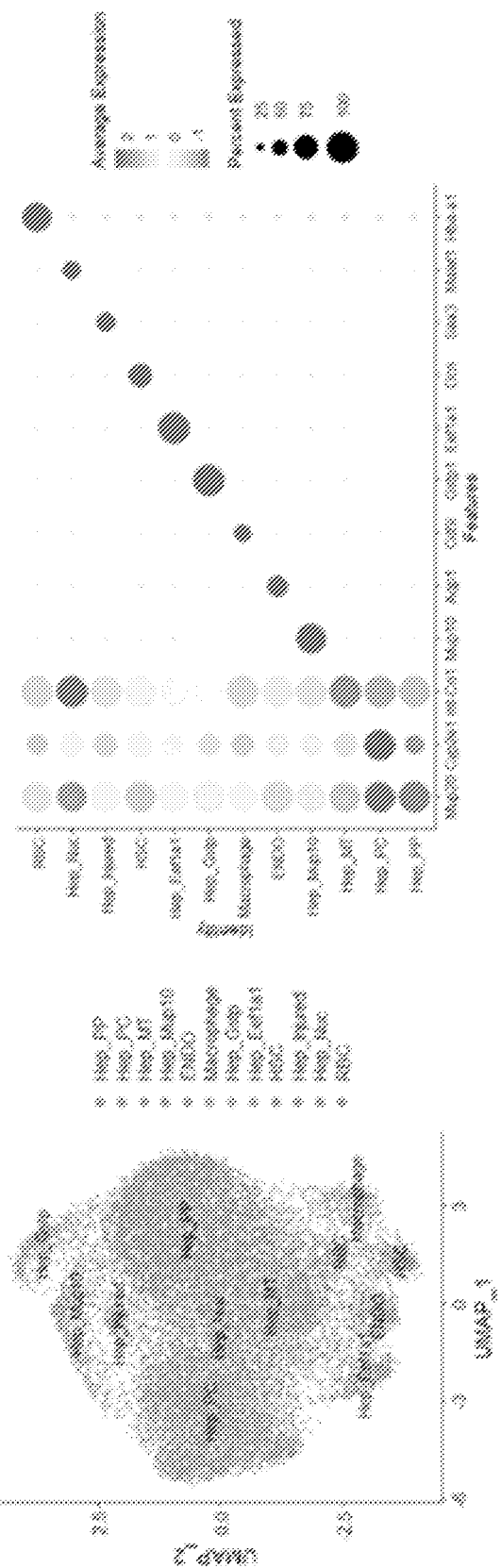
Figure 20V:
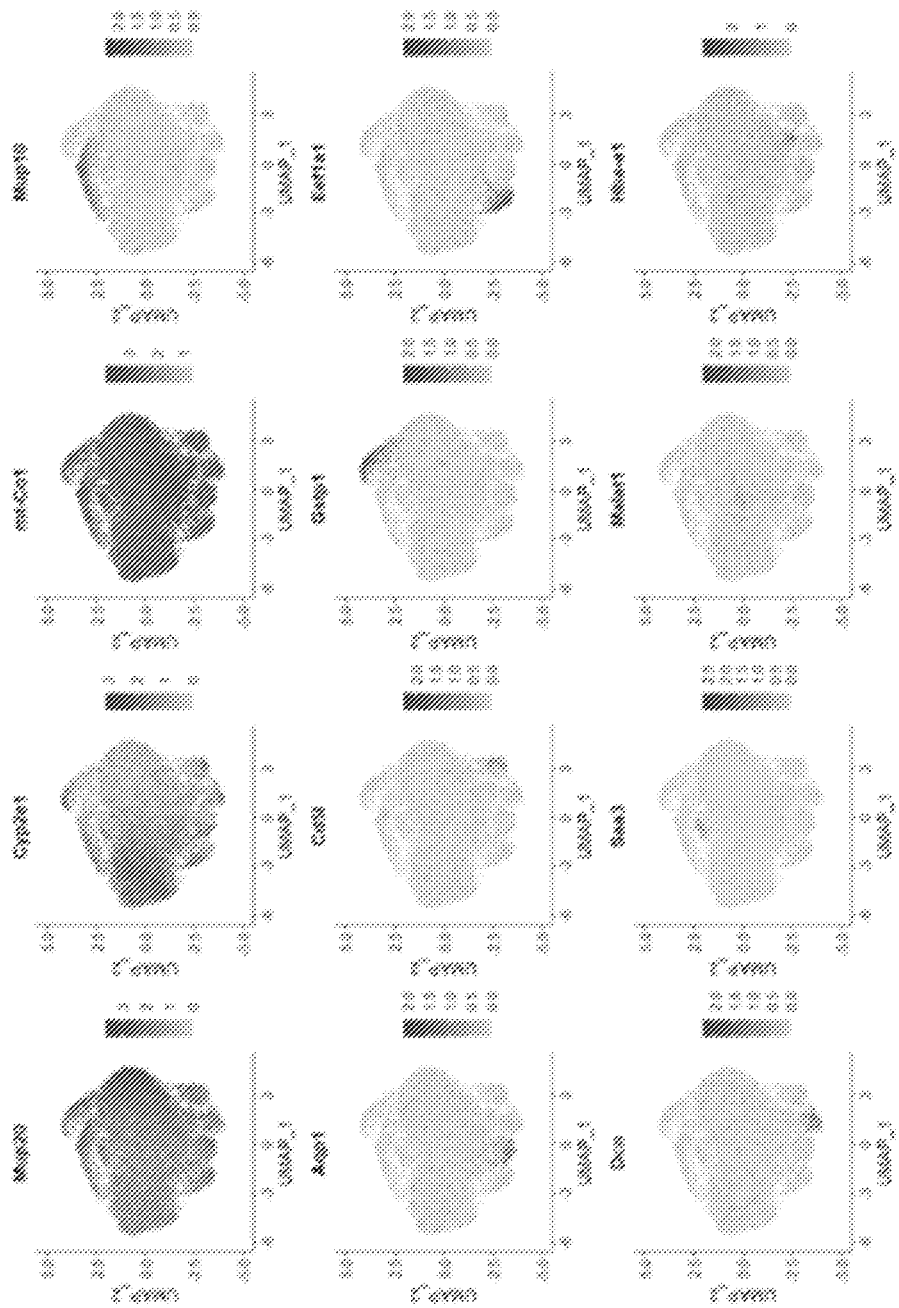
Figure 21A:
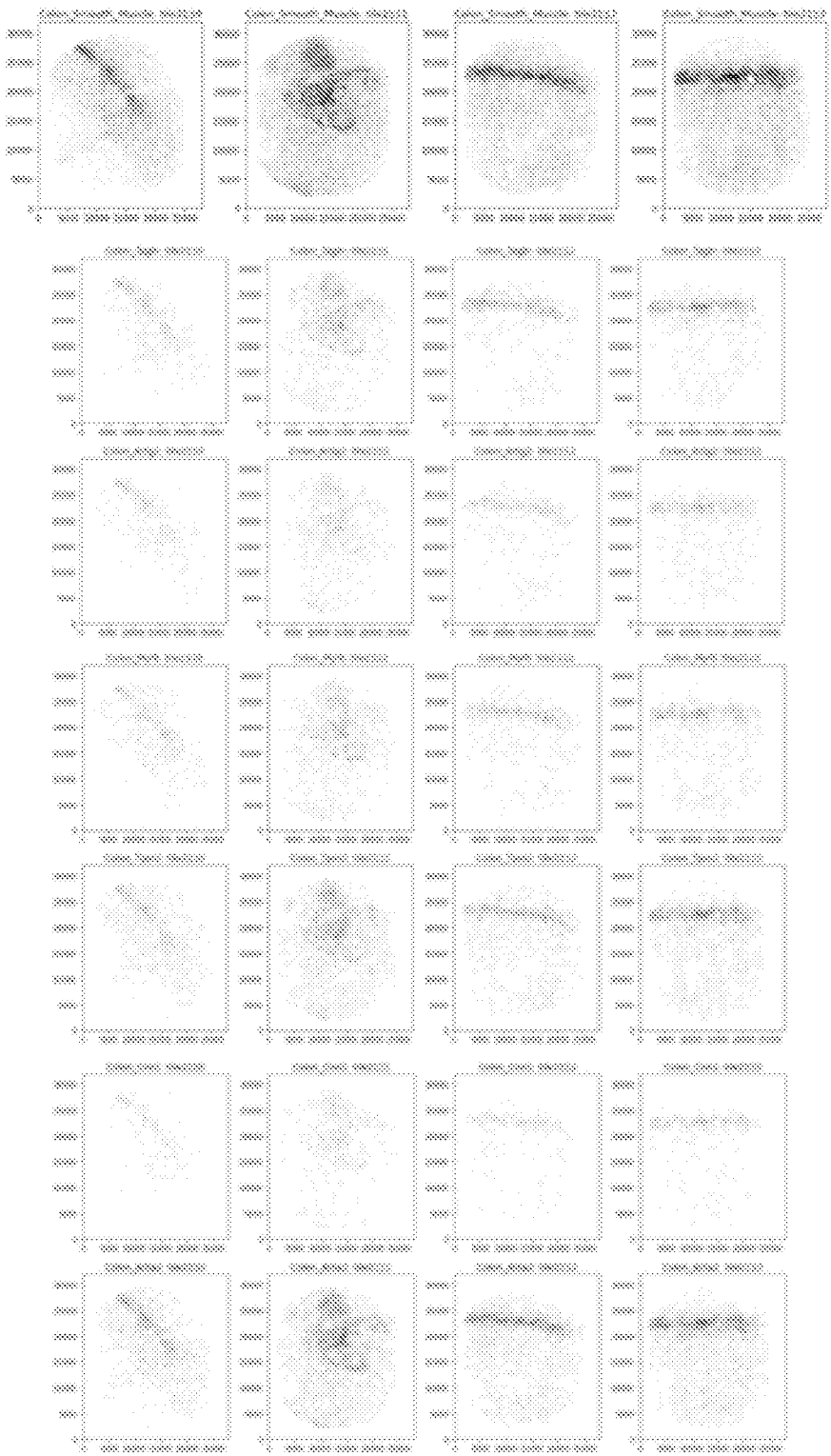
FIGS. 21A-J. Spatial Expression Patterns of Different Colonic Cell Type Markers.
Figure 21B:
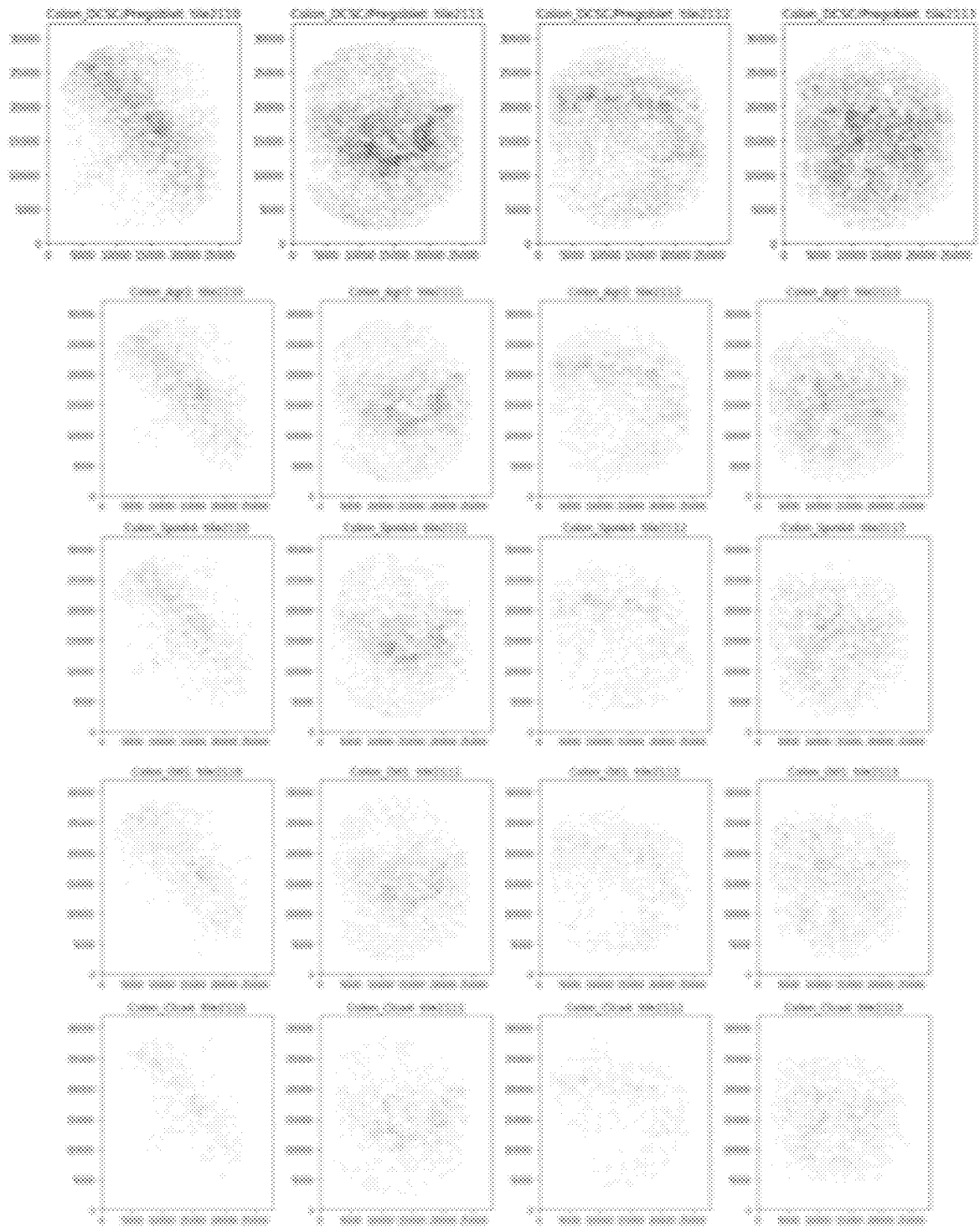
Figure 21C:
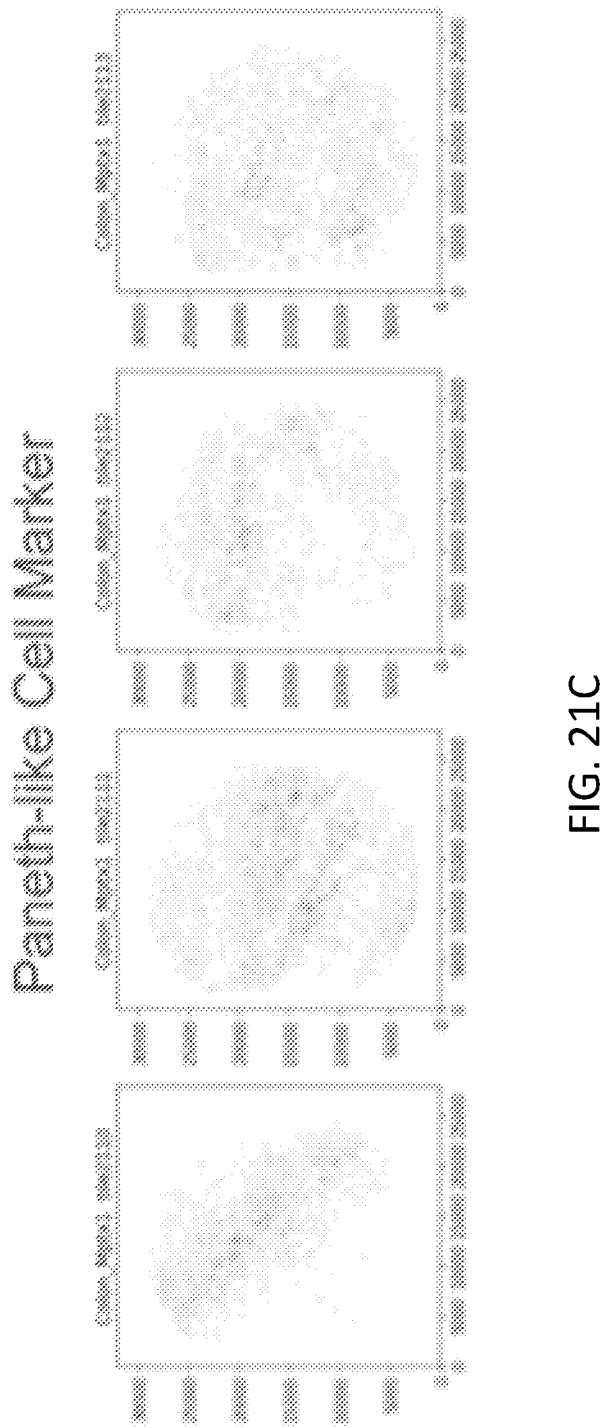
Figure 21D:
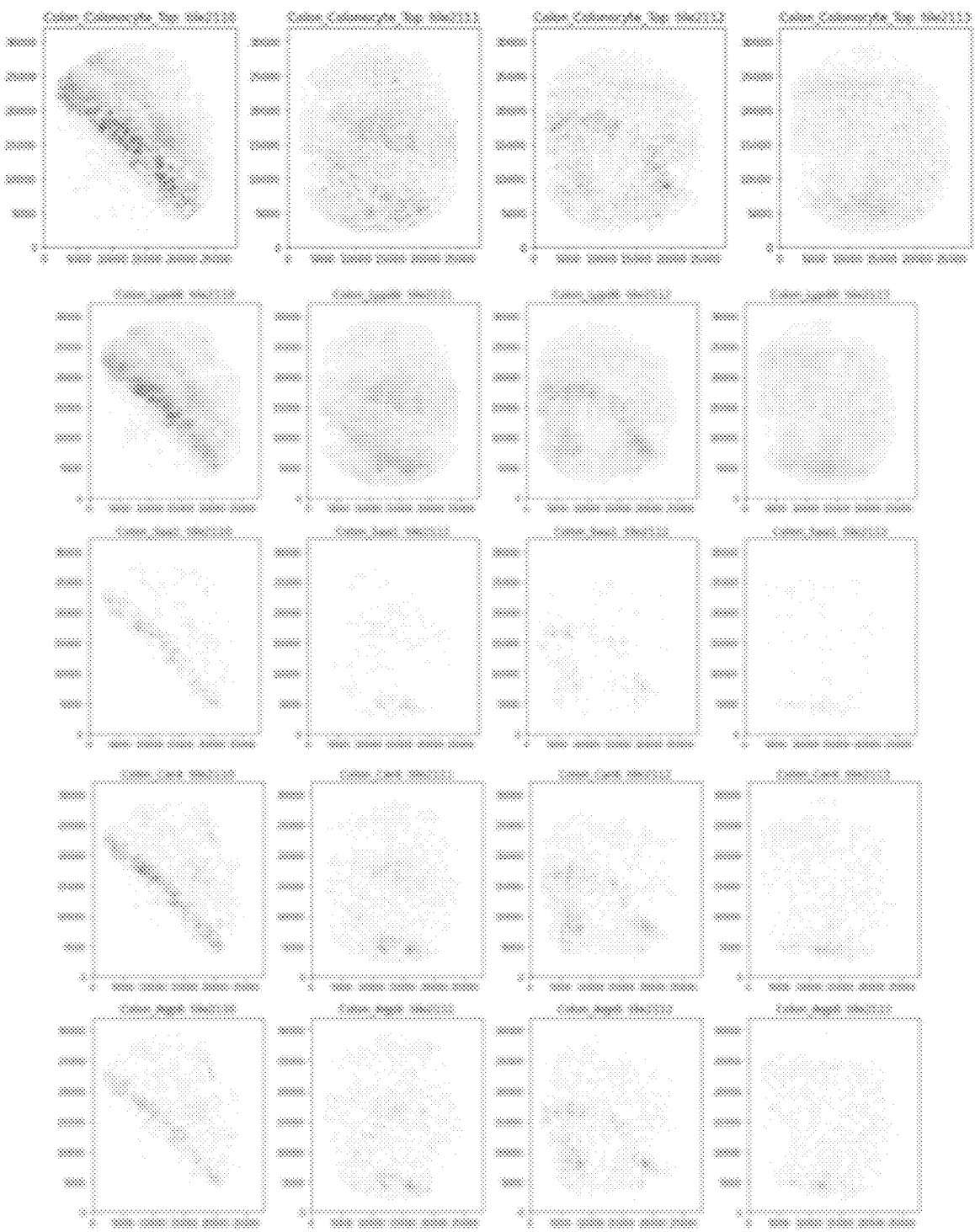
Figure 21E:
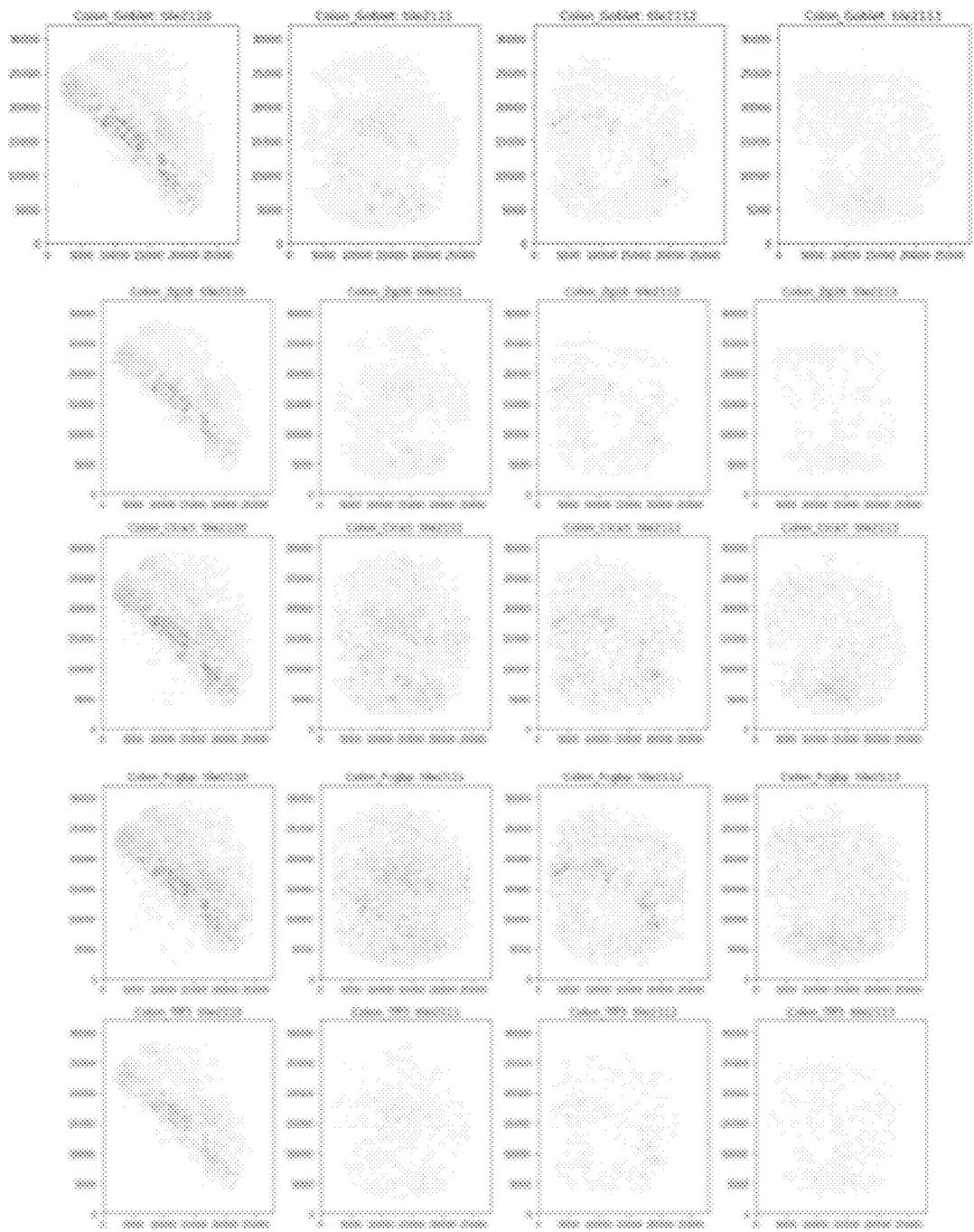
Figure 21F:
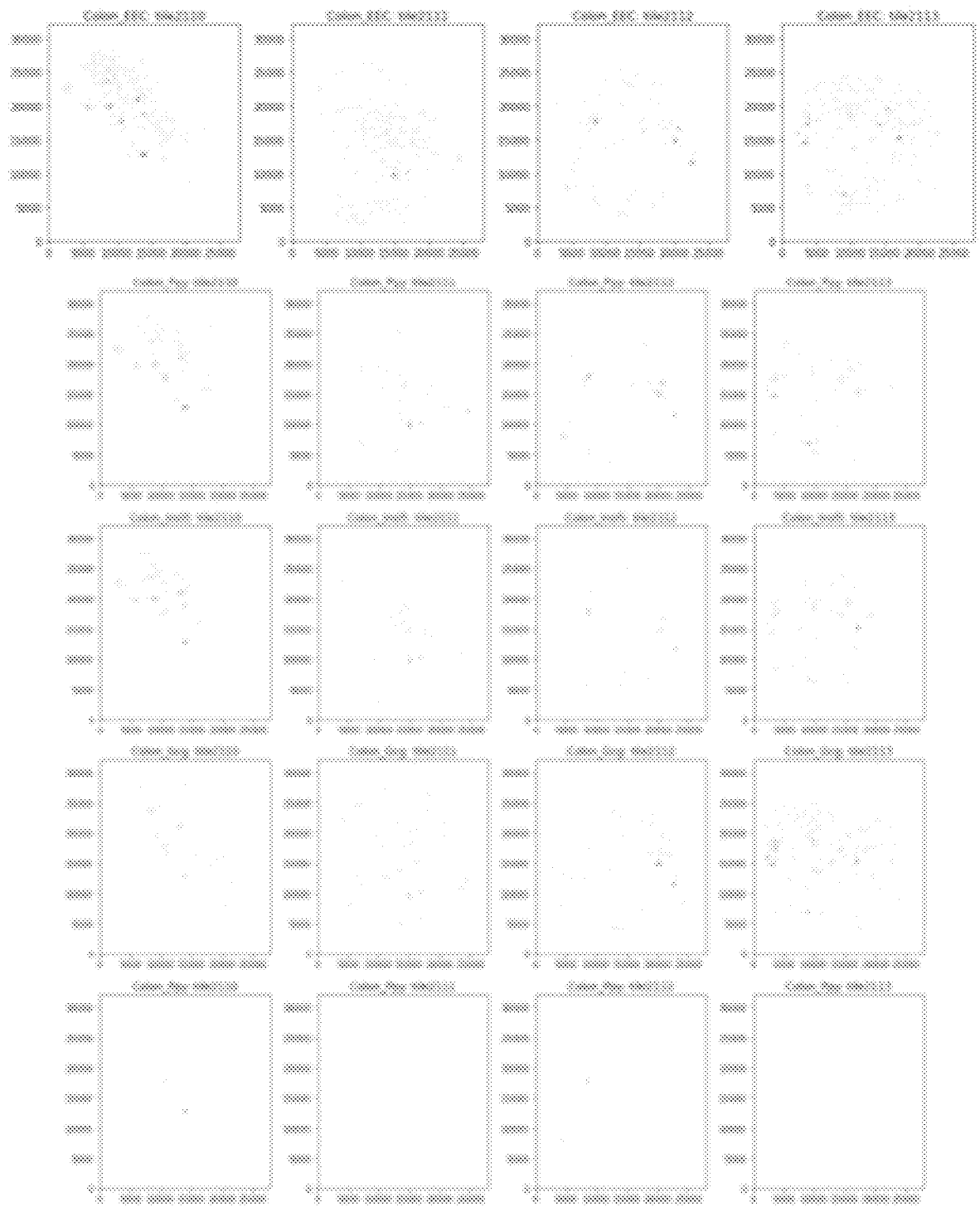
Figure 21G:
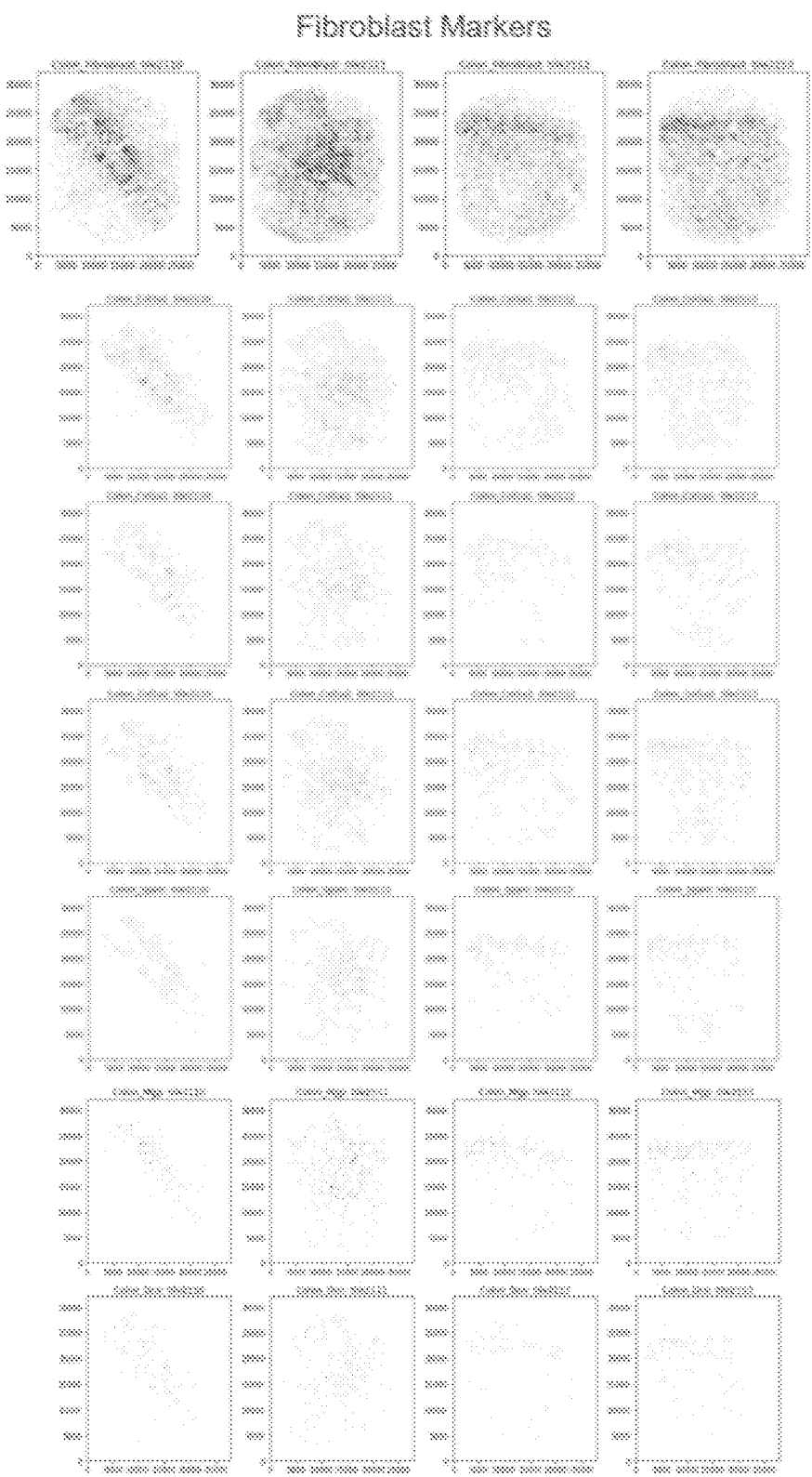
Figure 21H:
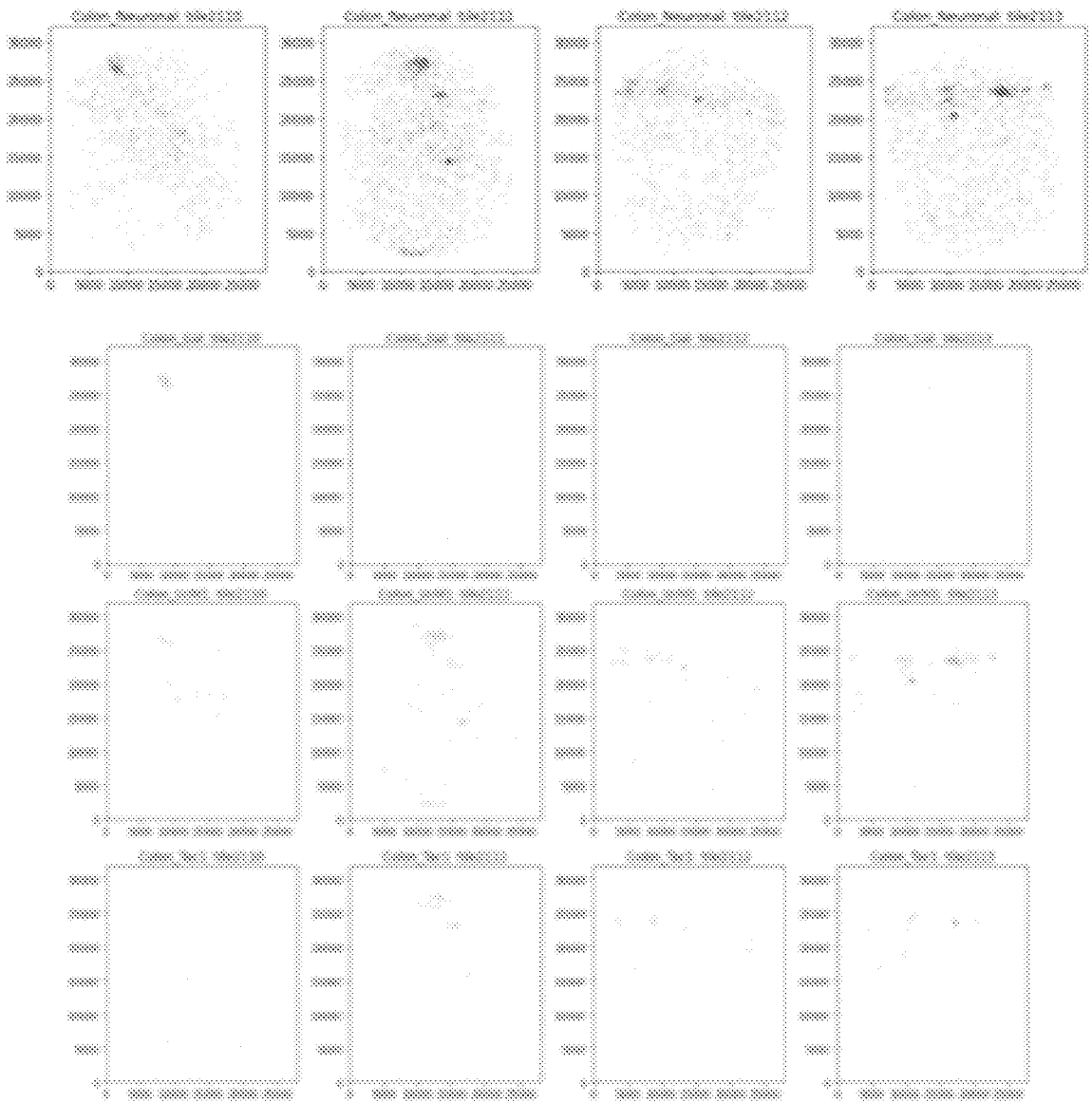
Figure 21I:
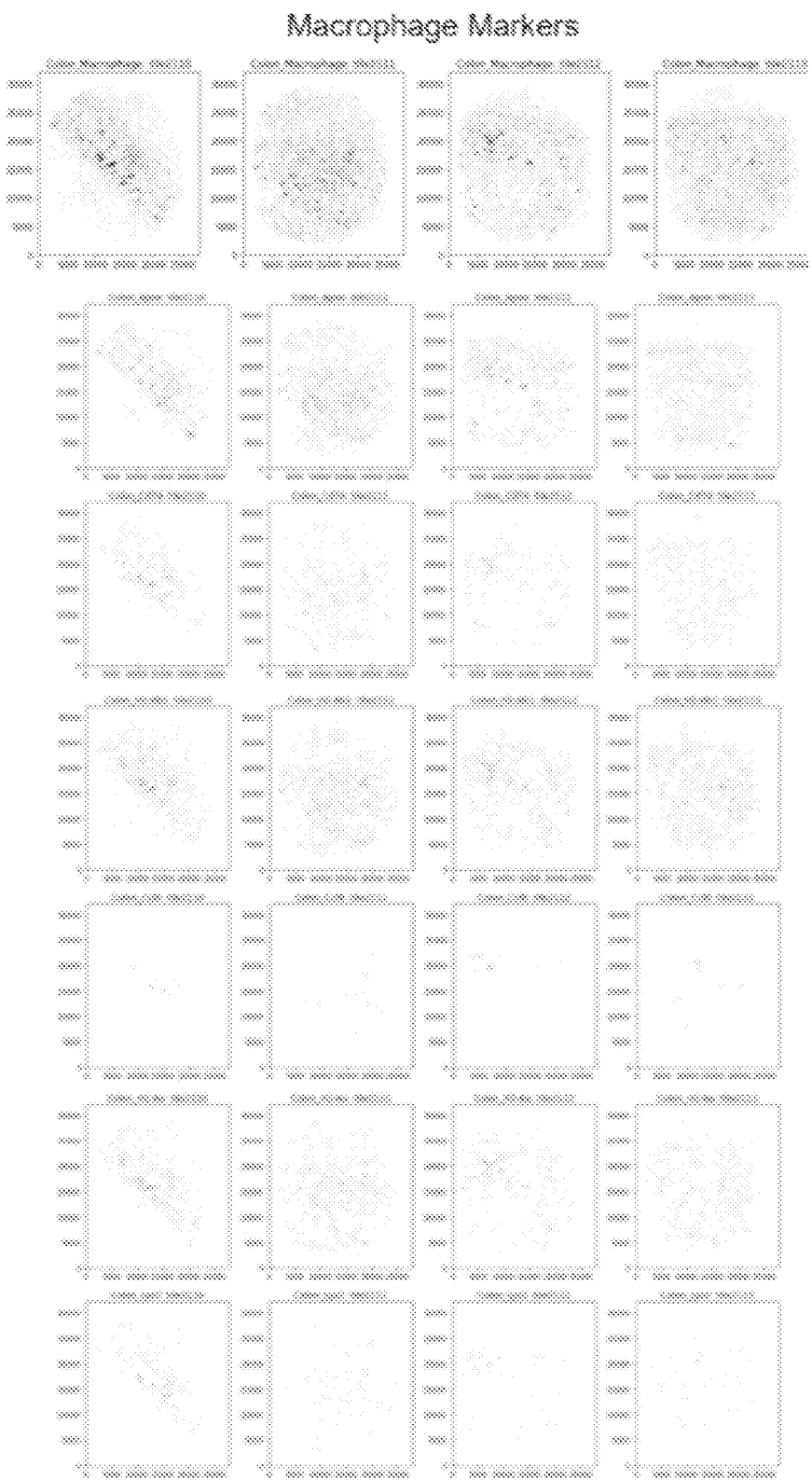
Figure 21J:
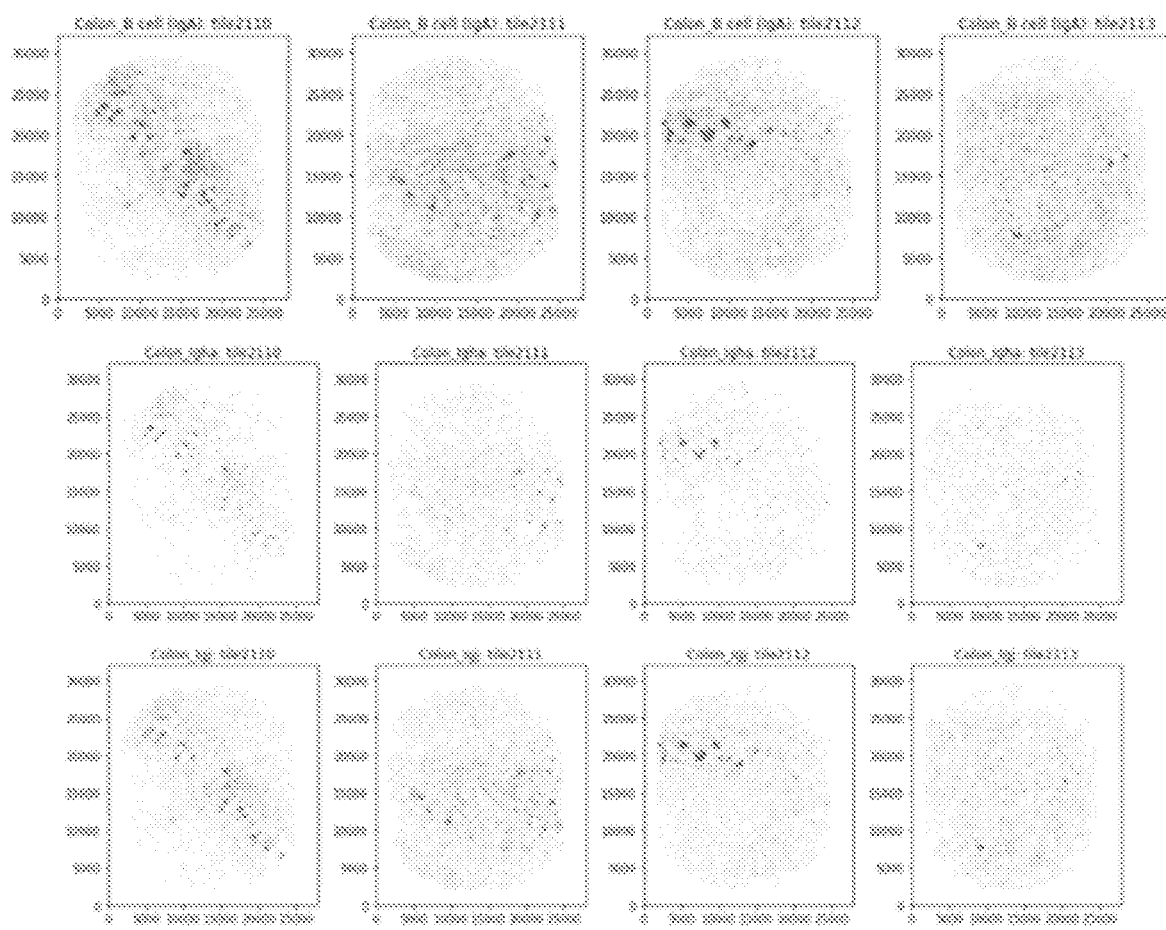

Seq-Scope detects non-parenchymal cell transcriptome from liver section Although hepatocytes are the major cellular component in the liver, non-parenchymal cells (NPC) such as macrophages (M4; blue), hepatic stellate cells (HSC; dark green), endothelial cells (ENDO; orange), and red blood cells (RBC; red) can be found in a small portion of the histological area (FIG. 15F) (Ben-Moshe and Itzkovitz, 2019). Due to their small sizes, these cells were not easily isolated through H&E-based image segmentation assays; H&E-based segmentation assay failed to reveal the NPC transcriptome except around the portal vein area (gray clusters in FIGS. 15C and 15D), where RBCs and M4s often accumulate in large quantities (Dou et al., 2020). Therefore, alternatively, the Seq-Scope dataset was segmented with a uniform grid consisting of 10 mm-sided squares (FIGS. 20P-20S). Cell-type mapping analysis of the gridded Seq-Scope dataset identified the grids that correspond to these NPC cell types (FIGS. 15G and 20T), based on the expression of cell-type-specific markers (FIGS. 20T-20V). Although most of the histological space was occupied by the hepatocellular area (Hep_PP and Hep_PC), the small and fragmented spaces scattered throughout the section represented the NPC area (FIG. 15H). The locations of the M4 and ENDO grids (FIG. 15I, first and second panels) were consistent with the spatial location of their corresponding cell-type-specific marker expression (FIG. 15I, arrows in the third panel) and the histologically identified M4 and sinusoid areas (FIG. 15I, arrows in the fourth panel) that are located around the segmentation boundaries (FIG. 15I, arrows in the fifth panel). Therefore, histology-guided cell segmentation analysis and histology-agnostic square gridding analysis complemented each other in identifying different cell types.

Identification of Hepatocyte Subpopulations undergoing Tissue Injury Response: Clustering also identified minor hepatocyte subpopulations expressing hepatocyte injury response genes (Saa1-3 and Cxcl9; FIG. 4L) [29, 30], a subset of major urinary proteins (Mup10, Mup14 and Mup7), a translation elongation factor (Eef1a1) that was formerly associated with hepatocarcinogenesis [31], and a subset of ribosomal proteins (Rpl15, Rpl35 and their matching pseudogenes). These clusters were spatially scattered throughout the liver sections (FIG. 14F), although the cluster expressing injury response markers showed a localized expression patterns. In spatial plotting analysis, expression of the liver injury markers substantially overlapped with Alb, confirming that they are hepatocyte subpopulations with altered transcriptome.

Processing the normal liver data through smaller grids, including 7 μm (FIG. 14G-14L) and 5 μm (FIG. 14M-14R) square grids, also robustly identified hepatocyte zonation, parenchymal/non-parenchymal cells and hepatocyte subpopulations, confirming that the observations described here are significant and reproducible.

Transcriptomic Details of Histopathology Associated with Liver Injury: Data presented above confirm that the described technique reveals the transcriptome heterogeneity and spatial complexity of the normal liver at various scales. To address whether this technique could also reveal pathological details of transcriptome dysregulation in diseased livers, the recently developed mouse model of early-onset liver failure that was provoked by excessive mTORC1 signaling was used [32]. This model (Tsc1$^{\Delta hep}$/Depdc5$^{\Delta hep}$ mice or TD mice) is characterized by a widespread hepatocellular oxidative stress, leading to localized liver damage, inflammation and fibrotic responses [32].

The cellular components of the TD liver were first evaluated using the gridded Seq-Scope dataset (FIG. 16A-16D). Most cell types identified from the normal liver, such as PP/PC hepatocytes and NPCs, were also discovered from the TD liver (FIG. 17A, FIG. 16E, and FIG. 16F).

Figure 16F:
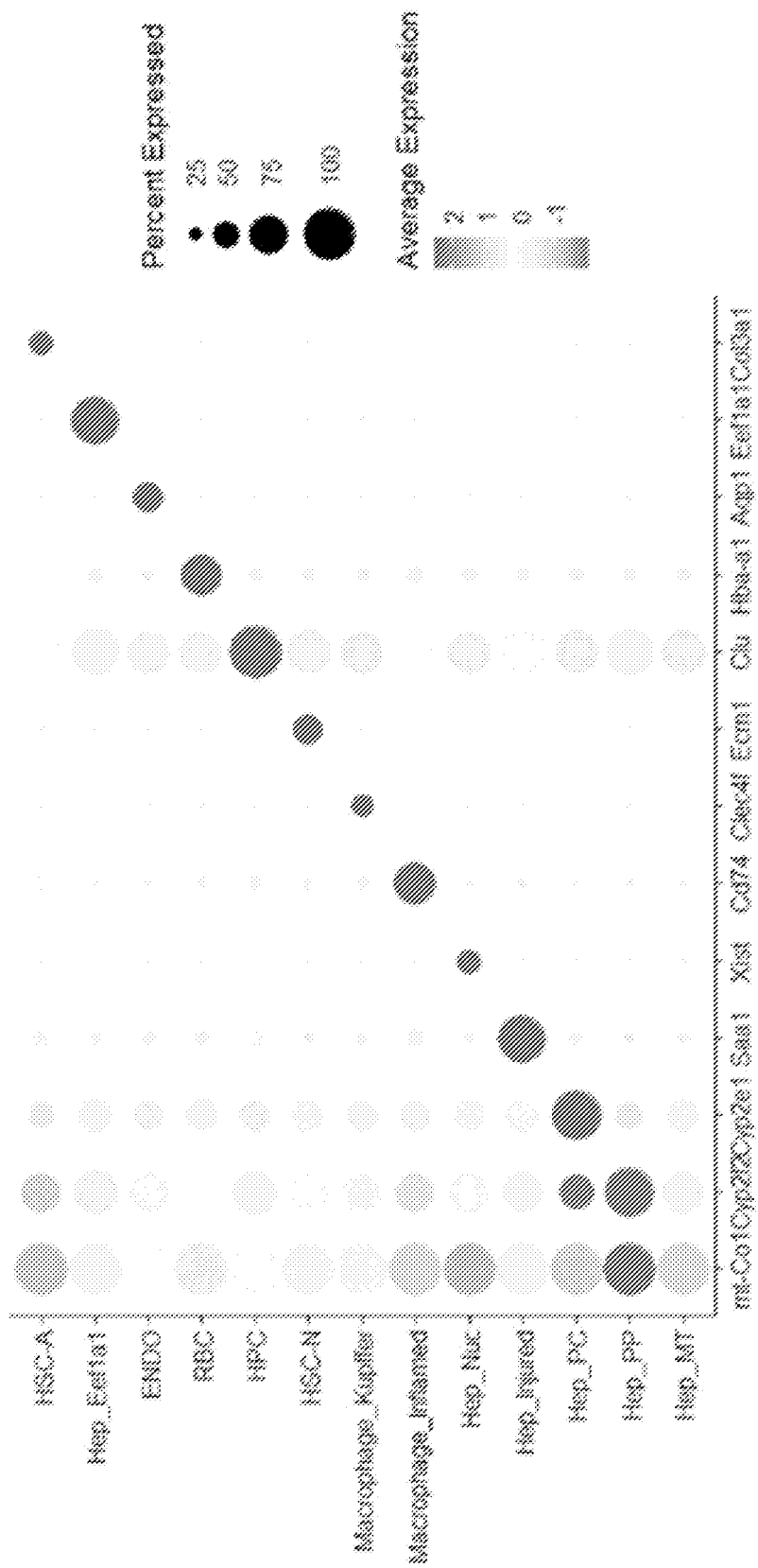
Figure 16G:
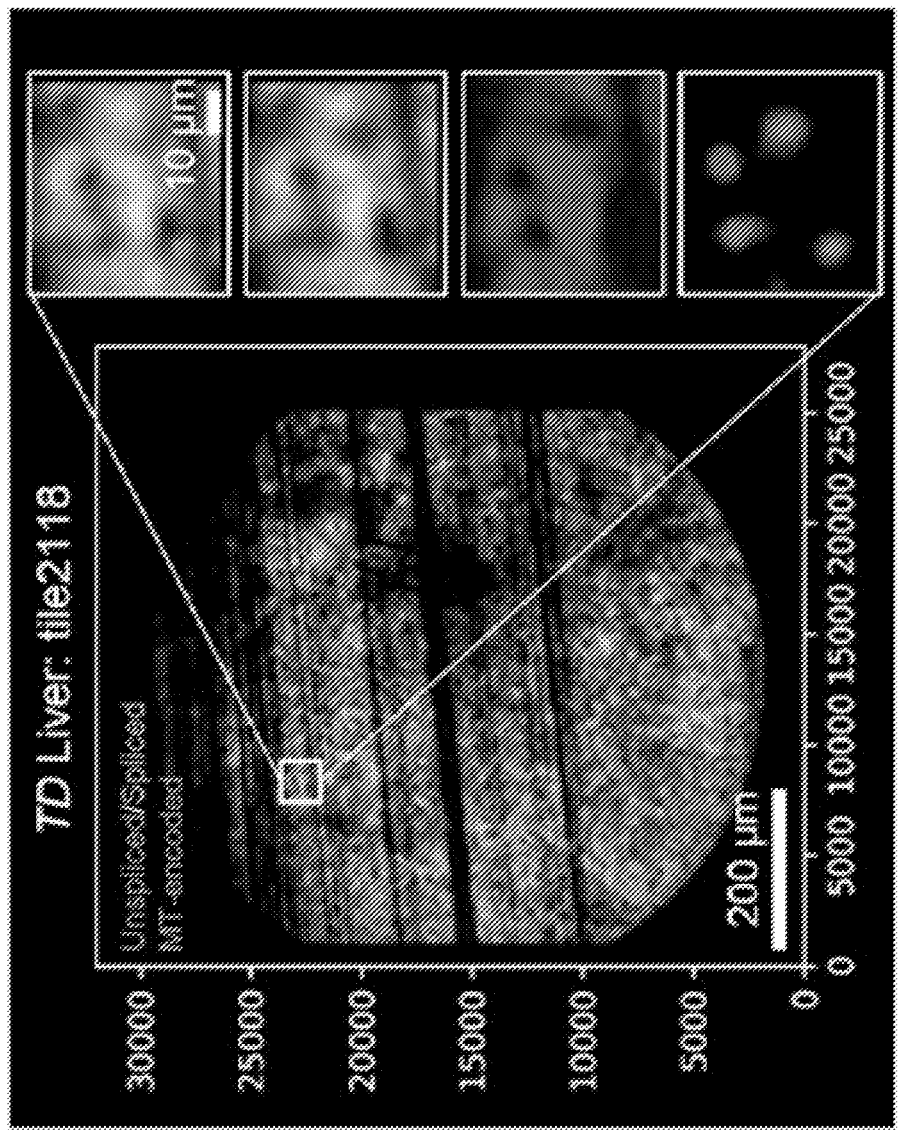
(FIG. 16G) Spatial plots of unspliced, spliced and mitochondrial transcripts visualize subcellular structures.
Figure 16H:
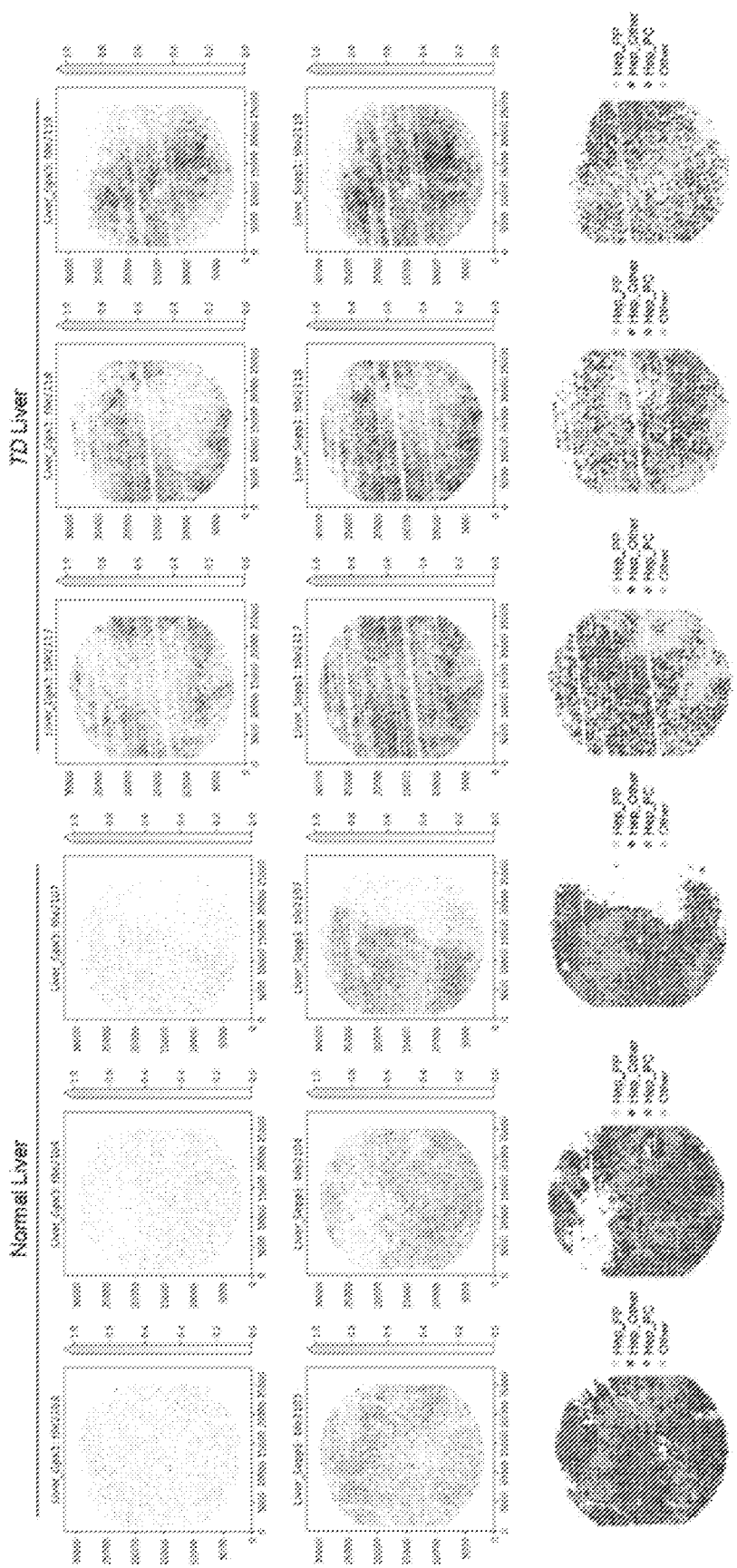
(FIG. 16H) Expression of oxidative stress-responsive genes, Gpx3 and Sepp1, was examined in normal and TD liver using spatial plotting. Hepatocyte zonation is plotted in the bottom panel as a reference. Gpx3 and Sepp1 were specifically induced in PP hepatocytes of TD liver.

Nuclear, cytoplasmic, and mitochondrial structures were also visualized through the spatial plotting of unspliced, spliced, and mtRNA transcripts, respectively (FIG. 16G). Former bulk RNA-seq results showed that the TD liver upregulates oxidative stress signaling pathways. Consistent with this, Seq-Scope identified that the TD liver expressed elevated levels of several antioxidant genes such as Gpx3 and Sepp1. Interestingly, induction of these genes was robust in PP hepatocytes, whereas the upregulation was not pronounced in PC hepatocytes (FIG. 16H). Therefore, the oxidative stress response of the TD liver was PP-specific.

In the TD liver, some NPC populations, such as M4s and HSCs, were greatly increased and differentiated into subpopulations. M4s were differentiated into homeostatic and inflamed populations (M4-Kupffer and M4-Inflamed). M4-Kupffer expressed Kupffer cell-specific markers such as Clec4f, whereas M4-Inflamed expressed pro-inflammatory markers such as Cd74 and MHC-II components (FIG. 17B). Likewise, HSCs were also differentiated into normal and activated HSCs (HSC-N and HSC-A). HSC-A exhibited elevated levels of fibrotic markers such as collagens and alpha-smooth muscle actins (Acta2). In contrast, HSC-N expressed a different set of extracellular proteins, such as Ecm1 and Dcn (FIG. 17B), which were also expressed by HSCs residing in the normal liver. The TD liver also exhibited emerging novel cell populations. Hepatocytes exhibiting injury responses (Hep_Injured) expressed serum amyloid proteins (FIG. 16F), a marker for liver injury. Although the Hep_Injured population was observed in a minor subset of normal liver hepatocytes (FIGS. 15C and 15D, black clusters, and 20T-20V), it became much more prevalent in the TD liver dataset (FIG. 17A and FIG. 16E).

Figure 16I:
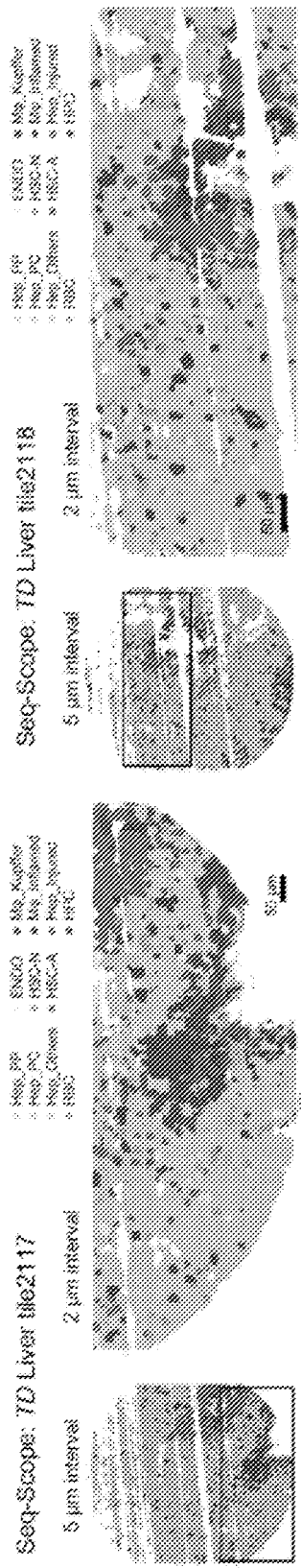
(FIG. 16I) Multi-scale cell type mapping analysis using sliding windows with 5 mm and 2 mm intervals.
Figure 16J:
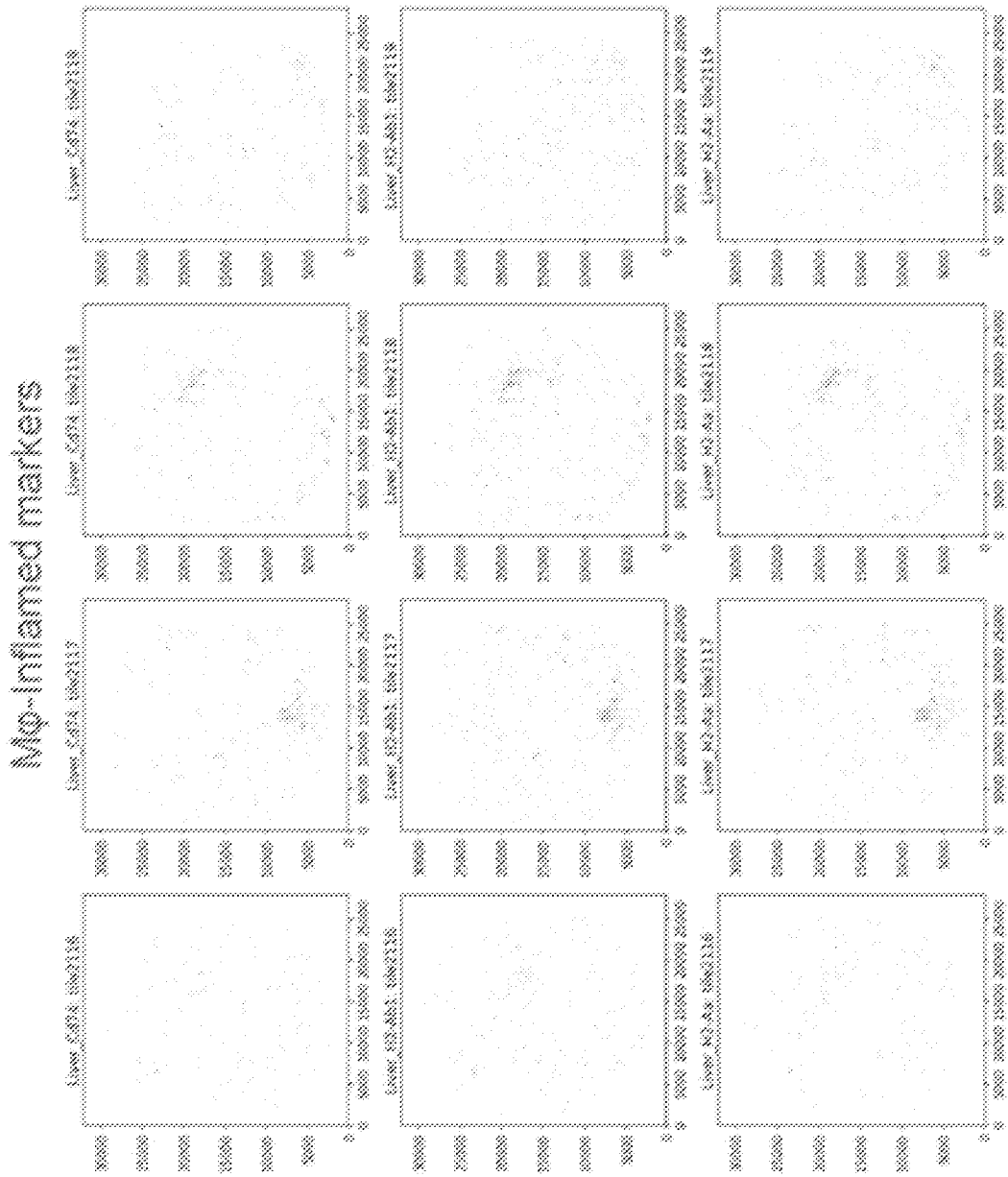
Figure 16K:
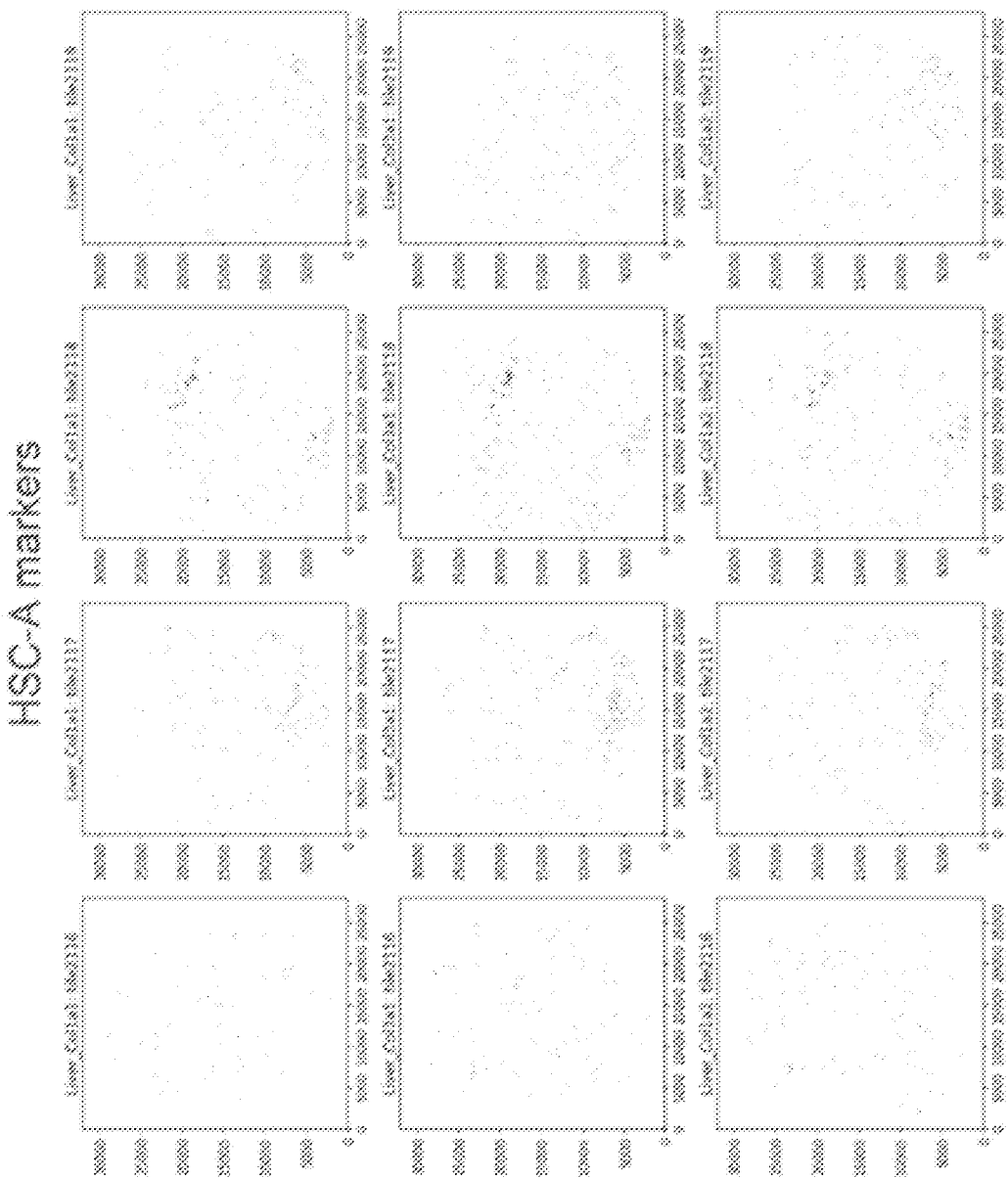
Figure 16L:
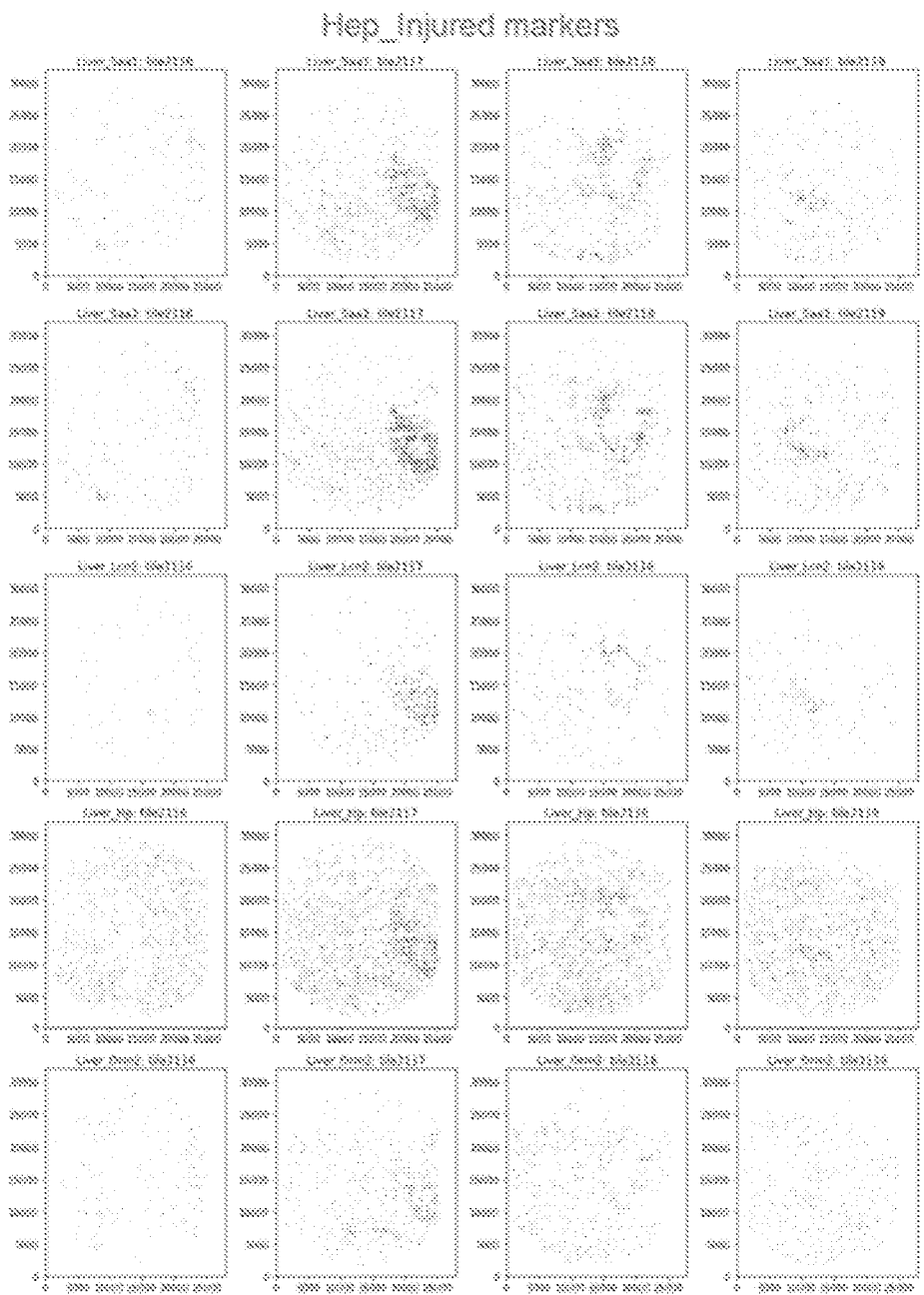
Figure 16M:
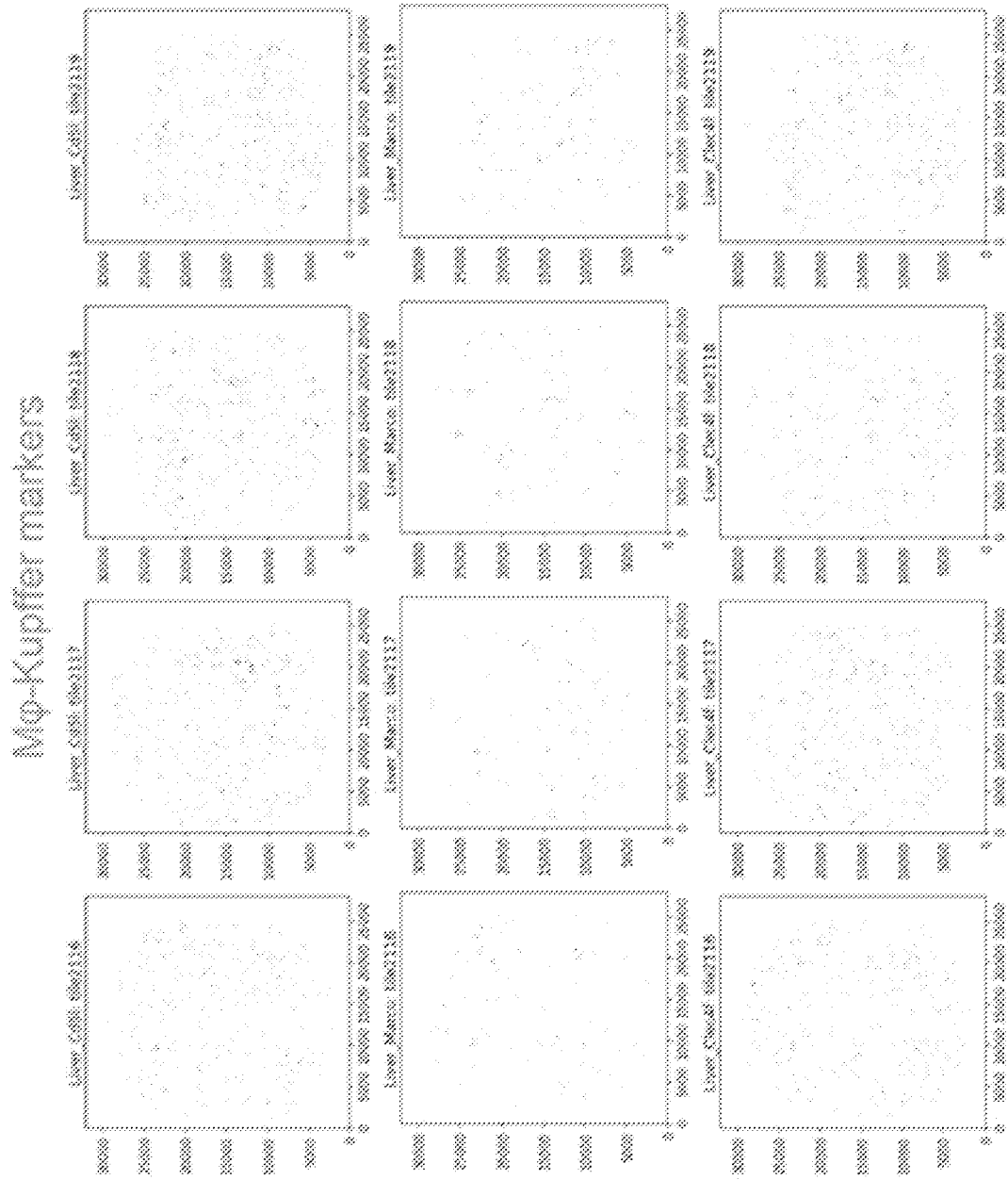
Figure 16N:
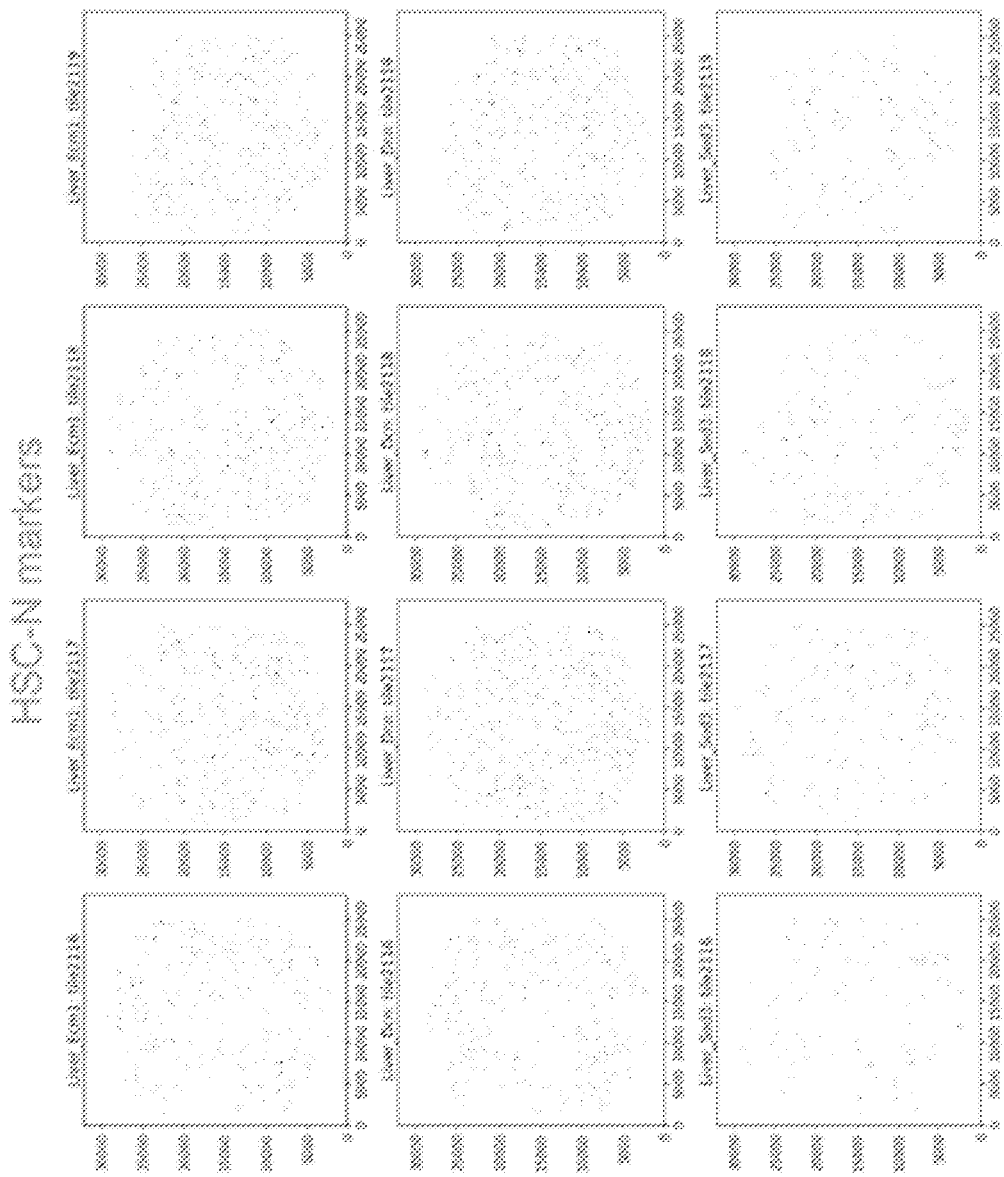
Figure 16O:
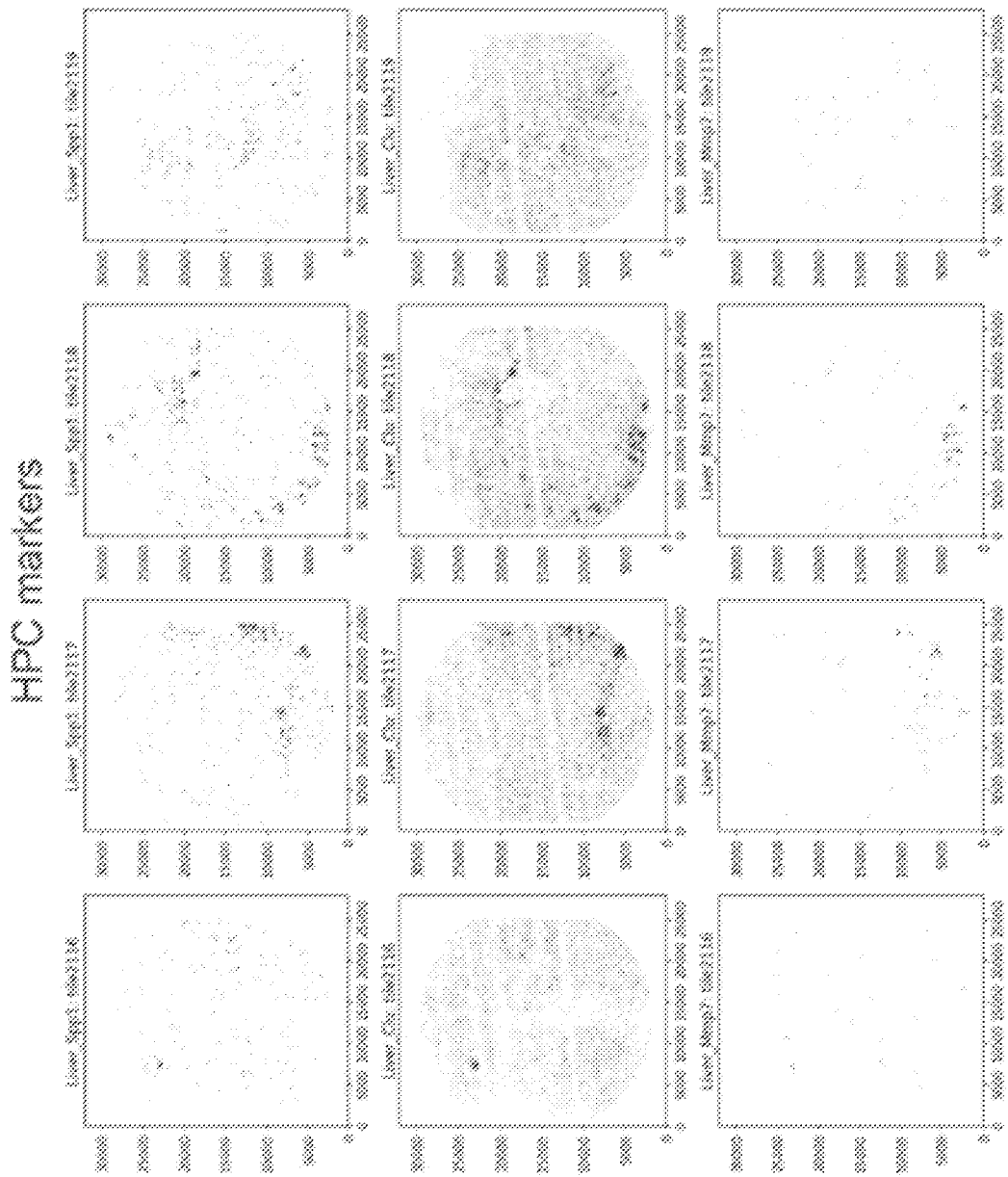

Hepatic progenitor cells (HPC) expressed a unique set of genes such as Clu, Mmp7, Spp1, and Epcam (FIG. 17B). Among these genes, Spp1 and Epcam were formerly reported to be expressed by injury-responding HPCs. Interestingly, these populations of M4-Inflamed, HSC-A, Hep_Injured, and HPC were concentrated around the injury and inflammation sites, identified from the H&E histology images (FIG. 17C; dotted rectangles). Therefore, it is likely that these cell types have an immediate pathophysiological connection with the liver injury observed in the TD liver. Through multiscale sliding windows analysis (see STAR Methods), a fine spatial map of different cell types was generated (FIG. 16I). The results indicated that dead hepatocytes (asterisks in FIGS. 17C-G) were surrounded by M4-Inflamed, which were subsequently surrounded by Hep_Injured (FIG. 17D). In contrast, M4-Kupffer was more uniformly distributed throughout the liver section (FIG. 17D). These observations are consistent with the spatial plotting of cell-type-specific markers (FIG. 17EE) and suggest the transcriptomic structure of liver injury histopathology (FIG. 17F).]

To independently confirm these observations through orthogonal technology, immunofluorescence confocal imaging of the cell-type-specific markers (Cd74, Saa1/2, and Clec4f) (FIGS. 17B and 16J-16O) was performed. The result revealed a similar histopathological structure (FIG. 17G) Cd74-positive cells surrounded the region where no live cells were found (yellow asterisks), and Saa1/2 marked the hepatocellular injury response around the inflamed region. The Kupffer cell marker Clec4f was not associated with the injury site and was scattered throughout the space (FIG. 17G). These results support the initial observations from the Seq-Scope data (FIGS. 17D-17F). TD liver also exhibits fibrotic responses. In the active fibrosis area, M4-Inflamed and HSC-A were very tightly intermingled with each other (FIGS. 17H and 17I). In contrast, M4-Kupffer did not show specific spatial interaction and could be found in both fibrotic and non-fibrotic areas (FIGS. 17H and 17I). These observations (FIG. 17J) were again reproduced with immunofluorescence imaging; the tight co-localization between M4-Inflamed and HSC-A (FIG. 17K), as well as the non-specific distribution of M4-Kupffer (FIG. 17L), were confirmed by visualizing Cd74, Acta2, and Clec4f proteins. In addition to HSC-A, HPCs also interacted with M4-Inflamed in the Seq-Scope data (FIGS. 17M and 17N), consistent with their known functional interactions. The interaction between HPC and M4-Inflamed was also observed in immunofluorescence imaging (FIG. 17O). These results highlight the utility of Seq-Scope in identifying cell types associated with specific histopathological structures and identifying their specific cell type markers. These results also demonstrate that Seq-Scope can reveal the microscopic structure of transcriptome phenotypes in a way similar to immunofluorescence microscopy.

Seq-Scope Visualizes Histological Layers of Colonic Wall

The colon is another gastrointestinal organ with complex tissue layers, histological zonation structure, and diverse cellular components. Using the colon, it was next examined whether Seq-Scope can examine the spatial transcriptome in a non-hepatic tissue. The colonic wall is histologically divided into the colonic mucosa and the external muscle layers. The colonic mucosa consists of the epithelium and lamina propria, and the epithelium is further divided into the crypt-base, transitional, and surface layers (FIG. 18A). Clustering analysis of the gridded Seq-Scope dataset (FIGS. 18A-18E) revealed transcriptome phenotypes corresponding to these layers (FIG. 18B) and visualized their spatial locations (FIGS. 18C and 18F).

Seq-Scope Identifies Individual Cellular Components from Colon Tissue

Figure 6A:
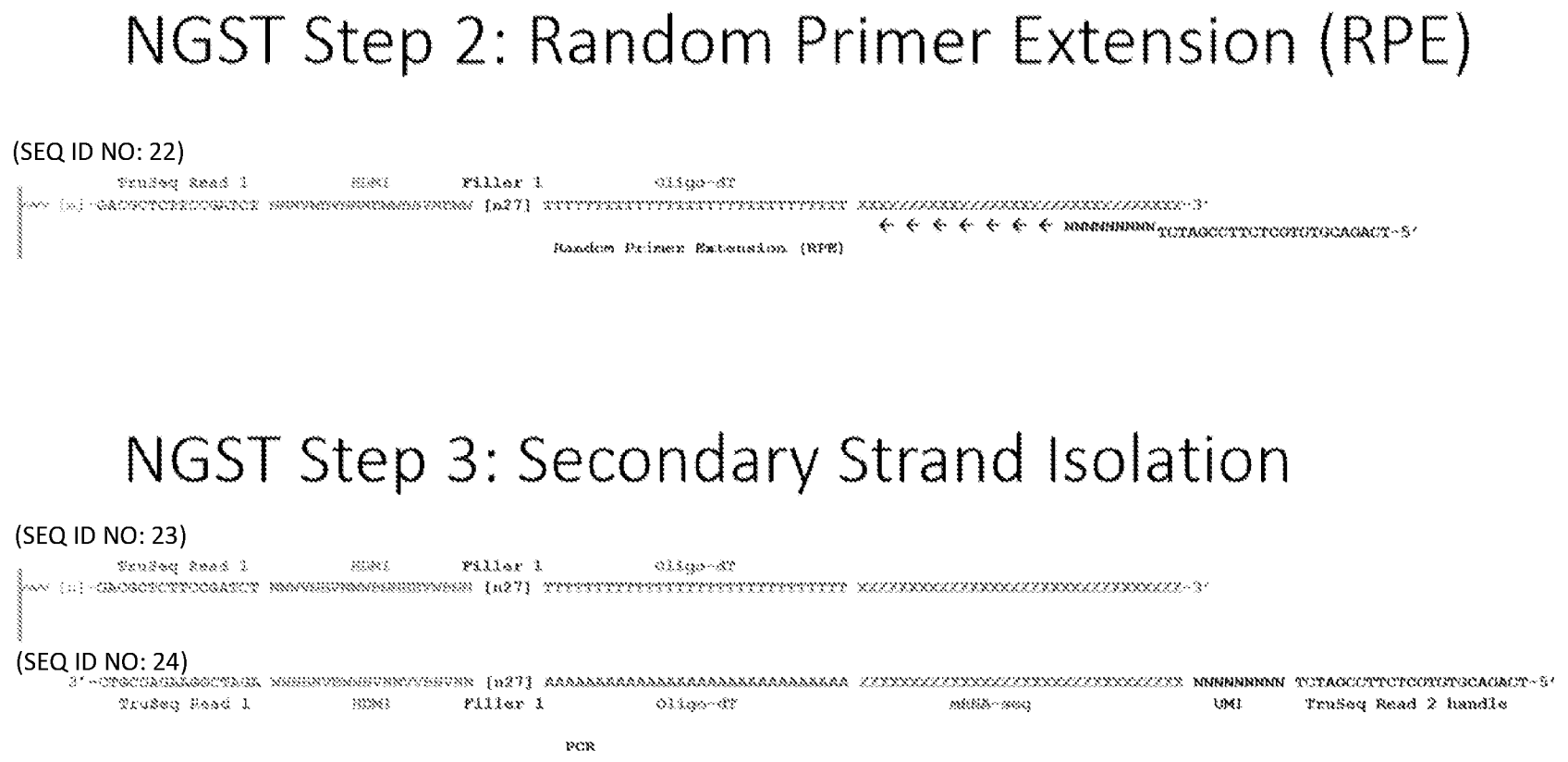

In addition to visualizing the layer structure, Seq-Scope also revealed the various colonic epithelial and non-epithelial cell types (FIGS. 18D-18I and 19F-19H). In the crypt base, stem/dividing, deep crypt secretory cell (DCSC) and Paneth-like cell phenotypes (FIGS. 18E, 18F, and 19G) were identified. The stem/dividing cells expressed higher levels of ribosomal proteins while expressing lower levels of other epithelial cell-type markers (FIG. 18J). DCSCs expressed secretory cell markers, such as Agr2, Spink4, and Oit1 (FIG. 18J), whereas Paneth-like cells expressed Mptx1, a recently identified marker of the Paneth cell in the small intestine. Seq-Scope also identified distinct cell types at the surface of the colonic mucosa (FIGS. 18D-18F). The top layer of the epithelial cells expressed surface colonocyte markers, such as Aqp8, Car4, and Saa1 (FIG. 18J). Some of the epithelial cells expressed goblet cell-specific markers, such as Zg16, Fcgbp, and Tff3 (FIG. 18J). In addition, Seq-Scope also identified enteroendocrine cells (EEC) expressing hormones, such as glucagon, peptide YY, insulin-like peptide, and CCK (FIG. 18J). Below the epithelium, there are connective tissue layers, including the lamina propria, submucosa, and external muscle layers. Seq-Scope identified many non-epithelial cell types from these layers, including smooth muscle, fibroblasts, enteric neurons, M4s, and B cells (FIGS. 18G-6I). These results indicate that Seq-Scope can transcriptomically recognize most of the major cell types present in the normal colonic wall.

Seq-Scope Performs Microscopic Analysis of Colonic Spatial Transcriptome

Figure 22A:
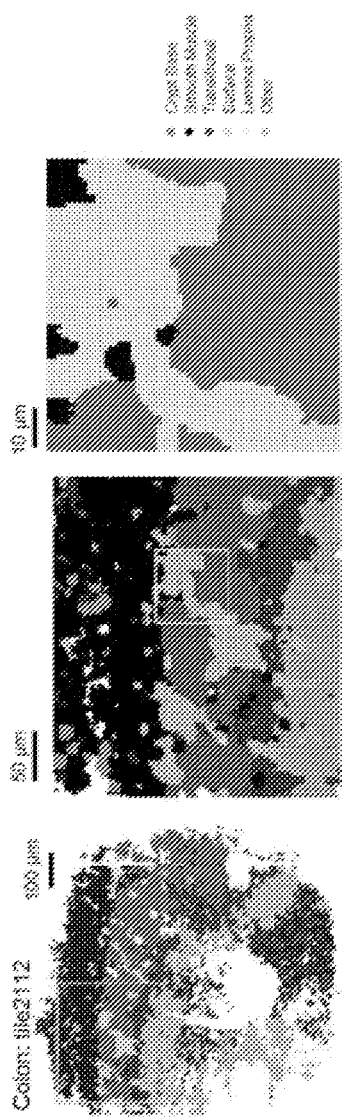
FIGS. 22A-H. Seq-Scope enables microscopic analysis of colon spatial transcriptome.
Figure 22B:
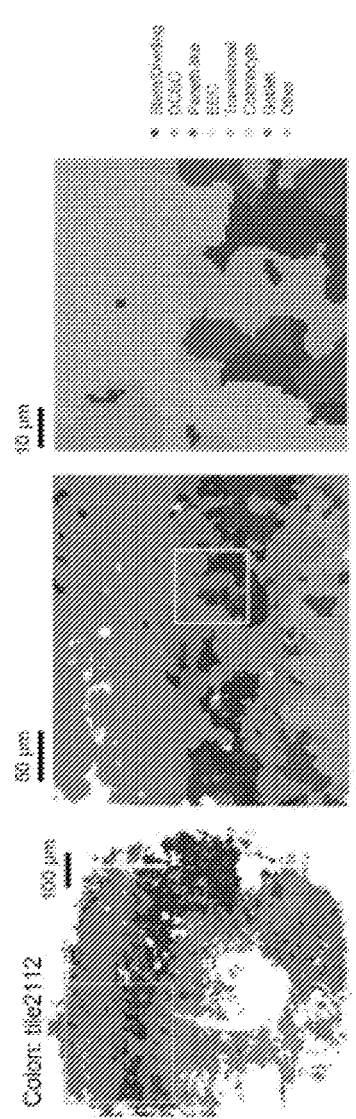
Figure 22C:
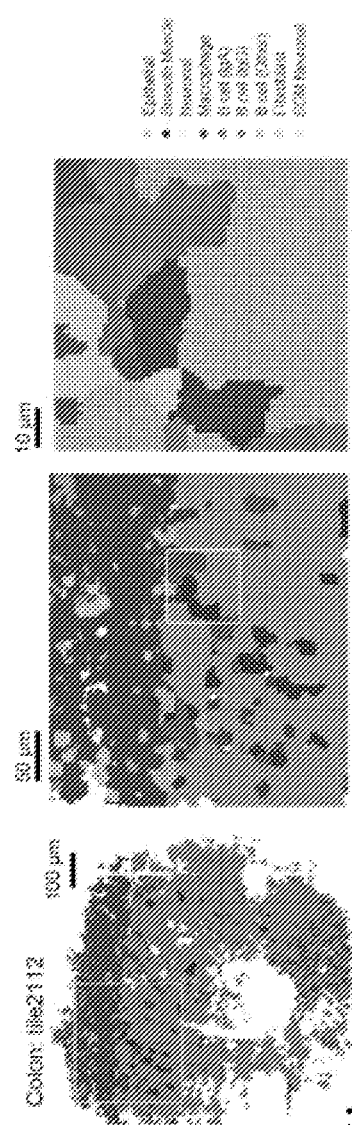
Figure 22D:
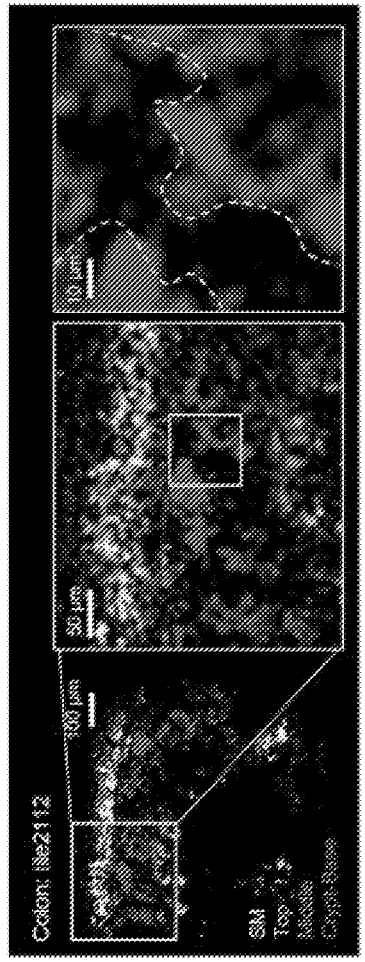
Figure 22E:
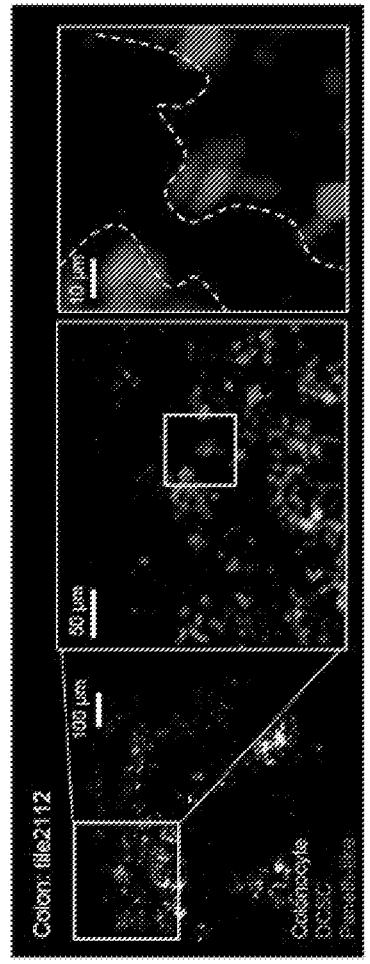
Figure 22F:
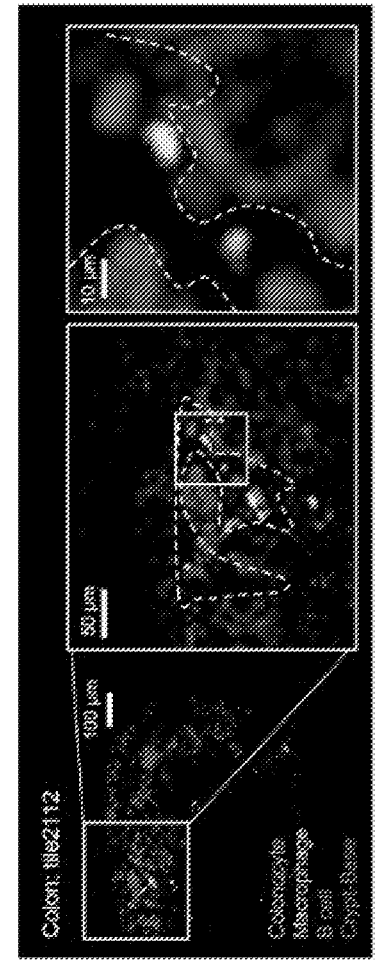
Figure 22G:
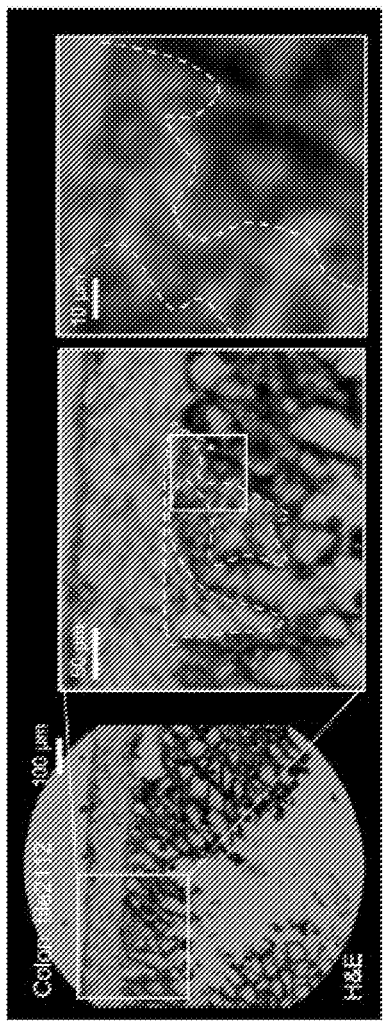
Figure 22H:
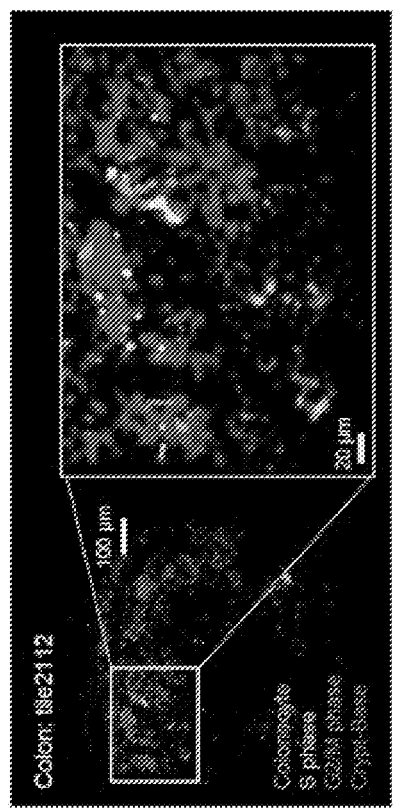

To take advantage of Seq-Scope's high-resolution data, a multiscale sliding windows analysis (FIG. 22A-C) and spatial plotting of cluster markers (FIG. 22D-7F and FIG. 21), focusing on the same region of the colonic wall. Multiscale sliding windows analysis drew a clear line between different cellular compartments (FIG. 22A-C); the original gridding analysis (10 mm) or analysis with smaller grids (5 mm) did not reveal this level of high-resolution detail. The sliding windows cluster assignments (FIG. 22A-C) were congruent with the spatial plotting of the relevant cluster marker genes (FIG. 22D-F) and H&E histology data (FIG. 22G). For instance, in all of these data, B cells and M4s were confined to the lamina propria, whereas crypt base cell markers were confined to the epithelium (separated by dotted lines in FIG. 22D-G). The B cells and M4s are often in very close proximity (FIG. 22C and FIG. 22F), likely due to their functional interactions (Spencer and Sollid, 2016). Genes specifically expressed in S and G2/M cell-cycle phases (Nestorowa et al., 2016) were highly expressed in the crypt base area where stem/dividing cells are located (Levine and Haggitt, 1989), however, their expression was lower in the surface area (FIG. 22H).

Discussion

The technology described herein is the only available molecular barcoding technology that can perform the microscopic examination of spatial transcriptome. The data presented here demonstrate that methods described herein are capable of visualizing histological organization of transcriptome architecture at multiple scales, including the gross tissue zonation level, cellular component level and even subcellular level. Due to its ultra-high resolution output, this technology was able to draw a clear boundary between different tissue zones, cell types and subcellular components. Previously existing technologies could not provide this level of clarity due to its low resolution output and/or inefficiency in transcriptome capture. In the current study, a single pixel area, which is below 1 $\mu m^2$, can capture up to 10-100 unique transcripts at just around 70% (liver) and 42% (colon) saturation of library examination, leading to approximately 1,000 unique transcripts per 100 $\mu m^2$ area. Therefore, in addition to providing an unprecedented sub-micrometer resolution, this technique can reveal high-quality transcriptome information. The high resolution and transcriptome output performances are the basis of how the technique described herein was able to visualize so many biologically-relevant ST features from liver and colon slides.

Several factors could have contributed to Seq-Scope's high transcriptome capture efficiency. First, the dense and tight arrangement of barcoded clusters in Seq-Scope could have increased the transcriptome capture rate because they almost eliminated "blind spot" areas between the spatial features. Second, unlike some methods that produce a bumpy array surface, Seq-Scope produces a flat array surface, enabling direct interaction between the capture probe and tissue sample. Third, solid-phase amplification, limited by molecular crowding, might have provided the two-dimensional concentration of RNA-capture probes ideal for the molecular interaction with tissue-derived RNA. Finally, biochemical strategies specific to our protocol, such as the secondary strand synthesis, retrieval, and amplification methods, could have increased the yield of transcriptome recovery.

Another benefit of the technique described herein is its scalability and adaptability. The MiSeq platform was used herein for the HDMI-array generation; however, virtually any sequencing platforms using spatially localized amplification, such as Illumina platforms including GAIIx, HiSeq, NextSeq and NovaSeq, could be used for generation of the HDMI-array. The established technologies for DNA sequencing could be repurposed to provide high-resolution spatial barcoding. For instance, although MiSeq has fragmented imaging areas that are limited to the 0.8 mm×1 mm rectangular space, HiSeq2500 (Rapid Run) and NovaSeq can provide approximately 90 $mm^2$ and 800 $mm^2$ of uninterrupted imaging area that can be used for HDMI-array production and sequencing. Newer sequencing methods, such as NovaSeq, are based on a patterned flow cell technology [49], which could provide a more defined and confident spatial information for the HDMI-encoded clusters. Furthermore, through these combinations, the field of view provided by the technique could be dramatically expanded.

In terms with the cost, current MiSeq-based HDMI-array can be generated at approximately $150 per $mm^2$. The cost could be reduced further down to $11 per $mm^2$ in HiSeq2500 or $2.6 per mm² in NovaSeq, based on the current cost of sequencing. 30- and 40-nucleotide random seed sequence could provide a 1 quintillion and 1 septillion barcode diversities, respectively, which should be enough for spatially barcoding the wide imaging area surfaces. In terms with turnaround time, the HDMI-array generation takes less than a day, and library preparation could be completed within two days (three days in total). The procedure is straightforward and not laborious or technically demanding; correspondingly, a single researcher can handle multiple samples at the same time. Therefore, the methods escribed herein can make ultra-high-resolution ST accessible for any types and scales of basic science and clinical work.

The methods provided herein have a potential to complement the current scRNA-seq approaches for solid tissues. scRNA-seq for solid tissues is seriously limited by tissue dissociation and single cell sorting procedures, which creates a very harsh condition for most types of cells. Labile cell populations in the solid tissue will lyse during tissue dissociation, and as a result, certain cell populations may be either over- or under-represented in the final dataset. Furthermore, there are many cell types, such as elongated myofibers and neurons, lipid-laden adipocytes and cells tightly joined by extracellular matrix and tight junctions, which are not amendable for conventional scRNA-seq analysis. Even the cell types that can survive through single cell dissociation and sorting may change their transcriptome substantially during the scRNA-seq procedures. For instance, gross tissue dissociation may activate injury and inflammation-associated gene signatures that are not observed in the cells' native conditions. By capturing transcriptome directly from a tissue slice, it is possible capture transcriptome signatures from such difficult types of cells. Indeed, the liver dataset revealed a couple of novel hepatocyte subpopulations undergoing tissue injury response, which were not formerly detectable through scRNA-seq of normal and diseased liver tissues [22-24]. This exemplifies the utility of this technique in identifying novel cell types from a solid tissue that were undetectable from traditional scRNA-seq; therefore, it also has a potential to complement and improve the existing scRNA-seq technologies.

Exposing the cluster surface was initially challenging. In the liver dataset, scratch-associated data loss was often observed due to the damages during disassembly. When generating the colon dataset, damage was minimized by protecting the HDMI-array with hydrogel filling. Therefore, the colon result was almost scratch-free and revealed higher numbers of UMI per area than the liver result.

Data binning with 10 mm grids performed well for identifying various cell types from the liver and colon datasets, whereas smaller grids did not perform well. To overcome this limitation and fully utilize Seq-Scope's high resolution, three independent approaches were employed: (1) histology-guided image segmentation assay for spatial single cell analysis, (2) multiscale sliding windows analysis for high-resolution cell type mapping, and (3) direct spatial plotting to monitor spatial gene expression at high resolution. The results from these analyses demonstrated the utility of Seq-Scope in performing high-resolution spatial single cell/subcellular analysis and identifying biological information that former technologies were unable to approach. These results also indicate that Seq-Scope has the potential to improve and complement current scRNA-seq approaches. scRNA-seq for solid tissues requires extensive tissue dissociation and single-cell sorting procedures. These procedures create very harsh conditions, which may eliminate labile cell populations and induce stress responses. Several cell types, such as elongated myofibers, lipid-laden adipocytes, and cells tightly joined by the extracellular matrix and tight junctions, are not amendable for conventional scRNA-seq. By capturing the transcriptome directly from a frozen tissue slice, Seq-Scope can capture single-cell transcriptome signatures from cell types that have previously been difficult to work with.

In sum, described herein are systems and methods that enables the transcriptome imaging at microscopic resolution. A single run of the method describe herein could produce microscopic imaging data that are equivalent to RNA in situ hybridization of 25,000 genes. This vast amount of information provided by this technique would not only accelerate scientific discoveries but may also lead to development of new paradigm in molecular diagnosis.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

Any patents and publications referenced herein are herein incorporated by reference in their entireties.

REFERENCES

1. Mazzarini, M., et al., *Evolution and new frontiers of histology in bio-medical research*. Microsc Res Tech, 2020.
2. Callea, F., et al., *From immunohistochemistry to in situ hybridization*. Liver, 1992. 12(4 Pt2):p.290-5.
3. Asp, M., J. Bergenstrahle, and J. Lundeberg, *Spatially Resolved Transcriptomes—Next Generation Tools for Tissue Exploration*. Bioessays, 2020. 42(10): p. e1900221.
4. Liao, J., et al., *Uncovering an Organ's Molecular Architecture at Single-Cell Resolution by Spatially Resolved Transcriptomics*. Trends Biotechnol, 2020.
5. Crosetto, N., M. Bienko, and A. van Oudenaarden, *Spatially resolved transcriptomics and beyond*. Nat Rev Genet, 2015. 16(1): p. 57-66.
6. Bergenstrahle, J., L. Larsson, and J. Lundeberg, *Seamless integration of image and molecular analysis for spatial transcriptomics workflows*. BMC Genomics, 2020. 21(1): p. 482.
7. Salmen, F., et al., *Barcoded solid-phase RNA capture for Spatial Transcriptomics profiling in mammalian tissue sections*. Nat Protoc, 2018. 13(11): p. 2501-2534.
8. Stahl, P. L., et al., *Visualization and analysis of gene expression in tissue sections by spatial transcriptomics*. Science, 2016. 353(6294): p. 78-82.
9. Stickels, R. R., et al., *Highly sensitive spatial transcriptomics at near-cellular resolution with Slide-seqV2*. Nat Biotechnol, 2020.
10. Vickovic, S., et al., *High-definition spatial transcriptomics for in situ tissue profiling*. Nat Methods, 2019. 16(10): p. 987-990.
11. Rodriques, S. G., et al., *Slide-seq: A scalable technology for measuring genome-wide expression at high spatial resolution*. Science, 2019. 363(6434): p. 1463-1467.

12. Liu, Y., et al., *High-Spatial-Resolution Multi-Omics Sequencing via Deterministic Barcoding in Tissue.* Cell, 2020. 183(6): p. 1665-1681 e18.
13. Bergenstråhle, L., et al., *Super-resolved spatial transcriptomics by deep data fusion.* bioRxiv, 2020: p. 2020.02.28.963413.
14. Baccin, C., et al., *Combined single-cell and spatial transcriptomics reveal the molecular, cellular and spatial bone marrow niche organization.* Nat Cell Biol, 2020. 22(1): p. 38-48.
15. Asp, M., et al., *A Spatiotemporal Organ-Wide Gene Expression and Cell Atlas of the Developing Human Heart.* Cell, 2019. 179(7): p. 1647-1660 e19.
16. Zhou, Y., et al., *Encoding Method of Single-cell Spatial Transcriptomics Sequencing.* Int J Biol Sci, 2020. 16(14): p. 2663-2674.
17. Bentley, D. R., et al., *Accurate whole human genome sequencing using reversible terminator chemistry.* Nature, 2008. 456(7218): p. 53-9.
18. Bahar Halpern, K., et al., *Nuclear Retention of mRNA in Mammalian Tissues.* Cell Rep, 2015. 13(12): p. 2653-62.
19. Baratta, J. L., et al., *Cellular organization of normal mouse liver: a histological, quantitative immunocytochemical, and fine structural analysis.* Histochem Cell Biol, 2009. 131(6): p. 713-26.
20. Stuart, T., et al., *Comprehensive Integration of Single-Cell Data.* Cell, 2019. 177(7): p. 1888-1902 e21.
21. Ben-Moshe, S. and S. Itzkovitz, *Spatial heterogeneity in the mammalian liver.* Nat Rev Gastroenterol Hepatol, 2019. 16(7): p. 395-410.
22. Halpern, K. B., et al., *Single-cell spatial reconstruction reveals global division of labour in the mammalian liver.* Nature, 2017. 542(7641): p. 352-356.
23. Aizarani, N., et al., *A human liver cell atlas reveals heterogeneity and epithelial progenitors.* Nature, 2019. 572(7768): p. 199-204.
24. Park, S. R., et al., *Holistic Characterization of Single Hepatocyte Transcriptome Responses to High Fat Diet.* Am J Physiol Endocrinol Metab, 2020.
25. Xiong, X., et al., *Landscape of Intercellular Crosstalk in Healthy and NASH Liver Revealed by Single-Cell Secretome Gene Analysis.* Mol Cell, 2019. 75(3): p. 644-660 e5.
26. de Haan, W., et al., *Unraveling the transcriptional determinants of liver sinusoidal endothelial cell specialization.* Am J Physiol Gastrointest Liver Physiol, 2020. 318(4): p. G803-G815.
27. Tee, L. B., et al., *Dual phenotypic expression of hepatocytes and bile ductular markers in developing and preneoplastic rat liver.* Carcinogenesis, 1996. 17(2): p. 251-9.
28. Werner, M., et al., *All-In-One: Advanced preparation of Human Parenchymal and Non-Parenchymal Liver Cells.* PLoS One, 2015. 10(9): p. e0138655.
29. Sack, G. H., Jr., *Serum Amyloid A (SAA) Proteins.* Subcell Biochem, 2020. 94: p. 421-436.
30. Saiman, Y. and S. L. Friedman, *The role of chemokines in acute liver injury.* Front Physiol, 2012. 3: p. 213.
31. Abbas, W., A. Kumar, and G. Herbein, *The eEF1A Proteins: At the Crossroads of Oncogenesis, Apoptosis, and Viral Infections.* Front Oncol, 2015. 5: p. 75.
32. Cho, C. S., et al., *Concurrent activation of growth factor and nutrient arms of mTORC1 induces oxidative liver injury.* Cell Discov, 2019. 5: p. 60.
33. Levine, D. S. and R. C. Haggitt, *Normal histology of the colon.* Am J Surg Pathol, 1989. 13(11): p. 966-84.
34. Farkas, A. E., et al., *Cryosectioning Method for Microdissection of Murine Colonic Mucosa.* J Vis Exp, 2015 (101): p. e53112.
35. Haber, A. L., et al., *A single-cell survey of the small intestinal epithelium.* Nature, 2017. 551(7680): p. 333-339.
36. Moor, A. E., et al., *Spatial Reconstruction of Single Enterocytes Uncovers Broad Zonation along the Intestinal Villus Axis.* Cell, 2018. 175(4): p. 1156-1167 e15.
37. Altmann, G. G., *Morphological observations on mucus-secreting nongoblet cells in the deep crypts of the rat ascending colon.* Am J Anat, 1983. 167(1): p. 95-117.
38. Sasaki, N., et al., *Reg4+ deep crypt secretory cells function as epithelial niche for Lgr5+ stem cells in colon.* Proc Natl Acad Sci USA, 2016. 113(37): p. E5399-407.
39. Rothenberg, M. E., et al., *Identification of a cKit(+) colonic crypt base secretory cell that supports Lgr5(+) stem cells in mice.* Gastroenterology, 2012. 142(5): p. 1195-1205 e6.
40. Park, S. W., et al., *The protein disulfide isomerase AGR2 is essential for production of intestinal mucus.* Proc Natl Acad Sci USA, 2009. 106(17): p. 6950-5.
41. Parikh, K., et al., *Colonic epithelial cell diversity in health and inflammatory bowel disease.* Nature, 2019. 567(7746): p. 49-55.
42. Fischer, H., et al., *Differential expression of aquaporin 8 in human colonic epithelial cells and colorectal tumors.* BMC Physiol, 2001. 1: p. 1.
43. Borenshtein, D., et al., *Decreased expression of colonic Slc26a3 and carbonic anhydrase iv as a cause of fatal infectious diarrhea in mice.* Infect Immun, 2009. 77(9): p. 3639-50.
44. Eckhardt, E. R., et al., *Intestinal epithelial serum amyloid A modulates bacterial growth in vitro and pro-inflammatory responses in mouse experimental colitis.* BMC Gastroenterol, 2010. 10: p. 133.
45. Okumura, R., et al., *Lypd8 promotes the segregation of flagellated microbiota and colonic epithelia.* Nature, 2016. 532(7597): p. 117-21.
46. Pelaseyed, T., et al., *The mucus and mucins of the goblet cells and enterocytes provide the first defense line of the gastrointestinal tract and interact with the immune system.* Immunol Rev, 2014. 260(1): p. 8-20.
47. Nestorowa, S., et al., *A single-cell resolution map of mouse hematopoietic stem and progenitor cell differentiation.* Blood, 2016. 128(8): p. e20-31.
48. Spencer, J. and L. M. Sollid, *The human intestinal B-cell response.* Mucosal Immunol, 2016. 9(5): p. 1113-24.
49. Singer, G. A. C., et al., *Comprehensive biodiversity analysis via ultra-deep patterned flow cell technology: a case study of eDNA metabarcoding seawater.* Sci Rep, 2019. 9(1): p. 5991.
50. Stoeckius, M., et al., *Simultaneous epitope and transcriptome measurement in single cells.* Nat Methods, 2017. 14(9): p. 865-868.
51. Hughes, T. K., et al., *Second-Strand Synthesis-Based Massively Parallel scRNA-Seq Reveals Cellular States and Molecular Features of Human Inflammatory Skin Pathologies.* Immunity, 2020. 53(4): p. 878-894 e7.
52. Storm, A. J. and P. A. Jensen, *Designing Randomized DNA Sequences Free of Restriction Enzyme Recognition Sites.* Biotechnol J, 2018. 13(1).

53. Ro, S. H., et al., *Tumor suppressive role of sestrin2 during colitis and colon carcinogenesis.* Elife, 2016. 5: p. 12204.
54. Dobin, A., et al., *STAR: ultrafast universal RNA-seq aligner.* Bioinformatics, 2013. 29(1): p. 15-21.
55. La Manno, G., et al., *RNA velocity of single cells.* Nature, 2018. 560(7719): p. 494-498.
56. Bolte, S. and F. P. Cordelieres, *A guided tour into subcellular colocalization analysis in light microscopy.* J Microsc, 2006. 224(Pt 3): p. 213-32.
57. Becht, E., et al., *Dimensionality reduction for visualizing single-cell data using UMAP.* Nat Biotechnol, 2019. 37: p. 38-44.

I claim:

1. A method of generating a spatial transcriptomics gene expression image having subcellular resolution, comprising:

a. providing a flat array surface comprising high density clusters of probes, wherein each probe comprises a spatial barcode sequence and a capture domain, and wherein a location of each cluster on said flat array surface is known;

b. contacting said flat array surface with a tissue section under conditions such that RNA from cells in said tissue section hybridizes to said capture domain of said probes;

c. reverse transcribing target sequences from said RNA on 3' ends of said probes;

d. generating second strand copies of said probes and eluting said second strand copies from said array;

e. generating a sequencing library from eluted second strand copies;

f. sequencing said sequencing library to generate sequencing data; and g. generating a spatial transcriptomics gene expression image having subcellular resolution from said sequencing data.

2. The method of claim 1, wherein each probe in a given cluster comprises an identical spatial barcode sequence, and wherein said spatial barcode sequence for each cluster is unique.

3. The method of claim 1, wherein said flat array surface comprises 0.5-2 million clusters per 1 mm$^2$ of surface.

4. The method of claim 3, wherein said flat array surface comprises about 1.5 million clusters per 1 mm$^2$ of surface.

5. The method of claim 1, wherein each cluster comprises at least 200 probes.

6. The method of claim 1, wherein each cluster comprises at least 500 probes.

7. The method of claim 1, wherein each cluster comprises at least 800 probes.

8. The method of claim 1, wherein each cluster has a diameter of 500-1200 nm.

9. The method of claim 8, wherein each cluster has an average diameter of 0.6 μm.

10. The method of claim 1, wherein said flat array surface comprises a material selected from glass, silicon, poly-L-lysine coated materials, nitrocellulose, polystyrene, cyclic olefin copolymers (COCs), cyclic olefin polymers (COPs), polyacrylamide, polypropylene, polyethylene and polycarbonate.

11. The method of claim 1, wherein said capture domain is identical for each probe.

12. The method of claim 1, wherein said capture domain comprises a poly-T oligonucleotide comprising at least 10 deoxythymidine residues.

13. The method of claim 1, wherein each probe further comprises a sequencing barcode.

14. The method of claim 1, wherein each probe further comprises one or more filler sequences.

15. The method of claim 1, wherein each probe further comprises a unique molecular identifier (UMI) barcode sequence.

16. The method of claim 1, wherein each probe further comprises a cleavage domain comprising a binding site for a restriction endonuclease.

17. The method of claim 1, further comprising imaging the tissue before or after reverse transcribing target sequences from said RNA on 3' ends of said probes.

18. The method of claim 17, further comprising correlating the identified location of each cluster on said flat array surface with a corresponding location within said tissue section.

19. The method of claim 1, wherein the distance between centers of said clusters is 1 μm or less.

20. The method of claim 1, wherein said clusters are produced by bridge amplification.

* * * * *

SEQUENCE LISTING

```
Sequence total quantity: 42
SEQ ID NO: 1              moltype = DNA  length = 185
FEATURE                   Location/Qualifiers
source                    1..185
                          mol_type = other DNA
                          organism = Synthetic construct
SEQUENCE: 1
caagcagaag acggcatacg agattctttc cctacacgac gctcttccga tctnnvnnvn  60
nvnnvnnvnn nnntcttgtg actacagcac cctcgactct cgcttttttt ttttttttt  120
tttttttttt tttaaagact ttcaccagtc catgatgtgt agatctcggt ggtcgccgta  180
tcatt                                                              185

SEQ ID NO: 2              moltype = DNA  length = 197
FEATURE                   Location/Qualifiers
source                    1..197
                          mol_type = other DNA
                          organism = Synthetic construct
SEQUENCE: 2
caagcagaag acggcatacg agattctttc cctacacgac gctcttccga tctnnvnbvn  60
nvnnvnnvn vnnvnnvnnv nnnnntcttg tgactacagc accctcgact ctcgcttttt  120
tttttttttt tttttttttt tttttaaaga ctttcaccag tccatgatgt gtagatctcg  180
gtggtcgccg tatcatt                                                 197

SEQ ID NO: 3              moltype = DNA  length = 83
FEATURE                   Location/Qualifiers
source                    1..83
                          mol_type = other DNA
                          organism = Synthetic construct
SEQUENCE: 3
atcatggact ggtgaaagtc tttaaaaaaa aaaaaaaaaa aaaaaaaaaa aaagcgagag  60
tcgagggtgc tgtagtcaca aga                                          83

SEQ ID NO: 4              moltype = DNA  length = 32
FEATURE                   Location/Qualifiers
source                    1..32
                          mol_type = other DNA
                          organism = Synthetic construct
SEQUENCE: 4
tcagacgtgt gctcttccga tctnnnnnnn nn                                32

SEQ ID NO: 5              moltype = DNA  length = 20
FEATURE                   Location/Qualifiers
source                    1..20
                          mol_type = other DNA
                          organism = Synthetic construct
SEQUENCE: 5
tctttcccta cacgacgctc                                              20

SEQ ID NO: 6              moltype = DNA  length = 20
FEATURE                   Location/Qualifiers
source                    1..20
                          mol_type = other DNA
                          organism = Synthetic construct
SEQUENCE: 6
tcagacgtgt gctcttccga                                              20

SEQ ID NO: 7              moltype = DNA  length = 49
FEATURE                   Location/Qualifiers
source                    1..49
                          mol_type = other DNA
                          organism = Synthetic construct
SEQUENCE: 7
aatgatacgg cgaccgagat ctacactctt tccctacacg acgctcttc              49

SEQ ID NO: 8              moltype = DNA  length = 55
FEATURE                   Location/Qualifiers
source                    1..55
                          mol_type = other DNA
                          organism = Synthetic construct
```

```
SEQUENCE: 8
caagcagaag acggcatacg agatgtgact ggagttcaga cgtgtgctct tccga        55

SEQ ID NO: 9               moltype = DNA   length = 145
FEATURE                    Location/Qualifiers
source                     1..145
                           mol_type = other DNA
                           organism = Synthetic construct
SEQUENCE: 9
caagcagaag acggcatacg agattctttc cctacacgac gctcttccga tcthnnbnbn    60
bnbnbnbnbn nnncccgttc gcaacatgtc tggcgtcata gaattccgca gtccaggtgt   120
agatctcggt ggtcgccgta tcatt                                          145

SEQ ID NO: 10              moltype = DNA   length = 43
FEATURE                    Location/Qualifiers
source                     1..43
                           mol_type = other DNA
                           organism = Synthetic construct
SEQUENCE: 10
ctggactgcg gaattctatg acgccagaca tgttgcgaac ggg                      43

SEQ ID NO: 11              moltype = DNA   length = 66
FEATURE                    Location/Qualifiers
source                     1..66
                           mol_type = other DNA
                           organism = Synthetic construct
SEQUENCE: 11
aaaaaaaaaa aaaaaaaaaa aaaaaaaaaa nnnnnnnnct atgacgccag acatgttgcg    60
aacggg                                                                66

SEQ ID NO: 12              moltype = DNA   length = 190
FEATURE                    Location/Qualifiers
source                     1..190
                           mol_type = other DNA
                           organism = Synthetic construct
SEQUENCE: 12
caagcagaag acggcatacg agattctttc cctacacgac gctcttccga tctnnnvnbv    60
nnnbnnbbvn bnnccttatgt tcttatgcgg taggagctgt gtacgttttt tttttttttt   120
tttttttttt tttttctaga tcagtagagg atagaggcca cgtgtagatc tcggtggtcg   180
ccgtatcatt                                                           190

SEQ ID NO: 13              moltype = DNA   length = 185
FEATURE                    Location/Qualifiers
source                     1..185
                           mol_type = other DNA
                           organism = Synthetic construct
SEQUENCE: 13
caagcagaag acggcatacg agattctttc cctacacgac gctcttccga tctnnvnnvn    60
nvnnvnnvnn nnntcttgtg actacagcac cctcgactct cgcttttttt tttttttttt   120
tttttttttt tttaaagact ttcaccagtc catgatgtgt agatctcggt ggtcgccgta   180
tcatt                                                                185

SEQ ID NO: 14              moltype = DNA   length = 190
FEATURE                    Location/Qualifiers
source                     1..190
                           mol_type = other DNA
                           organism = Synthetic construct
SEQUENCE: 14
caagcagaag acggcatacg agattctttc cctacacgac gctcttccga tctnnnvnbv    60
nnnbnnbbvn bnnccttatgt tcttatgcgg taggagctgt gtacgttttt tttttttttt   120
tttttttttt tttttctaga tcagtagagg atagaggcca cgtgtagatc tcggtggtcg   180
ccgtatcatt                                                           190

SEQ ID NO: 15              moltype = DNA   length = 278
FEATURE                    Location/Qualifiers
source                     1..278
                           mol_type = other DNA
                           organism = Synthetic construct
SEQUENCE: 15
caagcagaag acggcatacg agattctttc cctacacgac gctcttccga tctnnnvnbv    60
nnnbnnbbvn bnnccttatgt tcttatgcgg taggagctgt gtacgttttt tttttttttt   120
tttttttttt tttttctaga tcagtagagg atagaggcca cgtgtagatc tcggtggtcg   180
ccgtatcatt gaatacaaga atacgccatc ctcgacacat gcaaaaaaaa aaaaaaaaaa   240
aaaaaaaaaa aagatctagt catctcctat ctccggtg                           278

SEQ ID NO: 16              moltype = DNA   length = 303
FEATURE                    Location/Qualifiers
```

```
                        source              1..303
                                            mol_type = other DNA
                                            organism = Synthetic construct
SEQUENCE: 16
caagcagaag acggcatacg agattctttc cctacacgac gctcttccga tctnnnvnbv      60
nnnbnnbbvn bnncttatgt tcttatgcgg taggagctgt gtacgttttt tttttttttt     120
tttttttttt ttttttctaga tcagtagagg atagaggcca cgtgtagatc tcggtggtcg    180
ccgtatcatt ctagannnbn vbnnnvnnvv bnvnngaata caagaatacg ccatcctcga     240
cacatgcaaa aaaaaaaaaa aaaaaaaaaa aaaaaagat ctagtcatct cctatctccg      300
gtg                                                                   303

SEQ ID NO: 17          moltype = DNA   length = 271
FEATURE                Location/Qualifiers
source                 1..271
                       mol_type = other DNA
                       organism = Synthetic construct
SEQUENCE: 17
caagcagaag acggcatacg agattctttc cctacacgac gctcttccga tctnnnvnbv      60
nnnbnnbbvn bnncccgttc gcaacatgtc tggcgtcata tttttttttt tttttttttt    120
tttttttttt ctagacgcag tccaggtgta gatctcggtg gtcgccgtat cattctagan    180
nnbnvbnnnv nnvvbnvnng ggcaagcgtt gtacagaccg cagtataaaa aaaaaaaaaa    240
aaaaaaaaaa aaaaaagatc tgcgtcaggt c                                   271

SEQ ID NO: 18          moltype = DNA   length = 222
FEATURE                Location/Qualifiers
source                 1..222
                       mol_type = other DNA
                       organism = Synthetic construct
SEQUENCE: 18
caagvagaag acggcatacg agatgcctgt ccgcggaagc agtggtatca acgcagagta      60
cnnbnbnbnb nbnbnnbndn ncccgttcgc aacatgtctg gcgtcataga attccgcagt    120
ccaggtgtag atctcggtgg tcgccgtatc atttcatgnn vnvnvnvnvn vnnnvhnnngg   180
gcaagcgttg tacagaccgc agtatcttaa ggcgtacagg tc                       222

SEQ ID NO: 19          moltype = DNA   length = 175
FEATURE                Location/Qualifiers
source                 1..175
                       mol_type = other DNA
                       organism = Synthetic construct
SEQUENCE: 19
caagvagaag acggcatacg agatgcctgt ccgcggaagc agtggtatca acgcagagta      60
cnnbnbnbnb nbnbnnbndn ncccgttcgc aacatgtctg gcgtcatagg ggcaagcgtt    120
gtacagaccg cagtatcnnn nnnnnaaaaa aaaaaaaaaa aaaaaaaaaa aaaaa         175

SEQ ID NO: 20          moltype = DNA   length = 147
FEATURE                Location/Qualifiers
source                 1..147
                       mol_type = other DNA
                       organism = Synthetic construct
SEQUENCE: 20
caagvagaag acggcatacg agatgcctgt ccgcggaagc agtggtatca acgcagagta      60
cnnbnbnbnb nbnbnnbndn ncccgttcgc aacatgtctg gcgtcatagn nnnnnnnttt    120
tttttttttt tttttttttt tttttt                                          147

SEQ ID NO: 21          moltype = DNA   length = 124
FEATURE                Location/Qualifiers
source                 1..124
                       mol_type = other DNA
                       organism = Synthetic construct
SEQUENCE: 21
gacgctcttc cgatctnnnv nbvnnnbnnb bvnbnntttt tttttttttt tttttttttt      60
tttttttaaaa aaaaaaaaa aaaaaaaaaa aannnnnnnn nnnnnnnnnn nnnnnnnnnn     120
nnnn                                                                  124

SEQ ID NO: 22          moltype = DNA   length = 130
FEATURE                Location/Qualifiers
source                 1..130
                       mol_type = other DNA
                       organism = Synthetic construct
SEQUENCE: 22
gacgctcttc cgatctnnnv nbvnnnbnnb bvnbnntttt tttttttttt tttttttttt      60
tttttnnnn nnnnnnnnnn nnnnnnnnnn nnnnnnnnnn nnnnnntct agccttctcg      120
tgtgcagact                                                            130

SEQ ID NO: 23          moltype = DNA   length = 98
FEATURE                Location/Qualifiers
source                 1..98
                       mol_type = other DNA
                       organism = Synthetic construct
```

```
SEQUENCE: 23
gacgctcttc cgatctnnnv nbvnnnbnnb bvnbnnttttt tttttttttt tttttttttt   60
ttttttnnnn nnnnnnnnnn nnnnnnnnnn nnnnnnnn                           98

SEQ ID NO: 24           moltype = DNA   length = 130
FEATURE                 Location/Qualifiers
source                  1..130
                        mol_type = other DNA
                        organism = Synthetic construct
SEQUENCE: 24
ctgcgagaag gctagannnb nvbnnnvnnv vbnvnnaaaa aaaaaaaaaa aaaaaaaaaa   60
aaaaaannnn nnnnnnnnnn nnnnnnnnnn nnnnnnnnnn nnnnnntct agccttctcg  120
tgtgcagact                                                        130

SEQ ID NO: 25           moltype = DNA   length = 162
FEATURE                 Location/Qualifiers
source                  1..162
                        mol_type = other DNA
                        organism = Synthetic construct
SEQUENCE: 25
gacgctcttc cgatctctgc gagaaggcta gannnbnvbn nnvnnvvbnv nnaaaaaaaa   60
aaaaaaaaaa aaaaaaaaaa aannnnnnnn nnnnnnnnnn nnnnnnnnnn nnnnnnnnnn  120
nnntctagcc ttctcgtgtg cagacttcag acgtgtgctc tt                    162

SEQ ID NO: 26           moltype = DNA   length = 244
FEATURE                 Location/Qualifiers
source                  1..244
                        mol_type = other DNA
                        organism = Synthetic construct
SEQUENCE: 26
nnnvnbvnnn bnnbbvnbnn tttttttttt tttttttttt tttttttttt nnnnnnnnnn   60
nnnnnnnnnn nnnnnnnnnn nnnnnnnnnn nagatcggaa gagcacacgt ctgactgcga  120
gaaggctaga nnnbnvbnnn vnnvvbnvnn aaaaaaaaa aaaaaaaaaa aaaaaaaaaa   180
nnnnnnnnnn nnnnnnnnnn nnnnnnnnnn nnnnnnnnnn ntctagcctt ctcgtgtgca  240
gact                                                              244

SEQ ID NO: 27           moltype = DNA   length = 260
FEATURE                 Location/Qualifiers
source                  1..260
                        mol_type = other DNA
                        organism = Synthetic construct
SEQUENCE: 27
aatgatacgg cgaccaccga gatctacact ctttccctac acgacgctct tccgatctga   60
cgctcttccg atctnnnvnb vnnnbnnbbv nbnnnnnnnn nnnagatcgg aagagcacac  120
gtctgactgc gagaaggcta gannnbnvbn nnvnnvvbnv nnnnnnnnnn ntctagcctt  180
ctcgtgtgca gactcaagca gaagacggca tacgagatnn nnnnnngtga ctggagttca  240
gacgtgtgct cttccgatct                                             260

SEQ ID NO: 28           moltype = DNA   length = 306
FEATURE                 Location/Qualifiers
source                  1..306
                        mol_type = other DNA
                        organism = Synthetic construct
SEQUENCE: 28
aatgatacgg cgaccaccga gatctacact ctttccctac acgacgctct tccgatctnn   60
nvnbvnnnbn nbbvnbnnnn nnnnnnnaga tcggaagagc acacgtctga actccagtca  120
cnnnnnnnna tctcgtatgc cgtcttctgc ttgttactat gccgctggtg gctctagatg  180
tgagaaaggg atgtgctgcg agaaggctag annnbnvbnn nvnnvvbnvn nnnnnnnnnn  240
tctagccttc tcgtgtgcag acttgaggtc agtgnnnnnn nntagagcat acggcagaag  300
acgaac                                                            306

SEQ ID NO: 29           moltype = DNA   length = 275
FEATURE                 Location/Qualifiers
source                  1..275
                        mol_type = other DNA
                        organism = Synthetic construct
SEQUENCE: 29
caagcagaag acggcatacg agattctttc cctacacgac gctcttccga tctnnvnnvn   60
nvnnvnnvnn nnntcttgtg actacagcac cctcgactct cgcttttttt tttttttttt  120
tttttttttt tttaaagact ttcaccagtc catgatgtgt agatctcggt ggtcgccgta  180
tcattagaac actgatgtcg tgggagctga gagcgaaaaa aaaaaaaaaa aaaaaaaaaa  240
aaaaaaaaaa tttctgaaag tgggtacagg tacta                            275

SEQ ID NO: 30           moltype = DNA   length = 275
FEATURE                 Location/Qualifiers
source                  1..275
                        mol_type = other DNA
                        organism = Synthetic construct
```

```
SEQUENCE: 30
caagcagaag acggcatacg agattctttc cctacacgac gctcttccga tctnnvnnvn   60
nvnnvnnvnn nnntcttgtg actacagcac cctcgactct cgctttttt tttttttttt  120
tttttttttt tttaaagact ttcaccagtc catgatgtgt agatctcggt ggtcgccgta  180
tcattagaac actgatgtcg tgggagctga gagcgaaaaa aaaaaaaaaa aaaaaaaaaa  240
aaaaaaaaaa tttctgaaag tgggtacagg tacta                             275

SEQ ID NO: 31              moltype = DNA   length = 133
FEATURE                    Location/Qualifiers
source                     1..133
                           mol_type = other DNA
                           organism = Synthetic construct
SEQUENCE: 31
caagcagaag acggcatacg agattctttc cctacacgac gctcttccga tctnnvnnvn   60
nvnnvnnvnn nnntcttgtg actacagcac cctcgactct cgctttttt tttttttttt  120
tttttttttt ttt                                                     133

SEQ ID NO: 32              moltype = DNA   length = 203
FEATURE                    Location/Qualifiers
source                     1..203
                           mol_type = other DNA
                           organism = Synthetic construct
SEQUENCE: 32
caagcagaag acggcatacg agattctttc cctacacgac gctcttccga tctnnvnnvn   60
nvnnvnnnnn tcttgtgact acagcaccct cgactctcgc tttttttttt tttttttttt  120
tttttttttt nnnnnnnnnn nnnnnnnnnn nnnnnnnnnn nnnnnnnnnn nnnnnnnnnn  180
nnnnnnnnna aaaaaaaaaa aaa                                          203

SEQ ID NO: 33              moltype = DNA   length = 221
FEATURE                    Location/Qualifiers
source                     1..221
                           mol_type = other DNA
                           organism = Synthetic construct
SEQUENCE: 33
caagcagaag acggcatacg agattctttc cctacacgac gctcttccga tctnnvnnvn   60
nvnnvnnnnn tcttgtgact acagcaccct cgactctcgc tttttttttt tttttttttt  120
tttttttttt nnnnnnnnnn nnnnnnnnnn nnnnnnnnnn nnnnnnnnnn nnnnnnnnnn  180
nnnnnnnnnt cagacgtctg ctcttccgat ctnnnnnnnn n                      221

SEQ ID NO: 34              moltype = DNA   length = 221
FEATURE                    Location/Qualifiers
source                     1..221
                           mol_type = other DNA
                           organism = Synthetic construct
SEQUENCE: 34
caagcagaag acggcatacg agattctttc cctacacgac gctcttccga tctnnvnnvn   60
nvnnvnnnnn tcttgtgact acagcaccct cgactctcgc tttttttttt tttttttttt  120
tttttttttt nnnnnnnnnn nnnnnnnnnn nnnnnnnnnn nnnnnnnnnn nnnnnnnnnn  180
nnnnnnnnnt cagacgtctg ctcttccgat ctnnnnnnnn n                      221

SEQ ID NO: 35              moltype = DNA   length = 460
FEATURE                    Location/Qualifiers
source                     1..460
                           mol_type = other DNA
                           organism = Synthetic construct
SEQUENCE: 35
aatgatacgg cgaccaccga gatctacact ctttccctac acgaggctct ctttccctac   60
acgacgctct tccgatctnn vnnvnnvnnv nnvnnnnntc ttgtgactac agcaccctcg  120
actctcgctt tttttttttt tttttttttt tttttttnn nnnnnnnnnn nnnnnnnnnn  180
nnnnnnnnnn nnnnnnnnnn agatcggaag agcacacgtc tgaagaaagg gatgtgctgc  240
gagaaggcta gannbnnbnn bnnbnnbnnn nnagaacact gatgtcgtgg gagctgagag  300
cgaaaaaaaa aaaaaaaaaa aaaaaaaaa aannnnnnnn nnnnnnnnnn nnnnnnnnnn  360
nnnnnnnnnn nnntctagc cttctcgtgt gcagactcaa gcagaagacg gcatacgaga  420
tnnnnnnnng tgactggagt tcagacgtgt gctcttccga                        460

SEQ ID NO: 36              moltype = DNA   length = 495
FEATURE                    Location/Qualifiers
source                     1..495
                           mol_type = other DNA
                           organism = Synthetic construct
SEQUENCE: 36
aatgatacgg cgaccaccga gatctacact ctttccctac acgacgctct tccgatctnn   60
vnnvnnvnnv nnvnnnnntc ttgtgactac tacagcaccc tcgactctcg ctttttttt  120
tttttttttt tttttttttt tnnnnnnnnn nnnnnnnnnn nnnnnnnnnn nnnnnnnnnn  180
```

```
nnnagatcgg aagagcacac gtctgaactc cagtcacnnn nnnnnatctc gtatgccgtc    240
ttctgcttgt tactatgccg ctggtggctc tagatgtgag aaagggatgt gctgcgagaa    300
ggctagannb nnbnnbnnbn nbnnnnnaga acactgatgt cgtgggagct gagagcgaaa    360
aaaaaaaaaa aaaaaaaaaa aaaaaannn nnnnnnnnnn nnnnnnnnnn nnnnnnnnnn    420
nnnnnnnnnt ctagccttct cgtgtgcaga cttgaggtca gtgnnnnnnn ntagagcata    480
cggcagaaga cgaac                                                     495

SEQ ID NO: 37           moltype = DNA    length = 145
FEATURE                 Location/Qualifiers
source                  1..145
                        mol_type = other DNA
                        organism = Synthetic construct
SEQUENCE: 37
caagcagaag acggcatacg agattctttc cctacacgac gctcttccga tcthnnbnbn     60
bnbnbnbnbn nnncccgttc gcaacatgtc tggcgtcata gaattccgca gtccaggtgt    120
agatctcggt ggtcgccgta tcatt                                          145

SEQ ID NO: 38           moltype = DNA    length = 189
FEATURE                 Location/Qualifiers
source                  1..189
                        mol_type = other DNA
                        organism = Synthetic construct
SEQUENCE: 38
caagcagaag acggcatacg agattctttc cctacacgac gctcttccga tctnnvnnvn     60
nvnnvnnvnn nnncccgttc gcaaccatgt ctggcgtcat agaattccgc agtccaggtg    120
tagatctcgg tggtcgccgt atcattgggc aagcgttgta cagaccgcag tatcttaagg    180
cgtcaggtc                                                            189

SEQ ID NO: 39           moltype = DNA    length = 214
FEATURE                 Location/Qualifiers
source                  1..214
                        mol_type = other DNA
                        organism = Synthetic construct
SEQUENCE: 39
caagcagaag acggcatacg agattctttc cctacacgac gctcttccga tctnnvnnvn     60
nvnnvnnvnn nnncccgttc gcaaccatgt ctggcgtcat agaattccgc agtccaggtg    120
tagatctcgg tggtcgccgt atcattctag annbnnbnnb nnbnnbnnnn ngggcaagcg    180
ttgtacagac cgcagtatct taaggcgtca ggtc                                214

SEQ ID NO: 40           moltype = DNA    length = 101
FEATURE                 Location/Qualifiers
source                  1..101
                        mol_type = other DNA
                        organism = Synthetic construct
SEQUENCE: 40
caagcagaag acggcatacg agattctttc cctacacgac gctcttccga tctnnvnnvn     60
nvnnvnnvnn nnncccgttc gcaacatgtc tggcgtcata g                        101

SEQ ID NO: 41           moltype = DNA    length = 167
FEATURE                 Location/Qualifiers
source                  1..167
                        mol_type = other DNA
                        organism = Synthetic construct
SEQUENCE: 41
caagcagaag acggcatacg agattctttc cctacacgac gctcttccga tctnnvnnvn     60
nvnnvnnvnn nnncccgttc gcaacatgtc tggcgtcata ggggcaagcg ttgtacagac    120
cgcagtatcn nnnnnnaaaa aaaaaaaaaa aaaaaaaaa aaaaaaa                   167

SEQ ID NO: 42           moltype = DNA    length = 167
FEATURE                 Location/Qualifiers
source                  1..167
                        mol_type = other DNA
                        organism = Synthetic construct
SEQUENCE: 42
caagcagaag acggcatacg agattctttc cctacacgac gctcttccga tctnnvnnvn     60
nvnnvnnvnn nnncccgttc gcaacatgtc tggcgtcata ggggcaagcg ttgtacagac    120
cgcagtatcn nnnnnnttt tttttttttt tttttttttt ttttttt                   167
```